(12) United States Patent
Matthews et al.

(10) Patent No.: US 9,193,781 B2
(45) Date of Patent: Nov. 24, 2015

(54) HEPATITIS C VIRUS ANTIBODIES

(75) Inventors: David J. Matthews, London (GB);
David G. Williams, London (GB);
Arvind Patel, Glasgow (GB)

(73) Assignees: MEDICAL RESEARCH COUNCIL, London (GB); MEDICAL RESEARCH COUNCIL TECHNOLOGY, London (GB)

( * ) Notice: Subject to any disclaimer, the term of this patent is extended or adjusted under 35 U.S.C. 154(b) by 399 days.

(21) Appl. No.: 12/809,050

(22) PCT Filed: Dec. 17, 2008

(86) PCT No.: PCT/IB2008/003952
§ 371 (c)(1),
(2), (4) Date: Sep. 9, 2010

(87) PCT Pub. No.: WO2009/081285
PCT Pub. Date: Jul. 2, 2009

(65) Prior Publication Data
US 2011/0002926 A1    Jan. 6, 2011

Related U.S. Application Data

(60) Provisional application No. 61/006,066, filed on Dec. 17, 2007.

(51) Int. Cl.
| | | |
|---|---|---|
| *C12P 21/08* | (2006.01) | |
| *C07K 16/00* | (2006.01) | |
| *G01N 33/53* | (2006.01) | |
| *C07K 16/10* | (2006.01) | |
| *G01N 33/50* | (2006.01) | |
| *G01N 33/576* | (2006.01) | |

(52) U.S. Cl.
CPC ........... *C07K 16/109* (2013.01); *C07K 2316/96* (2013.01); *C07K 2317/24* (2013.01); *C07K 2317/56* (2013.01); *C07K 2317/92* (2013.01); *G01N 33/50* (2013.01); *G01N 33/576* (2013.01); *G01N 2333/186* (2013.01)

(58) Field of Classification Search
None
See application file for complete search history.

(56) References Cited

U.S. PATENT DOCUMENTS 6,372,216 B1 * 4/2002 Piazza ................. 424/161.1

FOREIGN PATENT DOCUMENTS

| WO | WO02/055560 | 7/2002 |
| WO | WO03/064473 | 8/2003 |
| WO | WO2006041866 | 4/2006 |
| WO | WO2006100449 | 9/2006 |

OTHER PUBLICATIONS

Keller et al., Clinical Microbiology Reviews, 2000, 13(4):602-614.*
Irshad et al., International Reviews of Immunology, 2008, 27:497-517.*
Tarr, Alexander W et al, "Determination of the human antibody response to the epitope defined by the hepatitis C virus-neutralizing monoclonal antibody AP33," The Journal of General Virology, 2007, vol. 88, pp. 2991-3001.
Owsianka, Ania et al, "Monoclonal antibody AP33 defines a broadly neutralizing epitope of the hepatitis C virus E2 glycoprotein," Journal of Virology, 2005, V. 79, No. 17, pp. 11095-11104.
Burioni, Roberto et al, "Nonneutralizing human antibody fragments against hepatitis C virus E2 glycoprotein modulate neutralization of binding activity of human recombinant Fabs," Virology, 2001, vo. 288, pp. 29-35.
Chan, Shiu-Wan et al, "Human recombinant antibodies specific for hepatitis C virus core and envelope E2 peptides from an immune phage display library," 1996, Journal of General Virology, vol. 77, pp. 2531-2539.
Gal-Tanamy, Meital et al, "In vitro selection of a neutralization-resistant hepatitis C virus escape mutant," Proceedings of the National Academy of Sciences, 2008, vol. 105, No. 49, pp. 19450-19455.
Hix, Rebecca "International Preliminary Report on Patentability and Written Opinion of the International Searching Authority—PCT/IB2008/003952" European Patent Office; Jul. 13, 2010; pp. 1-8.
Hix, Rebecca "International Search Report—PCT/IB2008/003952" European Patent Office; Jul. 2, 2010; pp. 1-7.
Tarr, et al. "Characterization of the Hepatitis C Virus E2 Epitope Defined by the Broadly Neutralizing Monoclonal Antibody AP33" Hepatology, vol. 43, No. 3, 2006; pp. 592-601.

* cited by examiner

*Primary Examiner* — Hong Sang
(74) *Attorney, Agent, or Firm* — Thomas G. Peterson; Bradley Arant Boult Cummings LLP

(57) ABSTRACT

This invention relates to humanized antibodies and fragments thereof which bind to hepatitis C virus E2 protein and methods of their use.

8 Claims, 49 Drawing Sheets

| | Canonical Residue | -111-1----------2-----1 |
|---|---|---|
| | Vernier Residue | *--**---****-- |
| | Interface Residue | -------IIII-------II-- |
| | Kabat Number | 2 24 26 27 28 29 30 37 39 45 47 48 49 67 69 71 73 78 91 93 94 103 |

| Name | VCI | FW | SEQ ID NO | |
|---|---|---|---|---|
| AP-33H | 22 | 86 | 69 | VVGDSITIKLYMGIIRTYYALW |
| U86525 | 14 | 61 | 70 | ........S.Q.WI.V.V.F..R. |
| S67826 | 14 | 61 | 70 | ........S.Q.WI.V.V.F..R. |
| 42071 | 14 | 61 | 70 | ........S.Q.WI.V.V.F..R. |
| 42069 | 14 | 61 | 70 | ........S.Q.WI.V.V.F..R. |
| 42068 | 14 | 61 | 70 | ........S.Q.WI.V.V.F..R. |
| L23563 | 14 | 61 | 71 | ........R.Q.WI.V.V.F..R. |
| S67827 | 14 | 60 | 70 | ........S.Q.WI.V.V.F..R. |
| 30188 | 14 | 60 | 71 | ........R.Q.WI.V.V.F..R. |
| 42072 | 14 | 60 | 70 | ........S.Q.WI.V.V.F..R. |
| 42070 | 14 | 60 | 70 | ........S.Q.WI.V.V.V..R. |
| 42075 | 14 | 60 | 70 | ........S.Q.WI.V.V.F..R. |
| 42073 | 14 | 60 | 70 | ........S.Q.WI.V.V.F..R. |
| 42074 | 14 | 60 | 70 | ........S.Q.WI.V.V.F..R. |
| AJ300800 | 14 | 60 | 72 | ....G....Q.WI.V.A.F..R. |
| AF062169 | 14 | 59 | 69 | ........Q.WI.VMV.F..R. |
| AF006528 | 14 | 58 | 73 | .....F..Q.WI.V.V.F..R. |
| U68226 | 14 | 57 | 74 | ...V....Q.WI.V.L.F..R. |
| 40567 | 14 | 56 | 74 | ...V....Q.WI.V.L.F..R. |
| AB066912 | 13 | 56 | 75 | ...G..S.Q.WI.V.V.F..R. |
| AB066903 | 13 | 60 | 75 | ...G..S.Q.WI.V.V.F..R. |
| AF062129 | 13 | 60 | 75 | ...G..S.Q.WI.V.V.F..R. |

Figure 15

| Kabat number | SEQ ID No | 1<br>1234567890 | 2<br>1234567890 | 3<br>12345 11 1<br>1234567890 | 4<br>12345AB67890 | 5<br>1234567890 | 6<br>12 2<br>12ABC3456789012 | 7<br>1234567890 | 8<br>1234567890 | 9<br>123456789012 | 10<br>1<br>ABC3456789012ABC34567890 | 11<br>1<br>1234567890123 |
|---|---|---|---|---|---|---|---|---|---|---|---|---|
| Canonical | | | | 1 111 1 | | | 2 22 | | 2 | 1 | | |
| Vernier | | * | | **** | *** | | | ***** | | ** | | * |
| Interface | | | | I I | I I I | | | | | I I I | I | I |
| CDR | | | | ******* | ********* | | ****************** | | | | *************************** | |
| AP-33VH | 76 | SEVQLQESGPESLVKPSQTLSLTCSVTGDSIITSGYWN | | | WIRKFPGNKLEYMGYIS | | YSGSTYNLSLRSISITRDTSKNQYYLQLNSVTTEDPATYY | | | CALITTTYA | | MDYWGQGTSVTVSS |
| U86525 | 77 | SQVQLQESGPGLVKPSETLSLTCTVSGDSISSYYWS | | | WIRQSPGKGLEWIGEMS | | YSGSTNYNPSLRSRVTIIDTSKNQFSLELRSSVTAADTAVYY | | | CARHDFWRT | | FDSWGQGTLVTVSS |
| S67826 | 78 | SQVQLQESGPGLVKPSETLSLTCTVSGDSISSYYWS | | | WIRQPPGRALEWIGYIY | | HGGSTNYSPSLKSRVTISVDTSKNQFSLRLSSVTAADTAMYY | | | CARDRHCSGGTCYG | | MDVWGQGTTVTVSS |
| 42071 | 79 | -QVQLQESGPGLVKPSETLSLTCTVSGDSISSYYWS | | | WIRQPPGRGLEWIGYIY | | HGGSTNYSPSLKSRVTISVDTSKNQFSLRLSSVTAADTAMYY | | | CARDRHCSGGTCYG | | MDVWGQGTTVTVSS |
| 42069 | 80 | -QVQLQESGPGLVKPSETLSLTCTVSGDSISSYYWS | | | WIRQPPGRALEWIGYIY | | HGGSTNYSPSLKSRVTISVDTSKNQFSLRLSSVTAADTAMYY | | | CARDRHCSGGTCYG | | MDVWGQGTTVTVSS |
| 42068 | 80 | -QVQLQESGPGLVKPSETLSLTCTVSGDSISSYYWS | | | WIRQPPGKGLEWIGYIY | | HGGSTNYSPSLKSRVTISVDTSKNQFSLRLSSVTAADTAMYY | | | CARDRHCSGGTCYG | | MDVWGQGTTVTVSS |
| L23563 | 81 | -QVQLQESGPGLMKPSETLSLTCSVSGDSIRSYYWS | | | WIRQPPGKGLEWIGYIY | | DTGSTNYNPSLKSRVTISVDTSKNRFSLKLRLTSLTAADTAVYY | | | CARYKQQI | | FDFWGQGILVTVSS |
| S67827 | 81 | -QVQLQESGPGLVKPSETLSLTCTVSGDSISSYYWS | | | WIRQPPGRALEWIGYIY | | HGGSTNYSPSLKSRVTISVDTSKNRFSLKLRLTSLTAADTAVYY | | | CARDRHCSGGTCYG | | MDVWGQGTTVTVSS |
| 30188 | 82 | -QVQLQESGPGLVKPSETLSLTCTVSGDSIRSYYWS | | | WIRQPPGKGLEWIGYIY | | DTGSTNYNPSLKSRVTISVDTSKNRFSLKLRSVTAADTAVYY | | | CARYKQQI | | FDEWGQGILVTVSS |
| 42072 | 82 | -QVQLQESGPGLVKPSETLSLTCTVSGDSISSYYWS | | | WIRQPPGRALEWIGYIY | | HGGSTNYSPSLKSRVTISVDTSKSQVSLRLSSVTAADTAMYY | | | CARDRHCSGGTCYG | | MDVWGQGTTVTVSS |
| 42070 | 83 | -QVQLQESGPGLVKPSETLSLTCTVSGDSISSYYWS | | | WIRQPPGRALEWIGYIY | | HGGSTNYSPSLKSRVTISVDTSKNQFSLRLSSVTAADTAMYY | | | CARDRHCSGGTCYG | | MDVWGQGTTVTVSS |
| 42075 | 82 | -QVQLQESGPGLVKPSETLSLTCTVSGDSISSYYWS | | | WIRQPPGRALEWIGYIY | | HGGSTNYSPSLKSRVTISVDTSKNQFSLRLSSVTAADTAMYY | | | CARDRHCSGGTCYG | | MDVWGQGTTVTVSS |
| 42073 | 82 | -QVQLQESGPGLVKPSETLSLTCTVSGDSISSYYWS | | | WIRQPPGRALEWIGYIY | | HGGSTNYSPSLKSRVTISVDTSKNQFSLRLSSVTAADTAMYY | | | CARDRHCSGGTCYG | | MDVWGQGTTVTVSS |
| 42074 | 82 | -QVQLQESGPGLVKPSETLSLTCTVSGDSISSYYWS | | | WIRQPPGRALEWIGYIY | | HGGSTNYSPSLKSRVTISVDTSKNQFSLRLSSVTAADTAMYY | | | CARDRHCSGGTCYG | | MDVWGQGTTVTVSS |
| AJ300800 | 84 | -EVQLLESGGGLVKPSETLSLTCTVSGGSITSYYWT | | | WIRQPPGKGLEWIGYIY | | NSVSTNYNPSVKSRVTISAHTSNQFSLNLFSVTAADTAVYY | | | CARGRRAYSSSWIP | | RDYWGQGTLVTVSS |
| AF062169 | 85 | SRVQLQESGPGLVKASETLSLTCTVSGDSITNYYWS | | | WIRQPPGKGLEWIGNTY | | SSGNANYNPSFRSVTMSVDTSRSQFSLKLSSVTAADTAVYY | | | CARVHFDFGAKRKT | | FDYWGQGTLVTVSS |
| AF006528 | 86 | -QVQLQQWGAGLLKPSETLSLTCAVYGGSFTDYYWS | | | WIRQPPGKDLEWIGEIN | | HSGNTNYNPSLTSRVTISRSVTISDTTKNHFSLKLRSVTAADTGVYY | | | CARLRQYGAKA | | GGYWGQGTLVTVSS |
| U68226 | 87 | -QVQLQESGPGLVKPSETLSLTCTVSGVSITNYFWS | | | WIRQTPGKGLEWIGYIY | | YSGSRNYNPSLKSRVVISLDTTKNHFSLKLRSVTRADTGVYY | | | CARHVRGGRLGDLSS | | ADSWGEGTLVTVSS |
| 40567 | 87 | -QVQLQESGPGLVKPSETLSLTCTVSGVSITNYFWS | | | WIRQTPGKGLEWIGYIY | | YSGSRNYNPSVKSRVVISLDTTKNHFSLKLRSVTAADTGVYY | | | CARHVRGGRLGDLSS | | ADSWGEGTLVTVSS |
| AB066912 | 88 | -QVQLQESGPGLVKPSETLSLTCTVSGGSISSYYWS | | | WIRQPPGKGLEWIGYTY | | YSGSTNYNPSLKSRVTILVDTSKNQFSLRLSSVTAADTAVYY | | | CARDEGNAWVGELSGG | | MDVWGQGTTVTVSS |

Figure 16

```
                                                                                    AP-33heavy.pro (SEQ ID NO: 89)
  1 ----------------EVQLQESGPSIVKPSQTLSLTCSVTGDSITSGYWNWIRKFP    s67826.pro (SEQ ID NO: 90)
  1 MKHLWFFLLLVAAPRWVLSQ............G.......E....T.S.....S.Y...S....QP.   U86525.pro (SEQ ID NO: 91)
  1 -------------------SQ............G.......E....S.....S.Y...S....QS.   42071.pro  (SEQ ID NO: 92)
  1 -------------------Q.............G.......E....T.S.....S.Y...S....QP.  s67827.pro (SEQ ID NO: 93)
  1 -------------------Q.............G.......E....T.S.....S.Y...S....QP.
                     50          60          70          80          90         100

42 GNKLEYMGYISYSGSTYYNLSLRSRISITRDTSKNQYYLQLNSVTTEDTATYYCALITT   AP-33heavy.pro
 61 .RA...WI...YHG....N.SP...K..VT.SV........FS.R..S....AA....M.....RDRHC   s67826.pro
 43 .KG...WI.CM.......N..P...K..VT.SV........FS.R..S....AA....M..V..RHDFW   U86525.pro
 42 .RG...WI...YHG....N.SP...K..VT.SV........FS.R..S....AA....M.....RDRHC   42071.pro
 42 .RA...WI...YHG....N.SP...K..VT.SV........FS.R..T....AA....M.....RDRHC   s67827.pro
                           110         120

102 T----YAMDYWGQGTSVTVSASTKGPSVFP          AP-33heavy.pro
121 SGGTC.G..V......T.....SG                s67826.pro
103 R----T-F.S.......                  S    U86525.pro
102 SGGTC.G..V......T.....S                 42071.pro
102 SGGTC.G..V......T.....SG                s67827.pro
```

A

Leader DNA sequence of germline gene VH 4-59

ATGAAACATCTGTGGTTCTTCCTTCTGCTGGTGGCAGCTCCCAGATGGGTCCTGTCC (SEQ ID NO: 94)

(SEQ ID NO: 95)

(SEQ ID NO: 96)

| | 1234567890123456789012345AB6789012345AB678901234567890123456789012ABC34567890123456789012ABC34567890ABCDEFGHIJKMNOPQRSTUVW123456789012 |
|---|---|
| Kabat: | v  -vvv==H1==  vvv==  ==H2==  -Kabat-  v v v v  vv====H3=  v |
| AP-33vh | EVQLQESGPGLVKPSQTLSLTCSVTGDSITS-GYWNIRKFPGNKLEYMGYISYSG-STYYNLSLRSISTRDTSKNQYYLQLNSVTTEDTATYYCALITTTYA------MDYWGQGTSVTVS- |
| CDR | S-GYWN(SEQ ID NO: 97)  YISYSG-STYYNLSLRS (SEQ ID NO: 98)  ITTTYA-MDY SEQ ID NO:99 |
| AP-33RHZ | QVQLQESGPGLVKPSETLSLTCTVSGDSISS-GYWNWIRQPPGRALEWIGYISYSG-STYYNLSLRSRVTISVDTSKNQFSLRLSSVTAADTAMYYCARITTTYA-MDYWGQGTTVTVSS |
| FW | QVQLQESGPGLVKPSETLSLTCTVSGDSIS  WIRQPPGRALEWIG  RVTISVDTSKNQFSLRLSSVTAADTAMYYCAR  WGQGTTVTVSS |
| s67826 | QVQLQESGPGLVKPSETLSLTCTVSGDSISS--YYWSWIRQPPGRALEWIGYIYHGG---STNYSPSLKSRVTISVDTSKNQFSLRLSRVTAADTAMYYCARDRHCSGGTCYG------MDVWGQGTTVTVSS |

SEQ ID NO:1
SEQ ID NO: 100
SEQ ID NO: 101
SEQ ID NO: 64

B

| Region | DNA | Protein |
|---|---|---|
| VH4-59 leader | ATGAAACATCTGTGGTTCTTCCTTCTGCTGGTGGCAGCTCCCAGATGGGTCCTGTCC (SEQ ID NO: 94) | MKHLWFLLLVAAPRWVLS (SEQ ID NO: 102) |
| FW1 | Caggtgcagctgcagctcagtcagggcccaggactggtgaagccttcggagaccctgtccctcacctcactgtctctggtgactccatcagt (SEQ ID NO: 103) | QVQLQESGPGLVKPSETLSLTCTVSGDSIS (SEQ ID NO: 104) |
| CDR1 | AGTGGTTACTGGAAC (SEQ ID NO: 105) | SGYWN (SEQ ID NO: 97) |
| FW2 | atccggcagcccccagggagggcactggagtggataga (SEQ ID NO: 106) | WIRQPPGRALEWIG (SEQ ID NO: 107) |
| CDR2 | TACATAAGTTACAGTGGTAGCACTTACTACAATCTATCTCTCAGAAGT (SEQ ID NO: 108) | YISYSGSTYYNLSLRS (SEQ ID NO: 98) |
| FW3 | cgggtcaccatatcagtagacacgtctaagaaccagttctccctgaggctgagctctgtgaccgctgccgaca ccgccatgtattactgtgcgaga (SEQ ID NO: 109) | RVTISVDTSKNQFSLRLSSVTAADTAMYY CAR (SEQ ID NO: 110) |
| CDR3 | ATTACTACGACATACCTATGCTATGGACTAC (SEQ ID NO: 111) | ITTTYAMDY (SEQ ID NO: 99) |
| FW4 | tggggccaaggggaccacggtcaccgtctcc (SEQ ID NO: 112) | WGQGTTVTVS (SEQ ID NO: 113) |

| Sequence | FW Score | VCI score | SEQ ID NO. | VCI sequence |
|---|---|---|---|---|
| Kabat Number | | | | 2 4 35 36 38 44 46 47 48 49 64 66 68 69 71 87 98 |
| Canonical | | | | 1......2.2...1.. |
| Vernier | | | | **..******.* |
| Interface | | | | ...III..........II |
| AP-33K | 80 | 17 | 150 | ILWFQPLLIYGGRTFYF |
| 20404 | 58 | 16 | 150 | ...Y............. |
| 22255 | 56 | 15 | 150 | ...Y........G.... |
| 37659 | 68 | 14 | 150 | L..Y........G.... |
| 37657 | 67 | 13 | 150 | L..Y........G..F. |
| 4993 | 55 | 13 | 150 | L..Y........G..H. |
| S78338 | 67 | 13 | 151 | .M.Y.....K..G.... |

Figure 22

| Sequence | FW Score | VCI score | SEQ ID NO. | VCI sequence |
|---|---|---|---|---|
| Kabat Number | | | | 2 4 35 36 38 44 46 47 48 49 50 64 66 68 69 71 87 98 |
| Canonical | | | | 1.......2.2...1.. |
| Vernier | | | | **..*******.* |
| Interface | | | | ...III.........II |
| AP-33K | 80 | 17 | 152 | IIWFQPIIIYGGRTFYF |
| X61125 | 59 | 16 | 152 | ............G.... |
| AB095284 | 56 | 15 | 152 | ...Y........G.... |
| AY685279 | 59 | 15 | 152 | ...Y........G.... |
| AY247656 | 58 | 15 | 152 | ...Y........G.... |
| AB095279 | 57 | 15 | 152 | ...Y........G.... |
| Z18845 | 58 | 15 | 152 | ...Y........G.... |
| AY685271 | 57 | 15 | 152 | ...Y........G.... |
| 4752 | 58 | 15 | 152 | ...Y........G.... |
| M88499 | 59 | 15 | 152 | ...Y........G.... |
| 19218 | 54 | 15 | 152 | ...Y........G.... |
| X72444 | 54 | 15 | 152 | ...Y........G.... |
| AJ399873 | 55 | 15 | 152 | ...Y........G.... |
| 24310 | 57 | 15 | 152 | ...Y........G.... |
| Z37344 | 57 | 15 | 152 | ...Y........G.... |
| BC034141 | 55 | 15 | 152 | ...Y........G.... |
| AB095290 | 56 | 15 | 152 | ...Y........G.... |
| AX112586 | 56 | 15 | 152 | ...Y........G.... |
| AX044468 | 58 | 15 | 152 | ...Y........G.... |
| BC029444 | 56 | 15 | 152 | ...Y........G.... |
| 26509 | 56 | 15 | 152 | ...Y........G.... |

```
          10                20                30                40                50                60                70
----+----|----+----|----+----|----+----|----+----|----+----|----+----|----+----|----+----|----+----|----+----|----+----|----+----|----+----|
--METDTLLLWVLLLWVPGSTGNIVLTQSPVSLAVSLGQRATISCRASESVDGYGN--SFLHWFQQKPGQPPKLLIYLAS   AP33Kappa_chimeric.pro
SK.VLQ.QVFIS....IS.AS.D.......D..S....E.V.VN.KL.Q..LHSS.KQNY.A......N........W..   x61125.seq
-------------------------------D......S.VSA.V.D.V..T....QGIS-------W.A......KA..A.. AB095284.seq
-------------------------------E......S..SA.V.D.V..T....Q.IS-------Y.N......KA..A.. AY685279.seq
-------------------------------E......S..SA.V.D.V..T.Q..QDIS-------NY.N.Y....KA..D.. AY247656.seq 80                90               100               110               120
----+----|----+----|----+----|----+----|----+----|----+----|----+----|----+----|----+----|
NINSGVPARFSGSGSRTDFTLTIDPVEADDAATYYCQQ--NNVDPWTFGGGTKLEIK   (SEQ ID NO: 169)   AP33Kappa_chimeric.pro
ARQ......M.....G.E.S....SSLQ.E.V.V.....-YYDSTY......Q..N   (SEQ ID NO: 170)   x61125.seq
S.Q......S.....G.........SSLQPE.S..S...--T.SF.I...Q..R..   (SEQ ID NO: 154)   AB095284.seq
S.Q......S.....G.........SSLQPE.F.......S-YSTLMY...Q....   (SEQ ID NO: 155)   AY685279.seq
..ET.....S.....G......F..SSLQPE.FG......--Y.TY.L........   (SEQ ID NO: 156)   AY247656.seq
```

Figure 24

| Sequence | VCI score | FW Score | SEQ ID NO. | VCI sequence |
|---|---|---|---|---|
| Kabat Number | | | | 2 4 35 36 38 44 46 47 48 49 64 65 68 69 71 87 98 |
| Canonical | | | | 1.......2.2...1.. |
| Vernier | | | | **..******.* |
| Interface | | | | ...III.........II |
| AP-33K | 17 | 80 | 150 | IIWFQPLLIYGGRTFYF |
| AB064133 | 15 | 60 | 171 | ILWFQPRLIYGGGTFYF |
| X72448 | 15 | 60 | 171 | ILWFQPRLIYGGGTFYF |
| 19224 | 15 | 60 | 171 | ILWFQPRLIYGGGTFYF |
| AY685280 | 15 | 59 | 150 | IMWFQPLLIYGGGTFYF |
| AB064090 | 15 | 59 | 171 | ILWFQPRLIYGGGTFYF |
| AX829088 | 15 | 58 | 150 | ILWFQPLLIYGGGTFFF |
| AB064137 | 15 | 58 | 171 | ILWFQPRLIYGGGTFYF |
| AB064135 | 15 | 58 | 150 | ILWYQPLLIYGGGTFYF |
| AB064093 | 15 | 58 | 150 | ILWYQPLLIYGGETFYF |
| AB064136 | 15 | 57 | 150 | ILWYQPLLIYGGGTFYF |
| X93714 | 15 | 57 | 150 | IMWFQPLLIYGGGTFYF |
| AJ241401 | 15 | 56 | 150 | ILWYQPLLIYGGGTFYF |
| 26509 | 15 | 56 | 150 | ILWYQPLLIYGGGTFYF |
| U21021 | 15 | 56 | 150 | IMWFQPLLIYGGGTFYF |
| AJ241387 | 15 | 56 | 150 | ILWYQPLLIYGGGTFYF |
| U21043 | 15 | 56 | 150 | ILWYQPLLIYGGGTFYF |
| U21040 | 15 | 56 | 150 | IMWFQPLLIYGGGTFYF |
| DQ187590 | 15 | 56 | 150 | ILWYQPLLIYGGGTFYF |
| AJ496517 | 15 | 55 | 150 | ILWYQPLLIYGGGTFYF |
| Y12698 | 15 | 55 | 150 | IMWFQPLLIYGGGTFYF |

Figure 25

SEQ ID NO: 203

```
Measure   Position   Value   Cutoff   signal peptide?
  max. C      21       0.962   0.32     YES
  max. Y      21       0.881   0.33     YES
  max. S      13       0.991   0.87     YES
  mean S     1-20      0.942   0.48     YES
       D     1-20      0.912   0.43     YES
# Most likely cleavage site between pos. 20 and 21: AYG-DI
(SEQ ID NO: 291)
```

SEQ ID NO: 204

```
 Measure   Position   Value   Cutoff   signal peptide?
 max. C      23       0.918   0.32     YES
 max. Y      23       0.845   0.33     YES
 max. S      16       0.986   0.87     YES
 mean S     1-22      0.925   0.48     YES
      D     1-22      0.885   0.43     YES
Most likely cleavage site between pos. 22 and 23: ARC-EI
(SEQ ID NO: 292)
```

SEQ ID NO: 205

```
>Sequence              length = 50
# Measure   Position   Value   Cutoff   signal peptide?
  max. C    20         0.883   0.32     YES
  max. Y    21         0.803   0.33     YES
  max. S    13         0.982   0.87     YES
  mean S    1-20       0.917   0.48     YES
       D    1-20       0.860   0.43     YES
# Most likely cleavage site between pos. 20 and 21: SSG-EI
(SEQ ID NO: 293)
```

| SEQ ID NO:2 | AP-33 VK | v v<br>NIVLTQSPVSLAVSLGQRATISCRASESVDG--YGNSFLHWFQQKPGQPPKLLIYLASNLNSGVPARFSGSGSRTDFTLTIDPVEADDAATYYCQQNNVDP----WTFGGGTKLEI-R |
|---|---|---|
| | CDR | RASESVDG--YGNSFLH (SEQ ID NO:206) LASNLNS (SEQ ID NO:207) QQNNVDP----WT (SEQ ID NO:208) |
| SEQ ID NO:4 | Ap-33RKA | DIVLTQSPDSLSVSLGERVTVNCRASESVDG--YGNSFLHWFQQNPGQPPKLLIYLASNLNSGVPARFMGSGSGTEFSLTISSLQAEDVAVYYCQQNNVDP----WTFGQGTKLEI-N |
| SEQ ID NO:209 | FW | DIVLTQSPDSLSVSLGERVTVNC WFQQNPGQPPKLLIY GVPARFMGSGSGTEFSLTISSLQAEDVAVYYC FGQGTKLEI N |
| SEQ ID NO:210 | x61125 | DIVLTQSPDSLSVSLGERVTVNCKLSQSVLHSSNKQNYLAWFQQNPGQPPKLLIYWASARQSGVPARFMGSGSGTEFSLTISSLQAEDVAVYYCQQYYDST------YTFGQGTKLEI-N |

B

| Region | DNA | Protein |
|---|---|---|
| B3 leader | ATGGACATGAGGGTCCCTGCAGCTCCTGGGGCTCCTGCAGCTCTGGGCTCCCAGATGT (SEQ ID NO: 211) | MDMRVPAQLLGLLLQLWLSGARC (SEQ ID NO:218) |
| X61125 FW1 | Gacatcgtgctgacccagtctccagactccctgtctgtctctgggcgagagggtcaccgtcaactgc (SEQ ID NO:212) | DIVLTQSPDSLSVSLGERVTVNC (SEQ ID NO:219) |
| AP-33 CDR1 | AGAGCCAGTGAAAGTGTTGATGGTTATGGCAATAGTTTTCTGCAC (SEQ ID NO:213) | RASESVDGYGNSFLH (SEQ ID NO:206) |
| X61125 FW2 | AGAGCCAGTGAAAGTGTTGATGGTTATGGCAATAGTTTTCTGCAC (SEQ ID NO:213) | WFQQNPGQPPKLLIY (SEQ ID NO:220) |
| AP-33 CDR2 | CTTGCATCCAACCTAAACTCT (SEQ ID NO:214) | LASNLNS (SEQ ID NO:207) |
| X61125 FW3 | gggtccctgcccgattcatggcagcggctctggacagaattcagtctcaccatcagcagcctgcaggctgaagatgtggcagtttattactgt (SEQ ID NO:215) | GVPARFMGSGSGTEFSLTISSLQAEDVAVYYC (SEQ ID NO:221) |
| AP-33 CDR3 | CAGCAAAATAATGTGGACCCGTGGACG (SEQ ID NO:216) | QQNNVDPWT (SEQ ID NO:208) |
| X61125 FW4 | tttggccaggggaccaagctggagatcaac (SEQ ID NO:217) | FGQGTKLEIN (SEQ ID NO:222) |

| | | v v | ======L1====== vvvv==L2=== v v vv v ======L3===== v |
|---|---|---|---|
| SEQ ID NO:2 | AP-33 VK CDR | | EIVLTQSPVSLAVSLGQRPATISCRASESVDG--YGNSFLHWFQQKPGQPPKLLIYLASNLNSGVPARFSGSGSRTDFTLTIDPVEADDAATYYCQQNNVDP-----WTFGGGTKLEI-K |
| | | | RASESVDG--YGNSFLH(SEQ ID NO:206)  LASNLNS(SEQ ID NO:207)  QQNNVDP------WT(SEQ ID NO:208) |
| SEQ ID NO:223 | Ap-33RKA | | EIVLTQSPSSLSASVGDRVTITCRASESVDG--YGNSFLHWFQQKPGKAPKLLIYLASNLNSGVPSRFSGSGSRTDFTLTISSLQPEDFATYYCQQNNVDP-----WTFGQGTKLEI-K |
| SEQ ID NO:224 | FW | | EIVLTQSPSSLSASVGDRVTITC  WFQQKPGKAPKLLIY  GVPSRFSGSGSRTDFTLTISSLQPEDFATYYC  FGQGTKLEI-K |
| SEQ ID NO:155 | AY685279 | | EIVLTQSPSSLSASVGDRVTITCRLKSQSIS-----SYLNWFQQKPGKAPKLLIYAASSLQSGVPSRFSGSGSRTDFTLTISSLQPEDFATYYCQQSYSTL----MYTFGQGTKLEI-K |

B

| Region | DNA | Protein |
|---|---|---|
| B3 leader | ATGGACATGAGGGTCCCCGCTCAGCTCCTGGGGCTCCTGCTACTCTGGCTCCGAGGTGCCAGATGT (SEQ ID NO:225) | MDMRVPAQLLGLLLWLRGARC (SEQ ID NO:230) |
| AY685279 FW1 | gaaatagtgttgacgcagtctccatcctccctgtctgcatctgtaggagacagagtcaccatcacttgc (SEQ ID NO:226) | EIVLTQSPSSLSASVGDRVTITC (SEQ ID NO:231) |
| AP-33 CDR1 | AGAGCCAGTGAAAGTGTTGATGGTTATGGAATAGTTTTCTCAC (SEQ ID NO:213) | RASESVDGYGNSFLH (SEQ ID NO:206) |
| AY685279 FW2 | tggtTtcagcagcagaaaccaggaaagcccctaagctcctgatctat (SEQ ID NO:227) | WFQQKPGKAPKLLIY (SEQ ID NO:232) |
| AP-33 CDR2 | CTTGCATCCAACTAAACTCT (SEQ ID NO:214) | LASNLNS (SEQ ID NO:207) |
| AY685279 FW3 | gggtccctcaagttcagtggcagtggatctCggacagatttcactctcaccatcagcagtctgcaacctgaaga tttgcaacttactactgt (SEQ ID NO:228) | GVPSRFSGSGSRTDFTLTISSLQP EDFATYYC (SEQ ID NO:233) |
| AP-33 CDR3 | CAGCAAAATAATGGGACCCGTGGACG (SEQ ID NO:216) | QQNNVDPWT (SEQ ID NO:208) |
| AY685279 FW4 | tttggccaggggaccaagctggagatcaaa (SEQ ID NO:229) | FGQGTKLEIN (SEQ ID NO:222) |

| SEQ ID NO:2 | AP-33 VK | v v | vvvv==L1=====vv | vvv==L2=== | v v vv v | ======L3======v |
|---|---|---|---|---|---|---|
| | CDR | NIVLTQSPVSLAVSLGQRATISCRASESVDG--YGNSFLHWFQQKPGQPPKLLIYLASNLNSGVPARFSGSGSRTDFTLTIDPVEADDAATYYCQQNNVDP------WTFGGGTKLEIK | | | | |
| | | RASESVDG--YGNSFLH (SEQ ID NO:206) LASNLNS (SEQ ID NO:207) QQNNVDP-----WT (SEQ ID NO:208) | | | | |
| SEQ ID NO:234 | AP33R3 | EIVLTQSPLSLPVTLGQPASISCRASESVDG--YGNSFLHWFQQRPGQSPRRLIYLASNLNSGVPDRFSGSGSGTDFTLKISRVEAEDVGVYYCQQNNVDP-----WTFGGGTKVEIK | | | | |
| SEQ ID NO:235 | FW | EIVLTQSPLSLPVTLGQPASISC | | WFQQRPGQSPRRLIY | GVPDRFSGSGSGTDFTLKISRVEAEDVGVYYC | FGGGTKVEIK |
| SEQ ID NO:192 | AB064133 | EIVLTQSPLSLPVTLGQPASISCRSSQSLVYS-DGNTYLNWFQQRPGQSPRRLIYKVSNWDSGVPDRFSGSGSGTDFTLKISRVEAEDVGVYYCMQGTHW------LTFGGGTKVEIK | | | | |

B

| Region | DNA | Protein |
|---|---|---|
| VKII-A17leader | ATGAGGCTCCCTGCTGCTCAGCTCCTCAGGGCTCCTCTGGGTCCCAGGATCCAGTGGG SEQ ID NO:236 | MRLPAQLLGLLMLWVPGSSG SEQ ID NO:241 |
| AB064133 FW1 | GAAATTGTGCTGACTCAGTCTCCACTCTCCCTGCCCGTCACCCTTGGACAGCCGGCCTCCATCTCCTGC SEQ ID NO:237 | EIVLTQSPLSLPVTLGQPASISC SEQ ID NO:242 |
| AP-33 CDR1 | AGAGCCAGTGAAAGTGTTGATGGTTATGGCAATAGTTTTCTGCAC SEQ ID NO:213 | RASESVDGYGNSFLH SEQ ID NO:206 |
| AB064133 FW2 | TGGTTTCAGCAGAGGCCAGGCCAATCTCCAAGGCGCCTAATTTAT SEQ ID NO:238 | WFQQRPGQSPRRLIY SEQ ID NO:243 |
| AP-33 CDR2 | CTTGCATCCAACCTAAACTCT SEQ ID NO:214 | LASNLNS SEQ ID NO:207 |
| AB064133 FW3 | GGGGTCCCAGACAGATTCAGCGGCAGTGGGTCAGGCACTGATTTCACACTGAAAATCAGCAGGGTGGAGGCTGAGGATGTTGGGGTTTATTACTGC SEQ ID NO:239 | GVPDRFSGSGSGTDFTLKISRVEAEDVGVYYC SEQ ID NO:244 |
| AP-33 CDR3 | CAGCAAAATAATGTGGACCCGTGGACG SEQ ID NO:216 | QQNNVDPWT SEQ ID NO:208 |
| AB064133 FW4 | TTCGGCGGAGGGACCAAGGTGGAGATCAAA SEQ ID NO:240 | FGGGTKVEIK SEQ ID NO:245 |

Figure 33

| Region | DNA | Protein |
|---|---|---|
| VKI-018 leader | ATGGACATGAGGGTCCCTGCTCAGCTCCTGGGGCTCCTGCTGCTCTGGCTCTCAGGTGCCAGATGT SEQ ID NO:246 | MDMRVPAQLLGLLLWLSGARC SEQ ID NO:218 |
| AB064072 FW1 | GACATCGTGATGACCCAGTCTCCAGACTCCCTGGCTGTGTCTCTGGGTGAGAGGGCCACCATCAACTGC SEQ ID NO:247 | DIVMTQSPDSLAVSLGERATINC SEQ ID NO:251 |
| AP-33 CDR1 | AGAGCCAGTGAAAGTGTTGATGGTTATGGCAATAGTTTTCTGCAC SEQ ID NO:213 | RASESVDGYGNSFLH SEQ ID NO:206 |
| AB064072 FW2 | TGGTACCAGCAGAAACCGGGACAGCCTCCTAAGTTGCTCATTTAC SEQ ID NO:248 | WYQQKPGQPPKLLIY SEQ ID NO:252 |
| AP-33 CDR2 | CTTGCATCCAACCTAAACTCT SEQ ID NO:214 | LASNLNS SEQ ID NO:207 |
| AB064072 FW3 | GGGGTCCCTGACCGATTCAGTGGCAGCGGGTCTGGGACAGATTTCACTCTCACCATCAGCAGCCTGCAGGCCGA AGATGTGGCAGTGTATTACTGT SEQ ID NO:249 | GVPDRFSGSGSGTDFTLTISSLQAEDV AVYYC SEQ ID NO:253 |
| AP-33 CDR3 | CAGCAAAATAATGTGGACCCGTGGACG SEQ ID NO:216 | QQNNVDPWT SEQ ID NO:208 |
| AB064072 FW4 | TTTGGCCAGGGGACCAAGCTGGAGATCAAA SEQ ID NO:250 | FGQTKLEIK SEQ ID NO:254 |

Figure 34

A   AP-33RKA DNA sequence with leader

ATGGACATGAGGGTCCCTGCTCAGCTCTGGGGCTCCTGCAGCTCTGCAGTCTGGCTCTCCGGCGCCAGATGTGACATGTGTCGACCCAGTCCCAGACTCCCTGTCTGT
CTCTGGGGAGAGGGTCACCGTCAACCTGCAGAGACAGTCAACTGCAGAAAGTGTTGATGTTATGGCACAGAGCCAGTGAAAGTGTTATGGCAATAGTTT
TCTGCACCTTGCATCCAACCTAAACTCTGGGGTCCTGCCGATTCATGGGCAGCGGGGTCTGGACAGAATTCAGTCTCACCATCAGCAGCCTGCAGGCTGAAGATGTGG
CAGTTTATTACTGTCAGCAAAATAATGTTGACGGTGAACGTTTGGCCAGGGGACCAAGCTGGAGATCAAC(SEQ ID NO: 255)

B   AP-33RK2 DNA sequence with leader

ATGGACATGAGGGTCCCCGTCAGTCTGGGGCTCTGCTACTCTGGCTCTGCAGCTCTGCAGAGTGTGCCAGATGTGCCAGATGTGAAATAGTGTGAGCAGTCTCCATCTCCCTGTCTGCAT
CTGTAGGAGACAGAGTCACCATCACTTGCAGAGACAGTCAACTGCAGAAAGTGTGATGGTTCAGCAGAAACCAGGAAAGCCCCCTAAGCTCCT
GATCTATCTTGCATCCAACCTAAACTCTGGGGTCCATCAAGGTTCAGTGCCAGTTCAGGTCAGATTTCACTCTCACCATCAGCAGTCTGCAACCTGAAGATTTTGC
AACTTACTACTGTCAGCAAAATAATGTGGACCAGGGGACCAAGCTTGGCCAGGGGACCAAGCTGGAGATCAAA(SEQ ID NO: 256)

C   AP33RK3 DNA sequence with leader

ATGAGGCTCCCTGCTCAGCTCCTGGGGCTGCTAATGCTCTGGGTCTGCCAGGAATCCAGTGGGAATTGTGCTGACTCAGTCTCCACTCTCCCTGCCCGTCACCC
TTGGACAGCCGGCCTCCATCCTCTGCAGAGCCAGTGAAAGTTGTGATGGTTATGGCAATAGTTTCTGCACTGGTTTCAGCAGAGGCCAGGCCATCTCCAAGGCGCT
AATTTATCTTGCATCCAACCTAAACTCTGGGGTCCCAGACAGATTCAGGCCAGTCAGGCCACTGATTTCACACTGAAAATCAGCAGGGTGAGGCTGAGGATGTT
GGGGTTTATTACTGCGCAGCAAATATAATGTGGACCCGTTCGGCGGAGGGACCAAGGTGGAGATCAAA(SEQ ID NO: 257)

D   AP33RK4 DNA sequence with leader

ATGGACATGAGGGTCCCTGCTCAGCTCCTGGGGCTCCTGCAGCTCTGGgCCTCAGGGCCAGATGTGACATCGTGATGACCCAGTCTCCAGACTCCCTGGCTG
TGTCTCTGGGCGAGAGGGCCACCATCAACTGCAGAGCCAGTGAAAGTGTTGATGTTATGGCAATAGTTTCTGCACTGGTatCAGCAGAAACCGGACAGCC
TCCTAAGTTGCTCATTTACCTGCATCCAACCTAACTCTGGGGTCCCTGACCGATTCAGTGGCAGCGGGGTCTGGACAGATTTCACTCTCACCATCAGCAGC
CTGCAGGCCGAAGATGTGGCAGTGTATTACTGTCAGCAAATAATGTGAGCCGTGGACGTTTGGCCAGGGGACCAAGCTGGAGATCAAA(SEQ ID NO: 258)

Figure 39
A
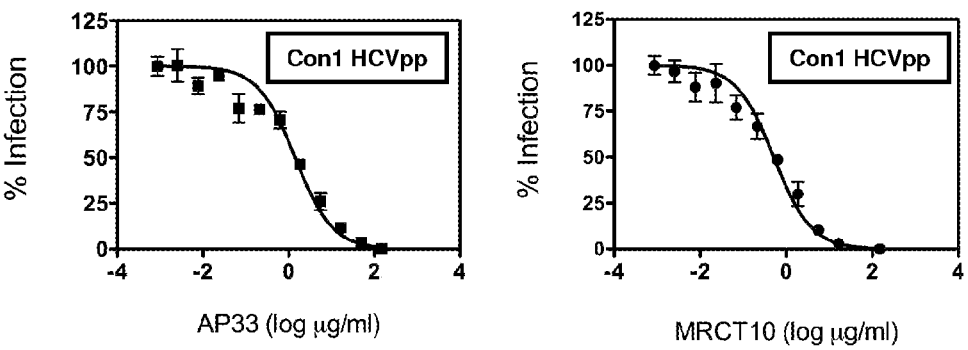
B
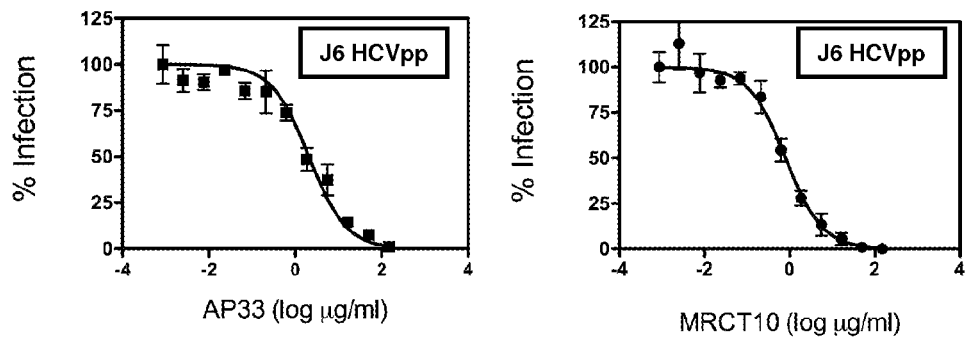
C
| | EC$_{50}$ (µg/ml) | |
|---|---|---|
| | AP33 | MRCT10 |
| Con1 HCVpp | 1.417 | 0.511 |
| J6 HCVpp | 2.066 | 0.793 |

Figure 40
A
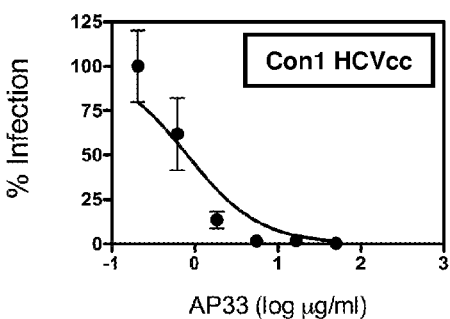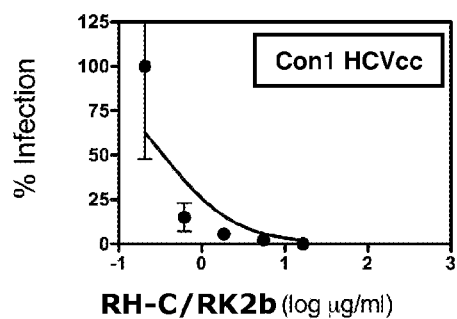
B
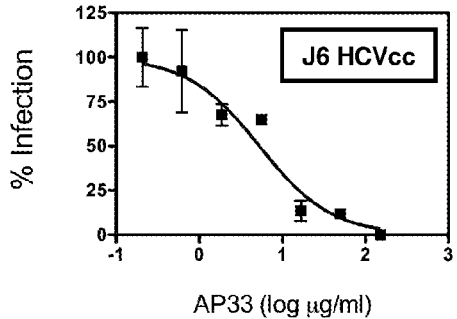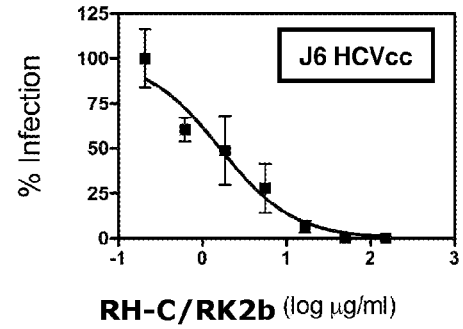
C
|  | EC$_{50}$ (μg/ml) | |
|---|---|---|
|  | AP33 | RH-C/RK2b |
| Con1 HCVcc | 0.812 (n=1) | 0.72 ± 0.38 (n=2) |
| J6 HCVcc | 8 ± 3.77 (n=7) | 1.7 ± 0.3 (n=4) |

Figure 41
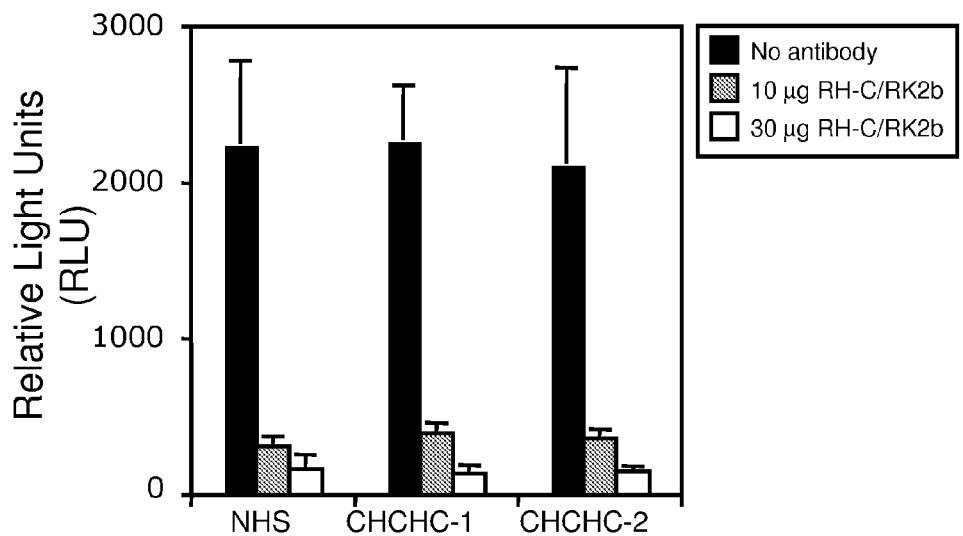
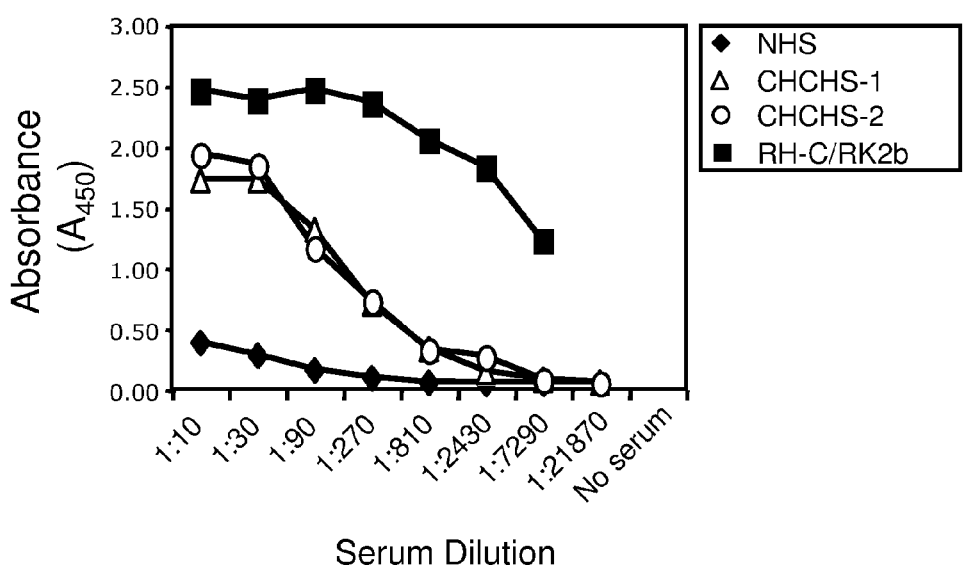

Figure 42A

SEQ ID NO: 1: Amino acid sequence of AP-33 heavy chain
SEQ ID NO: 21: Nucleic acid sequence of AP-33 heavy chain

```
5'  GAGGTGCAGCTTCAGGAGTCAGGACCTAGCCTCGTGAAACCTTCTCAGACTCTGTCCCTCACCTGTTCTGTCACTGGCGACTCCATCACCAGTGGTTACTGGAACTGGAT
                                                                                                                    110
3'  CTCCACGTCGAAGTCCTCAGTCCTGGATCGGAGCACTTTGGAAGAGTCTGAGACAGGAGTGGACAAGACAGTGACCGCTGAGGTAGTGGTCACCAATGACCTTGACCTA
1   Glu Val Gln Leu Gln Glu Ser Gly Pro Ser Leu Val Lys Pro Ser Gln Thr Leu Ser Leu Thr Cys Ser Val Thr Gly Asp Ser Ile Thr Ser Gly Tyr Trp Asn Trp Ile

5'  CCCGAAATTCCCAGCCAATAAACTTGACTACATGGGATACATAAGTTACAGTGGTAGCACTTACTACAATCTATCTCTGACAAGTCGCATCTCCATCACTCGAGACACAT
                                                                                                                    220
3'  GGGCTTTAAGGGTCGGTTATTTGAACTGATGTACCCTATGTATTCAATGTCACCATCGTGAATGATGTTAGATAGAGAGTCTTCAGCGTAGAGGTAGTGAGCTCTGTGTA
1   Arg Lys Phe Pro Gly Asn Lys Leu Glu Tyr Met Gly Tyr Ile Ser Tyr Ser Gly Ser Thr Tyr Tyr Asn Leu Ser Leu Arg Ser Arg Ile Ser Ile Thr Arg Asp Thr

5'  CCAAGAATCAGTACTACCTGCAGTTGAATTCTGTGACTACTGAGGACACAGCCACATATTACTGTGCGCTCATTACTACGACTACCTATGCTATGGACTACTGGGGTCAA
                                                                                                                    330
3'  GGTTCTTAGTCATGATGGACGTCAACTTAAGACACTGATGACTCCTGTGTCGGTGTATAATGACACGCGAGTAATGATGCTGATGGATACGATACCTGATGACCCCAGTT
1   Ser Lys Asn Gln Tyr Tyr Leu Gln Leu Asn Ser Val Thr Thr Glu Asp Thr Ala Thr Tyr Tyr Cys Ala Leu Ile Thr Thr Thr Thr Tyr Ala Met Asp Tyr Trp Gly Gln

5'  GGAACCTCAGTCACCGTCTCC
                                                                                                                    351
3'  CCTTGGAGTCAGTGGCAGAGG
1   Gly Thr Ser Val Thr Val Ser
```

SEQ ID NO: 2: Amino acid sequence of AP-33 Kappa chain
SEQ ID NO: 22: Nucleic acid sequence of AP-33 Kappa chain

```
5'  AACATTGTGCTGACCCAATCTCCAGTTTCTTTGGCTGTGTCTCTGGGGCAGAGGGCCACCATTTCCTGCAGAGCCAGTGAAAGTGTTGATGGTTATGGCAATAGTTTTCT
                                                                                                                    110
3'  TTGTAACACGACTGGGTTAGAGGTCAAAGAAACCGACACAGAGACCCCGTCTCCCGGTGGTAAAGGACGTCTCGGTCACTTTCACAACTACCAATACCGTTATCAAAAGA
1   Asn Ile Val Leu Thr Gln Ser Pro Val Ser Leu Ala Val Ser Leu Gly Gln Arg Ala Thr Ile Ser Cys Arg Ala Ser Glu Ser Val Asp Gly Tyr Gly Asn Ser Phe Leu

5'  GCACTGGTTCCAGCACAAACCAGCACAGCCACCCAAACTCCTCATCTATCTTGCATCGAACCTAAACTCTGCCGTCCCTGCCAGGTTCAGTGGCAGTGGGTCTACGACAG
                                                                                                                    220
3'  CGTGACCAAGGTCGTCTTTGGTCCTGCGGTGGGTTTGAGGAGTAGATAGAACGTAGGTTGGATTTGAGACCCCAGGGACGGTCCAAGTCACCGTCACCCAGATCCTGTC
1   His Trp Phe Gln Gln Lys Pro Gly Gln Pro Pro Lys Leu Leu Ile Tyr Leu Ala Ser Asn Leu Asn Ser Gly Val Pro Ala Arg Phe Ser Gly Ser Gly Ser Arg Thr

5'  ACTTCACCCTCACCATTGATCCTGTGGAGGCTGATGATGCTGCAACCTATTACTGTCAGCAAAATAATGTGGACCCGTGGACGTTCGGTGGAGGCACCAAGCTGGAAATC
                                                                                                                    330
3'  TGAAGTGGGAGTGGTAACTAGGACACCTCCGACTACTACGACGTTGGATAATGACAGTCGTTTTATTACACCTGGGCACCTGCAAGCCACCTCCGTGGTTCGACCTTTAG
1   Asp Phe Thr Leu Thr Ile Asp Pro Val Glu Ala Asp Asp Ala Ala Thr Tyr Tyr Cys Gln Gln Asn Asn Val Asp Pro Trp Thr Phe Gly Gly Gly Thr Lys Leu Glu Ile

5'  AAA
                                                                                                                    333
3'  TTT
1   Lys
```

Figure 42B

SEQ ID NO: 3: Amino acid sequence of AP33RHA
SEQ ID NO: 23: Nucleic acid sequence of AP33RHA

SEQ ID NO: 4: Amino acid sequence of AP33RKA
SEQ ID NO: 24: Nucleic acid sequence of AP33RKA

SEQ ID NO: 5: Amino acid sequence of AP33RKAbd
SEQ ID NO: 25: Nucleic acid sequence of AP33RKAbd

Figure 42C

SEQ ID NO: 6: Amino acid sequence of AP33RK2
SEQ ID NO: 26: Nucleic acid sequence of AP33RK2

```
5'  gaaatagtgttgacgcagtctccatcctccctgtctgcatctgtaggagacagagtcaccatcac__gcAGAGCCAGTGAAAGTGTTGATGGTTATGGCAATAGTTTTCT
o   ++++|++++|++++|++++|++++|++++|++++|++++|++++|++++|++++|++++|++++|++++|++++|++++|++++|++++|++++|++++|++++|++++|    110
3'  cttatcacaactgcgtcagaggtaccaggggacagacgtagacatcctctgtctcagtggtagtgaacgTCTCGGTCACTTTCACAACTACCAATACCGTTATCAAAAGA
1   Glu Ile Val Leu Thr Gln Ser Pro Ser Ser Leu Ser Ala Ser Val Gly Asp Arg Val Thr Ile Thr Cys Arg Ala Ser Glu Ser Val Asp Gly Tyr Gly Asn Ser Phe Leu 5'  GCACtggtatcagcagaaaccagggacagcccctaagctcctgatctatCTTGCATCCAACCTAAACTCTggggtcccatcaaggttcagtggcagtggatctgggacag
o   ++++|++++|++++|++++|++++|++++|++++|++++|++++|++++|++++|++++|++++|++++|++++|++++|++++|++++|++++|++++|++++|++++|    220
3'  CGTGaccatagtcgtctttggtcccttttcggggattcgaggactagataGAACGTAGGTTGGATTTGAGacccagggtagttccaagtcaccgtcacctagaccctgtc
1   His Trp Tyr Gln Gln Lys Pro Gly Lys Ala Pro Lys Leu Leu Ile Tyr Leu Ala Ser Asn Leu Asn Ser Gly Val Pro Ser Arg Phe Ser Gly Ser Gly Ser Gly Thr 5'  atttcactctcaccatcagcagtctgcaacctgaagattttgcaacttactactgtCAGCAAAATAATGTGGAcCCGTGGACttttTggccagggggaccaagctggagatc
o   ++++|++++|++++|++++|++++|++++|++++|++++|++++|++++|++++|++++|++++|++++|++++|++++|++++|++++|++++|++++|++++|++++|    330
3'  taaagtgagagtggtagtcgtcagacgttggactgctaaaacgttgaatgatgacaGTCGTTTTATTACACCTgGGCACCTGaaaAccggtccccctggttcgacctctag
1   Asp Phe Thr Leu Thr Ile Ser Ser Leu Gln Pro Glu Asp Phe Ala Thr Tyr Tyr Cys Gln Gln Asn Asn Val Asp Pro Trp Thr Phe Gly Gln Gly Thr Lys Leu Glu Ile 5'  aaac
o   ++++                                                                                                             334
3'  tttg
1   Lys
```

SEQ ID NO: 7: Amino acid sequence of AP33RK2bc
SEQ ID NO: 27: Nucleic acid sequence of AP33RK2bc

```
5'  gaaatagtgttgacgcagtctccatcctccctgtctgcatctgtaggagacagagtcaccatcacttgcAGAGCCAGTGAAAGTGTTGATGGTTATGGCAATAGTTTTCT
o   ++++|++++|++++|++++|++++|++++|++++|++++|++++|++++|++++|++++|++++|++++|++++|++++|++++|++++|++++|++++|++++|++++|    110
3'  ctttatcacaactgcgtcagaggtaggagggacagacgtagacatcctctgtctcagtggtagtgaacgTCTCGGTCACTTTCACAACTACCAATACCGTTATCAAAAGA
1   Glu Ile Val Leu Thr Gln Ser Pro Ser Ser Leu Ser Ala Ser Val Gly Asp Arg Val Thr Ile Thr Cys Arg Ala Ser Glu Ser Val Asp Gly Tyr Gly Asn Ser Phe Leu 5'  GCACtggtTtcagcagaaaccagggaaagcccctaagctcctgatctatCTTGCATCCAACCTAAACTCTggggtcccatcaaggttcagtggcagtggatctCggacag
o   ++++|++++|++++|++++|++++|++++|++++|++++|++++|++++|++++|++++|++++|++++|++++|++++|++++|++++|++++|++++|++++|++++|    220
3'  CGTGaccaAagtcgtcttttggtcccttcggggattcgaggactagataGAACGTAGGTTGGATTTGAGAcccagggtagttccaagtcaccgtcacctagaGcctgtc
1   His Trp Phe Gln Gln Lys Pro Gly Lys Ala Pro Lys Leu Leu Ile Tyr Leu Ala Ser Asn Leu Asn Ser Gly Val Pro Ser Arg Phe Ser Gly Ser Gly Ser Arg Thr 5'  atttcactctcaccatcagcagtctgcaacctgaagattttgcaacttactactgtCAGCAAAATAATGTGGAcCCGTGGACTttTggccagggggaccaagctggagatc
o   ++++|++++|++++|++++|++++|++++|++++|++++|++++|++++|++++|++++|++++|++++|++++|++++|++++|++++|++++|++++|++++|++++|    330
3'  taaagtgagagtggtagtcgtcagacgttggacttctaaaacgttgaatgatgacaGTCGTTTTATTACACCTgGGCACCTGaaaAccggtccccctggttcgacctctag
1   Asp Phe Thr Leu Thr Ile Ser Ser Leu Gln Pro Glu Asp Phe Ala Thr Tyr Tyr Cys Gln Gln Asn Asn Val Asp Pro Trp Thr Phe Gly Gln Gly Thr Lys Leu Glu Ile 5'  aaa
o   +++                                                                                                              333
3'  ttt
1   Lys
```

SEQ ID NO: 8: Amino acid sequence of AP33RK3
SEQ ID NO: 28: Nucleic acid sequence of AP33RK3

```
5'  GAAATTGTGCTGACTCAGTCTCCACTCTCCCTGCCCGTCACCCTTGGACAGCCGGCCTCCATCTCCTGCAGAGCCAGTGAAAGTGTTGATGGTTATGGCAATAGTTTTCT
o   ++++|++++|++++|++++|++++|++++|++++|++++|++++|++++|++++|++++|++++|++++|++++|++++|++++|++++|++++|++++|++++|++++|    110
3'  CTTTAACACGACTGAGTCAGAGGTGAGAGGGACGGGCAGTGGGAACCTGTCGGCCGGAGGTAGAGGACGTCTCGGTCACTTTCACAACTACCAATACCGTTATCAAAAGA
1    E  I  V  L  T  Q  S  P  L  S  L  P  V  T  L  G  Q  P  A  S  I  S  C  R  A  S  E  S  V  D  G  Y  G  N  S  F  L

5'  GCACTGGTTTCAGCAGAGGCCAGGCCAATCTCCAAGGCtCCTAATTTATCTTGCATCCAACCTAAACTCTGGGGTCCCAGACAGATTCAGCGGCAGCGGaTCAaggACTG
o   ++++|++++|++++|++++|++++|++++|++++|++++|++++|++++|++++|++++|++++|++++|++++|++++|++++|++++|++++|++++|++++|++++|    220
3'  CGTGACCAAAGTCGTCTCCGGTCCGGTTAGAGGTTCCGaGGATTAAATAGAACGTAGGTTGGATTTGAGACCCCAGGGTCTGTCTAAGTCGCCGTCgCCtAGttccTGAC
1    H  W  F  Q  Q  R  P  G  Q  S  P  R  L  L  I  Y  L  A  S  N  L  N  S  G  V  P  D  R  F  S  G  S  G  S  R  T 5'  ATTTCACACTGAAAATCAGCAGaGTGGAGGCTGAGGATGTTGGGGTTTATTACTGCCAGCAAAATAATGTGGAcCCGTGGACtTTCGGCGGAGGGACCAAAGTGGAGATC
o   ++++|++++|++++|++++|++++|++++|++++|++++|++++|++++|++++|++++|++++|++++|++++|++++|++++|++++|++++|++++|++++|++++|    330
3'  TAAAGTGTGACTTTTAGTCGTCtCACCTCCGACTCCTACAACCCCAAATAATGACGGtCGTTTTATTACACCtgGGCACCTGCAAGCCGCCTCCCTGGTTtCACCTCTAG
1    D  F  T  L  K  I  S  R  V  E  A  E  D  V  G  V  Y  Y  C  Q  Q  N  N  V  D  P  W  T  F  G  G  G  T  K  V  E  I 5'  AAACGTGAGTGGATCCCGCG
o   ++++|++++|++++|++++|                                                                                              350
3'  TTTGCACTCACCTAGGGCGC
1    K  R  E  W  I  P  R
```

Figure 42D

SEQ ID NO: 9: Amino acid sequence of AP33RK4
SEQ ID NO: 29: Nucleic acid sequence of AP33RK4

SEQ ID NO: 10: Amino acid sequence of AP33RHbcdefgh
SEQ ID NO: 30: Nucleic acid sequence of AP33RHbcdefgh

SEQ ID NO: 11: Amino acid sequence of AP33RHI
SEQ ID NO: 31: Nucleic acid sequence of AP33RHI

Figure 42E

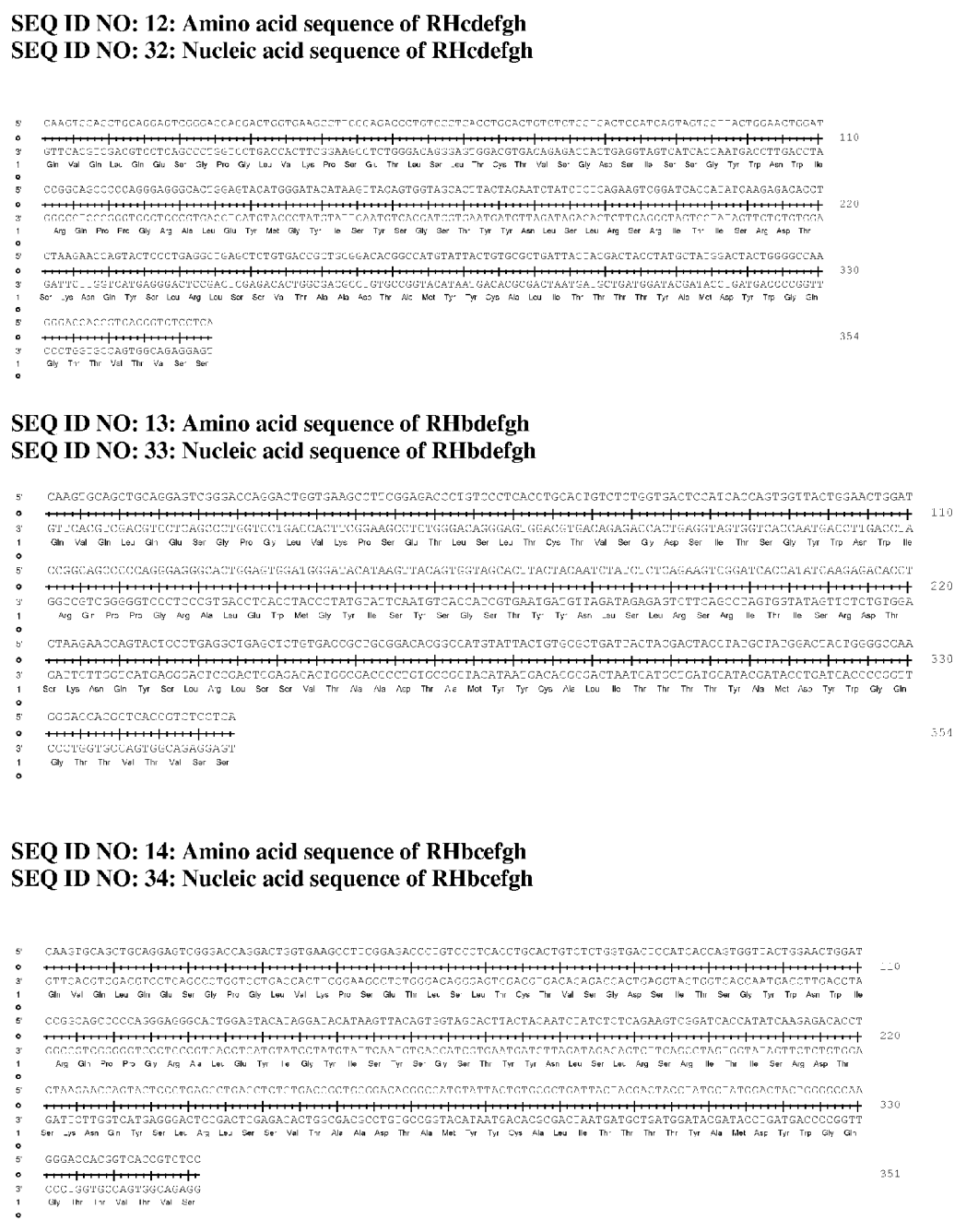

SEQ ID NO: 12: Amino acid sequence of RHcdefgh
SEQ ID NO: 32: Nucleic acid sequence of RHcdefgh

SEQ ID NO: 13: Amino acid sequence of RHbdefgh
SEQ ID NO: 33: Nucleic acid sequence of RHbdefgh

SEQ ID NO: 14: Amino acid sequence of RHbcefgh
SEQ ID NO: 34: Nucleic acid sequence of RHbcefgh

Figure 42F

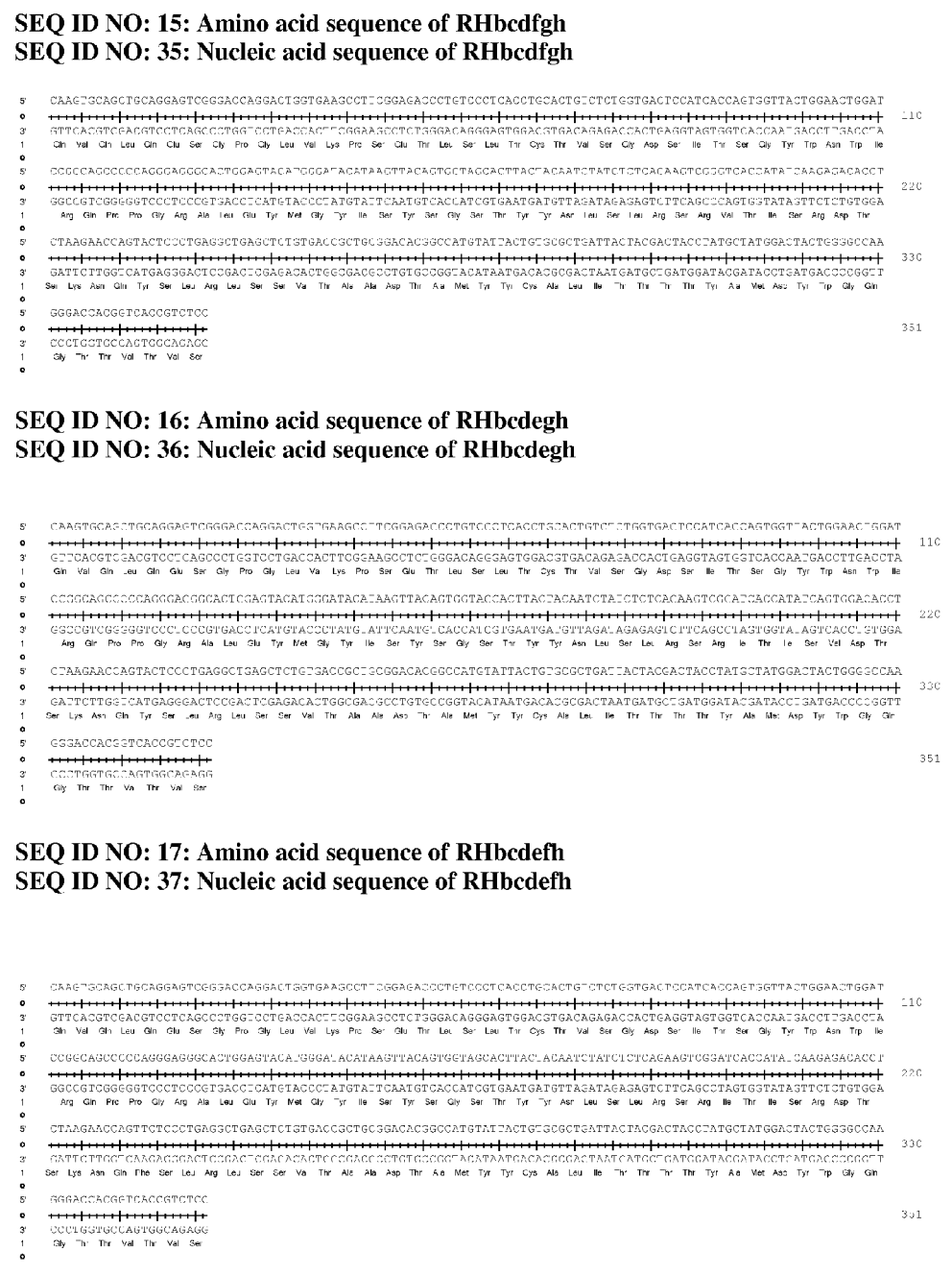

SEQ ID NO: 15: Amino acid sequence of RHbcdfgh
SEQ ID NO: 35: Nucleic acid sequence of RHbcdfgh

SEQ ID NO: 16: Amino acid sequence of RHbcdegh
SEQ ID NO: 36: Nucleic acid sequence of RHbcdegh

SEQ ID NO: 17: Amino acid sequence of RHbcdefh
SEQ ID NO: 37: Nucleic acid sequence of RHbcdefh

Figure 42G

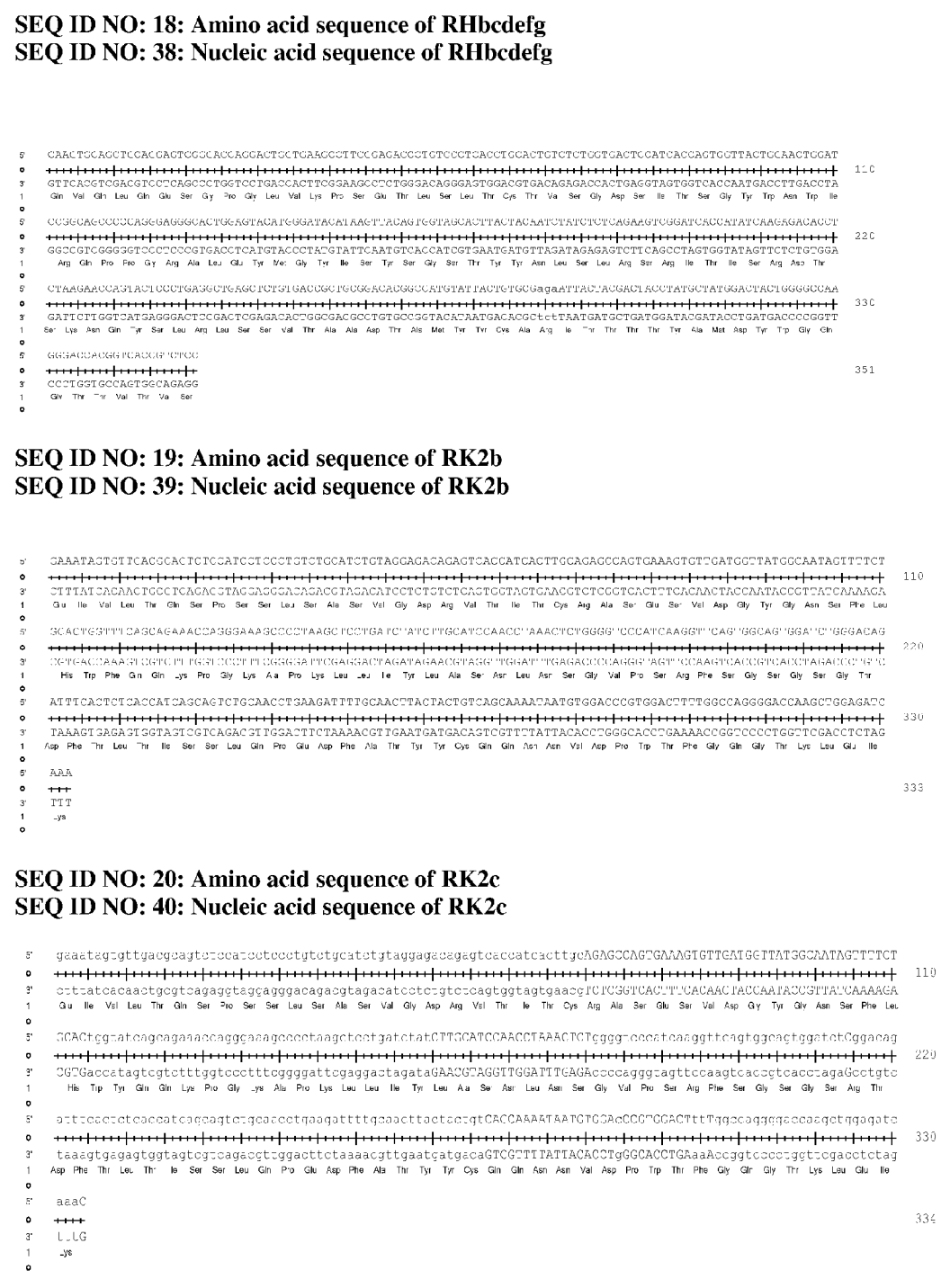

SEQ ID NO: 18: Amino acid sequence of RHbcdefg
SEQ ID NO: 38: Nucleic acid sequence of RHbcdefg

SEQ ID NO: 19: Amino acid sequence of RK2b
SEQ ID NO: 39: Nucleic acid sequence of RK2b

SEQ ID NO: 20: Amino acid sequence of RK2c
SEQ ID NO: 40: Nucleic acid sequence of RK2c

HEPATITIS C VIRUS ANTIBODIES

CROSS-REFERENCE TO RELATED APPLICATIONS

This application claims the priority benefit of U.S. Provisional Application 61/006,066 filed Dec. 17, 2007, which is hereby incorporated herein by reference in its entirety.

FIELD OF THE INVENTION

This invention relates to therapeutic humanized antibodies and fragments thereof that retain broad spectrum inhibitory effect on HCV infection of the parent murine monoclonal antibody and methods of their use.

BACKGROUND OF THE INVENTION

HCV is a positive strand RNA virus belonging to the Flaviviridae family. It is the major cause of non-A non-B viral hepatitis. HCV has infected approximately 200 million people and current estimates suggest that as many as 3 million individuals are newly infected each year. Approximately 80% of those infected fail to clear the virus; a chronic infection ensues, frequently leading to severe chronic liver disease, cirrhosis and hepatocellular carcinoma. Current treatments for chronic infection are ineffective and there is a pressing need to develop preventative and therapeutic vaccines.

Due to the error-prone nature of the RNA-dependent RNA polymerase and the high replicative rate in vivo, HCV exhibits a high degree of genetic variability. HCV can be classified into six genetically distinct genotypes and further subdivided into at least 70 subtypes, which differ by approximately 30% and 15% at the nucleotide level, respectively. A significant challenge for the development of vaccines will be identifying protective epitopes that are conserved in the majority of viral genotypes and subtypes. This problem is compounded by the fact that the envelope proteins, the natural target for the neutralizing response, are two of the most variable proteins.

The envelope proteins, E1 and E2, are responsible for cell binding and entry. They are N-linked glycosylated transmembrane proteins with an N-terminal ectodomain and a C-terminal hydrophobic membrane anchor. In vitro expression experiments have shown that E1 and E2 proteins form a non-covalent heterodimer, which is proposed to be the functional complex on the virus surface. Due to the lack of an efficient culture system, the exact mechanism of viral entry is unknown. That said, there is mounting evidence that entry into isolated primary liver cells and cell lines requires interaction with the cell surface receptors CD81 and Scavenger Receptor Class B Type 1 (SR-B1), although these receptors alone are not sufficient to allow viral entry.

Current evidence suggests that cell mediated immunity is pivotal in clearance and control of viral replication in acute infection. However, surrogate models of infection, such as animal infection and cell and receptor binding assays, have highlighted the potential role of antibodies in both acute and chronic infection. Unsurprisingly, neutralizing antibodies recognize both linear and conformational epitopes. The majority of antibodies that demonstrate broad neutralization capacity are directed against conformational epitopes within E2. Induction of antibodies recognizing conserved conformational epitopes is extremely relevant to vaccine design, but this is likely to prove difficult, as the variable regions appear to be immuno-dominant. One such immuno-dominant linear epitope lies within the first hypervariable region of E2 (HVR1). The use of conserved HVR1 mimotopes has been proposed to overcome problems of restricted specificity, but it is not yet known whether this approach will be successful.

A region immediately downstream of HVR1 contains a number of epitopes. One epitope, encompassing residues 412-423 and defined by the monoclonal antibody AP33, inhibits the interaction between CD81 and a range of presentations of E2, including soluble E2, E1E2 and virus-like particles. See Owsianka A. et al., *J Gen Virol* 82:1877-83 (2001).

WO 2006/100449 teaches that the monoclonal antibody designated AP33 can bind to and neutralize each of the six known genotypes 1-6 of HCV. Accordingly, it is deduced that the epitope targeted by AP33 is cross-reactive with all of genotypes 1-6 of HCV, indicating it as a target for anti-HCV ligands and as an immunogen for raising anti-HCV antibodies.

AP33 is a mouse antibody, and as such is likely to raise a human anti-mouse antigenic response (HAMA) in human patients if used therapeutically for multiple administrations. There is accordingly a need for an antibody which shares the cross-reactivity of AP33, but which possesses reduced antigenicity in human subjects.

BRIEF SUMMARY OF THE INVENTION

The present invention relates to an improved therapeutic humanized antibody that retains broad spectrum inhibitory effect on HCV infection. The humanization of AP33 has been shown to be technically problematic, and the generation of humanized AP33 has led to the following developments.

During the humanization of the AP33 monoclonal antibody, the inventors encountered problems relating to poor expression levels of the humanized variable light chain domain. There is no human ortholog for the mouse light chain. The L1 loop cannot be matched and to a human kappa chain and this is normally a key component of the humanization process. Despite several modifications to the variable light chain domains, such as removing potential splice site mutations and exchanging leader sequences, none of these modifications were effective in restoring expression levels above background even though such modifications have previously been reported to be effective in improve expression levels. Surprisingly, the inventors eventually identified a variable light chain domain, designated herein as RK2b, which not only expresses well but also possesses good light chain binding activity.

The inventors have also discovered that the retention of W at position 47 is required for optimal activity of the humanized variable heavy chain domain. This is surprising because in the mouse (chimeric) antibody it does not appear to be of importance whether the amino acid at position 47 is W (the human residue) or Y (the mouse residue). In the humanized variable heavy chain domain the amino acid at position 47 should be W for optimal activity. In direct contrast, all of the other important framework residues, i.e. the vernier and canonical residues, need to be mutated to mouse donor residues for optimal activity.

The inventors have moreover surprisingly discovered that the humanized antibody described herein is at least as effective as AP33 at inhibiting HCV infection. Usually, when an antibody is humanized a decrease in activity is expected due to the replacement of murine framework which forms the environment surrounding the CDRs with a human framework. In the present invention, however, replacement of the murine frameworks has resulted in an increase in activity. Advantageously, the antibody of the present invention not only has the advantages associated with humanization (e.g.

rendering it less immunogenic in human subjects) but also retains the broad spectrum of neutralizing cross-reactivity against HCV species.

In a first aspect, therefore, there is provided a variable light chain domain of a humanized AP33 antibody comprising or consisting of the amino acid sequence set forth in any of SEQ ID NO:6, SEQ ID NO:7, SEQ ID NO:19, or SEQ ID NO:20. In some embodiments, the variable light chain domain of a humanized AP33 antibody binds hepatitis C virus E2 protein.

In a second aspect, there is provided a variable heavy chain domain of a humanized AP33 antibody comprising or consisting of the amino acid set forth in SEQ ID No. 3. SEQ ID No 3 represents murine CDRs grafted onto a human framework. Advantageously, the human framework is modified by backmutation at one or more of positions 30, 48, 67, 71 78 and 94 thereof, to match the equivalent positions in the mouse genome.

Suitably, the amino acid mutations are substitutions, for example S30T, I48M, V67I, V71R, F78Y and R94L. In the forgoing, the mouse residue is represented second and the human residue first; thus, in the humanization procedure, residue 30 is T in the original AP33 framework, S in the human framework employed, and T in the backmutated, humanized antibody framework.

In some embodiments, the variable heavy chain domain comprises or consists of the amino acid sequence as set forth in any of SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. In some embodiments, the variable heavy chain domain of a humanized AP33 antibody binds hepatitis C virus E2 protein.

In a third aspect, there is provided a humanized antibody or humanized antibody fragment comprising the variable light chain domain described in the first aspect of the invention. In some embodiments, the humanized antibody or humanized antibody fragment comprising the variable light chain domain binds hepatitis C virus E2 protein. In some embodiments, the humanized antibody fragment is an antigen binding fragment.

In a fourth aspect, there is provided a humanized antibody or humanized antibody fragment comprising the variable heavy chain domain of the second aspect of the invention. In some embodiments, the humanized antibody or humanized antibody fragment comprising the variable heavy chain domain binds hepatitis C virus E2 protein. In some embodiments, the humanized antibody fragment is an antigen binding fragment.

In a fifth aspect, there is provided a humanized antibody or humanized antibody fragment comprising a light chain and a heavy chain, wherein the variable region of the light chain and the variable region of the heavy chain are as defined in the first and second aspects above. In some embodiments, the humanized antibody or humanized antibody fragment comprising the variable region of the light chain and variable region of the heavy chain binds hepatitis C virus E2 protein. In some embodiments, the humanized antibody fragment thereof is selected from the group consisting of a Fab fragment, a Fab' fragment, a F(ab')$_2$ fragment, a scFv, a Fv, and a diabody. In some embodiments, the humanized antibody fragment is an antigen binding fragment.

In a sixth aspect, there is provided a nucleic acid sequence encoding the variable light chain domain.

Suitably, the nucleic acid sequence encoding the variable light chain domain comprises or consists of the sequence set forth in any of SEQ ID NO:26, SEQ ID NO:27, SEQ ID NO:39, or SEQ ID NO:40.

In a seventh aspect, there is provided a nucleic acid sequence encoding the variable heavy chain domain.

Suitably, the variable heavy chain domain comprises or consists of the sequence set forth in any of SEQ ID NO:30, SEQ ID NO:31, SEQ ID NO:32, SEQ ID NO:33, SEQ ID NO:34, SEQ ID NO:35, SEQ ID NO:36, SEQ ID NO:37, or SEQ ID NO:38.

In an eighth aspect, there is provided a nucleic or an amino sequence encoding the humanized antibody or humanized antibody fragment as described herein.

In a ninth aspect, there is provided a nucleic acid sequence complementary to the nucleic acid sequence(s) described herein.

In a tenth aspect, there is provided a nucleic acid sequence that is capable of hybridizing to the nucleotide sequence(s) described herein.

In an eleventh aspect, there is provided a construct or a vector comprising the nucleic acid sequence(s) described herein. In some embodiments, the vector further comprises an expression control sequence operatively linked to the nucleic acid encoding the variable heavy chain region and/or the variable light chain region. Suitably, said vector is an expression vector.

In some embodiments, there is provided a recombinant cell containing the construct or vector of the eleventh aspect. In some embodiments, the cell is a eukaryotic cell. In some embodiments, the eukaryotic cell is a CHO cell.

In an twelfth aspect, there is provided an amino sequence encoding the variable heavy chain described herein.

In a thirteenth aspect, there is provided an amino sequence encoding the humanized antibody or humanized antibody fragment as described herein.

In a fourteenth aspect, there is provided an amino acid sequence comprising the sequence set forth in any of SEQ ID NO:6, SEQ ID NO:7, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20.

In a fifteenth aspect, there is provided a process for preparing a humanized antibody comprising the steps of: (a) providing a host cell transformed with either: (i) a first expression vector which encodes the variable light chain domain and a second expression vector which encodes the variable heavy chain domain according to the preceding aspects; or (ii) a single expression vector which encodes both the variable light chain domain according to and the variable heavy chain domain according to the preceding aspects; (b) culturing said host cell under such conditions that each chain is expressed; and (c) optionally isolating the humanized antibody formed by assembly of the expressed chains.

In some embodiments, there is provided a method of producing a humanized antibody, or antigen binding fragment thereof, comprising growing a recombinant cell containing the nucleic acid of the eighth aspect such that the encoded variable heavy chain region and/or variable light chain region are expressed by the cell; and recovering the expressed the humanized antibody or antigen binding fragment thereof. In some embodiments, the method further comprises isolating and/or purifying the recovered humanized antibody or antigen binding fragment thereof.

In a sixteenth aspect, there is provided a humanized antibody obtained or obtainable by this process.

In a seventeenth aspect, there is provided a pharmaceutical composition comprising a pharmaceutically acceptable carrier or diluent and, as active ingredient, the humanized antibody or the humanized antibody fragment as described herein.

In an eighteenth aspect, there is provided a method for the treatment and/or prevention of the hepatitis C virus infection, comprising the use of the humanized antibody or the humanized antibody fragment or the pharmaceutical composition as described herein. In some embodiments, the hepatitis C virus infection is an acute hepatitis C virus infection. In some embodiments, the hepatitis C virus infection is a chronic hepatitis C virus infection. In some embodiments, treatment of the hepatitis C virus infection comprises reducing viral load and/or viral titer. In some embodiments, the method further comprises administering a second therapeutic agent.

Suitably, the method for the treatment and/or prevention of hepatitis C virus infection comprises administering an effective amount of the humanized antibody or humanized antibody thereof or the pharmaceutical composition to a subject in need thereof In a nineteenth aspect, there is provided the humanized antibody or the fragment thereof or the pharmaceutical composition for use in the treatment and/or prevention of hepatitis C virus infection in a subject. In some embodiments, the hepatitis C virus infection is an acute hepatitis C virus infection. In some embodiments, the hepatitis C virus infection is a chronic hepatitis C virus infection. In some embodiments, the use in treatment of hepatitis C virus infection comprises reducing viral load and/or viral titer.

In a twentieth aspect, there is provided the use of the humanized antibody or the fragment thereof or the pharmaceutical composition in the manufacture of a composition for the treatment and/or prevention of hepatitis C virus infection in a subject. In some embodiments, the hepatitis C virus infection is an acute hepatitis C virus infection. In some embodiments, the hepatitis C virus infection is a chronic hepatitis C virus infection. In some embodiments, treatment of hepatitis C virus infection comprises reducing viral load and/or viral titer. In some embodiments, the use further comprises administering a second therapeutic agent.

In a twenty-first aspect, there is provided an assay method for identifying an agent that improves or enhances the efficacy of the neutralizing activity of the humanized antibody or fragment thereof against hepatitis C virus, comprising the steps of: (a) providing the humanized antibody or fragment thereof; (b) contacting said humanized antibody or fragment thereof with an agent to be tested; and (c) determining whether the agent improves or enhances the efficacy of the humanized antibody or fragment thereof in neutralizing the infectivity of hepatitis C virus.

In some embodiments, an assay method for identifying an agent that improves or enhances the efficacy of the neutralizing activity of the humanized antibody or antigen binding fragment thereof against hepatitis C virus is provided herein, comprising the steps of: (a) contacting said humanized antibody or antigen binding fragment thereof with an agent to be tested; and (b) determining whether the agent improves or enhances the efficacy of the humanized antibody or antigen binding fragment thereof in neutralizing the infectivity of hepatitis C virus. In some embodiments, the agent improves or enhances the efficacy of the humanized antibody or antigen binding fragment thereof in neutralizing the infectivity of hepatitis C virus is compared to a suitable control. In some embodiments, the suitable control is the humanized antibody or fragment thereof in the absence of the agent.

There is provided in a twenty-second aspect, an agent obtained or obtainable by this method.

There is also provided, in a twenty-third aspect a method for determining the presence of hepatitis C virus in a sample, comprising the use of the humanized antibody or humanized antibody fragment described herein.

Suitably, the method comprises the step of contacting a sample from a subject with the humanized antibody or humanized antibody fragment. In some embodiments, the method further comprises comparing to a suitable control. In some embodiments, the suitable control is an antibody which does not recognize HCV. In some embodiments, the suitable control is a sample known to contain HCV.

BRIEF DESCRIPTION OF THE DRAWINGS

FIG. 13 (previously Table 7 in 61/006,066) shows Comparison of Vernier Canonical and Interface residues in AP33 H and L chains (SEQ ID NOs: 1 & 2, respectively) with the donor sequences. 'Vern/CDR' indicates vernier residues (v) and CDRs (-===-). Light grey highlighting indicates CDRs. Black highlighting with white text indicates VCI residues. Dark gray highlighting with bolded text differences between the VCI residues found in AP33 and 567826 (SEQ ID NO: 64), X61125(SEQ ID NO: 65), AB064133 (SEQ ID NO: 67), AB064072(SEQ ID NO: 68) and AY685279 (SEQ ID NO: 66), FIG. 14 (previously Table 8 in 61/006,066) shows a comparison of the VCI residues in AP33 VH and selected human $V_H$ genes. Twenty human $V_H$ sequences with best VCI scores, and matching CDR1 and 2 sizes compared to AP33VH. "." indicates residue identical to that in AP33VH. Black highlighting with white text indicates sites that differ in potential donor frameworks. VCI/FW score indicates number of VCI or FW residues identical to AP33VH. Light grey highlighting, dark grey highlighting with bolded text, and no highlighting with bolded text indicate non-conservative, conservative, and acceptable canonical alternative residues, respectively. (SEQ ID NOs: 69-75).

FIG. 15 (previously Table 9 in 61/006,066) shows a comparison of AP33VH (SEQ ID NO: 76) with selected human $V_H$ protein sequences (SEQ ID NOs: 77-88). This is a comparison of twenty human $V_H$ sequences as in FIG. 14. Grey highlighting denotes Pro residues. Dark grey highlighting with bolded text denotes Cys residues.

FIG. 16 (previously Table 10 in 61/006,066) shows a ClustalW alignment of the best four human $V_H$ sequences (SEQ ID NOs: 89-93). Black highlighting with white text indicates CDRs, and grey highlighting and dark grey highlighting with bolded text show differences between donor candidates outside the CDRs.

FIGS. 18A-B (previously Table 12 in 61/006,066) show AP33RHA protein and DNA sequence generation. FIG. 18A shows AP33RHA protein sequence graft (SEQ ID NOs: 64, & 97-101), and FIG. 18B shows AP33RHA DNA sequence graft (SEQ ID NOs: 94, 97-99, & 102-113). Dark grey highlighting with bolded text indicates CDRs.

FIG. 19 (previously Table 14 in 61/006,066) shows DNA and Protein sequence of AP33RHA (SEQ ID NOs: 115 & 116, respectively). Light grey boxes show nucleotide changes that remove cryptic splice sites.

FIG. 20 (previously Table 15 in 61/006,066) (SEQ ID NOs: 117-149) shows AP33 VK comparison with germline human VK genes, V gene segment only of AP33VK and human germline genes. Comparison of AP33VK with human germline V genes shows that this CDR1 length is not represented by any human VK gene. No human germline kappa genes have the same size CDR1 loop. CDR1 loop is denoted with black highlighting and white text. Highlighted and/or bolded residues highlight the differences between a conserved proline with V genes with short CDR1 loops and those with longer loops.

FIG. 21 (previously Table 16 in 61/006,066) shows VCI scores of human VK with same CDR1 size. Only 6 "human", VK sequences with matching canonical loop lengths found in the database were either phage or humanized antibodies. "." indicates residue identical to that in AP33VK. VCI/FW score indicates number of VCI or FW residues identical to AP33VK. Black highlighting with white letters in AP33K indicates unconserved residues. (SEQ ID NOs: 150 & 151)

FIG. 22 (previously Table 17 in 61/006,066) shows Human VK (including different CDR1 lengths) with high VCI scores. Twenty human VK sequences with best VCI scores and matching CDR2 size compared to AP33VK. "." indicates residue identical to that in AP33VK. VCI/FW score indicates number of VCI or FW residues identical to AP33VK. Black highlighting with white letters in AP-33K indicates sites that differ in potential donor framework. (SEQ ID NO: 152)

FIG. 23A-B. FIG. 23A (previously Table 18A in 61/006,066) shows AP33 VK and human VK sequences with non-matching CDR1 size. Cys, Pro and CDRs are indicated by dark grey highlighting with bolded text, black highlighting with white text, and light grey highlighting, respectively (SEQ ID NOs: 2, & 153-168). FIG. 23B (previously Table 18B in 61/006,066) shows ClustalW alignment of AP33 VK (SEQ ID NO: 169) and human sequences with non-matching CDR1 size (SEQ ID NOs: 154-156, 170). Identity of residue to AP33 is indicated by a dot and grey highlights CDRs and their differences in length. Black highlighting with white text indicates a difference in a VCI residue, grey with bolded text is a non-conservative change in X61125 (SEQ ID NO: 170) or AY685279 (SEQ ID NO: 155). FW4 KLEIN (SEQ ID NO: 289) of X61125 is very unusual and is likely to be a sequencing artifact, and may be KLEIK (SEQ ID NO: 290). KLEIK (SEQ ID NO: 290) in AP33 is a common motif.

FIG. 24 (previously Table 19 in 61/006,066) shows VCI of AP33 VK and non-VK4 human VK sequences with longer CDR1 (SEQ ID NOs: 150 & 171). Twenty human VK nonVK4 sequences with best VCI scores, matching CDR2 size and longer CDR1 compared to AP33VK. VCI/FW score indicates number of VCI or FW residues identical to AP33VK.

Figure 25:
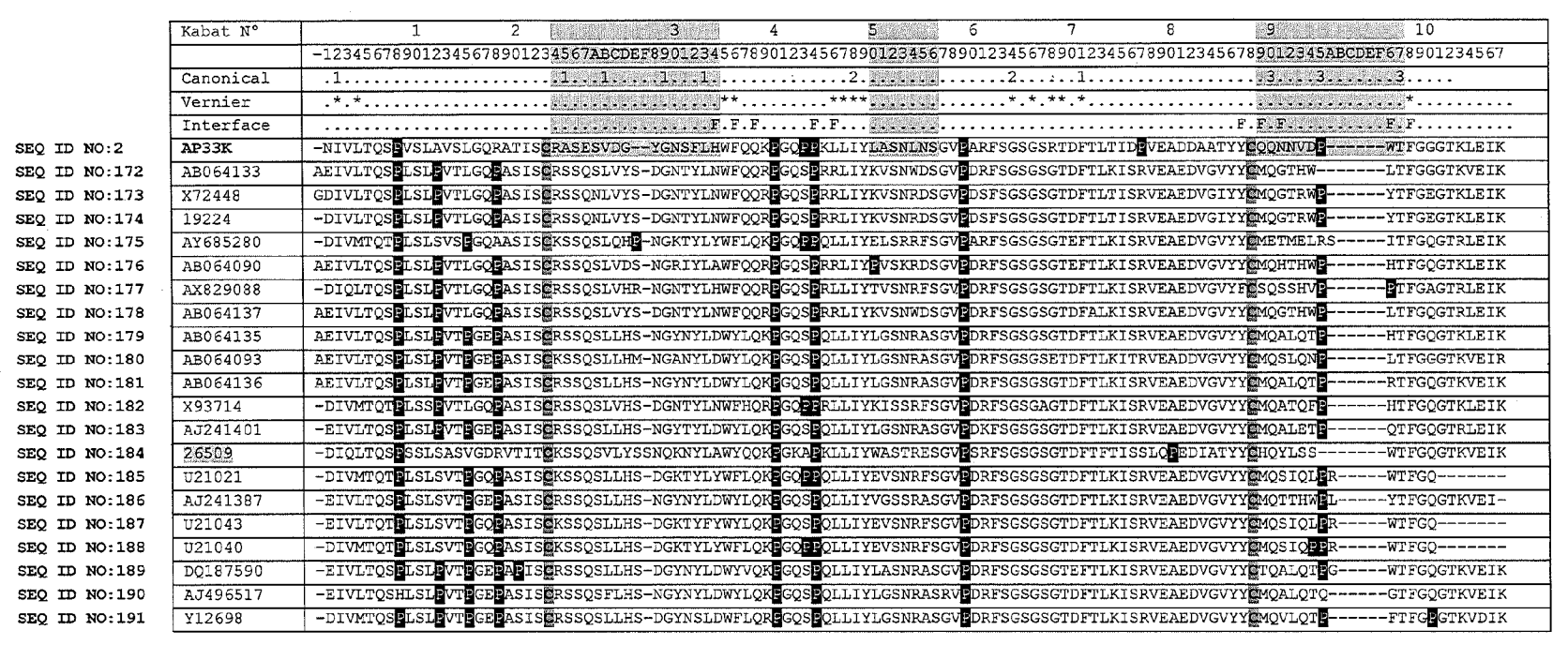

FIG. 25 (previously Table 20 in 61/006,066) shows AP33 VK and human VK non-VK4 sequences with larger CDR1 (SEQ ID NOs: 2, 172-191). Cys, Pro and CDRs are indicated by dark grey highlighting with bolded text, black highlighting with white text, and light grey highlighting, respectively.

FIGS. 30A and B (previously Table 25 in 61/006,066) show generation of AP33RKA sequence. FIG. 30A shows AP33RKA protein sequence graft (SEQ ID NOs: 2, 4, 206-210). FIG. 30B shows AP33RKA DNA sequence graft with VKIV B3 leader (SEQ ID NOs: 206-208, 211-222). CDRs are highlighted.

FIGS. 31A-B (previously Table 26 in 61/006,066) show generation of AP33RK2 sequence. FIG. 31A shows AP33RK2 protein sequence graft (SEQ ID NOs: 2, 155, 206-208, 223, 224). FIG. 31B shows AP33RK2 DNA sequence generation (SEQ ID NOs: 206-208, 213, 214, 216, 222, 225-233). CDRs are highlighted.

FIGS. 32A-B (previously Table 27 in 61/006,066) show generation of AP33RK3 sequence. FIG. 32A shows AP33RK3 protein sequence graft (SEQ ID NOs: 2, 192, 206-208, 234, 235). FIG. 32B shows AP33RK3 DNA sequence generation (SEQ ID NOs: 206-208, 213, 214, 216, 236-245). CDRs are highlighted.

FIG. 33 (previously Table 28 in 61/006,066) shows AP33RK4 DNA sequence generation (SEQ ID NOs: 206-208, 213, 214, 216, 218, 246-254). CDRs are highlighted.

FIGS. 34A-D (previously Table 29 in 61/006,066) show AP33RKA (SEQ ID NO: 255), AP33RK2 (SEQ ID NO: 256), AP33RK3 (SEQ ID NO: 257), and AP33RK4 (SEQ ID NO: 258) DNA sequence with leader. CDRs are highlighted.

FIG. 36 (previously Table 31 in 61/006,066) shows DNA (sense:—SEQ ID NO: 261; anti-sense:—SEQ ID NO: 262) and protein (SEQ ID NO: 263) sequence of AP33RK2 with leader. Light grey boxes represent changed nucleotides to remove cryptic splice sites or unwanted BamHI sites.

Figure 38:
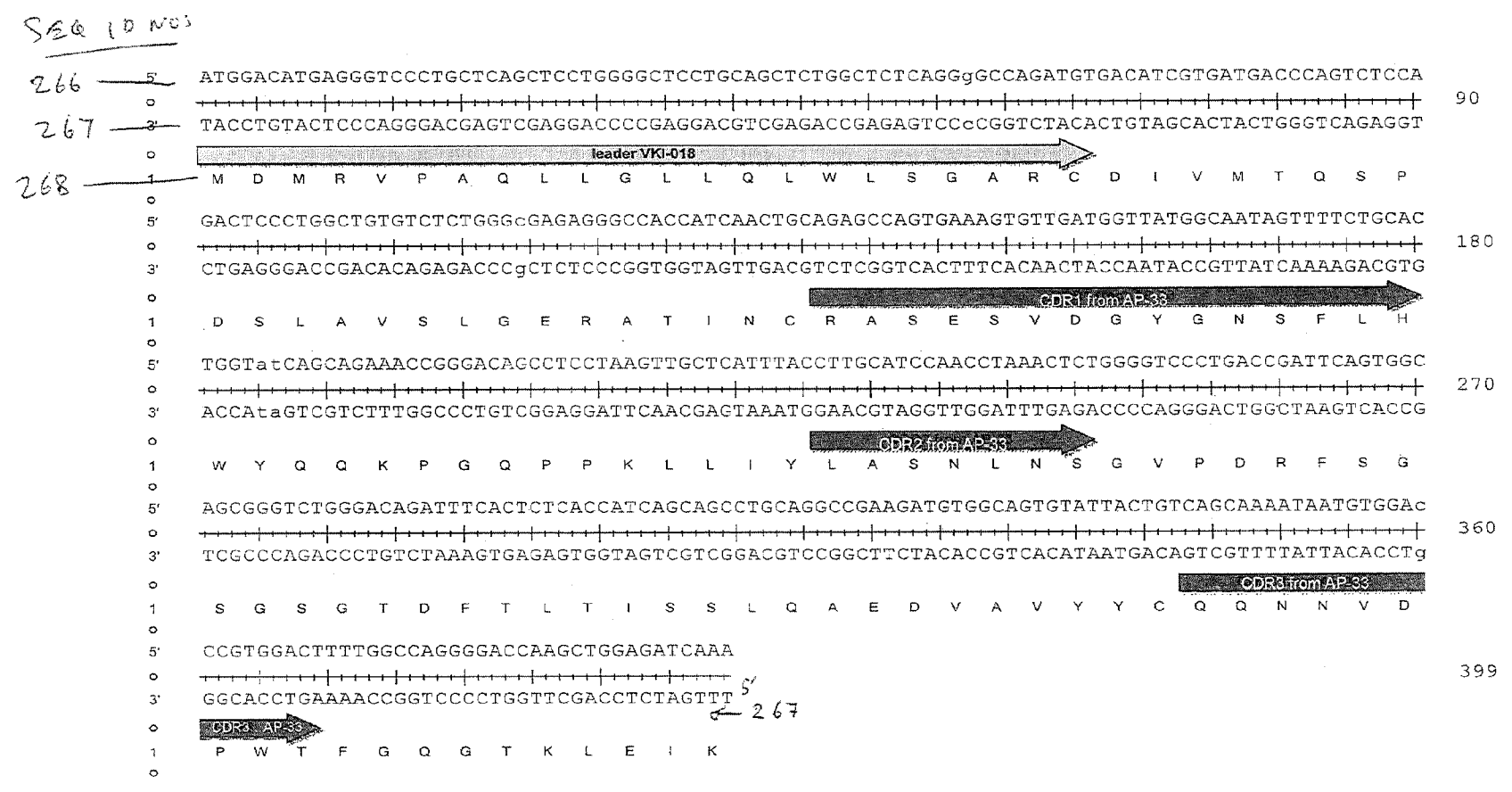

FIG. 38 (previously Table 33 in 61/006,066) shows DNA (sense:—SEQ ID NO: 266; anti-sense:—SEQ ID NO: 267) and protein (SEQ ID NO: 268) sequence of AP33RK4 construct.

FIGS. 39A-C. FIG. 39A shows AP33 and RH-C/RK2b neutralization of Con1 HCVpp as measured by percent infection. FIG. 39B shows AP33 and RH-C/RK2b neutralization of J6 HCVpp as measured by percent infection. FIG. 39C shows the $EC_{50}$ (µg/ml) of AP33 and RH-C/RK2b using Con1 and J6 HCVpp.

FIGS. 40A-C. FIG. 40A shows AP33 and RH-C/RK2b neutralization of Con1 HCVcc as measured by percent infection. FIG. 40B shows AP33 and RH-C/RK2b neutralization of J6 HCVcc as measured by percent infection. FIG. 40C shows the $EC_{50}$ (µg/ml) of AP33 and RH-C/RK2b using Con1 and J6 HCVcc.

FIGS. 41A-B. FIG. 41A shows the results of a neutralization assay using Con1 HCVpp in the presence of RH-C/RK2b and 10% normal human serum (NHS) or sera from chronic HCV-infected patients (CHCHS-1 and CHCHC-2). FIG. 41B shows level of binding of NHS, CHCHS-1, CHCHS-2, and RH-C/RK2b to Con1 HCV E1E2-reactive antibodies by ELISA assay using lysates from GT1b (Con1) E1E2-transfected 293T cells as measured by absorbance ($A_{450}$).

FIG. 42A-G shows the amino acid and nucleotide sequences of humanized antibody variable chains of Table 8 (SEQ ID NOs: 1-40, 269-288).

DETAILED DESCRIPTION OF THE INVENTION

I Antibodies

Figure 1:
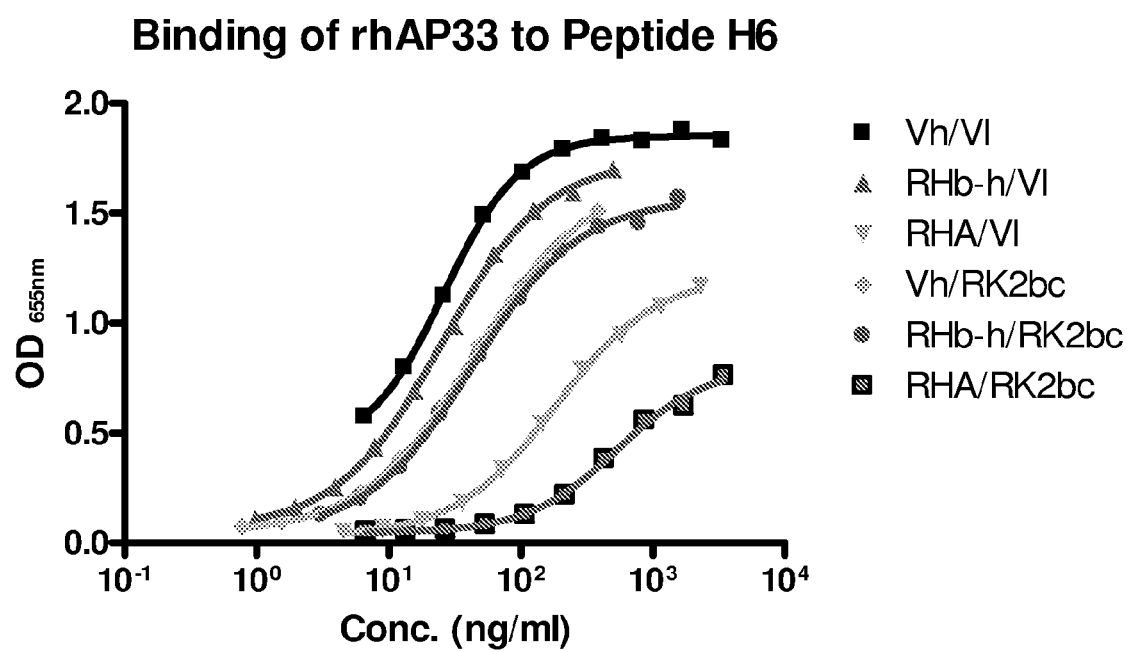
FIG. 1 shows the binding of humanized and chimeric antibody to the AP33 mimotope H6. To compare relative binding of the chimeric antibody to the humanized heavy and light chains COS7 cells were transfected with a series of chimeric and humanized heavy and light chain constructs and the supernatants were used to compare binding to the mimotope H6. The binding of the mimotope peptide H6 to chimeric (Vh/Vl) and humanized antibodies RHb-h/RK2bc and RHA/RK2bc or mixtures of humanized and chimeric antibodies RHA/Vl, RHb-h/Vl or Vh/RK2bc were measured by ELISA.

Antibodies are naturally occurring immunoglobulin molecules which have varying structures, all based upon the immunoglobulin fold. For example, IgG antibodies such as AP33 have two 'heavy' chains and two 'light' chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody or fragment thereof to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of*

*Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

In some embodiments, the hypervariable regions are the amino acid residues of an antibody which are responsible for antigen-binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196: 901-917 (1987)).

Each V region typically comprises three complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies, such as AP33, have antigen binding sites which are defined by $V_H$ and $V_L$ domains in cooperation. Certain antibodies, such as camel and shark antibodies, lack light chains and rely on binding sites formed by heavy chains only, Single domain engineered immunoglobulins can be prepared in which the binding sites are formed by heavy chains or light chains alone, in absence of cooperation between $V_H$ and $V_L$.

Throughout the present specification and claims, unless otherwise indicated, the numbering of the residues in the constant domains of an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody. The residues in the V region are numbered according to Kabat numbering unless sequential or other numbering system is specifically indicated.

The antibody or antibody fragment described herein may be isolated or purified to any degree. As used herein, "isolated" means that that antibody or antibody fragment has been removed from its natural environment. In some embodiments, contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Purified" means that the antibody or antibody fragment has been increased in purity, such that it exists in a form that is more pure than it exists in its natural environment and/or when initially synthesized and/or amplified under laboratory conditions. Purity is a relative term and does not necessarily mean absolute purity.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., *PNAS* (USA) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulates homeostasis of immunoglobulins.

WO00/42072 (Presta) describes antibody variants with improved or diminished binding to FcRs. The content of that patent publication is specifically incorporated herein by reference. See, also, Shields et al., *J. Biol. Chem.* 9(2): 6591-6604 (2001).

For binding affinity to FcRn, in one embodiment, the EC50 or apparent Kd (at pH 6.0) of the antibody is ≤900 nM, more preferably ≤90 nM. For increased binding affinity to FcγRIII (F158; i.e., low-affinity isotype), in one embodiment the EC50 or apparent Kd≤10 nM, and for FcγRIII (VI 58; high-affinity) the EC50 or apparent Kd≤3 nM. Methods of measuring binding to FcRn are known (see, e.g., Ghetie 1997, Hinton 2004) as well as described below. Binding to human FcRn in vivo and serum half life of human FcRn high affinity binding polypeptides can be assayed, e.g., in transgenic mice or transfected human cell lines expressing human FcRn, or in primates administered with the Fc variant polypeptides. In certain embodiments, the humanized antibody described herein further comprises amino acid alterations in the IgG Fc and exhibits increased binding affinity for human FcRn over an antibody having wild-type IgG Fc, by at least 60 fold, at least 70 fold, at least 80 fold, more preferably at least 100 fold, preferably at least 125 fold, even more preferably at least 150 fold to about 170 fold.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551 and WO99/51642. The contents of those patent publications are specifically incorporated herein by reference. See, also, Idusogie et al., *J. Immunol.* 164: 4178-4184 (2000).

As used herein, reference to "about" a value Or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Humanized Antibodies

The present invention provides a humanized anti-HCV antibody based on AP33. Generally, the antibody will comprise at least three recognizable CDRs or hypervariable loops and at least three, preferably four, recognizable framework regions, and will retain the ability to bind HCV E2 protein. The antibody also comprises a light chain constant region and/or a heavy chain constant region, preferably both.

The term "humanized antibody" refers to an antibody that includes at least one humanized antibody chain (i.e., at least one humanized light or heavy chain—such as at least one humanized variable light or variable heavy chain).

The term "humanized antibody chain" (i.e., a "humanized immunoglobulin light chain" or "humanized immunoglobulin heavy chain") refers to an antibody chain (i.e., a light or heavy chain, respectively) having a variable region that includes a variable framework region (substantially) from an acceptor human antibody and complementarity determining regions (CDRs) (e.g., at least one CDR, preferably two CDRs, more preferably three CDRs) substantially from a non-human donor antibody (e.g., a mouse antibody), and optionally further includes constant regions (e.g. at least one constant region or portion thereof, in the case of a light chain, and preferably three constant regions in the case of a heavy chain) of human origin. In addition, one or more residues of the acceptor framework may be mutated to match the residues present in the donor framework, to increase binding affinity.

The term "humanized variable region" (e.g. "humanized light chain variable region" or "humanized heavy chain variable region") refers to a variable region that includes a variable framework region substantially from a human antibody and complementarity determining regions (CDRs) substantially from a non-human antibody.

The non-human donor antibody is or is derived from the monoclonal antibody designated as AP33. The hybridoma secreting the AP33 monoclonal antibody is the subject of a deposit under the Budapest Treaty at the European Collection of Cell Cultures (ECACC, CAMR Porton Down, Salisbury, Wiltshire. SP4 9JG; date of deposit 27 Jan. 2006; accession number 05122101).

Humanized antibodies are less immunogenic than murine or chimeric antibodies. Chimeric antibodies are antibodies that include an entire non-human antibody variable region linked to a human constant region. Thus, in chimeric antibodies, the variable region is from the non-human donor, and the constant region is human. Chimeric antibodies and methods for making them are described in, for example, *Proc. Natl. Acad. Sci*, USA, 81: 6841-6855 (1984). Although they can be less immunogenic than a mouse monoclonal antibody, administrations of chimeric antibodies have been associated with human immune responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. One example is the replacement of a Fc region with that of a different isotype.

Humanized antibodies include CDR-grafted antibodies, which are antibodies that include the CDRs from a non-human "donor" antibody linked to the framework region from a human "acceptor" antibody. Generally, CDR-grafted antibodies include more human antibody sequences than chimeric antibodies because they include variable region (framework) sequences from human acceptor antibodies, rather than from the non-human donor. Thus, for example, a CDR-grafted humanized antibody of the invention can comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in *Nature*, 321: 522-525 (1986). Methods that can be used to produce humanized antibodies also are described in, for example, U.S. Pat. Nos. 5,721,367 and 6,180,377.

In some embodiments, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. In some embodiments, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. In some embodiments, the number of these amino acid substitutions in the FR are no more than 6 in the H chain, and in the L chain, no more than 3. In some embodiments, the humanized antibody also will comprise at least a portion of an immunoglobulin constant region (Fe), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

CDR-grafted antibodies may suffer a loss in binding activity, due to the disruption of the CDR environment. In order to partially correct this, CDR grafting may be supplemented with mutations to the framework regions, designed to restore antigen-binding activity. See, for example, EP0239400.

The humanized antibody may be a "veneered antibody" which is a humanized antibody that has been engineered to replace certain solvent-exposed amino acid residues so as to reduce their immunogenicity or enhance their function. Veneering may comprise identifying solvent-exposed residues in the non-human framework region and replacing at least one of them with the corresponding surface residues from a human framework region. Veneering can be accomplished by any suitable engineering technique.

The humanized antibody may be a heteroantibody. Heteroantibodies are two or more antibodies, or antibody binding fragments (Fab) linked together, each antibody or fragment having a different specificity.

Details on antibodies, humanized antibodies, human engineered antibodies, and methods for their preparation can be found in *Antibody Engineering*, Springer, New York, N.Y., 2001. Further details on humanization of antibodies is summarized in for example Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693,762, WO 90/07861, and U.S. Pat. No. 5,225,539.

In one embodiment, there is provided a variable light chain domain of a humanized AP33 antibody comprising the amino acid sequence set forth in any of in any of SEQ ID NO:6, SEQ ID NO:7, SEQ ID NO:19, or SEQ ID NO:20.

In another embodiment, there is provided a variable heavy chain domain of a humanized AP33 antibody comprising amino acid mutations at positions 30, 48, 67, 71 78 and 94 of SEQ ID No. 3.

The amino acid mutation may be obtained by substitution of one or more amino acid residue(s). In certain circumstances, a deletion or insertion may be tolerated. Mutation can be carried out using standard techniques such as for example site directed mutagenesis.

Suitably, the amino acid mutations are substitutions.

In another embodiment, the variable heavy chain domain according comprises the amino acid sequence as set forth in any of SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18.

There is also provided a humanized antibody or humanized antibody fragment comprising the variable light chain domain.

There is also provided a humanized antibody or humanized antibody fragment comprising the variable heavy chain domain.

There is also provided a humanized antibody or humanized antibody fragment comprising a light chain and a heavy chain, wherein the variable region of the light chain and the variable region of the heavy chain are as defined herein.

In some embodiments, the humanized antibody or fragment thereof comprises a variable heavy chain domain selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18 and a variable light chain domain selected from the group consisting of SEQ ID NO:6, SEQ ID NO:7, SEQ ID NO:19, and SEQ ID NO:20.

In some embodiments, the variable heavy chain domain is selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18 and the variable light chain domain is SEQ ID NO:6. In some embodiments, the variable heavy chain domain is selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18 and the variable light chain domain is SEQ ID NO:7. In some embodiments, the variable heavy chain domain is selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18 and the variable light chain domain is SEQ ID NO:19. In some embodiments, the variable heavy chain domain is SEQ ID NO:13 and the variable light chain domain is SEQ ID NO:19. In some embodiments, the variable heavy chain domain is selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18 and the variable light chain domain is SEQ ID NO:20.

In some embodiments, the humanized antibody or fragment thereof described herein binds to HCV. In some embodiments, the humanized antibody or fragment thereof is capable of binding to HCV E2 protein, soluble HCV E2 protein, or a heterodimer of HCV E1 protein and HCV E2 protein. In some embodiments, the humanized antibody or fragment thereof binds HCV E2 protein. In some embodiments, the HCV E2 protein is from one or more of the HCV genotypes selected from the group consisting of genotype 1 (e.g., genotype 1a and genotype 1b), genotype 2 (e.g., genotype 2a, genotype 2b, genotype 2c), genotype 3 (e.g., genotype 3a), genotype 4, genotype 5, and genotype 6. In some embodiments, the humanized antibody or fragment thereof inhibits the interaction of HCV E2 protein with CD81. In some embodiments, the humanized antibody or fragment thereof prevents and/or inhibits HCV entry into the cell. In some embodiments, the cell is a liver cell, e.g., hepatocyte.

In some embodiments, the humanized antibody or fragment thereof binds to soluble HCV E2 protein with a binding affinity of between 1-100 nM. In some embodiments, the binding affinity is between about any of 1-10 nM, 10-50 nM, or 50-100 nM. In some embodiments, the binding affinity is about 5 nM or about 50 nM. In some embodiments, the humanized antibody or fragment thereof binds to HCV E1/HCV E2 heterodimer with a binding affinity of between 1-100 nM. In some embodiments, the binding affinity is between about any of 1-10 nM, 10-50 nM, or 50-100 nM. In some embodiments, the binding affinity is about 5 nM or about 50 nM. In some embodiments, the binding affinity of the antibody can, for example, be determined by the Scatchard analysis described in Munson et al., *Anal. Biochem.*, 107:220 (1980).

In some embodiments, the humanized antibody or fragment thereof described herein inhibits HCV infection. In some embodiments, the humanized antibody or fragment thereof described herein inhibits HCV pseudoparticle (HCVpp) infection. Suitably, the humanized antibody as described herein is capable of inhibiting HCV pseudoparticle infection wherein the IC50 of infectious titers in the presence of said humanized antibody as judged by the HCVpp neutralization assay is: at least about 0.032 for genotype 1 (1a H77 20); at least about 1.6 for genotype 1 (1A20.8); at least about 0.9 for genotype 1 (1B5.23); at least about 3 for genotype 2 (2B1.1); at least about 0.41 for genotype 3a (F4/2-35); at least about 0.41 for genotype 4 (4.21.16); at least about 0.41 for genotype 6 (6.5.8); and at least 0.053 for genotype 5 (5.15.11). In some embodiments, the humanized antibody or fragment thereof as described herein is capable of inhibiting HCV pseudoparticle infection wherein the IC50 of infectious titers in the presence of said humanized antibody as judged by the HCVpp neutralization assay is any of less than about 0.41, less than about 0.137, or about 0.32 for genotype 1 (1a H77 20), about 1.6 for genotype 1 (1A20.8), about 0.9 for genotype 1 (1B5.23), about 3 for genotype 2 (2B1.1), about 0.64 for genotype 2 (2a JFH1), about 0.51 for genotype 2 (2A2.4), less than about 0.41 for genotype 3 (3a F4/2-35), less than about 0.41 for genotype 4 (4.21.16), about 0.053 for genotype 5 (5.15.11), or less than about 0.41 for genotype 6 (6.5.8).

In some embodiments, the humanized antibody as described herein is capable of inhibiting HCVpp infection wherein the $BC_{50}$ of infectious titers in the presence of said humanized antibody as judged by the HCVpp neutralization assay is: at least about 0.511 for genotype 1b or at least about 0.793 for genotype 2a.

Suitably, the IC90 of infectious titers in the presence of said humanized antibody as judged by the HCVpp neutralization assay is: at least about 0.6 for genotype 1 (1a H77 20); at least about 15 for genotype 1 (1A20.8); at least about 8.3 for genotype 1 (1B5.23); at least about 15 for genotype 2 (2B1.1); at least about 2.15 for genotype 3a (D4/2-35); at least about 0.92 for genotype 4 (4.21.16); at least about 1.8 for genotype 6 (6.5.8); and at least 0.82 for genotype 5 (5.15.11). In some embodiments, the humanized antibody or fragment thereof as described herein is capable of inhibiting HCV pseudoparticle infection wherein the IC90 of infectious titers in the presence of said humanized antibody as judged by the HCVpp neutralization assay is any of less than about 0.41, about 2.4, or about 0.6 for genotype 1 (1a H77 20), about 15 for genotype 1 (1A20.8), about 8.3 for genotype 1 (1B5.23), greater than about 15 for genotype 2 (2B1.1), about 7 for genotype 2 (2a JFH1), about 0.51 for genotype 2 (2A2.4), less than about 0.41 for genotype 3 (3a F4/2-35), less than about 6 for genotype 4 (4.21.16), about 0.82 for genotype 5 (5.15.11), or less than about 1.8 for genotype 6 (6.5.8).

In some embodiments, the humanized antibody or fragment thereof described herein inhibit recombinant cell culture-derived HCV (HCVcc) infection. In some embodiments, the humanized antibody as described herein is capable of inhibiting HCVcc infection wherein the $EC_{50}$ of infectious titers in the presence of said humanized antibody as judged by the HCVpp neutralization assay is: at least about 0.72 for genotype 1b or at least about 1.7 for genotype 2a.

In some embodiments, the humanized antibody or fragment thereof exhibits one or more of the above characteristics.

Antibody Engineering

Several techniques for engineering antibodies are known in the art. Generally, antibodies are rendered less immunogenic by transferring CDRs from a donor (non-human) antibody to an acceptor (human) antibody framework; this procedure is known as CDR grafting, or humanization. A disadvantage of this procedure is that, as a result of differences between donor and acceptor frameworks, binding activity may be impaired or lost. Moreover, a certain amount of immunogenicity may be retained by the CDRs themselves. Various complementary and alternative techniques, including veneering, resurfacing, SDR transfer and deimmunization have been proposed to address these problems.

In some embodiments, a humanized antibody described herein has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321: 522-525 (1986); Reichmann et al., *Nature,* 332:323-327 (1988); Verhoeyen et al., *Science,* 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.,* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody humanization has been described in, for example, EP460167, EP682040, U.S. Pat. No. 5,530,101, U.S. Pat. No. 5,585,089, U.S. Pat. No. 5,693,761, U.S. Pat. No. 5,693,762, U.S. Pat. No. 5,766,886, U.S. Pat. No. 5,821,337, U.S. Pat. No. 5,859,205, U.S. Pat. No. 5,886,152, U.S. Pat. No. 5,887,293, U.S. Pat. No. 5,955,358, U.S. Pat. No. 6,054,297 and U.S. Pat. No. 6,180,370. These methods all involve redesigning the variable region of an antibody so that the amino acid residues responsible for conferring the antigen binding specificity are integrated into the framework regions of a human antibody variable region.

In some cases the immunogenic portions of a non-human antibody are replaced by residues from a human antibody (e.g., U.S. Pat. No. 5,712,120). Alternatively the residues on the surface of the antibody variable domain can be replaced by residues from a human antibody to "resurface" the non-human variable domain (e.g., U.S. Pat. No. 5,639,641). Resurfacing was suggested by Padlan (1991, EP0519596) and is also termed "veneering". In this procedure the solvent-accessible residues of a first (equivalent of the donor—source of CDRs) antibody are replaced by residues from a second ("acceptor") antibody. Typically, the second antibody is a human antibody. The solvent inaccessible residues, CDRs, inter-domain contact residues, and residues immediately flanking the CDRs all remain as in the first antibody. This strategy is intended to mimic the surface of a second antibody while retaining all of the packing and interface interactions from the first antibody, which may aid in retention of full antigen binding activity. This should reduce the number of B cell epitopes (and may also reduce some T epitopes), leading to lower immunogenicity.

The solvent accessible residues are identified by inspection of high-resolution structures of antibodies. Other regions of the antibody which may be relevant to humanization: buried residues which make contact with the CDRs and are different between the murine and human antibodies (in such cases the rodent residue is used); the N-terminal regions which are positioned near the CDRs for both domains and may play a role in antigen binding; electrostatic interactions, which may also play a part even at long distance. The choice of surface residues to be substituted is determined by homology matching between the first antibody variable domains and those of available sequences (either individual or consensus sequences) from the second species.

U.S. Pat. No. 5,639,641 and EP0592106A1 describe alternative methods for resurfacing. Here solvent accessible residues that should be altered to those of a second species are identified using a similar procedure to that of Padlan, but analyzing a larger number of structures to obtain average accessibility for each location. Residues that have accessibility above a certain level are examined and are changed for that from an antibody from the species where the antibody is to be used. The choice of residue to be substituted can be from an antibody with overall homology or from the antibody with highest homology taking into consideration only the solvent accessible residues.

A humanization method described in WO93/17105 and U.S. Pat. No. 5,766,686 identifies low risk residues that can usually safely be altered to the human equivalent. These residues tend to be solvent accessible, Therefore, if only solvent accessible residue are altered, this process would resemble a resurfacing method.

Two further procedures have been described that have the net effect of providing a resurfaced or veneered antibody; see EPO438310A1 and EP0519596A1.

A further technique seeks to identify and remove T cell epitopes (called "detope") so that T help for an immune response is unavailable or reduced, leading to a minimal immune response to the introduced antibody (see U.S. Pat. No. 5,712,120; EP0699755A2). It is also possible that B cell epitopes are abolished in this process.

Antibody humanization techniques are also taught in "Antibody Engineering" (Eds. Kontermann and Dhubel), Chapter 40 p567-592 (O'Brien and Jones).

In some embodiments, the humanized antibody may be an antibody fragment, such as a Fab, which is optionally conjugated with one or more cytotoxic agent(s) in order to generate an immunoconjugate. Alternatively, the humanized antibody may be a full length antibody, such as an full length IgG1 antibody.

Antibody Fragments

Also contemplated within the scope of the present invention are antibody fragments—such as humanized antibody fragments—capable of binding to a selected target, and including Fv, ScFv, Fab', F(ab)$_2$, dAbs, engineered antibodies including chimeric, CDR-grafted, and humanized antibodies, and artificially selected antibodies produced using phage display or alternative techniques. Small fragments, such as dAbs, Fv, and ScFv, possess advantageous properties for diagnostic and therapeutic applications on account of their small size and consequent superior tissue distribution.

In some embodiments, the antibody fragments comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

In some embodiments, "Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

In some embodiments, fragments of the humanized antibodies described herein are provided. In some embodiments, the humanized antibody fragments are antigen binding fragments. In some embodiments, the antigen binding fragments of the humanized antibody bind to HCV. In some embodiments, the antigen binding fragments of the humanized antibody are capable of binding to HCV E2 protein, soluble HCV E2 protein, or a heterodimer of HCV E1 protein and HCV E2 protein. In some embodiments, the HCV E2 protein is from one or more of the HCV genotypes selected from the group consisting of genotype 1 (e.g., genotype 1a and genotype 1b), genotype 2 (e.g., genotype 2a, genotype 2b, genotype 2c), genotype 3 (e.g., genotype 3a), genotype 4, genotype 5, and genotype 6.

Typically, these fragments exhibit specific binding to antigen with an affinity of at least $10^7$, and more typically $10^8$ or $10^9$. In some embodiments, the humanized antibody fragment binds to soluble HCV E2 protein with a binding affinity of between 1-100 nM. In some embodiments, the binding affinity is between about any of 1-10 nM, 10-50 nM, or 50-100 nM. In some embodiments, the binding affinity is about 5 nM or about 50 nM. In some embodiments, the humanized antibody or fragment thereof binds to HCV E1/HCV E2 heterodimer with a binding affinity of between 1-100 nM. In some embodiments, the binding affinity is between about any of 1-10 nM, 10-50 nM, or 50-100 nM. In some embodiments, the binding affinity is about 5 nM or about 50 nM. In some embodiments, the binding affinity of the antibody can, for example, be determined by the Scatchard analysis described in Munson et al., *Anal. Biochem.*, 107:220 (1980).

In some embodiments, these fragments exhibit (substantially) the same HCV neutralizing activity as the AP33 monoclonal antibody or the humanized antibody described herein. Humanized antibody fragments include separate heavy chains, light chains, Fab, Fab', F(abl)$_2$, Fabc, and Fv. Fragments are produced by recombinant DNA techniques or by enzymatic or chemical separation of intact immunoglobulins.

In some embodiments, the humanized antibody fragments are functional fragments. "Functional fragments" of the humanized antibodies described herein such as functional fragments of the humanized AP33 antibody are those fragments that retain binding to HCV with substantially the same affinity as the intact full length molecule from which they are derived and show biological activity as measured by in vitro or in vivo assays such as those described herein. In some embodiments, the functional fragment neutralizes and/or inhibits HCV as shown by HCVpp and/or HCVcc neutralization assays. In some embodiments, the humanized antibody fragment prevents and/or inhibits the interaction of HCV E2 protein with CD81. In some embodiments, the humanized antibody fragment prevents and/or inhibits, HCV entry into the cell. In some embodiments, the cell is a liver cell, e.g., hepatocyte.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific. Antigen-binding antibody fragments can be produced by enzymatic or chemical separation of intact immunoglobulins Fragments can also be produced by recombinant DNA techniques (e.g., King et al, 1992 *Biochem. J.* 281, 317-323; Carter et al, 1992 *Biotechnology* 10, 163-167). Segments of nucleic acids encoding selected fragments are produced by digestion of full-length coding sequences with relevant restriction enzymes, or by de novo synthesis.

For example, a F(ab')$_2$ fragment can be obtained from an IgG molecule by proteolytic digestion with pepsin at pH 3.0-3.5 using standard methods such as those described in Harlow & Lane (1988 "Antibodies, A Laboratory Manual", Cold Spring Harbor Laboratory, NY).

Fab fragments may be obtained from F(ab')$_2$ fragments by limited reduction, or from whole antibody by digestion with papain in the presence of reducing agents.

The humanized antibodies may be characterized in a number of ways which will be apparent to those skilled in the art. These include physical measurements of their concentration by techniques such as ELISA, and of the antibody purity by SDS-PAGE. In addition the efficacy of the polypeptides can be determined by detecting the binding of the molecule to HCV E2 glycoprotein in solution or in a solid phase system such as ELISA, surface plasmon resonance (e.g., BIAcore) or immunofluorescence assays. More especially, the neutralizing capability of the polypeptide can be tested against HCV samples representative of the six known genotypes in a HCV pp-neutralizing assay as described herein, such as HCVpp and HCVcc neutralization assays.

Bispecific Antibodies

Bispecific antibodies are antibodies that have binding specificities for at least two different epitopes. Exemplary bispecific antibodies may bind to two different epitopes of the HCV. Other such antibodies may combine a HCV binding site with a binding site for another protein. Bispecific antibodies may also be used to localize cytotoxic agents to cells. These antibodies possess a HCV-binding arm and an arm which binds the cytotoxic agent (e.g., saporin, anti-interferon-a, *vinca* alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-Fc$_7$RIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a *facile* way of separation. This approach is disclosed in WO 94/04690. For further details of generating bispecific antibodies see, for example, Suresh et al., *Methods in Enzymology*, 121:210(1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')₂ fragments. These fragments are reduced in the presence of the dithiol complexing agent, sodium arsenite, to stabilize vicinal dithiols and prevent inter-molecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')₂ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl*, Acad. See. USA, 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the HCV binding antibodies described herein are contemplated. For example, it may be desirable to improve the binding affinity and/or other biological properties of the antibody. Amino acid sequence variants of the anti-HCV antibody such as humanized AP33 antibodies are prepared by introducing appropriate nucleotide changes into the anti-HCV antibody nucleic acid, or by peptide synthesis. Such modifications include, for example, deletions from, and/or insertions into and/or substitutions of, residues within the amino acid sequences of the anti-HCV antibody. Any combination of deletion, insertion, and substitution is made to arrive at the final construct, provided that the final construct possesses the desired characteristics. The amino acid changes also may alter post-translational processes of the anti-HCV antibody, such as changing the number or position of glycosylation sites.

A useful method for identification of certain residues or regions of the anti-HCV antibody that are preferred locations for mutagenesis is called "alanine scanning mutagenesis" as described by Cunningham and Wells in *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with HCV antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-HCV antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-HCV antibody with an N-terminal methionyl residue or the antibody fused to a cytotoxic polypeptide. Other insertional variants of the anti-HCV antibody molecule include the fusion to the N- or C-terminus of the anti-HCV antibody to an enzyme (e.g. for ADEPT) or a polypeptide which increases the serum half-life of the antibody.

Another type of variant is an amino acid substitution variant. These variants have at least one amino acid residue in the anti-HCV antibody molecule replaced by a different residue. The sites of greatest interest for substitutional mutagenesis include the hypervariable regions, but FR alterations are also contemplated. Conservative substitutions are shown in the Table below under the heading of "preferred substitutions". If such substitutions result in a change in biological activity, then more substantial changes, denominated "exemplary substitutions" in the Table, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry*, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues may be divided into groups based on common side-chain properties:

(1) hydrophobic: Norleucine, Met, Ala, Val, Leu, Ile;

(2) neutral hydrophilic. Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

Any cysteine residue not involved in maintaining the proper conformation of the anti-HCV antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and HCV. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. The humanized antibodies or fragments thereof may comprise non-amino acid moieties. For example, the humanized antibodies or fragments thereof may be glycosylated. Such glycosylation may occur naturally during expression of the humanized antibodies or fragments thereof in the host cell or host organism, or may be a deliberate modification arising from human intervention. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-HCV antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-HCV antibody.

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. J., *Immunol.* 148: 2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement mediated lysis and ADCC capabilities. See Stevenson et al., *Anti-Cancer Drug Design* 3:219-230 (1989).

For increasing serum half the serum half life of the antibody, amino acid alterations can be made in the antibody as described in US 2006/0067930.

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

Additionally or alternatively the humanized antibodies or fragments thereof may be subjected to other chemical modification. One such desirable modification is addition of one or more polyethylene glycol (PEG) moieties. Pegylation has been shown to increase significantly the half-life of various antibody fragments in vivo (Chapman 2002 *Adv. Drug Delivery Rev.* 54, 531-545). However, random Pegylation of antibody fragments can have highly detrimental effects on the binding affinity of the fragment for the antigen. In order to avoid this it is desirable that Pegylation is restricted to specific, targeted residues of the humanized antibodies or fragments thereof (see Knight et al, 2004 *Platelets* 15, 409-418 and Chapman, supra).

Screening for Antibodies with Desired Properties

Antibodies with certain biological characteristics may be selected as described in the Experimental Examples.

To screen for antibodies which bind to an epitope on the HCV E2 protein bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody binds the same site or epitope as an anti-HCV E2 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of HCV E2 protein can be used in competition assays with the test antibodies or with a test antibody and an antibody with a characterized or known epitope.

In some embodiments, antibodies can also be screen for their ability to neutralize an HCV infection. In some embodiments, neutralization of an HCV infection is based on a HCV pseudotyped particles (HCVpp) neutralization assay as described herein. HCVpp consist of unmodified HCV envelop glycoproteins assembled onto retroviral or lentiviral core particles. HCVpp infect hepatoma cell lines and hepatocytes in an HCV envelop protein-dependent matter. The presence of a marker gene packaged within the HCVpp allows fast and reliable determination of antibody-mediated neutralization. In some embodiments, neutralization of an HCV infection is based on a recombinant cell culture-derived HCV (HCVcc) neutralization assay infecting human hepatoma cell lines as described herein.

II. Polynucleotides

The present invention also provides polynucleotide(s). "Polynucleotide" or "nucleic acid" as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer.

For example, the polynucleotide may encode an entire immunoglobulin molecule chain, such as a light chain or a heavy chain. A complete heavy chain includes not only a heavy chain variable region ($V_H$) but also a heavy chain constant region ($C_H$), which typically will comprise three constant domains: $C_H1$, $C_H2$ and $C_H3$; and a "hinge" region. In some situations, the presence of a constant region is desirable. For example, where the antibody is desired to kill an HCV-infected cell, the presence of a complete constant region is desirable to activate complement. However, in other situations the presence of a complete constant region may be undesirable, The polynucleotide may encode a variable light chain and/or a variable heavy chain.

Other polypeptides which may be encoded by the polynucleotide include antigen-binding antibody fragments such as single domain antibodies ("dAbs"), Fv, scFv, Fab' and F(ab')$_2$ and "minibodies". Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above.

Whilst the encoded polypeptide will typically have CDR sequences identical or substantially identical to those of AP33, the framework regions will differ from those of AP33, being of human origin. The polynucleotide of the invention will thus preferably encode a polypeptide having a heavy and/or light chain variable region as described herein relative to the heavy and/or light chain (as appropriate) of AP33. If the encoded polypeptide comprises a partial or complete heavy and/or light chain constant region, this too is advantageously of human origin.

Preferably at least one of the framework regions of the encoded polypeptide, and most preferably each of the framework regions, will comprise amino acid substitutions relative to the human acceptor so as to become more similar to those of AP33, so as to increase the binding activity of the humanized antibody.

Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen or fifteen amino acid substitutions relative to the acceptor framework regions. Advantageously, the mutations are backmutations to match the residues present at the equivalent positions in the murine AP33 framework. Preferably, six backmutations are made in the heavy chain and one in the light chain.

Suitably, the polynucleotide and/or the polypeptide of the invention may be isolated and/or purified. In some embodiments, the polynucleotide and/or polypeptide are an isolated polynucleotide and/or polypeptide. The term isolated is intended to indicate that the molecule is removed or separated from its normal or natural environment or has been produced in such a way that it is not present in its normal or natural environment. In some embodiments, the polynucleotide and/or polypeptide are a purified polynucleotide and/or polypeptide. The term purified is intended to indicate that at least some contaminating molecules or substances have been removed.

Suitably, the polynucleotide and/or polypeptide are substantially purified, such that the relevant polynucleotide and/or polypeptide constitutes the dominant (i.e., most abundant) polynucleotide or polypeptide present in a composition.

The invention therefore employs recombinant nucleic acids comprising an insert coding for a heavy chain variable domain and/or for a light chain variable domain as described herein. By definition such nucleic acids comprise coding single stranded nucleic acids, double stranded nucleic acids consisting of said coding nucleic acids and of complementary nucleic acids thereto, or these complementary (single stranded) nucleic acids themselves.

Modification(s) may also be made outside the heavy chain variable domain and/or of the light chain variable domain of the AP33 antibody. Such a mutant nucleic acid may be a silent mutant wherein one or more nucleotides are replaced by other nucleotides with the new codons coding for the same amino acid(s). Such a mutant sequence may be a degenerate sequence. Degenerate sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly yeast, bacterial or mammalian cells, to obtain an optimal expression of the heavy chain variable domain and/or the light chain variable domain.

Sequence Identity or Sequence Homology

The present invention encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the antibody.

In the present context, a homologous sequence is taken to include an amino acid sequence which may be at least 75, 85, or 90% identical, preferably at least 95 or 98% identical to the subject sequence. Typically, the homologues will comprise the same active sites etc. as the subject amino acid sequence. Although homology can also be considered in terms of similarity (i.e., amino acid residues having similar chemical properties/functions), in the context of the present invention it is preferred to express homology in terms of sequence identity.

In the present context, a homologous sequence is taken to include a nucleotide sequence which may be at least 75, 85, or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e., amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al., (1999) Short Protocols in Molecular Biology, 4th Ed—Chapter 18), BLAST 2 (see *FEMS Microbiol Lett* 174(2): 247-50 (1999); *FEMS Microbiol Lett* 177 (1): 187-8(1999)), FASTA (Altschul et al., *J. Mol. Biol.* 403-410 (1990)) and AlignX for example. At least BLAST, BLAST 2 and FASTA are available for offline and online searching (see Ausubel et al., (1999) pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M, *Gene* 73(1), 237-244 (1988)).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment. See Table 2.

TABLE 2

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence is determined over the whole sequence.

Hybridization

In a further aspect, there is provided a nucleic acid sequence that is capable of hybridizing (e.g. specifically hybridizing) to the nucleotide sequence(s) described herein.

The term "hybridization" as used herein shall include "the process by which a strand of nucleic acid joins with a complementary strand through base pairing". Hybridization conditions are based on the melting temperature (Tm) of the nucleic acid binding complex, as taught in Berger and Kimmel (1987, Guide to Molecular Cloning Techniques, *Methods in Enzymology*, 152, Academic Press, San Diego Calif.), and confer a defined "stringency" as explained below.

Maximum stringency typically occurs at about 5° C. below Tm; high stringency at about 5° C. to 10° C. below Tm;

intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related sequences.

Suitably, the nucleic acid sequence(s) that is capable of hybridizing to the nucleotide sequence(s) described herein is a sequence that is capable of hybridizing under stringent conditions (e.g., 50° C. and 0.2×SSC {1×SSC=0.15 M NaCl, 0.015 M Na$_3$citrate pH 7.0}) to the nucleotide sequences described herein.

Suitably, the nucleic acid sequence(s) that is capable of hybridizing under high stringent conditions (e.g., 65° C. and 0.1×SSC {1×SSC=0.15 M NaCl, 0.015 M Na$_3$citrate pH 7.0}) to the nucleotide sequences presented herein.

The present invention also relates to nucleotide sequences that are complementary to sequences that can hybridize to the nucleotide sequences of the present invention (including complementary sequences of those presented herein).

Also included within the scope of the present invention are nucleotide sequences that are capable of hybridizing to the nucleotide sequences presented herein under conditions of intermediate to maximal stringency.

III. Expression of Recombinant Antibodies

Also provided are isolated nucleic acids encoding the anti-HCV antibodies and fragments thereof described herein such as the humanized AP33 antibodies, vectors and host cells comprising the nucleic acid, and recombinant techniques for the production of the antibody. The antibodies described herein may be produced by recombinant expression.

Nucleic acids encoding light and heavy chain variable regions as described herein are optionally linked to constant regions, and inserted into an expression vector(s). The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences.

Suitably, the expression control sequences are eukaryotic promoter systems in vectors capable of transforming or transfecting eukaryotic host cells (e.g., COS cells—such as COS 7 cells—or CHO cells). Once the vector has been incorporated into the appropriate host, the host is maintained under conditions suitable for high level expression of the nucleotide sequences, and the collection and purification of the cross-reacting antibodies.

These expression vectors are typically replicable in the host organisms either as episomes or as an integral part of the host chromosomal DNA.

Selection Gene Component—

Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362). In some embodiments, selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the nucleic acid encoding anti-HCV antibodies described herein such as the humanized AP33 antibodies, such as DHFR, thymidine kinase, metallothionein-I and -III, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody described herein, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

Signal Sequence Component—

The anti-HCV antibodies described herein such as the humanized AP33 antibodies may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. A signal sequence can be substituted with a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the anti-HCV antibodies described herein such as the humanized AP33 antibodies.

Origin of Replication—

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Promoter Component—

Expression and cloning vectors usually contain a promoter that is recognized by the host organism and is operably linked to the nucleic acid encoding an antibody described herein such as a humanized AP33 antibody. Promoters suitable for use with prokaryotic hosts include the phoA promoter, β-lactamase and lactose promoter systems, alkaline phosphatase promoter, a tryptophan (tip) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-HCV antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

The transcription of an anti-HCV antibody described herein such as the humanized AP33 antibody from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human .beta.-interferon cDNA in mouse cells under the control of a thymidine kinase promoter from herpes simplex virus. Alternatively, the Rous Sarcoma Virus long terminal repeat can be used as the promoter.

Enhancer Element Component—

Transcription of a DNA encoding the anti-HCV antibody described herein such as the humanized AP33 antibody by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the HCV binding antibody-encoding sequence, but is preferably located at a site 5' from the promoter.

Transcription Termination Component—

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. One useful transcription termination component is the bovine growth hormone polyadenylation region. See WO94/11026 and the expression vector disclosed therein.

The vectors containing the polynucleotide sequences (e.g., the variable heavy and/or variable light chain encoding sequences and optional expression control sequences) can be transferred into a host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity is most preferred, for pharmaceutical uses.

Constructs

The invention further provides a nucleic acid construct comprising a polynucleotide as described herein.

Typically the construct will be an expression vector allowing expression, in a suitable host, of the polypeptide(s) encoded by the polynucleotide. The construct may comprise, for example, one or more of the following: a promoter active in the host; one or more regulatory sequences, such as enhancers; an origin of replication; and a marker, preferably a selectable marker. The host may be a eukaryotic or prokaryotic host, although eukaryotic (and especially mammalian) hosts may be preferred. The selection of suitable promoters will obviously depend to some extent on the host cell used, but may include promoters from human viruses such as HSV, SV40, RSV and the like. Numerous promoters are known to those skilled in the art.

The construct may comprise a polynucleotide which encodes a polypeptide comprising three light chain hypervariable loops or three heavy chain hypervariable loops. Alternatively the polynucleotide may encode a polypeptide comprising three heavy chain hypervariable loops and three light chain hypervariable loops joined by a suitably flexible linker of appropriate length. Another possibility is that a single construct may comprise a polynucleotide encoding two separate polypeptides—one comprising the light chain loops and one comprising the heavy chain loops. The separate polypeptides may be independently expressed or may form part of a single common operon.

The construct may comprise one or more regulatory features, such as an enhancer, an origin of replication, and one or more markers (selectable or otherwise). The construct may take the form of a plasmid, a yeast artificial chromosome, a yeast mini-chromosome, or be integrated into all or part of the genome of a virus, especially an attenuated virus or similar which is non-pathogenic for humans.

The construct may be conveniently formulated for safe administration to a mammalian, preferably human, subject. Typically, they will be provided in a plurality of aliquots, each aliquot containing sufficient construct for effective immunization of at least one normal adult human subject.

The construct may be provided in liquid or solid form, preferably as a freeze-dried powder which, typically, is rehydrated with a sterile aqueous liquid prior to use.

The construct may be formulated with an adjuvant or other component which has the effect of increasing the immune response of the subject (e.g., as measured by specific antibody titer) in response to administration of the construct.

Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *Escherichia coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

Vectors may be transformed into a suitable host cell as described below to provide for expression of a polypeptide encompassed in the present invention. Thus, in a further aspect the invention provides a process for preparing polypeptides for use in the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter.

Vectors may contain one or more selectable marker genes which are well known in the art.

Host Cells

The invention further provides a host cell—such as a host cell in vitro—comprising the polynucleotide or construct described herein. The host cell may be a bacterium, a yeast or other fungal cell, insect cell, a plant cell, or a mammalian cell, for example.

The invention also provides a transgenic multicellular host organism which has been genetically manipulated so as to produce a polypeptide in accordance with the invention. The organism may be, for example, a transgenic mammalian organism (e.g., a transgenic goat or mouse line).

*E. coli* is one prokaryotic host that may be of use. Other microbial hosts include bacilli, such as *Bacillus subtilis*, and other enterobacteriaceae, such as *Salmonella, Serratia*, and various *Pseudomonas* species. In these prokaryotic hosts, one can make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may be used for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the humanized antibodies or fragments thereof as described herein and in some instances are preferred (See Winnacker, From Genes to Clones, VCH Publishers, N.Y., N.Y. (1987). For some embodiments, eukaryotic cells (e.g., COST cells) may be preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas.

In some embodiments, the host cell is a vertebrate host cell. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR(CHO, Urlaub et al., *Proc. Natl. Acad. Sci. USA* 77:4216 (1980)) or CHO-DP-12 line; mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Alternatively, antibody-coding sequences can be incorporated into transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Alternatively, the antibodies described herein can be produced in transgenic plants (e.g., tobacco, maize, soybean and alfalfa). Improved 'plantibody' vectors (Hendy et al. (1999) *J. Immunol. Methods* 231:137-146) and purification strategies coupled with an increase in transformable crop species render such methods a practical and efficient means of producing recombinant immunoglobulins not only for human and animal therapy, but for industrial applications as well (e.g., catalytic antibodies). Moreover, plant produced antibodies have been shown to be safe and effective and avoid the use of animal-derived materials. Further, the differences in glycosylation patterns of plant and mammalian cell-produced antibodies have little or no effect on antigen binding or specificity. In addition, no evidence of toxicity or HAMA has been observed in patients receiving topical oral application of a plant-derived secretory dimeric IgA antibody (see Larrick et al. (1998) *Res. Immunol.* 149:603-608).

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

Suitable host cells for the expression of glycosylated anti-HCV antibodies such as a humanized AP33 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10: 163467 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a C.sub.H3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

IV. Antibody Conjugates

The antibody may be conjugated to a cytotoxic agent such as a toxin or a radioactive isotope. In certain embodiments, the toxin is calicheamicin, a maytansinoid, a dolastatin, auristatin E and analogs or derivatives thereof, are preferable.

Preferred drugs/toxins include DNA damaging agents, inhibitors of microtubule polymerization or depolymerization and antimetabolites. Preferred classes of cytotoxic agents include, for example, the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins and differentiation inducers. Particularly useful members of those classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, N-(5,5-diacetoxypentyl)doxorubicin, morpholino-doxorubicin, 1-(2-choroehthyl)-1,2-dimethanesulfonyl hydrazide, $N^8$-acetyl spermidine, aminopterin methopterin, esperamicin, mitomycin C, mitomycin A, actinomycin, bleomycin, carminomycin, aminopterin, tallysomycin, podophyllotoxin and podophyllotoxin derivatives such as etoposide or etoposide phosphate, vinblastine, vincristine, vindesine, taxol, taxotere, retinoic acid, butyric acid, camptothecin, calicheamicin, bryostatins, cephalostatins, ansamitocin, actosin, maytansinoids such as DM-1, maytansine, maytansinol, N-desmethyl-4,5-desepoxymaytansinol, C-19-dechloromaytansinol, C-20-hydroxymaytansinol, C-20-demethoxymaytansinol, C-9-SH maytansinol, C-14-alkoxymethylmaytansinol, C-14-hydroxy or acetyloxymethlmaytansinol, C-15-hydroxy/acetyloxymaytansinol, C-15-methoxymaytansinol, C-18-N-demethylmaytansinol and 4,5-deoxymaytansinol, auristatins such as auristatin E, M, PHE and PE; dolostatin such as dolostatin A, dolostatin B, dolostatin C, dolostatin D, dolostatin E (20-epi and 11-epi), dolostatin G, dolostatin H, dolostatin I, dolostatin 1, dolostatin 2, dolostatin 3, dolostatin 4, dolostatin 5, dolostatin 6, dolostatin 7, dolostatin 8, dolostatin 9, dolostatin 10, deo-dolostatin 10, dolostatin 11, dolostatin 12, dolostatin 13, dolostatin 14, dolostatin 15, dolostatin 16, dolostatin 17, and dolostatin 18; cephalostatins such as cephalostatin 1, cephalostatin 2, cephalostatin 3, cephalostatin 4, cephalostatin 5, cephalostatin 6, cephalostatin 7,25'-epi-cephalostatin 7,20-epi-cephalostatin 7, cephalostatin 8, cephalostatin 9, cephalostatin 10, cephalostatin 11, cephalostatin 12, cephalostatin 13, cephalostatin 14, cephalostatin 15, cephalostatin 16, cephalostatin 17, cephalostatin 18, and cephalostatin 19.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Set. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene.

There are many linking groups known in the art for making antibody-maytansinoid conjugates, including, for example, those disclosed in U.S. Pat. No. 5,208,020 or EP Patent 0 425 235 B1, and Chari et al. *Cancer Research* 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Another immunoconjugate of interest comprises an anti-HCV antibody such as a humanized APP-33 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I, \alpha_2^I, \alpha_3^I$, N-acetyl$\gamma_1^I$, PSAG and $\theta^1_1$ (Hinman et al. *Cancer Research* 53: 3336-3342 (1993), Lode et al. *Cancer Research* 58: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Radioactive Isotopes

For selective destruction of an HCV infected cell, the antibody may comprise a highly radioactive atom. A variety of radioactive isotopes are available for the production of radioconjugated anti-HCV antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $Tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99m}$ or $I^{123}$, $Re^{186}$ $Re^{188}$ and $In^{111}$ can be attached via a cysteine residue in the peptide. Yttrium-90 can be attached via a lysine residue. The IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. *Cancer Research* 52: 127-131 (1992); U.S. Pat. No. 5,208,020) may be used.

V. Pharmaceutical Compositions

Pharmaceutical compositions useful in the present invention may comprise a therapeutically effective amount of the humanized antibody or fragment thereof and a pharmaceutically acceptable carrier, diluent or excipient (including combinations thereof).

Pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in *Remington's Pharmaceutical Sciences*, Mack Publishing Co. (A. R. Gennaro edit. 1985). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The choice of pharmaceutical carrier, excipient or diluent may be selected with regard to the intended route of administration and standard pharmaceutical practice. Pharmaceutical compositions may comprise as—or in addition to—the carrier, excipient or diluent any suitable binder(s), lubricant(s), suspending agent(s), coating agent(s) or solubilizing agent(s).

Preservatives, stabilizers, dyes and even flavoring agents may be provided in pharmaceutical compositions. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, pharmaceutical compositions useful in the present invention may be formulated to be administered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be administered by a number of routes.

The humanized antibody or fragment thereof may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g., as a carrier, diluent or solubilizer. Alpha-, beta- and gamma-cyclodextrins are most commonly used and suitable examples are described in WO-A-91/11172, WO-A-94/02518 and WO-A-98/55148.

The pharmaceutical composition also can be incorporated, if desired, into liposomes, microspheres, or other polymer matrices. Liposomes, for example, which consist of phospholipids or other lipids, are nontoxic, physiologically acceptable and metabolizable carriers that are relatively simple to make and administer.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macro emulsions. Such techniques are disclosed in *Remington's Pharmaceutical Sciences* 16th edition, Osol, A. Ed. (1980).

Sustained-release preparations may be prepared. Suitable examples of sustained-release preparations include semi-permeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

The humanized antibody or fragment thereof may even be prepared in situ in the subject being treated. In this respect, nucleotide sequences encoding said humanized antibody or fragment thereof may be delivered by use of non-viral techniques (e.g., by use of liposomes) and/or viral techniques (e.g., by use of retroviral vectors) such that the said protein is expressed from said nucleotide sequence.

The pharmaceutical compositions may be used in any of the methods described herein.

The pharmaceutical composition may be used among those subjects (e.g., humans) susceptible to infection with HCV i.e. to prevent or reduce/decrease the onset of HCV infection.

The pharmaceutical composition may be used among those subjects (e.g., humans) already infected with HCV i.e. to treat HCV infection. Such treatment may facilitate clearance of the virus from those subjects who are acutely or chronically infected including infected patients undergoing liver transplantation.

Thus, in a further aspect the invention provides a method for the treatment and/or prevention of hepatitis C virus infection, comprising the use of the humanized antibody or the humanized antibody fragment or the pharmaceutical composition. Suitably, an effective amount of the humanized antibody or humanized antibody thereof or the pharmaceutical composition is administered to the subject. In some embodiments, the humanized antibody or humanized antibody fragment is administered in a therapeutic effective amount to effect beneficial clinical results, including, but not limited to ameliorating one or more symptoms of HCV infections or aspects of HCV infection. In some embodiments, the humanized antibody or humanized antibody fragment is administered in a therapeutic effective amount to reduce viral titer and/or viral load of HCV.

There is also provided a humanized antibody of a fragment thereof or the pharmaceutical composition for use in the treatment and/or prevention of hepatitis C virus infection in a subject.

There is also provided the use of a humanized antibody of a fragment thereof or the pharmaceutical composition in the manufacture of a composition for the treatment and/or prevention of hepatitis C virus infection in a subject.

The antibody/ies may be administered, for example, in the form of immune serum or may more preferably be a purified recombinant or monoclonal antibody. Methods of producing sera or monoclonal antibodies with the desired specificity are routine and well-known to those skilled in the art. One skilled in the art understands that the antibody/ies can be administered by various routes including, for example, injection, intubation, via a suppository, orally or topically, the latter of which can be passive, for example, by direct application of an ointment or powder containing the antibodies, or active, for example, using a nasal spray or inhalant. The antibodies can also be administered as a topical spray, if desirable, in which case one component of the composition is an appropriate propellant.

The humanized antibodies and fragments thereof described herein can be administered to a subject in accord with known methods, such as by intravenous administration, e.g., as a bolus or by continuous infusion over a period of time, by subcutaneous, intramuscular, intraperitoneal, intracerobrospinal, intra-articular, intrasynovial, intrathecal, or inhalation routes, generally by intravenous or subcutaneous administration.

Preferably the administered antibody/antibodies are substantially purified (e.g., preferably at least 95% homogeneity, more preferably at least 97% homogeneity, and most preferably at least 98% homogeneity, as judged by SDS-PAGE).

Suitably, a passive immunization regime may conveniently comprise administration of the humanized antibody of fragment thereof as described herein and/or administration of antibody in combination with other antiviral therapeutic compounds. Recently such passive immunization techniques have been used safely to treat HIV infection (Armbruster et al, *J. Antimicrob. Chemother.* 54, 915-920 (2004); Stiegler & Katinger, *J. Antimicrob. Chemother.* 51, 757-759 (2003)).

The active or passive immunization methods of the invention should allow for the protection or treatment of individuals against infection with viruses of any of genotypes 1-6 of HCV, except for very occasional mutant isolates (such as that exemplified by UKN5.14.4, below) which contain several amino acid differences to that of the consensus peptide epitope defined above.

In some embodiments, the humanized antibody or fragment thereof can be administered in combination with a second therapeutic agent. In some embodiments, the second therapeutic agent is an antiviral therapeutic agent. In some embodiments, the humanized antibody or fragment thereof is administered in combination with, sequential to, concurrently with, consecutively with, rotationally with, or intermittently with a second therapeutic agent. In some embodiment, the administration of the combination of a humanized antibody or fragment thereof and a second therapeutic agent ameliorates one or more symptom of HCV, reduces and/or suppresses viral titer and/or viral load, and/or prevents HCV more than treatment with the humanized antibody or fragment thereof or second therapeutic agent alone.

VI. Diagnosis

In yet a further aspect, there is provided a diagnostic test apparatus and method for determining or detecting the presence of HCV in a sample. The apparatus may comprise, as a reagent, one or more humanized antibodies or fragments thereof as described herein. The antibody/ies may, for example, be immobilized on a solid support (e.g., on a microtiter assay plate, or on a particulate support) and serve to "capture" HCV particles from a sample (e.g., a blood or serum sample or other clinical specimen—such as a liver biopsy). The captured virus particles may then be detected by, for example, adding a further, labeled, reagent which binds to the captured virus particles. Conveniently, the assay may take the form of an ELISA, especially a sandwich-type ELISA, but any other assay format could in principle be adopted (e.g., radioimmunoassay, Western blot) including immunochromatographic or dipstick-type assays.

For diagnostic purposes, the humanized antibodies or fragments thereof as described herein may either be labeled or unlabelled. Unlabelled antibodies can be used in combination with other labeled antibodies (second antibodies). Alternatively, the antibodies can be directly labeled. A wide variety of labels may be employed—such as radionuclides, fluors, enzymes, enzyme substrates, enzyme cofactors, enzyme inhibitors, ligands (particularly haptens), etc. Numerous types of immunoassays are available and are well known to those skilled in the art.

Since the humanized antibodies or fragments thereof as described herein can bind to HCV from any of genotypes 1-6, the assay apparatus and corresponding method should be capable of detecting in a sample HCV representative from any of these genotypes.

In some embodiments, the sample is compared to a control sample. In some embodiments, the control sample is from an individual known to be infected with HCV. In some embodiments, the individual is known to infected with one or more HCV genotypes selected from the group consisting of genotype 1 (e.g., genotype 1a and genotype 1b), genotype 2 (e.g., genotype 2a, genotype 2b, genotype 2c), genotype 3 (e.g., genotype 3a), genotype 4, genotype 5, and genotype 6. In some embodiments, the control sample is from an individual known not to be infected with HCV.

In some embodiments, any of the methods of treatment described are based on the determination or detection of HCV in a sample by any of the humanized antibodies or fragments thereof described herein. As used herein, "based upon" includes (1) assessing, determining, or measuring the subject's characteristics as described herein (and preferably selecting a subject suitable for receiving treatment); and (2) administering the treatment(s) as described herein.

In some embodiments a method is provided for identifying an individual suitable or not suitable (unsuitable) for treatment with the humanized antibody or fragment thereof
Agent In a further aspect, there is provided an assay method for identifying an agent that improves or enhances the efficacy of the neutralizing activity of the humanized antibody or fragment thereof as described herein.

Provided herein is an assay method for identifying an agent that improves or enhances the efficacy of the neutralizing activity of the humanized antibody or fragment thereof against hepatitis C virus, comprising the steps of: (a) contacting said humanized antibody or antigen binding fragment thereof with an agent to be tested; and (b) determining whether the agent improves or enhances the efficacy of the humanized antibody or antigen binding fragment thereof in neutralizing the infectivity of hepatitis C virus.

In some embodiments, the ability of the agent to improve or enhance the efficacy of the neutralizing activity of the humanized antibody or fragment thereof against hepatitis C virus is compared to a control. In some embodiments, the control is the humanized antibody or fragment thereof in the absence of the agent. In some embodiments, the control is humanized antibody or fragment thereof with a placebo, e.g., water, saline, sugar water, etc.

As used herein, the term "agent" may be a single entity or it may be a combination of entities.

The agent may be an organic compound or other chemical. The agent may be a compound, which is obtainable from or produced by any suitable source, whether natural or artificial. The agent may be an amino acid molecule, a polypeptide, or a chemical derivative thereof, or a combination thereof. The agent may even be a polynucleotide molecule—which may be a sense or an anti-sense molecule. The agent may even be an antibody.

The agent may be designed or obtained from a library of compounds, which may comprise peptides, as well as other compounds, such as small organic molecules.

By way of example, the agent may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetics, a derivatized agent, a peptide cleaved from a whole protein, or a peptides synthesized synthetically (such as, by way of example, either using a peptide synthesizer or by recombinant techniques or combinations thereof, a recombinant agent, an antibody, a natural or a non-natural agent, a fusion protein or equivalent thereof and mutants, derivatives or combinations thereof.

Typically, the agent will be an organic compound. Typically the organic compounds will comprise two or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the agent comprises at least one cyclic group. The cyclic group may be a polycyclic group, such as a non-fused polycyclic group. For some applications, the agent comprises at least the one of said cyclic groups linked to another hydrocarbyl group.

The agent may contain halo groups. Here, "halo" means fluoro, chloro, bromo or iodo.

The agent may contain one or more of alkyl, alkoxy, alkenyl, alkylene and alkenylene groups—which may be unbranched- or branched-chain.

VII. Therapeutic Uses

The humanized anti-HCV antibodies and fragments thereof or a pharmaceutical composition comprising same are useful in reducing, eliminating, or inhibiting HCV infection and can be used for treating any pathological condition that is characterized, at least in part, by HCV infection. The humanized antibodies and fragments thereof and/or the pharmaceutical composition can be used for treating a HCV infection. The humanized antibodies and fragments thereof and/or the pharmaceutical composition can also be used in methods for preventing a HCV infection, The term "hepatitis C virus" or "HCV" is well understood in the art and refers to a virus which is a member of the genus *Hepacivirus* of the family flaviviridae. HCV is a lipid enveloped virus having a diameter of approximately 55-65 nm in diameter with a positive strand RNA genome. The hepatitis C virus species is classified into six genotypes (1-6) with several subtypes within each genotype. In some embodiments, the subject is infected with one or more HCV genotypes selected from the group consisting of genotype 1 (e.g., genotype 1a and genotype 1b), genotype 2 (e.g., genotype 2a, genotype 2b, genotype 2c), genotype 3 (e.g., genotype 3a), genotype 4, genotype 5, and genotype 6. In North America, genotype 1a predominates followed by 1b, 2a, 2b, and 3a. In Europe, genotype 1b is predominant followed by 2a, 2b, 2c, and 3a. Genotypes 4 and 5 are found almost exclusively in Africa.

Provided herein are methods for treating a hepatitis C virus infection in a human, comprising administering an effective amount of the humanized antibody fragment thereof described herein. In some embodiments, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, and/or increasing the quality of life.

In some embodiments, the humanized anti-HCV antibodies and fragments thereof described herein or a pharmaceutical composition comprising same are useful in methods of treating an acute HCV infection. In some embodiments, treating an acute HCV infection includes reducing, eliminating, or inhibiting an acute HCV infection. The term "acute hepatitis C virus infection" or "acute HCV infection," as used herein, refers to the first 6 months after infection with HCV. In some embodiments, a subject with an acute HCV infection will not develop any symptoms (i.e., free of acute HCV infection symptoms). Between 60% to 70% of subjects with acute HCV infection develop no symptoms during the acute phase. In some embodiments, an subject with acute HCV infection will develop symptoms. In some embodiments, the methods of treatment described herein ameliorate (e.g., reduce incidence of, reduce duration of, reduce or lessen severity of) of one or more symptoms of acute HCV infection. In the minority of patients who experience acute phase symptoms, the symptoms are generally mild and nonspecific, and rarely lead to a specific diagnosis of hepatitis C. Symptoms of acute hepatitis C infection include decreased appetite, fatigue, abdominal pain, jaundice, itching, and flu-like symptoms. In some embodiments, the subject with acute HCV infection is infected with HCV of the genotype 1. Treatment during the acute HCV injection of genotype 1 has a greater than 90% success rate with half the treatment time required for chronic infections.

In some embodiments, the humanized anti-HCV antibodies and fragments thereof described herein or a pharmaceutical composition comprising same are useful in methods of treating a chronic HCV infection. In some embodiments, treating an chronic HCV infection includes reducing, eliminating, or inhibiting a chronic HCV infection. The term "chronic hepatitis C virus infection" or "chronic HCV infection," as used herein, refers to as infection with HCV which persisting for more than six months. In some embodiments, the methods of treatment described herein ameliorate (e.g., reduce incidence of, reduce duration of, reduce or lessen severity of) of one or more symptoms of chronic HCV infection. Symptoms of chronic HCV infection include fatigue, marked weight loss, flu-like symptoms, muscle pain, joint pain, intermittent low-grade fevers, itching, sleep disturbances, abdominal pain (especially in the right upper quadrant), appetite changes, nausea, diarrhea, dyspepsia, cognitive changes, depression, headaches, and mood swings. Once chronic HCV has progressed to cirrhosis, signs and symptoms may appear that are generally caused by either decreased liver function or increased pressure in the liver circulation, a condition known as portal hypertension. Possible signs and symptoms of liver cirrhosis include ascites, bruising and bleeding tendency, bone pain, varices (especially in the stomach and esophagus), fatty stools (steatorrhea), jaundice, and a syndrome of cognitive impairment known as hepatic encephalopathy. In some embodiments, the chronic HCV infection may result in hepatocellular carcinoma (HCC). Chronic HCV infection can be further divided into two types (either or both of which are included in the methods of treatment provided herein) chronic active HCV infection and chronic persistent HCV infection. Chronic active HCV infection is HCV which is cause active damage to the liver. Chronic persistent HCV infection is a chronic HCV infection which is not currently causing damage to the liver, although pre-existing liver damage may be present.

In some embodiments, the humanized antibodies or fragments thereof may be administered to the subject infected with HCV prior to, concurrent with, or subsequent to a liver transplant.

In some embodiments of any of the methods of treating, the humanized anti-HCV antibodies and fragments thereof described herein or a pharmaceutical composition comprising same are useful in methods of treatment including suppressing one or more aspects of a HCV infection. In some embodiments, the HCV infection is a chronic HCV infection. In some embodiments, the HCV infection is an acute HCV infection. In some embodiments, the methods described herein suppress a HCV-associated laboratory finding (e.g., ALAT, AST, and GGTP levels in blood), viral replication, viral titer, viral load, or viremia.

In some embodiments, the methods described herein suppress or reduce viral titer. "Viral titer" is known in the art and indicates the amount of virus in a given biological sample. In some embodiments, the methods described herein suppress or reduce viremia. "Viremia" is known in the art as the presence of virus in the bloodstream and/or viral titer in a blood or serum sample. In some embodiments, the methods described herein suppress or reduce viral load. "Viral load" refers to the amount of hepatitis C virus in a person's blood. The results of a hepatitis C viral load test (known as a viral RNA test or HCV RNA test) are usually expressed as International Units/mL (IU/mL) or RNA copies/mL. A subject with a hepatitis C viral load of 1 million IU/mL or more is considered to have a high viral load. Amount of virus (e.g., viral titer or viral load) are indicated by various measurements, including, but not limited to amount of viral nucleic acid, the presence of viral particles, replicating units (RU), plaque forming units (PFU). Generally, for fluid samples such as blood and urine, amount of virus is determined per unit fluid, such as milliliters. For solid samples, such as tissue samples, amount of virus is determined per weight unit, such as grams. Methods for determining amount of virus are known in the art and are also described herein.

In some embodiments, the subject treated with the humanized antibodies and fragments thereof described herein and/or the pharmaceutical composition is at risk for rapid HCV infection progression. Factors that have been reported to influence the rate of HCV disease progression include age (increasing age associated with more rapid progression), gender (males have more rapid disease progression than females), alcohol consumption (associated with an increased rate of disease progression), HIV co-infection (associated with a markedly increased rate of disease progression), and fatty liver (the presence of fat in liver cells has been associated with an increased rate of disease progression).

In some embodiments of any of the methods, the subject produces anti-HCV antibodies. In some embodiments, the anti-HCV antibodies are detectable, e.g., the anti-HCV antibodies are detectable by ELISA. In some embodiments, the anti-HCV antibodies produced by the subject are neutralizing antibodies. In some embodiments, the anti-HCV antibodies produced by the subject are non-neutralizing antibodies.

The humanized antibodies and fragments thereof described herein and/or the pharmaceutical composition can also be used in methods for preventing a HCV infection. In some embodiments, the humanized antibodies and fragments thereof and/or the pharmaceutical composition can be used in methods for preventing a HCV infection in a subject susceptible to infection with HCV. In some embodiments, the humanized antibodies and fragments thereof and/or the pharmaceutical composition can also be used in methods for preventing a HCV infection in a subject exposed to or potentially exposed to HCV. "Exposure" to HCV denotes an encounter or potential encounter with HCV which could result in an HCV infection. Generally, an exposed subject is a subject that has been exposed to HCV by a route by which HCV can be transmitted. In some embodiments, the subject has been exposed to or potentially exposed to blood of a subject with an HCV infection or blood from a subject which may or may not be infected with HCV (i.e., HCV infection status of the blood exposure is unknown). HCV is often transmitted by blood-to-blood contact. In some embodiments, the subject has been exposed to or potentially exposed to HCV by, but not limited to, use of blood products (e.g., a blood transfusion), "needle stick" accidents, sharing drug needles, snorting drugs, a sexual partner, iatrogenic medical or dental exposure, needles used in body piercings and tattoos, or a child whose mother has an HCV infection. In some embodiments of the methods of prevention, the humanized antibodies and fragments thereof described herein will be administered at the time or within any of about one day, one week, or one month of the exposure or potential exposure to HCV.

In some embodiments of any of the methods described herein, the subject is a human or chimpanzee. In some embodiments, the subject is a human. HCV infects only human and chimpanzee.

In some embodiments of any of the methods described herein, the method comprises administering the humanized antibody or fragment thereof in combination with a second therapeutic agent. In some embodiments, the second therapeutic agent is an antiviral therapeutic agent. In some embodiments, the method comprises administering the humanized antibody or fragment thereof in combination with, sequential to, concurrently with, consecutively with, rotationally with, or intermittently with a second therapeutic agent. In some embodiment, the method comprising administering the combination of a humanized antibody or fragment thereof and a second therapeutic agent ameliorates one or more symptom of HCV, reduces and/or suppresses viral titer and/or viral load, and/or prevents HCV more than treatment with the humanized antibody or fragment thereof or second therapeutic agent alone.

In some embodiments of any of the methods, humanized antibody or fragment thereof comprises a variable heavy chain domain selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18 and a variable light chain domain selected from the group consisting of SEQ ID NO:6, SEQ ID NO:7, SEQ ID NO:19, and SEQ ID NO:20. In some embodiments, the fragment of the humanized antibody is selected from the group consisting of a Fab fragment, a Fab' fragment, a F(ab')$_2$ fragment, a scFv, a Fv, and a diabody. In some embodiments, the humanized antibody or fragment thereof binds to HCV. In some embodiments, the humanized antibody or fragment thereof is capable of binding to HCV E2 protein, soluble HCV E2 protein, or a heterodimer of HCV E1 protein and HCV E2 protein. In some embodiments, the humanized antibody or fragment thereof binds HCV E2 protein. In some embodiments, the HCV E2 protein is from one or more of the HCV genotypes selected from the group consisting of genotype 1 (e.g., genotype 1a and genotype 1b), genotype 2 (e.g., genotype 2a, genotype 2b, genotype 2c), genotype 3 (e.g., genotype 3a), genotype 4, genotype 5, and genotype 6. In some embodiments, the humanized antibody or fragment thereof inhibits the interaction of HCV E2 protein with CD81. In some embodiments, the humanized antibody or fragment thereof prevents and/or inhibits HCV entry into the cell. In some embodiments, the cell is a liver cell, e.g., hepatocyte.

VIIi. Monitoring the Course of Treatment

There is also provided methods of monitoring treatment in a patient suffering from or susceptible to HCV infection, i.e., for monitoring a course of treatment being administered to a patient. The methods can be used to monitor both therapeutic treatment on symptomatic patients and prophylactic treatment on asymptomatic patients. In particular, the methods are useful for monitoring passive immunization (e.g., measuring level of administered antibody).

Some methods involve determining a baseline value, for example, of the level or profile of HCV infection in a patient, before administering a dosage of agent, and comparing this with a value for the profile or level after treatment. Conveniently, the level or profile of HCV infection can de determined with the humanized antibody or fragment thereof as described herein. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

IX Clinical Trials

A single-dose phase I trial can be performed to determine the safety of the humanized antibody or fragment thereof or the pharmaceutical composition comprising same as described herein in subjects, preferably, humans. The humanized antibody or fragment thereof is administered in increasing dosages to different patients starting from about 0.01 the level of presumed efficacy, and increasing by a factor of three until a level of about 10 times the effective mouse dosage is reached.

A phase II trial can be further performed to determine therapeutic efficacy. Patients with HCV infection are selected. Other selection criteria are that patients are likely to survive the duration of the study and lack complicating issues such as use of concomitant medications that may interfere. Disease progression can be monitored using blood profiles of patients. Following baseline measurements, patients begin receiving treatment. They are randomized and treated with either the humanized antibody or fragment thereof or placebo in a blinded fashion. Patients are monitored at least every six months. Efficacy is determined by a significant reduction in progression of HCV infection in the treatment group relative to a placebo group.

X. Kits and Articles of Manufacture

Kits can also be supplied for use with the antibodies in the protection against or detection of a cellular activity or for the presence of a selected antigen. Thus, the humanized antibody/ies or fragments thereof may be provided, usually in a lyophilized form in a container, either alone or in conjunction with additional antibodies specific for the desired cell type.

The antibodies, which may be conjugated to a label or toxin, or unconjugated, are included in the kits with buffers, such as Tris, phosphate, carbonate, etc., stabilizers, biocides, inert proteins, e.g., serum albumin, or the like. Generally, these materials will be present in less than about 5% wt. based on the amount of antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition.

The invention also provides diagnostic kits, for example, research, detection and/or diagnostic kits. Such kits typically contain the humanized antibody or fragment thereof as described herein. Suitably, the antibody is labeled or a secondary labeling reagent is included in the kit. Preferably, the kit is labeled with instructions for performing the intended application, for example, for performing an in vivo imaging assay.

In some embodiments, the kit contains a package insert. Package insert refers to instructions customarily included in commercial packages of therapeutic products, which contain information about the indications, usage, dosage, administration, contraindications and/or warnings concerning the use of such therapeutic products. In one embodiment, the package insert indicates that the composition is used for treating a HCV infection. In some embodiments, the package insert provides instructions for using the humanized antibodies or fragments thereof in any of the methods of treatment, prevention, or diagnosis described herein.

Provided herein are articles of manufacture which comprise a humanized antibody or fragment thereof described herein. In some embodiments, the articles of manufacture comprise a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

XL General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

The invention will now be further described by way of Examples, which are meant to serve to assist one of ordinary skill in the art in carrying out the invention and are not intended in any way to limit the scope of the invention.

EXAMPLES

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation.

Example 1

Materials and Methods

Cloning of Humanized V genes

The heavy chain V regions (see Example 2) were cloned into pG1D200 via HindIII and ApaI restriction enzyme sites. Similarly, the light chain V regions were cloned into pKN100 via the HindIII and BamHI sites. pG1D200 vector were prepared for ligation by digesting 5 μg of DNA with 20 units of HindIII and ApaI in multicore (Promega) restriction digest buffer for 2 hrs at 37° C. Then 1 unit of shrimp alkaline phosphatase was added for 30 min at 37° C. and inactivated at 65° C. for 20 minutes. The vector preparation was then purified on a Qiaquick (Qiagen) column following manufacturer's instructions. The vector was eluted in 50 μl. Similarly pKN100 vector was prepared by digesting 5 μg of DNA with 20 units of HindIII and BamHI in buffer E (Promega) for 1 hour at 37° C. The DNA was treated with shrimp alkaline phosphatase and purified as described above. V region DNA including mutant V regions was supplied by GENART in the vectors pGA4 or pGA1. Insert DNAs (approx 4 ug) were digested as described above and the heavy and light chain fragments were purified from the vector by gel electrophoresis. The appropriate band was excised from the gel and purified on a Qiaquick column (Qiagen) and eluted in 50 μl following manufacturer's instructions. Ligations were carried out by mixing 1 μl of vector with either 1 or 3 μl of insert DNA in 1× ligase buffer (Promega) and 10 units of ligase (Promega). The reaction was incubated at 14° C. overnight and 2.5 μl were used to transform 50 μl of DH5a competent cells (Invitrogen).

Site directed Mutagenesis

Site directed mutagenesis was carried out by outsourcing the mutagenesis to GENEART AG except for the chimeric heavy chain mutants AP33 Y47W and Y47F. The chimeric heavy chain mutagenesis was carried out using the following oligonucleotides:

```
AP33_Y47F_F:  AATAAACTTGAGTTCATGGGATACATAAGT      (SEQ ID NO: 41)

AP33_Y47F_R:  ACTTATGTATCCCATGAACTCAAGTTTATT      (SEQ ID NO: 42)

AP33_Y47W_F:  GAATAAACTTGAGTGGATGGGATACATAAG      (SEQ ID NO: 43)

AP33_Y47W_R:  CTTATGTATCCCATCCACTCAAGTTTATTC.     (SEQ ID NO: 44)
```

The mutagenesis PCR reaction used oligonucleotides at a final concentration of 0.5 micro Molar, combined with 20 ng of VH.pG1D200 (Chimeric heavy chain construct) and 1× Fusion master mix (NEB). PCR conditions were: 98° C. for 30 sec then 12 cycles of 98° C. for 10 sec, 55° C. for 15 sec, 72° C. for 2 min 15 sec. Once the PCR reaction was complete, 20 units of DpnI were added to each PCR reaction for 1 hour at 37° C. 2 μl of the PCR digest mixture was used to transform 50 μl of XL-1 blue competent cells (Stratagene).

The recombinant chimeric and humanized heavy chains RHA, RHbcdefgh (RHb-h) and humanized light chains RKA and RK2bc were cloned into the antibody expression vectors pG1D200 and pKN100 respectively. Plasmid DNA was prepared using the appropriate Qiagen plasmid purification kit.

Electroporation

Cos7 cells were grown and split 1:3 on the day before transfection. Log phase Cos7 cells were trypsinised and washed in PBS and resuspended at $10^7$ cells/ml in PBS and 700 μl of cells aliquoted into electroporation cuvettes (Bio-Rad). 5 μg each of heavy and light chain constructs were mixed with the cells and electroporated at 1.9 KV and 25 μF. Cells were left for 10 minutes at room temperature to recover and added to 8 ml of DMEM with Glutamax (Invitrogen)/10% FCS/Penicillin 500 U/ml/Streptomycin 500 μg/ml on 10 cm2 tissue culture plates. The supernatant was harvested after 3 days and antibody concentration was analyzed by ELISA.

IgG1 ELISA

Maxisorp plates were coated with 0.4 μg/ml goat anti-human IgG antibody and stored at 4° C. for no more than 1 month. Before use, plates were washed three times in PBS/0.02% Tween 20 (v/v) then blocked in PBS/0.02% Tween 20 (v/v)/0.2% (w/v) BSA. Plates were washed as before and sample supernatant added over a concentration range using doubling dilutions and incubated at 37° C. for 1 hr. Plates were washed as before and incubated with goat anti-human kappa light chain peroxidase conjugate (Sigma) at 1:5000 dilution. Plates were washed, as before, then 150 μL of K Blue One-Step substrate Neogen) was added. After 10 minutes the reaction was stopped with 50 μL of Red Stop solution (Neogen) and the optical density was measured at 655 nm.

Peptide ELISA

ELISA plates (Nunc Maxisorp) were coated with streptavadin (Sigma 50677) (10 μg/ml in 100 mM $Na_2HPO_4$, 50 mM citric acid pH 5.0, 100 μl/well) and stored at 4° C. for up to one month. Before use, plates were washed three times in PBS/0.1%(v/v) Tween 20 and blocked with 200 μl of PBS/2% BSA (w/v) for one hour at 37° C. The plates were then washed as before and 100 μl peptide (0.5 μg/ml in SEC buffer) was added for one hour at 37° C. All peptides included the biotinylated linker sequence GSGK-biotin. The plate was washed as before and 100 μl antibody supernatant added in serial doubling dilutions in SEC buffer and incubated for one hour. Plate was washed as before and incubated for one hour at 37° C. with HRP conjugated anti-human kappa antibody (Sigma) at 1:5000 dilution (100 μl/well). The plates were washed as before and 150 μl for TMB One-Step K-Blue substrate (Neogen) added for 10 minutes and stored in the dark at room temperature. The reaction was stopped with 50 μl of Red Stop (Neogen). The optical density was measured at 655 nm.

Preparation of Antibody for HCVpp Infection Assays

In order to carry out HCVpp experiments, antibodies from COST cell transfection supernatants were purified and concentrated by Protein A purification. For each chimeric or humanized antibody: Prosep-vA beads (Millipore) were resuspended and 400 μl added to a 10 ml disposable chromatography column (Pierce) and washed with 20 ml of PBS. COST transfection supernatant (approximately 150 ml) was added to the column under gravity flow. The column was subsequently washed with PBS (20 ml) and eluted with 0.5 ml of Immunopure IgG Elution buffer (Pierce). The eluate was neutralized with 20 μl of 1 M Tris/HCL pH 7.6 and dialyzed in a 0.5 ml Slide-A-Lyser (Pierce) in 3 liters of PBS overnight at 4° C.

HCV Pseudoparticle Infection Assays

HCVpp for genotypes 1, 2, 3, 4, and 6 were made by transfecting HEK cells with plasmids encoding HCV glycoprotein sequences, MLV gag-pol and luciferase reporter, then the conditioned medium was concentrated and partially purified by ultracentrifugation through a cushion of 20% sucrose. See Owsianka A. et al., *J Virol* 79:11095-104 (2005). The HCVpp for genotype 5 was made in a similar way except that the partial purification step through a sucrose gradient was omitted since adversely affected infectivity of the genotype 5 pseudoparticles. Three-fold dilutions of each antibody in cell culture medium were mixed with HCVpp and the antibody/HCVpp mixtures were incubated at 37° C. for 1 h, and then added to human hepatomaHuh-7 target cells in triplicate wells. After 4 h incubation at 37° C., the inoculum was removed and replaced with fresh medium. After 3 days the cells were lysed and assayed for luciferase activity. Multiple wells were infected with HCVpp in the absence of antibody, and all the results are expressed as a percentage of this "no antibody" control. The genotypes for HCV used in the following experiments are shown in Table 3.

TABLE 3

(previously Table 1 in 61/006,066): The genotypes of HCV and the IC50 and IC90s of the chimeric and humanized antibodies.

| | Experiment 1 | | | | | |
|---|---|---|---|---|---|---|
| | Genotype | | | | | |
| IC units | 1a H77 20 | | 2a JFH1 | | 3a F4/2-35 | |
| (μg/ml) | IC50 | IC90 | IC50 | IC90 | IC50 | IC90 |
| Vh/Vl | <0.137 | 0.31 | 1.1 | 9.31 | 0.48 | 3.2 |
| RH B-H/RK2b | <0.41 | 0.73 | 2.7 | 22.1 | 1.15 | 8.3 |

TABLE 3-continued (previously Table 1 in 61/006,066): The genotypes of HCV and the IC50 and IC90s of the chimeric and humanized antibodies.

| | | | | | | | |
|---|---|---|---|---|---|---|---|
| RH-C/RK2b | <0.41 | <0.41 | 0.64 | 7 | | <0.41 | 2.15 |
| RH-H/RK2b | <0.41 | 1 | 3 | 26 | | 0.67 | 8.3 |

Experiment 2

| | Genotype | | | | | | | |
|---|---|---|---|---|---|---|---|---|
| IC units | 1a H77 20 | | 2A2.4 | | 4.21.16 | | 6.5.8 | |
| (μg/ml) | IC50 | IC90 | IC50 | IC90 | IC50 | IC90 | IC50 | IC90 |
| RH B-H/RK2b | 0.08 | 1 | 1.7 | 20 | 0.33 | 3.64 | <0.41 | 3.7 |
| RH-C/RK2b | <0.0137 | 0.24 | 0.51 | 6 | <0.41 | 0.92 | <0.41 | 1.8 |
| RH-H/RK2b | 0.06 | 1.2 | 3.33 | 26.67 | 0.33 | 5.3 | 0.79 | 18 |
| Vh/Vl | 0.018 | 0.28 | 0.88 | 6.67 | <0.137 | 0.83 | <0.137 | 3.7 |

Experiment 3

| | Genotype | | | | | | | |
|---|---|---|---|---|---|---|---|---|
| IC units | 1a H77 20 | | 1A20.8 | | 1B5.23 | | 2B1.1 | |
| (μg/ml) | IC50 | IC90 | IC50 | IC90 | IC50 | IC90 | IC50 | IC90 |
| Vh/Vl | 0.03 | 0.43 | 1.1 | 11.5 | 1.15 | 11 | 3 | >15 |
| RH-C/RK2b | 0.032 | 0.6 | 1.6 | 15 | 0.9 | 8.3 | 3 | >15 |

Experiment 4

| | Genotype 5.15.11 | |
|---|---|---|
| IC units | | |
| (μg/ml) | IC50 | IC90 |
| Vh/Vl | 0.088 | 1.11 |
| RH-C/RK2b | 0.053 | 0.82 |
| RH-H/RK2b | 0.37 | 8 |

Molecular Modelling AP33

The nearest VH and VK structures to AP33 in the RCSB protein databank were 1DQD_H (84% identity) and 1EGL_L (91% identity) respectively. The 1DQD_H VH and the 1EGL_L VK structures were combined into a single template structure. The AP33 sequences (Table 4) were aligned with the combined template sequences. The heavy chain and kappa light chain CDR lengths were identical to those of AP33 except for the H3 loop. A homology model of AP33 was generated based on this combined template using Modeler software. See Fiser A. et al., *Protein Sci* 9:1753-73 (2000); Fiser A. and Sali A., *Methods Enzymol* 374:461-91 (2003); and Sali A. and Blundell T L., *J Mol Biol* 234:779-815 (1993).

TABLE 4

(previously Table 2 in 61/006,066): Heavy and light protein sequence used to model the AP33 antibody.

AP33_H (117 amino acids)
EVQLQESGPSLVKPSQTLSLTCSVTGDSITSGYWNWIRKFPGNKLEYM

GYISYSGSTYYNLSLRSRISITRDTSKNQYYLQLNSVTTEDTATYYCA

LITTTTYAMDYWGQGTSVTVS (SEQ ID NO: 1)

AP33_L (111 amino acids)
NIVLTQSPVSLAVSLGQRATISCRASESVDGYGNSFLHWFQQKPGQPP

KLLIYLASNLNSGVPARFSGSGSRTDFTLTIDPVEADDAATYYCQQNN

VDPWTFGGGTKLEIK (SEQ ID NO: 2)

Results

HCV is described as belonging to six genotypes but is further subdivided into sub genotypes. Infected individuals carry a swarm of variant genotype descended from the initial infection. The region of the HCV protein E2 protein to which AP33 binds is unusually conserved among HCV genotypes so the AP33 antibody exhibits cross genotype specificity. It was therefore important to ensure the humanized AP33 retains species cross-reactivity.

The most effective method of testing the humanized antibody was to replicate the experiments carried out with AP33 (Yagnik A. T. et al., *Proteins* 40:355-66 (2000)) that show the blocking of HCV pseudoparticle infection of Huh-7 cells. However pseudo particle infection studies required relatively large amounts of antibody that would have caused logistical problems if applied to the large number of variants generated during the humanization process. Therefore peptide ELISA analysis was used to perform an initial screen of the antibody variants against a variety of HCV genotypes.

The D3 peptide is the sequence identified by Anonymous, *J Viral Hepatology* 6:35-47 (1999) as conserved among HCV genotypes; peptides B1, C1, H3 and G3 represents alternative HCV genotype variants and peptide H6 is a mimotope for AP33 identified by phage display. Each of these peptides was used as a probe to measure the success of the humanization and the sequence shown in Table 5.

TABLE 5

(previously Table 3 in 61/006,066): Peptides used
in the binding analysis of humanized AP33.

| PEPTIDE | SEQ ID NO. | GENO-NAME | TYPE |
|---|---|---|---|
| QLINTNGSWHINGSGK-biotin | 45 | D3 | All |
| N..........GSGK-biotin | 46 | B1 | 2b |
| ..........V.GSGK-biotin | 47 | C2 | 1a |
| ....S.......GSGK-biotin | 48 | H3 | 2a, 4 |
| ..V.........GSGK-biotin | 49 | G3 | 1a, 3 |
| VELRNLGGTWRPGSGK-biotin | 50 | H6 | Mimotope |

Example 2

Selection of a Human VH Framework for AP33RHA

Human VH sequences with highest identity to AP33 VH at Vernier, Canonical and VL Interface residues (VCI residues) and which have the same size of CDR1 and 2, are shown in FIG. 14 and are used to select the optimal donor framework. See Foote J. and Winter G., *J Mol Biol* 224:487-99 (1992) and Chothia C. et al., *J Mol Biol* 186:651-63 (1985). The FW identity scores are also shown. Sequences which are humanized antibodies, mouse antibodies or scFv have also been omitted, except for A03907, the D1.3 mouse anti-lysozyme VH. The interface residues tend to be buried, away from the CDRs, whereas Vernier and Canonical residues tend to be close to CDRs.

With respect to overall VCI identity, U86525 had the highest score (14 out of 17 for VCI score and 80 out of 86 for the framework score) (FIG. 14). The top 18 human sequences all had a VCI score of 14 whilst the framework scores varied from 61 out of 86 or less. The VCI residue differences that were the least conservative when compared to the mouse antibody sequences were at positions 71 and 94 (Kabat numbering).

Figure 13:
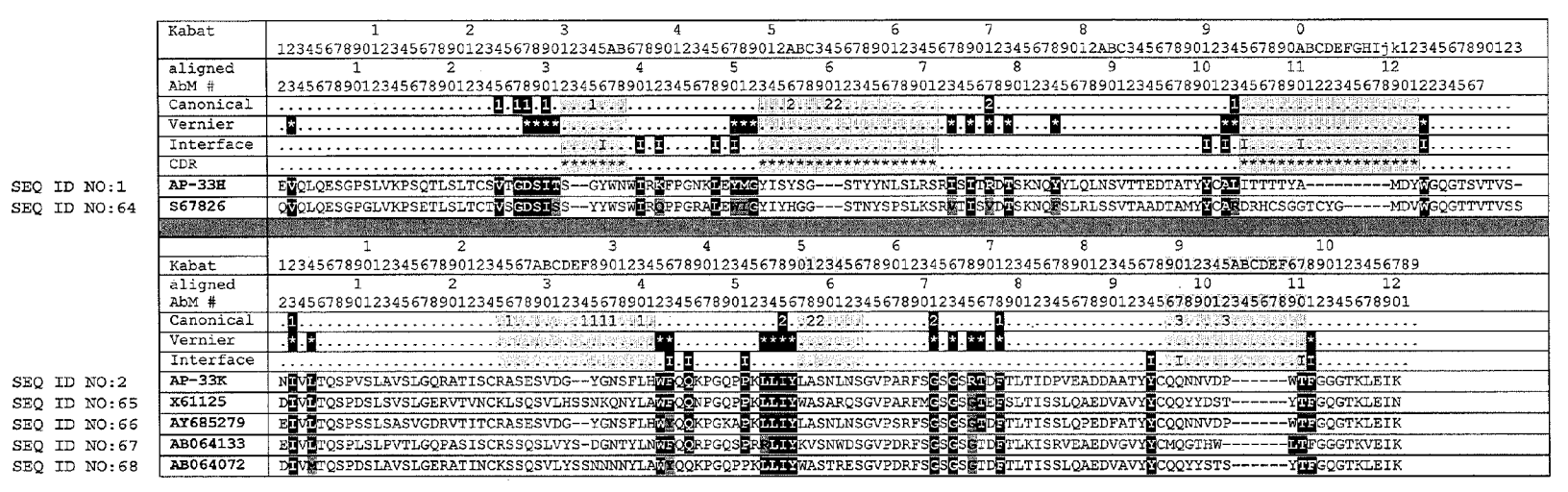

Analysis of the complete human VH sequences (FIGS. 15 and 16) showed that U86525, S67826, 42071, 42069, 42068, S67827 had no unusual Cys or Pro residues in the FW. However U86525 contained more non-conservative residue differences than S67826 (i.e., residues 23, 40, 81, and 92: using FIG. 16 numbering). The 567826 antibody VH, which was derived from a patient with a CLL lymphoma (Mierau R. et al., *Rheumatol Int* 12:23-31 (1992)), was therefore chosen to act as the framework acceptor for the donor mouse AP33 VH CDRs to produce AP33RHA. FIG. 13 shows the comparison between AP33H and S56827.

Example 3

Selection of a Leader Sequence for AP33RHA

Figure 17:
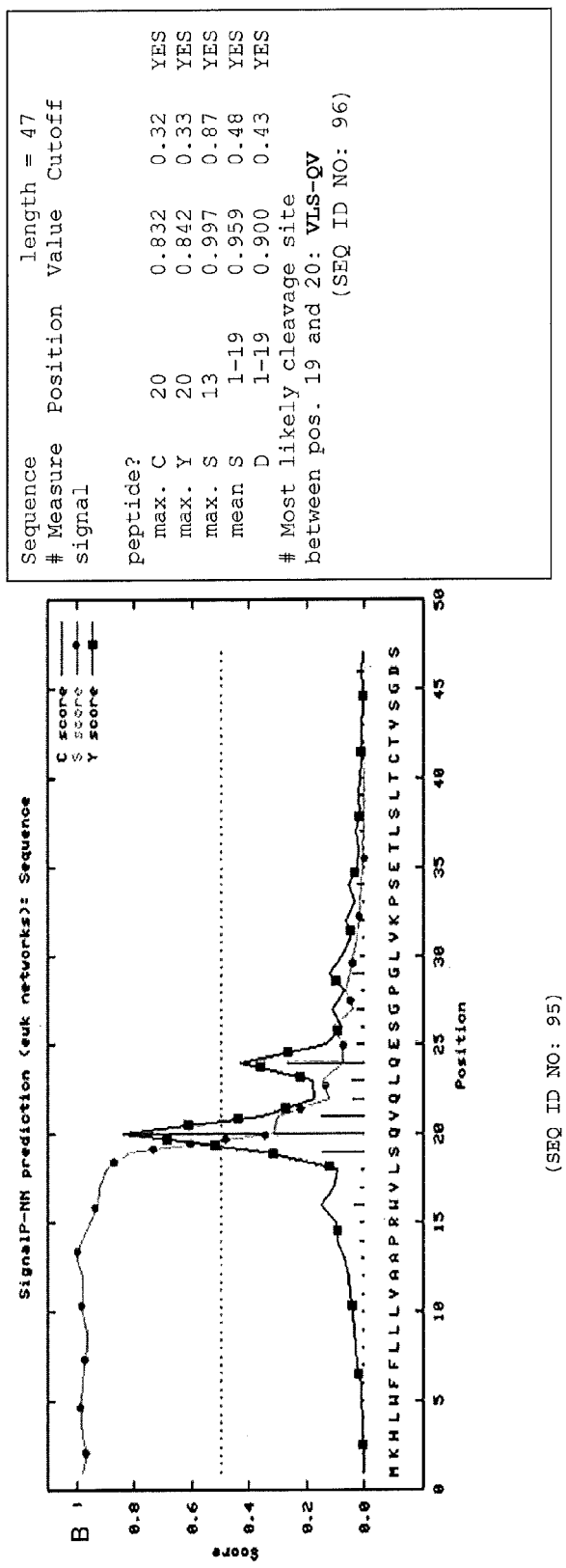
FIGS. 17A-B (previously Table 11 in 61/006,066) show AP33RHA leader selection (SEQ ID NO: 94) and SignalP results with VH4-59 leader and S67826 FW1 [14] (SEQ ID NOs: 95 & 96).
Figure 26:
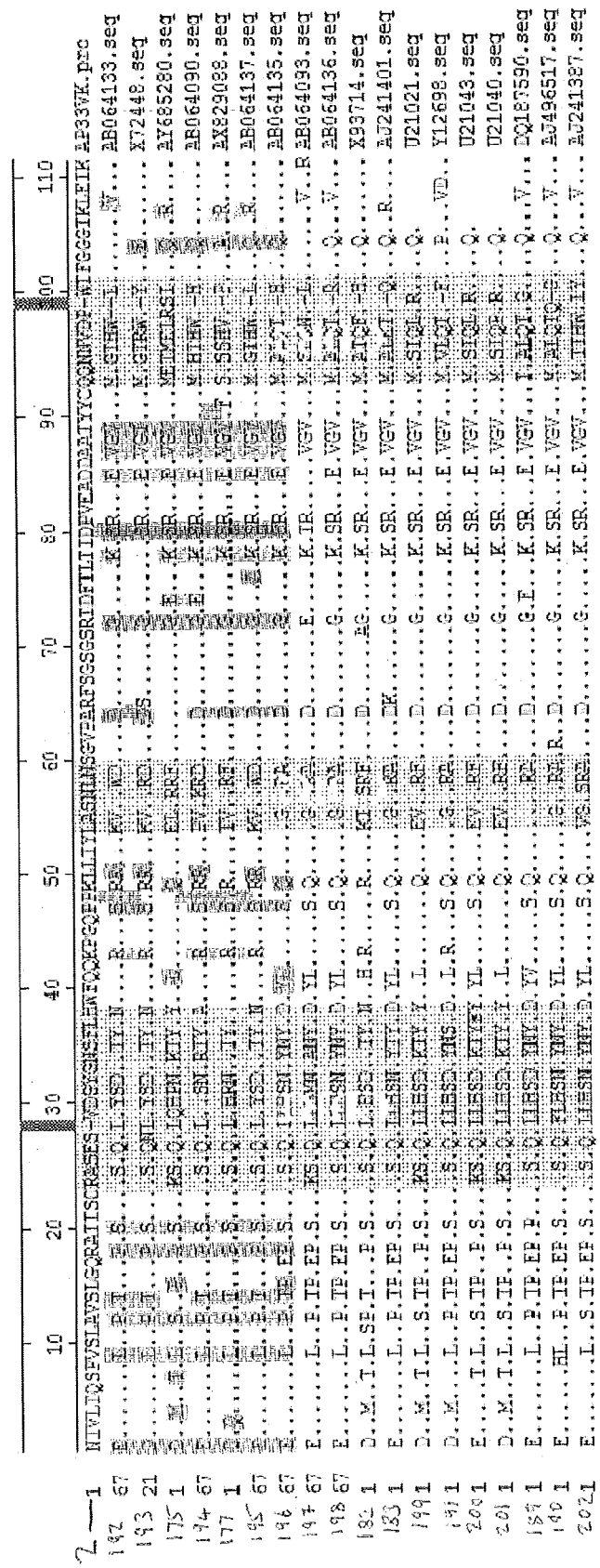
FIG. 26 (previously Table 21 in 61/006,066) shows ClustalW alignment of AP33 VK and non VK4 human sequences with larger CDR1(SEQ ID NOs: 2, 192-202). Residues identical to AP33VK are indicated by a dot. In the top 7 sequences, conservative changes are medium grey and non conservative changes are dark grey. CDRs are light grey.

The initial humanization is the graft of the Kabat CDRs 1, 2 and 3 from AP33VH into the acceptor S67826 Kabat FWs 1, 2, 3, 4 (FIG. 18). This sequence requires the addition of a signal peptide from the germline gene VH4-59 that has the closest sequence identity to S67826 (FIG. 17). We used the SignalP (Foote J. and Winter G., *J Mol Biol* 224:487-99 (1992)) (V2.0.b2) server to confirm that this leader (FIG. 17) would cut with signal peptidase when preceding the S67826 FW1 sequence. FIG. 18 shows the generation of AP33RHA protein and DNA sequence by intercalating the AP33 CDRs into the human FW. The DNA sequence of AP33RHA including its leader is shown below (previously Table 13 in 61/006, 066):

(SEQ ID NO: 114)
*ATGAAACATCTGTGGTTCTTCCTTCTGCTGGTGGCAGCTCCCAGATGGG*

*TCCTGTCC*caggtgcagctgcaggagtcgggcccaggactggtgaagcc ttcggagaccctgtccctcacctgcactgtctctggtgactccatcagt

AGTGGTTACTGGAACatccggcagccccagggagggcactggagtgga taggaTACATAAGTTACAGTGGTAGCACTTACTACAATCTATCTCTCAG

AAGTcgggtcaccatatcagtagacacgtctaagaaccagttctccctg aggctgagctctgtgaccgctgcggacacggccatgtattactgtgcga gaATTACTACGACTACCTATGCTATGGACTACtggggccaagggaccac ggtcaccgtctcc AP33RHA DNA sequence with leader. Italics, upper case text indicates leader sequence, lower case text indicates FW, and upper case, bolded text indicates CDR sequences.

Figure 19:
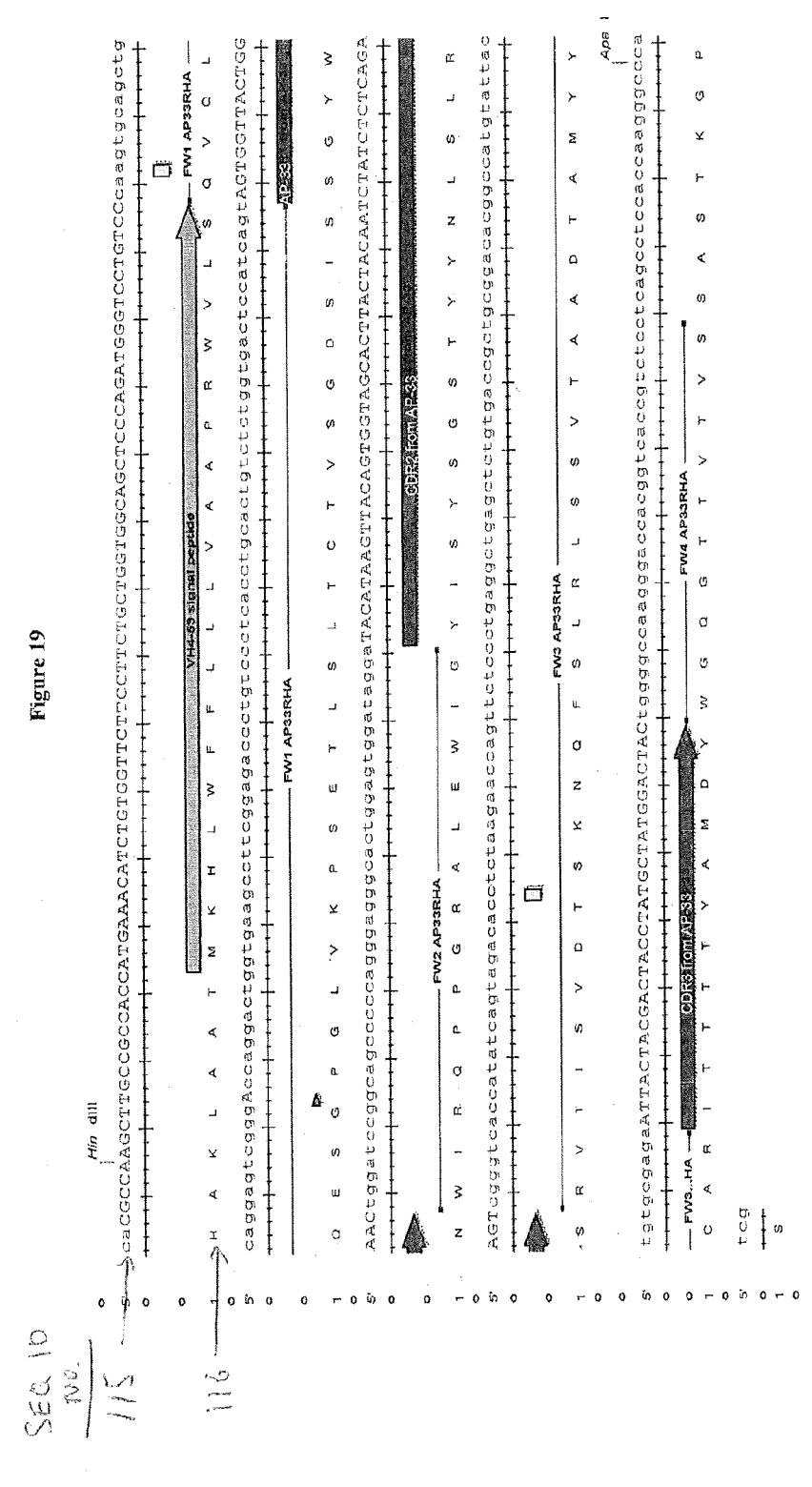

The completed protein and DNA sequence of the AP33RHA including the VH4-59 signal peptide is shown in FIG. 19.

Example 4

Selection of Human VK Frameworks for AP33RKA and AP33RK2

Figure 20:
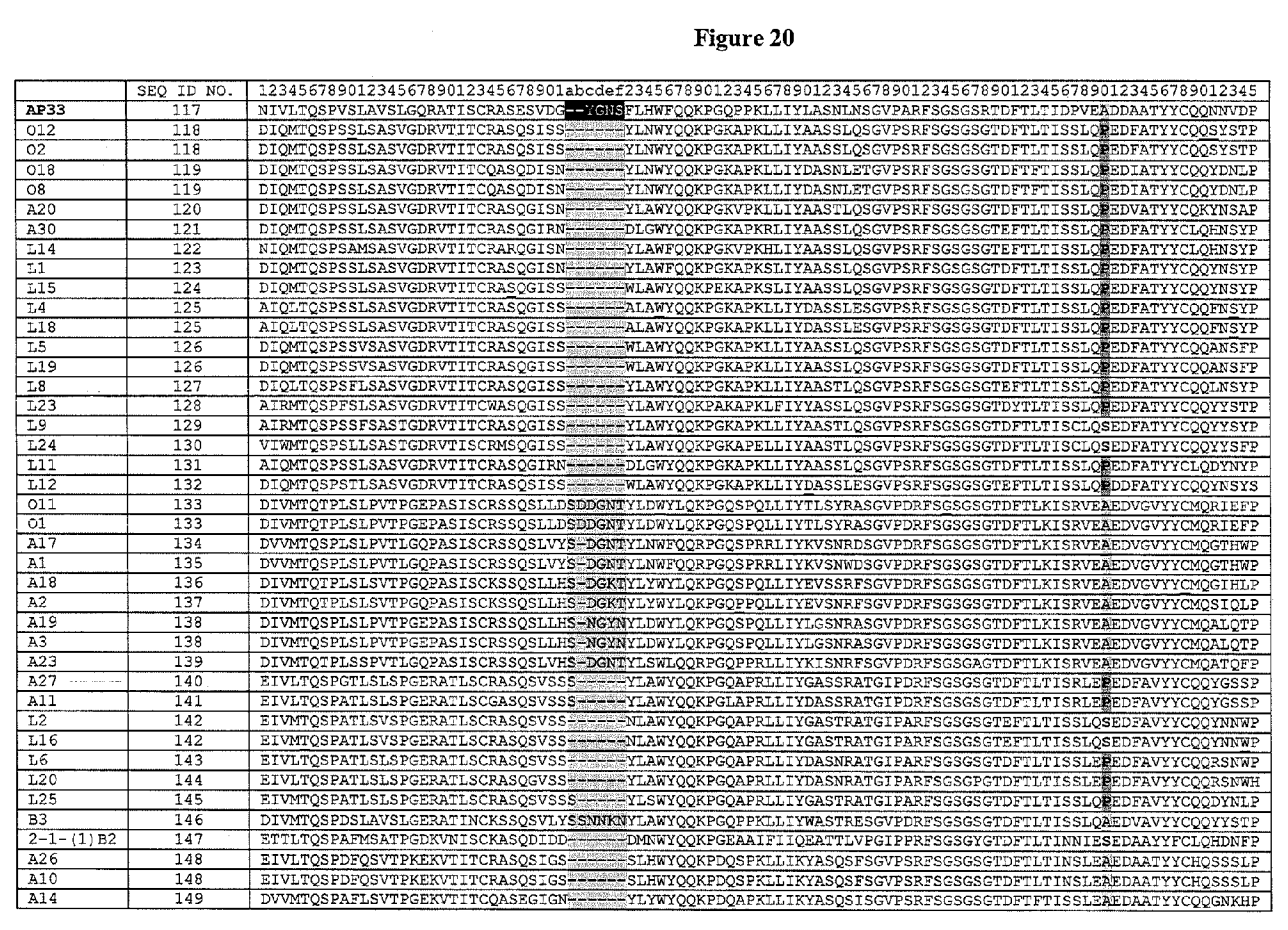

Comparison of human germline VK genes with AP33K revealed that there were none with the same canonical loop length for CDR1 (FIG. 20). Those sequences that were identified with the correct CDR1 loop length from our database of human light chain genes were either humanized antibodies or scFvs (FIG. 21). Human VK sequences with non-matching CDR1 lengths but with matching CDR2/3 lengths and highest identity to AP33 VK at Vernier, Canonical and VH Interface residues (VCI Score) were selected and are shown in FIG. 22 together with their scores of FW identity to AP33 VK. Sequences which are humanized antibodies, mouse antibodies or scFv have been omitted.

Figure 23A:
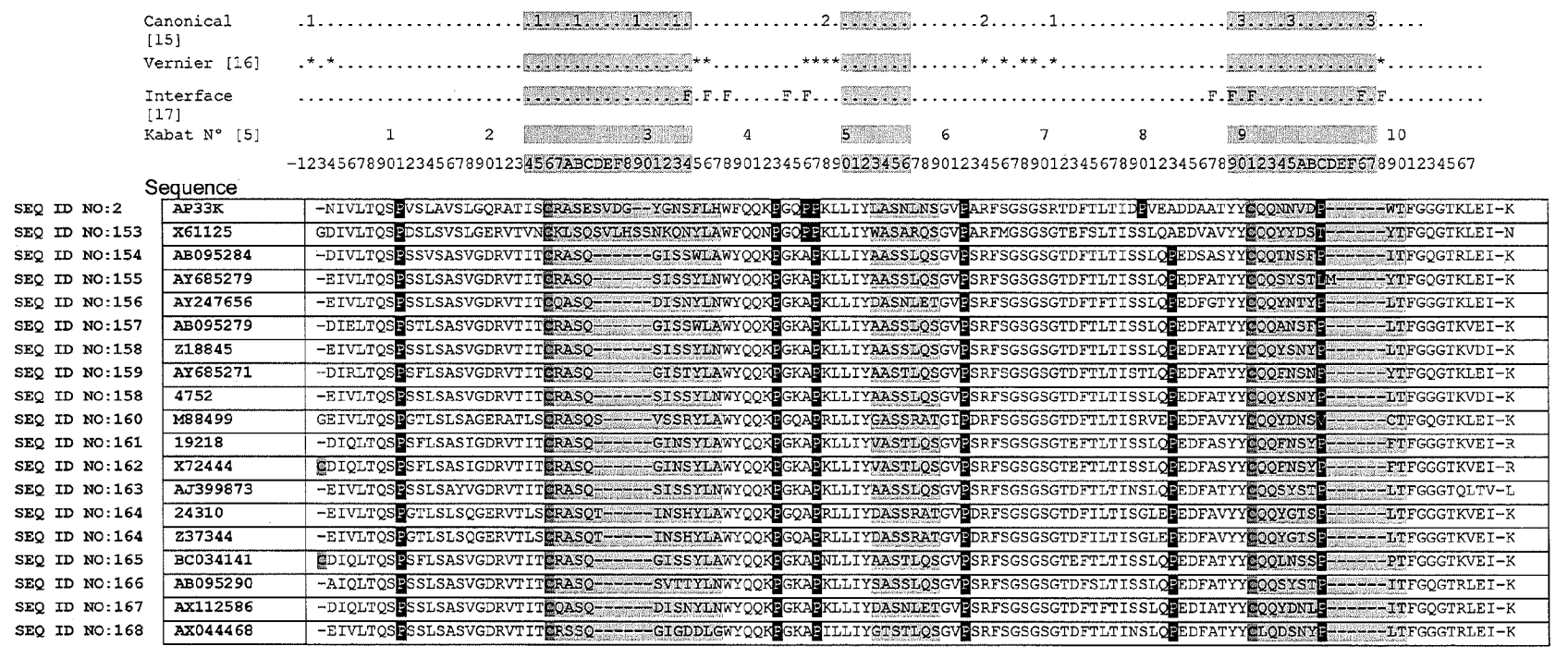

FIG. 23A shows the complete sequence of the human VK best matching AP33VK. The ClustalW alignment of these sequences is shown in FIG. 23B, and indicates the conserved residues. Due to the absence of a human canonical CDR1 loop length to match AP33, we chose two human frameworks with differing loop CDR1 lengths. Sequence X61125 (Chothia C. et al., *J Mol Biol* 186:651-63 (1985)) has the highest VCI score, CDR1 two residues longer than AP33 and an Alanine at position 80, matching AP33 VK. For these reasons we chose this sequence as the first donor framework to generate AP33RKA. AY685279 (Ghosh S. et al., *J Immunol* 174:2860-9 (2005)) has a CDR1 4-residues shorter than AP33 and a Proline at position 80 typical for that germline family. In addition, AY685279 has high VCI and framework scores and no unusual Proline or Cysteine residues in its sequence. Under these criteria AY685279 was chosen as the second framework donor to generate AP33RK2.

Example 5

Selection of Leader Sequences for AP33RKA and AP33RK2

Figure 27:
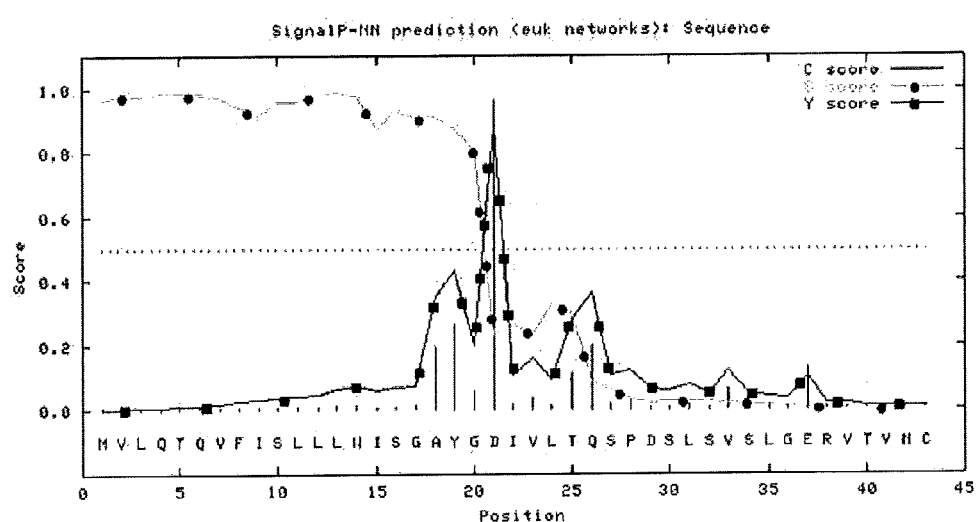
FIG. 27 (previously Table 22 in 61/006,066) (SEQ ID NOs: 203 & 291) shows AP33RKA design using human framework X61125 and AY685279. Predicted signal protease cleave result [20] with VKIV-B3 leader and X61125-ATGGACATGAGGGTCCCTGCTCAGCTCCTGGGGCTC-CTGCAGCTCT GGCTCTCcGGcGCCAGATGT (SEQ ID NO: 211).
Figure 28:
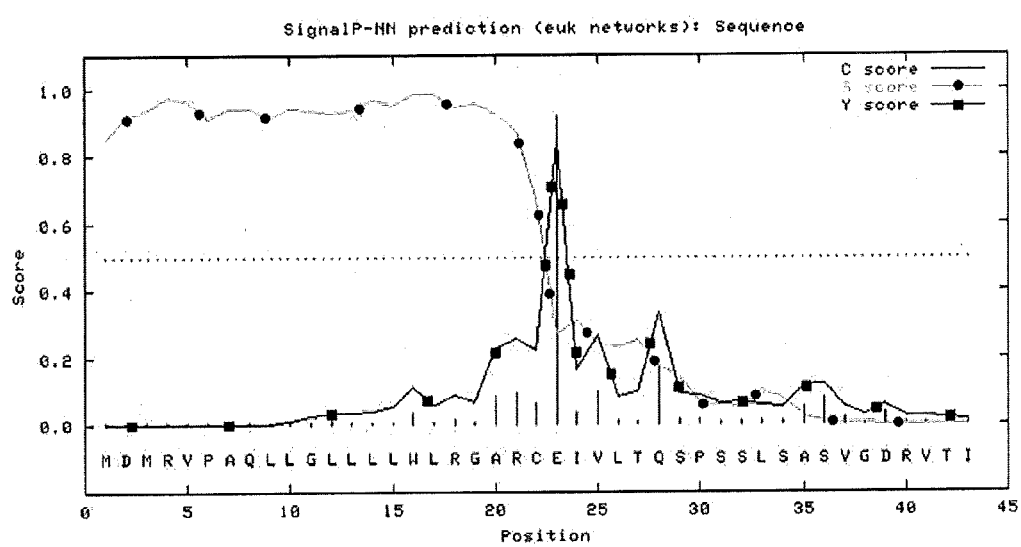
FIG. 28 (previously Table 23 in 61/006,066) (SEQ ID NOs: 204 & 292) shows predicted signal protease cleavage [21] result with VKI-012/02 leader and AY685279-ATGGACATGAGGGTCCCTGC TCAGCTCCTGGGGCTCCTG-CAGCTCTGGCTCTCcGGcGCCAGATGT (SEQ ID NO: 211).
Figure 29:
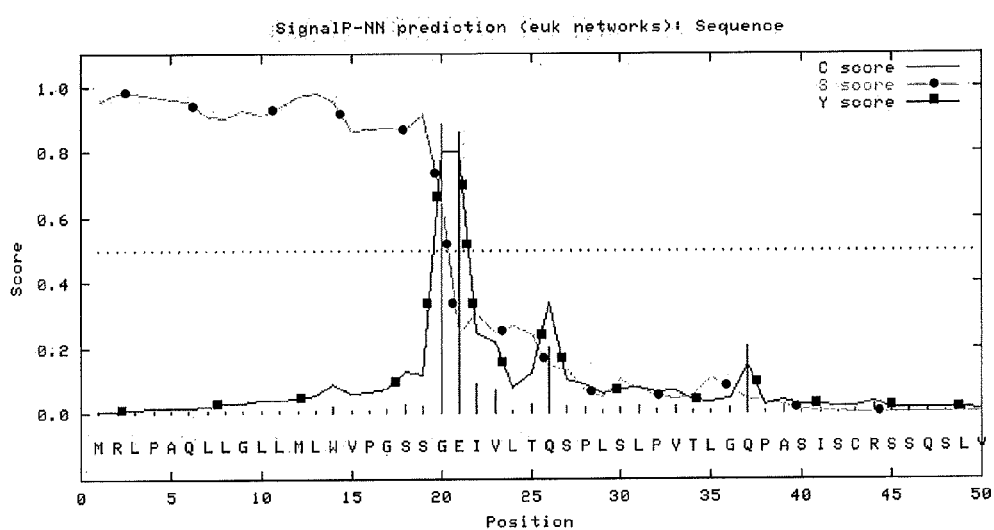
FIG. 29 (previously Table 24 in 61/006,066) (SEQ ID NOs: 205 & 293) shows predicted signal protease cleavage result [22] with VKII-A17 leader and AB064133 FW1.

The nearest human germline VK gene to X61125 is VKIV-B3, which would be the natural choice of leader sequence. The use of the predictive SignalP algorithm (Nielsen H. et al., *Protein Eng.* 10:1-6 (1997)) with this leader contiguous with FW1 of X61126 shows that signal protease cutting should be at the correct position (FIG. 27) Similarly, the germline gene nearest to AY685279 is VKI-012/02. Again, the leader sequence of VKI-012/02 when contiguous with FW1 of AY685279 is predicted to cut correctly (FIG. 28).

Example 6

Generation of AP33RKA, AP33RK2, AP33RK3 and AP33 RK4 Sequences

Figure 35:
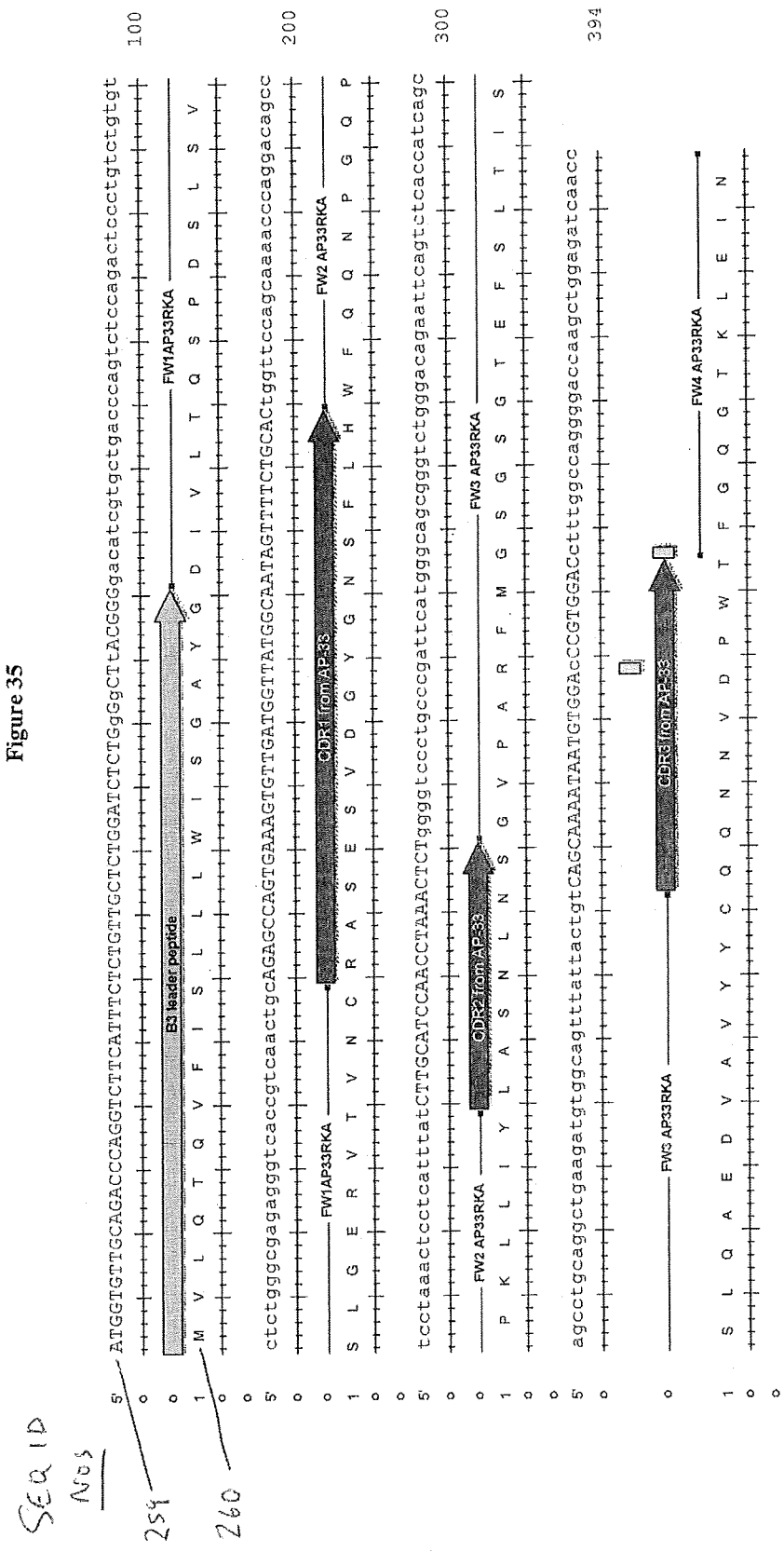
FIG. 35 (previously Table 30 in 61/006,066) shows DNA (SEQ ID NO: 259) and protein (SEQ ID NO: 260) sequence of AP33RKA with leader. Light grey boxes represent changed nucleotides to remove cryptic splice sites or unwanted BamHI sites.
Figure 36:
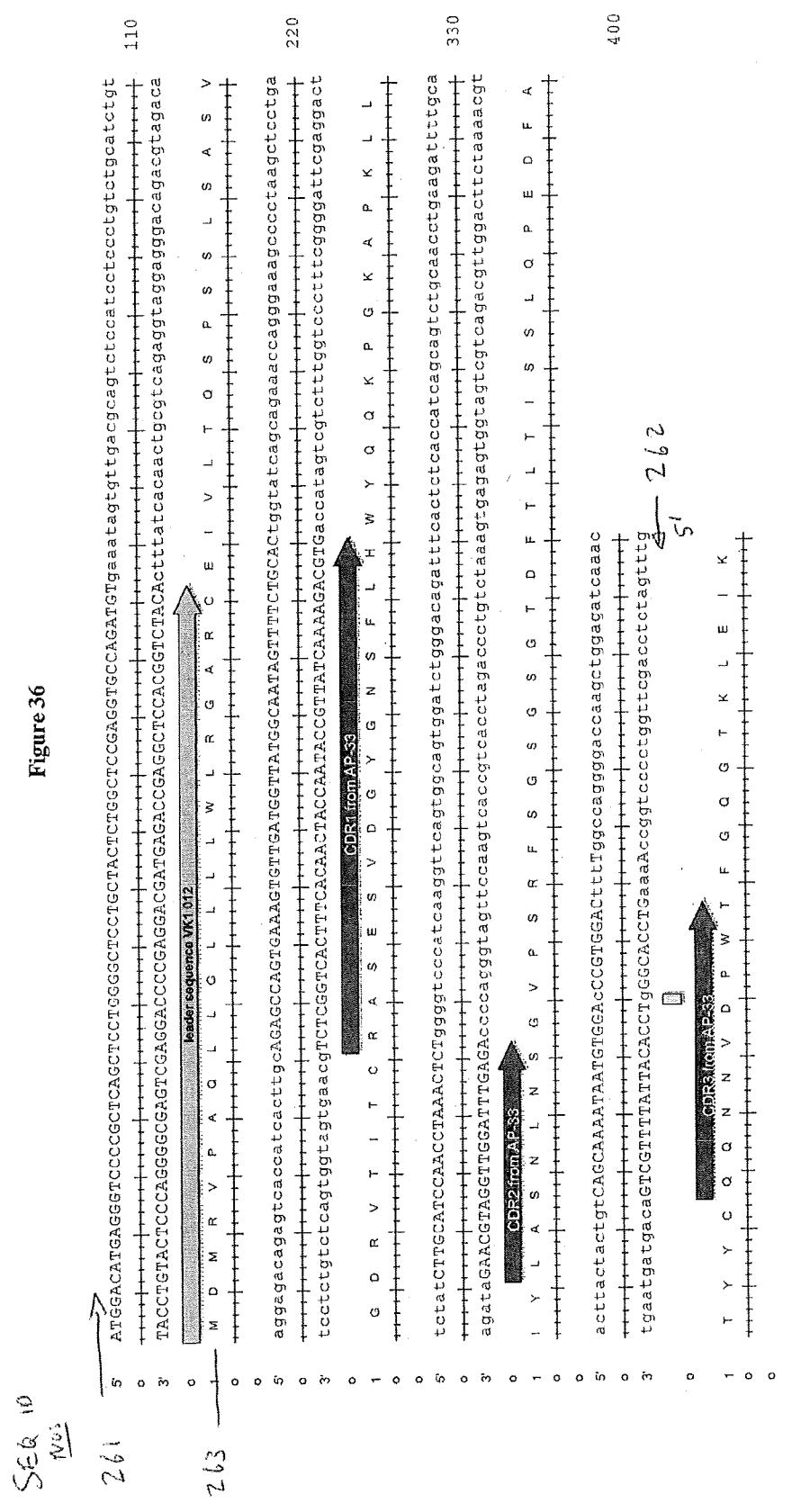
Figure 37:
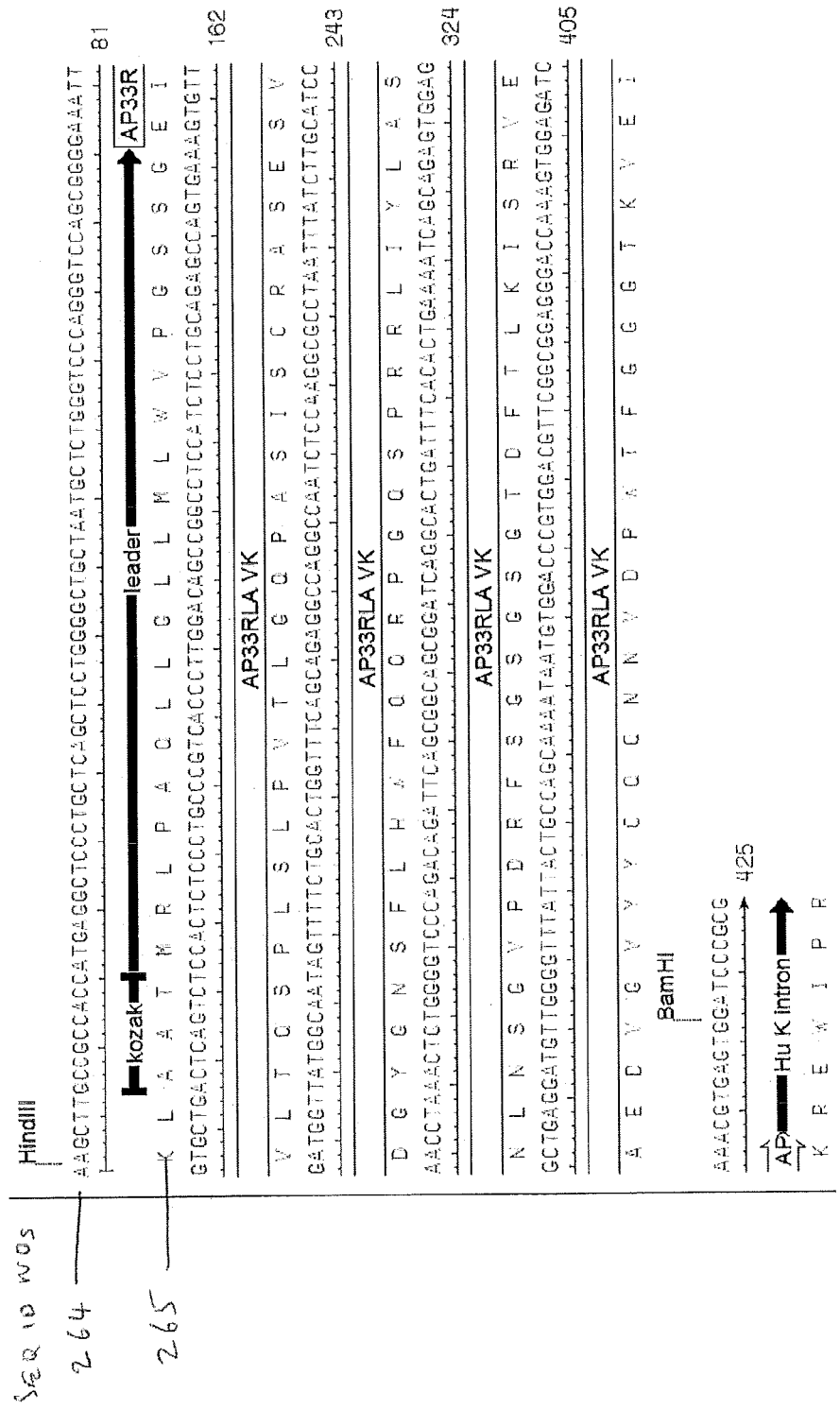
FIG. 37 (previously Table 32 in 61/006,066) shows DNA (SEQ ID NO: 264) and protein (SEQ ID NO: 265) sequence of AP33RK3 construct. NB AP33RLB has the two VCIs back mutated. No splice sites are generated by this.

Intercalating the protein and DNA sequences of AP33VK CDRs between FWs 1, 2, 3 and 4 of X611251 is shown in FIG. 30, together with the DNA sequence of the B3 leader (AP33RKA). Intercalating the protein and DNA sequences of AP33VK CDRs into FWs 1, 2, 3 and 4 of AY685279 is shown in FIG. 31, together with the DNA sequence of the VKI-012/02. The complete AP33RKA and AP33RK2 sequence with their respective leader sequences attached is shown in FIGS. 34-36.

Two further light chain frameworks were tested based on the human sequences AB064133 and AB064072 that became humanized kappa light chains RK3 and RK4, respectively. The selection of AB064133 is shown in FIGS. 24-26 and 29. The VCI residues are defined in FIG. 13, while the protein and DNA sequences for both RK3 and RK4 are shown in FIGS. 32-34 and 37-38. RK3 was chosen because it was a from a different germline family, i.e. V kappa 5. Although AB064072 was a member of the Kabat VKIV subgroup, which have historically been poorly expressed when used in recombinant antibody constructs, this specific human framework sequence had been shown previously to express well in our hands when part of a humanized antibody.

Example 7

Expression of Recombinant Heavy and Light Chains

Recombinant antibody V regions were expressed by transient transfection of Cos7 cells. Chimeric AP33 heavy or light chain DNA constructs were used as positive controls and co-transfected with the appropriate humanized antibody constructs chains. Initially the unmutated RHA and RHb-h (in which all seven unconserved vernier zone VC back-mutations) and RKAbd and RK2bc were tested. RK2bc has both conflicting VC residues back-mutated. The light chain RKA had two residues replaced; the VC residue Y36F, and since Asn is highly unusual at position 107, it was also replaced with Lys (RKAbd). It was noted that RKAbd expression was very low and below viable experimental and commercial levels (Table 9). In subsequent experiments modifications were made to RKAbd including removing potential splice sites mutation G380C and exchanging leader sequences from leader B3 to L11, shown in Table 6, which from our experience had worked efficiently in other light chain genes. In addition, others have reported that the amino acid substitution D9S was effective at rescuing expression of VKIV genes. See Saldanha J. W. et al. *J Mol Biol Immunol* 5391(22436): 487709-99719 (1992). None of these modifications were effective in restoring expression levels above background.

TABLE 6

(previously Table 4 in 61/006,066): The leader sequences for RKA.

| | |
|---|---|
| B3 leader sequence DNA | ATGGTGTTGCAGACCCAGGTCTTCATTTC TCTGTTGCTCTGGATCTCTGGGGCTTACG GG (SEQ ID NO: 51) |
| B3 leader sequence Protein | MVLQTQVFISLLLWISGAYG (SEQ ID NO: 52) |
| L11 leader sequence DNA | ATGGACATGAGGGTCCCCGCTCAGCTCCT GGGGCTCCTGCTGCTCTGGCTCCCAGGCG CCAGATGT (SEQ ID NO: 53) |
| L11 leader sequence Protein | MDMRVPAQLLGLLLLWLPGARC (SEQ ID NO: 54) |

TABLE 9

(previously Table 34 in 61/006,066): Expression of humanized light chains. COS 7 cells were transfected by the stated antibody constructs.

| Heavy Chain RHb-h | Antibody yield | Control transfection chimeric antibody ($V_H/V_L$) |
|---|---|---|
| RKAbd/VH | Not detected | 1008 ng/ml |
| RKAbd (leader plus D9S)/VH | Not detected | 1415 ng/ml |
| RK2bc/VL | 389 ng/ml | 3335 ng/ml |
| RK2bc/RHb-h | 1555 ng/ml | 3335 ng/ml |
| RK2b/RHb-h | 1552 ng/ml | 849 ng/ml |
| RK2b/RH-C | 1222 ng/ml | 1036 ng/ml |
| RK3/VH | 39 ng/ml | 1518 ng/ml |
| RK3/RHb-h | 2.3 ng/ml | 1518 ng/ml |
| RK4/RHb-h | 124 ng/ml | 5161 ng/ml |

Moreover, alternative light chain constructs RK3 and RK4 also show extremely low levels of expression (Table 9). Only RK2 can be expressed at levels suitable for producing a humanized antibody.

Example 8

The Binding of RHb-h/RK2bc to E2 Peptides

The supernatants from the Cos7 transfections were used to compare the binding of the humanized antibody RHb-h/RK2bc with the chimeric antibody. See FIG. 1.

The results from the antibody binding to the H6 mimotope suggest that the vernier zone (Foote J. and Winter G., *J Mol Biol* 224:487-99 (1992)) and canonical residues (Chothia C. et al., *J Mol Biol* 186:651-63 (1985), and Chothia C. et al., *Nature* 342:877-83 (1989)) introduced into RHA are necessary for binding. The H6 peptide binding of the antibody RHb-h/V1 was the closest to the chimeric antibody (Vh/V1) positive control and better than the fully humanized RHb-h/RK2bc antibody suggesting that the humanized light chain is not as good as the chimeric light chain. This is emphasized by the particularly poor binding of RHA/RK2bc when it is compared to the chimeric light chain RHA/V1.

The conclusion from this experiment is that the heavy chain RHb-h has retained much of the structural features in AP33 VH critical to antigen binding, but that the humanized light chain is less good. However, the absence of a human orthologue of the mouse light chain gene with the same L1 loop length was anticipated as a potential problem for humanization.

Example 9

The Interface Between the Heavy and Light Chains Mediated by Humanized Heavy Chain Interface Residue Q39 was not Responsible for the Suboptimal Binding One explanation for the poor function of the light chain was that the interface residues between the heavy and light chains were incompatible. See Chothia C. et al., *J Mol Biol* 186:651-63 (1985). The interface glutamine residues at position 39 was mutated back to the mouse equivalent, lysine, in RHb-h and the new heavy chain denoted as RHI.

Figure 2:
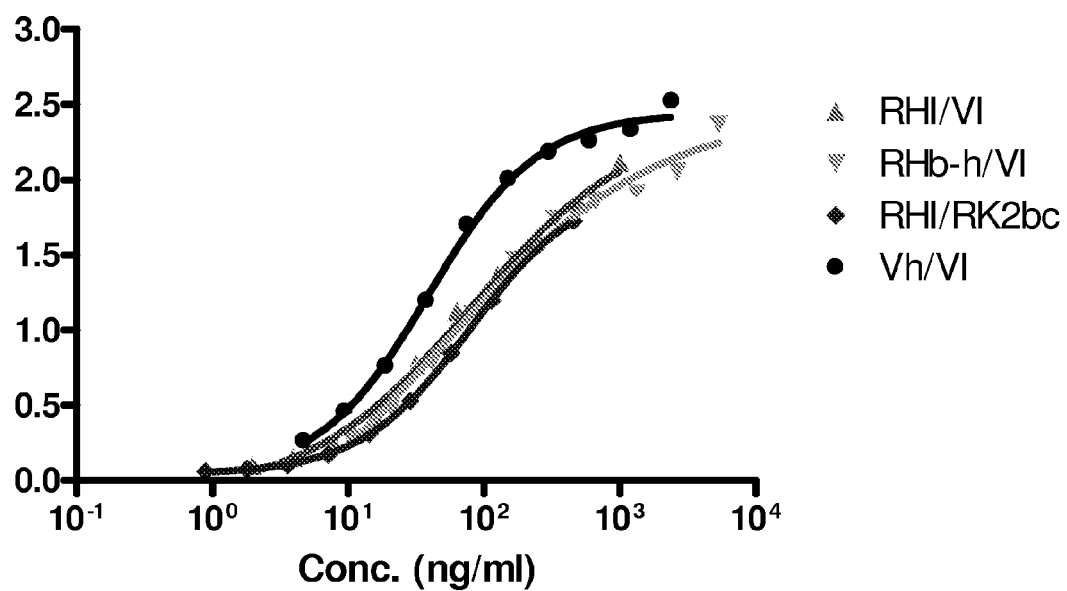
FIG. 2 shows the binding of AP33RHI to peptide H6. To determine if the heavy chain interface residue Q39 is responsible for the suboptimal binding to peptide H6 the binding of humanized heavy chain RHI (Q39K) was measured by ELISA. COS7 cells were transfected with a series of chimeric and RHI heavy and RK2b light chain constructs and the supernatants were used to compare binding to the mimotope H6. The binding of the mimotope peptide H6 to chimeric (Vh/Vl) and humanized antibodies RHb-h, RHI/RK2bc and mixtures of humanized and chimeric antibodies RHI/Vl or RHb-h/Vl were measured by ELISA.

The binding of RHI paired with RK2bc or the chimeric light chain failed to improve binding to the H6 peptide suggesting that the interface residue Q39K was not responsible for the suboptimal binding shown in FIG. 2.

Example 10

The Binding of RHb-h to a Range of E2 Peptides

Figure 3:
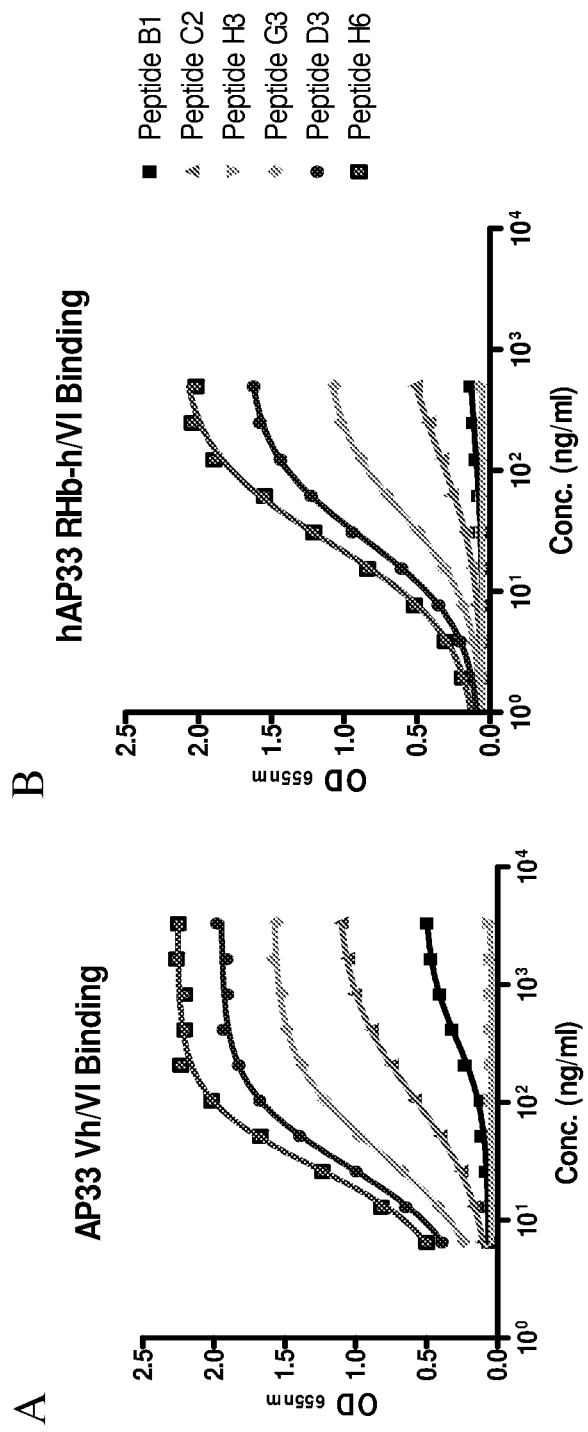
FIGS. 3A-B show the binding of Chimeric and humanized antibody to E2 peptides. To compare relative binding of the chimeric antibody to the humanized antibody RHb-h/Vl, COS7 cells were transfected with a series of chimeric and humanized antibody constructs. The antibody supernatants were subjected to ELISA and used to compare binding to the peptides described in Table 5.

In order to estimate the binding of the humanized antibody to different HCV genotypes the peptides shown in Table 5 were used as proxies for a spectrum of E2 variants. The peptide binding of RHb-h paired with the chimeric light chain, Vl, is shown in FIG. 3B. The results show that the humanized heavy chain binds a spectrum of peptides but is not as effective as the chimeric antibody, Vh/Vl, shown in FIG. 3A. Indeed the humanized antibody does not appear to bind peptide B1. The results indicated that replacing the unconserved canonical and vernier zone residues in the heavy chain was insufficient to retain the full spectrum of peptide antigen binding.

It is interesting to note that the peptides with variant AP33 epitopes have conserved changes, for example B1 replaces Gln to Asn and the peptides C2 and G3 are Ile to Val replacements. These conservative changes to smaller residues may represent a contraction of the epitope. This raises the possibility that the antigen contact residues on AP33 and the humanized antibody may be altered to give them greater reach. The effect of this could be to enhance the antibody's binding to those HCV genotypes which include the shorter epitope residues and that show weaker binding to AP33. It is also important to note that although the humanized antibody fails to bind the B1 peptide this sequence has not been found in infectious isolates of HCV.

Example 11

Identifying the Minimal Mutations to RK2

Figure 4:
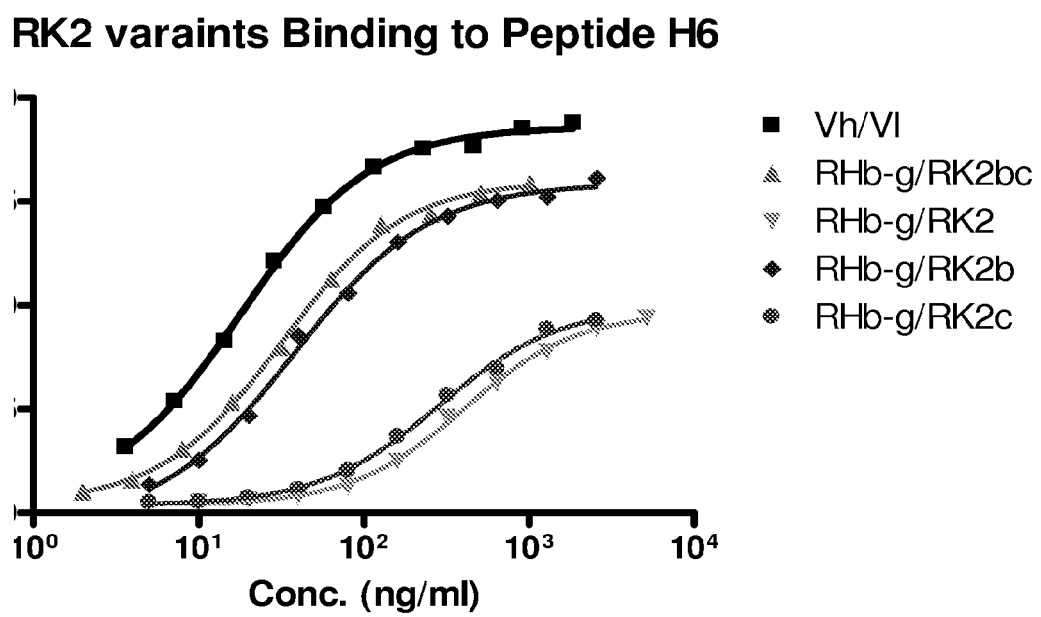
FIG. 4 shows the binding of RK2 variants to H6 peptide. The minimal number of mutations necessary for the humanized light chain RK2 to function was determined by comparing the binding of RHb-g with the light chains RK2, RK2b, and RK2c. The chimeric antibody Vh/Vl was included as a comparator to previous experiments. COS7 cells were transfected with a series of chimeric and humanized antibody constructs. The binding of antibody supernatants to the E2 peptides (Table 5) were measured by ELISA.

There were only 2 VC residues that were unconserved and were mutated in the RK2 light chain (mutation b (Y36F) and mutation c (G68R). Each VC mutation was back mutated to the human equivalent residue, Y36 and G68. The results (FIG. 4) show that mutation b is essential for light chain activity whereas mutation c is not.

Example 12

Identifying the Minimal Number of VC Changes Necessary for the Heavy Chain Humanization In order to identify the minimal number of VC mutations residues necessary for RHb-h humanization each mutation b, c, d, e, f, g, h was mutated back to the original human sequence, shown in Tables 7 and 8. See also FIG. 42A-G.

TABLE 7

(previously Table 5 in 61/006,066): Table of VC mutations.

| Antibody chain | Mutation name | Mouse residue | Human residue |
|---|---|---|---|
| RK2 | b | F36 | Y36 |
| RK2 | c | R68 | G68 |
| RH | b (S30T) | T30 | S30 |
| RH | c (W47Y) | Y47 | W47 |
| RH | d (I48M) | M48 | I48 |
| RH | e (V67I) | I67 | V67 |
| RH | f (V71R) | R71 | V71 |
| RH | g (F78Y) | Y78 | F78 |
| RH | h (R94L) | L94 | R94 |

TABLE 8

(previously Table 6 in 61/006,066): Humanized antibody mutants and there sequence identification.

| V gene name | V chain name | Mutations from parent sequence | Amino Acid SEQ ID NO | Nucleic Acid SEQ ID NO |
|---|---|---|---|---|
| AP33H heavy chain | VH | | SEQ ID NO: 1 | SEQ ID NO: 21 |
| AP33H light chain | Vl | | SEQ ID NO: 2 | SEQ ID NO: 22 |
| AP33RHA | RHA | None | SEQ ID NO: 3 | SEQ ID NO: 23 |
| AP33RKA | RKA | | SEQ ID NO: 4 | SEQ ID NO: 24 |
| AP33RKAbd | RKAbd | Y36F, N107K | SEQ ID NO: 5 | SEQ ID NO: 25 |
| AP33RK3 | RK3 | | SEQ ID NO: 8 | SEQ ID NO: 28 |
| AP33RK4 | RK4 | | SEQ ID NO: 9 | SEQ ID NO: 29 |
| RHbcdefgh | RHb-h | S30T, W47Y, I48M, V67I, V71R, F78Y, R94L | SEQ ID NO: 10 | SEQ ID NO: 30 |
| RHcdefgh | RH-B | W47Y, I48M, V67I, V71R, F78Y, R94L | SEQ ID NO: 12 | SEQ ID NO: 32 |
| RHcdefgh | RH-C | S30T, I48M, V67I, V71R, F78Y, R94L | SEQ ID NO: 13 | SEQ ID NO: 33 |
| RHcdefgh | RH-D | S30T, W47Y, V67I, V71R, F78Y, R94L | SEQ ID NO: 14 | SEQ ID NO: 34 |

TABLE 8-continued (previously Table 6 in 61/006,066): Humanized antibody mutants and there sequence identification.

| V gene name | V chain name | Mutations from parent sequence | Amino Acid SEQ ID NO | Nucleic Acid SEQ ID NO |
|---|---|---|---|---|
| RHcdefgh | RH-E | S30T, W47Y, I48M, V71R, F78Y, R94L | SEQ ID NO: 15 | SEQ ID NO: 35 |
| RHcdefgh | RH-F | S30T, W47Y, I48M, V67I, F78Y, R94L | SEQ ID NO: 16 | SEQ ID NO: 36 |
| RHcdefgh | RH-G | S30T, W47Y, I48M, V67I, V71R, R94L | SEQ ID NO: 17 | SEQ ID NO: 37 |
| RHcdefgh | RH-H | S30T, W47Y, I48M, V67I, V71R, F78Y | SEQ ID NO: 18 | SEQ ID NO: 38 |
| RHI | RHI | Q39K | SEQ ID NO: 11 | SEQ ID NO: 31 |
| RK2 | RK2 | none | SEQ ID NO: 6 | SEQ ID NO: 26 |
| RK2b | RK2b | Y36F | SEQ ID NO: 19 | SEQ ID NO: 39 |
| RK2c | RK2c | G68R | SEQ ID NO: 20 | SEQ ID NO: 40 |
| RK2bc | RK2bc | Y36F G68R | SEQ ID NO: 7 | SEQ ID NO: 27 |

Figure 5:
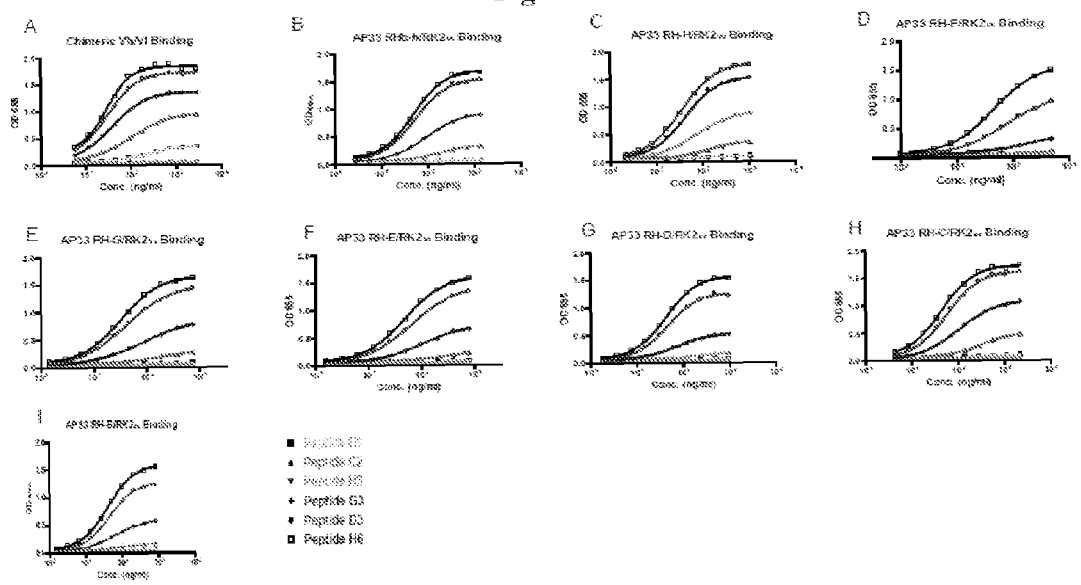
FIGS. 5A-I show the binding of E2 peptides to the humanized heavy chain VC variants. The minimal number of mutations necessary for the humanized heavy chain RHb-h to function was determined by comparing the binding of RHb-h with the back mutated heavy chains RH-B, RH-C, RH-D, RH-E, RH-F, RH-G and RH-H. The chimeric antibody Vh/Vl was included as a comparator to previous experiments and the humanized light chain RK2bc was used to pair with all the humanized heavy chains. COS7 cells were transfected with a series of chimeric and humanized antibody constructs. The binding of antibody supernatants to the E2 peptides (Table 5) were measured by ELISA.
Figure 6:
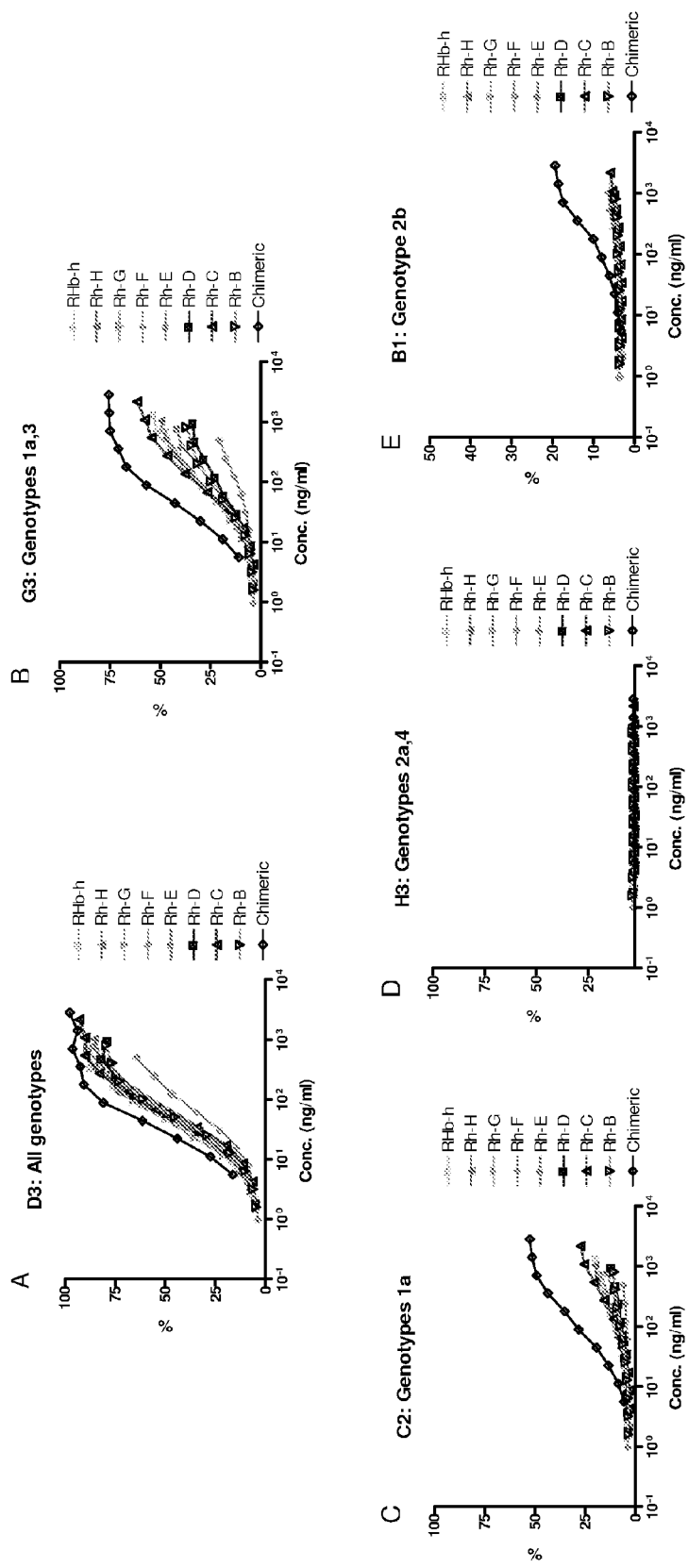
FIGS. 6A-E shows a comparison of humanized antibody VC mutants binding to E2 peptides using normalized data. The data from FIG. 5 was analyzed further by normalizing each data set as a percentage of H6 binding and each genotype grouped together.

The effect of the mutations was assessed by comparing the binding to the peptides described in Table 5 of different versions of the humanized antibody. The results are shown in FIG. 5 and normalized in FIG. 6 by expressing each data set as a percentage of the maximum binding to H6. The results from antibody RH-F suggested that the absence of the VC mutation F (V71R) significantly affected the binding of the antibody. Therefore, despite the presence of all other VC mutations from human to the mouse sequence, Arginine at position 71 is necessary for optimal binding. In all cases where binding could be detected, RH-F bound to the peptides more weakly. However, binding to peptide G3 by the back-mutated variants also identified the original mutations S30T (b), I48M (d) and V67I (e) as being important for binding affinity. Mutations F78Y (g) and R94L (h) were essentially indistinguishable (displaying only marginally less binding when back-mutated, when compared to the RHb-h standard) and so did not appear to be critical to peptide binding. However, antibody version RH-C resulted in an increased binding to peptides G3 and C2 over all other variants, including RHb-h (FIG. 6). In this case mutation c (W47Y) is not present and the human tryptophan residue is retained (but VC mutations S30T, I48M, V67I, V71R, F78Y, and R94L are present). On this basis the humanized antibody containing the heavy chain variant RH-C was chosen to be tested in the HCVpp assays and compared to RHb-h. The humanized antibody RH-H (where the mutation h (R94L) is not present) was also included for testing in the HCVpp assays. The R94L mutation is a canonical and vernier zone residue that supports the H3 loop and we wished to determine if disruption of the H3 loop adversely affected inhibition of HCVpp infection. These heavy chains were co-expressed with the humanized light chain variant RK2b.

Example 13

HCV Pseudoparticle Infection Assays

Figure 7:
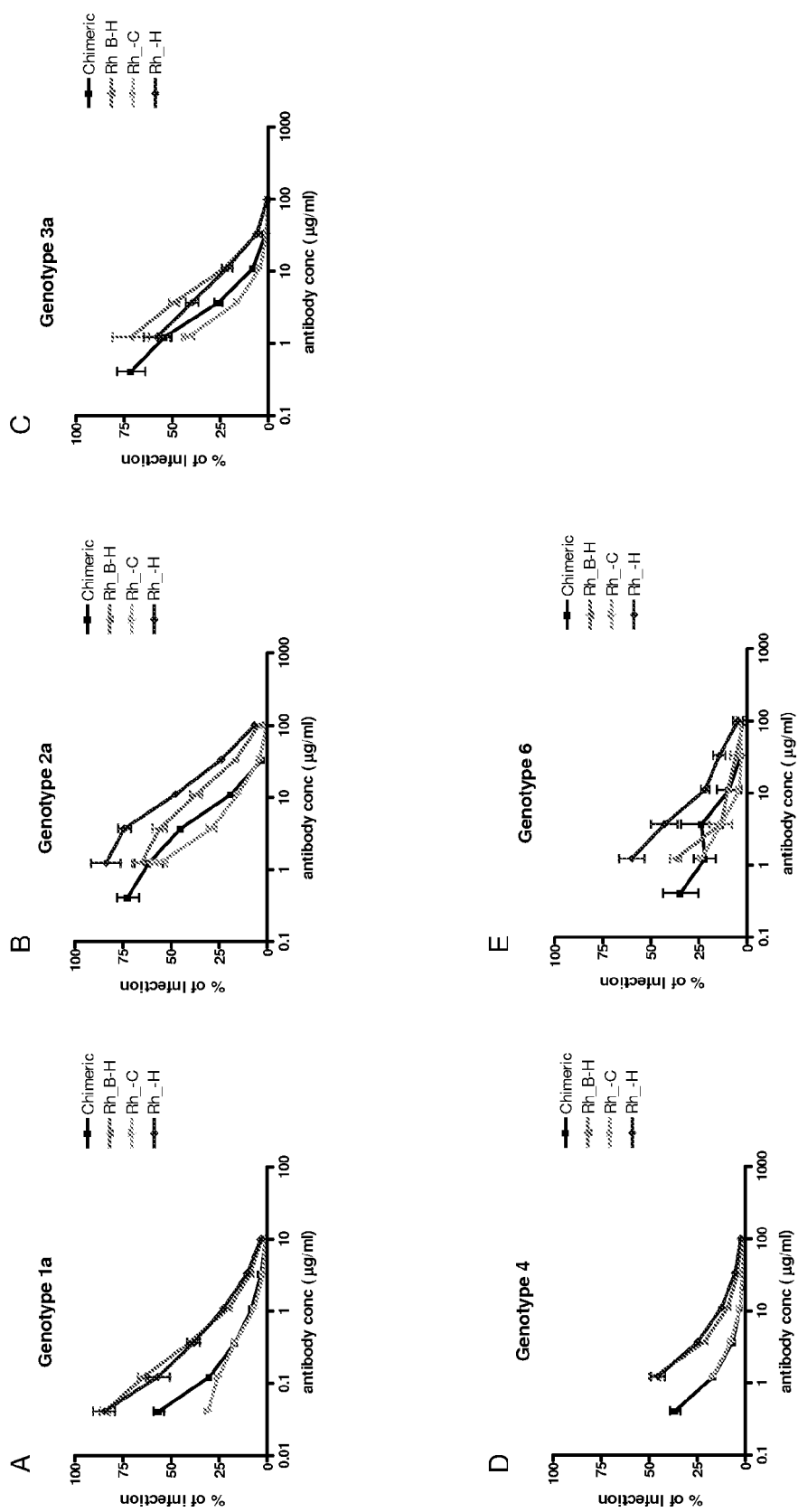
FIGS. 7A-E show that humanized AP33 antibodies inhibit HCVpp infection. Neutralization by chimeric AP33 or humanized antibodies of HCVpp derived from diverse genotypes. HCVpp were preincubated for 1 hour at 37° C. with different concentrations of purified chimeric AP33 or humanized antibodies prior to infection of Huh-7 cells. The neutralizing activity of the antibody is expressed as percentage of inhibition of the infectious titers.
Figure 8:
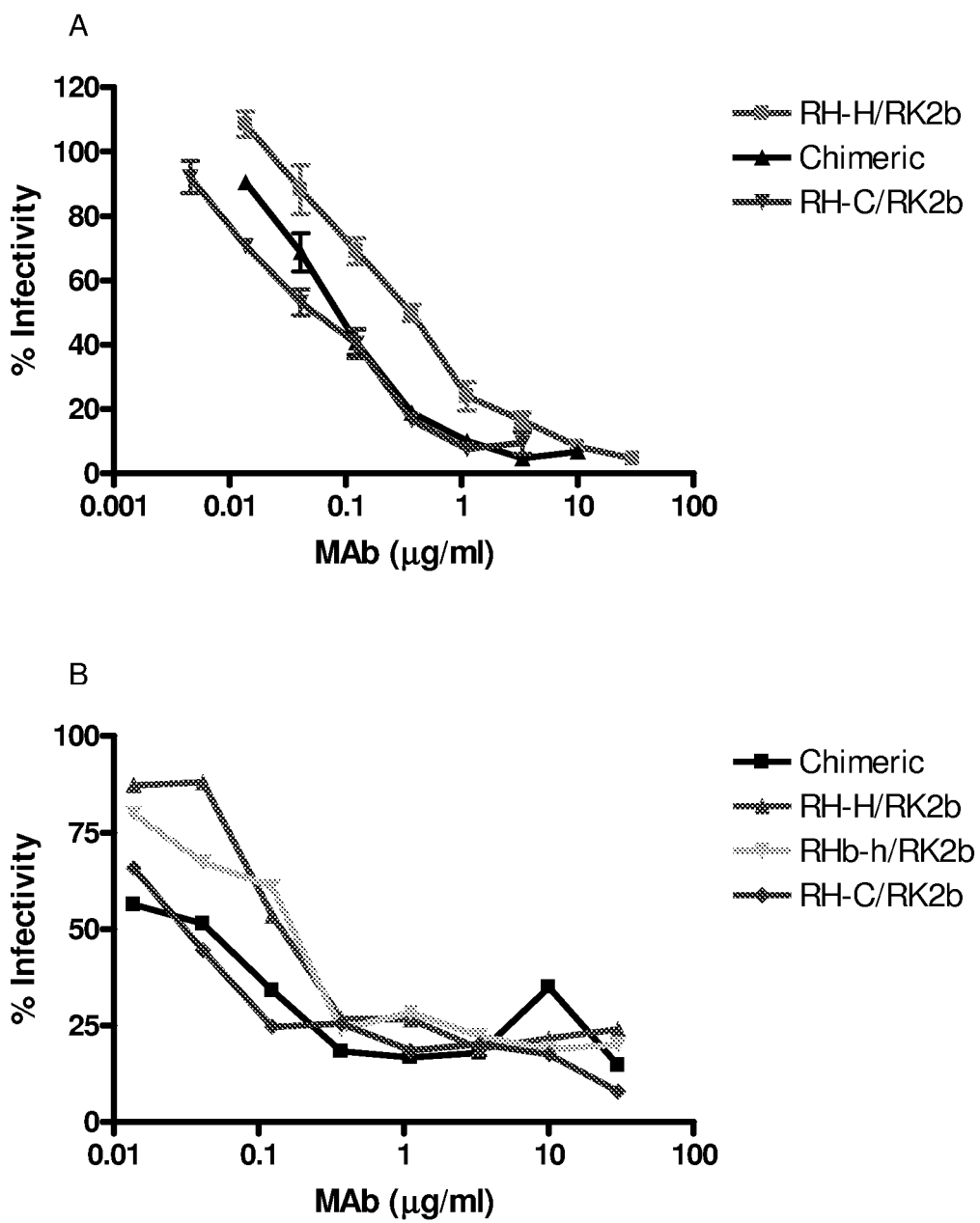
FIGS. 8A-B show the neutralization by chimeric AP33 or humanized antibodies of HCVpp derived from genotype 5. HCVpp were pre-incubated for 1 hour at 37° C. with different concentrations of purified chimeric AP33 or humanized antibodies prior to infection of Huh-7 cells. The neutralizing activity of the antibody is expressed as percentage of inhibition of the infectious titers. Results from two separate experiments are shown.

Three humanized antibodies were tested in the HCVpp infection assays. All humanized heavy chains were paired with light chain RK2b. Although the peptide binding data suggested little difference between the heavy chains RHb-h, RH-C and RH-H, the data shown in FIGS. 7 and 8 suggested that RH-C is the best inhibitor of HCVpp infection. The RH-C antibody was at least as effective as the positive control chimeric AP33, at inhibiting HCVpp infection but the other humanized antibodies RHb-h and RH-H were significantly less effective. The 1050 and IC90 for four experiments are shown in Table 3 and show that the humanized antibody shows very similar 1050 and IC90 values to that of the chimeric antibody across all genotypes.

Figure 9:
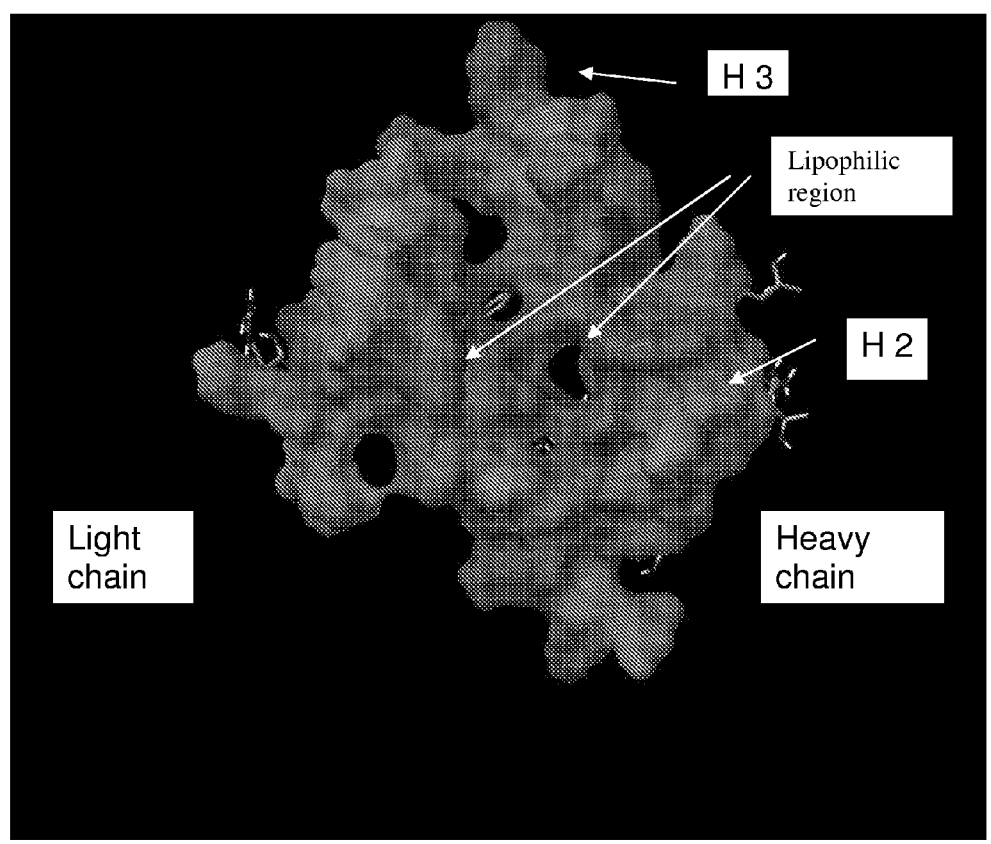
FIG. 9 shows the molecular model of AP33 showing the top view of the CDRs of AP33. The transparent Connolly surface shows the lipophilic regions in brown, Vernier and canonical residues are depicted as tapered sticks. The view is looking down on CDRs from above. The Loops H1, H2, L3, and L1 help to form a valley shaped structure that is lipophilic
Figure 10:
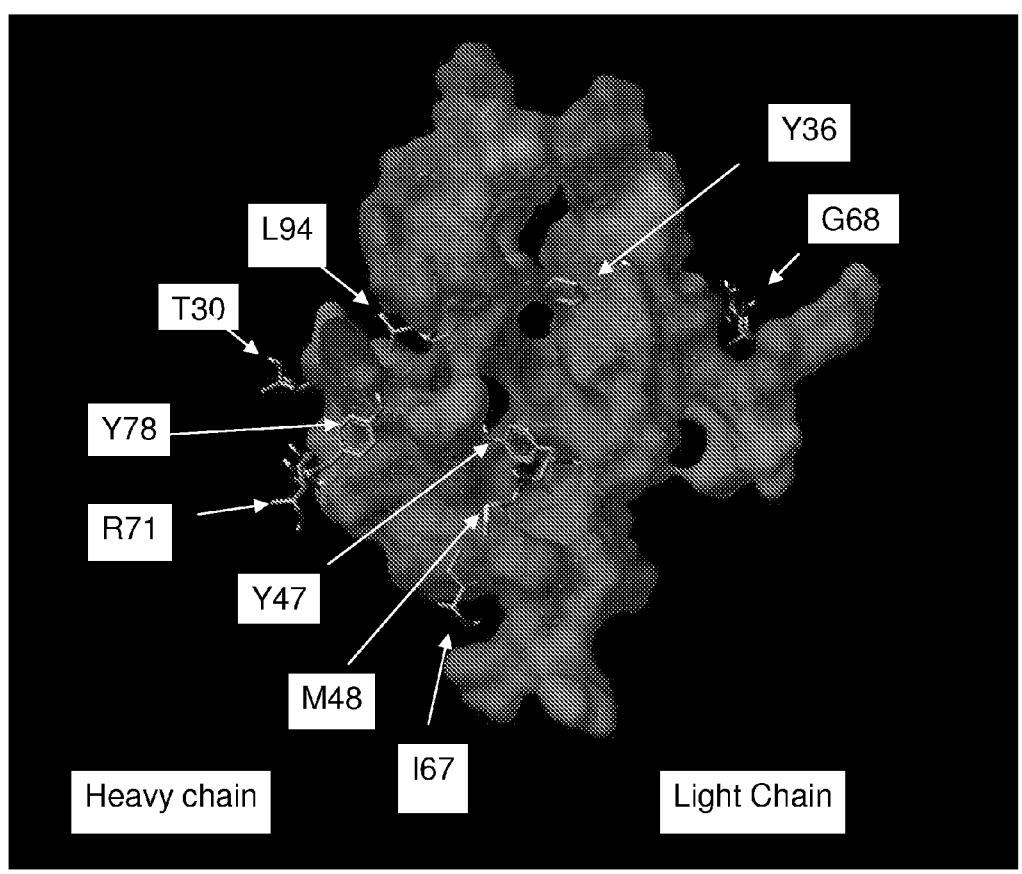
FIG. 10 shows the molecular model of AP33 showing the bottom view of the CDRs of AP33, The transparent Connolly surface shows the lipophilic regions in brown. Vernier and canonical residues are depicted as tapered sticks.

This result was unexpected since the location of the back-mutation in RH-C (i.e., residue position 47), is both a vernier and interface residue suggesting that the tryptophan residue found in the original human FW may either improve the interface between the heavy and light chains, or may better support the H2 loop, or may do both (FIGS. 9 and 10). In addition, the tryptophan residue may augment the lipophilic area identified in FIG. 9 and perhaps contribute to binding.

The tryptophan residue present in the AP33 epitope has been shown to be crucial for AP33 binding. See Tarr A. W. et al., *Hepatology* 43:592-601 (2006). The position of the mouse heavy chain residue Y47 is shown in FIG. 10 which also shows the positions of the vernier and canonical residues that have been mutated in the humanized antibody. The Y47 residue lies directly underneath a lipophilic region of the CDRs and it is a reasonable supposition that the Y47W mutation helps to fill a gap at the base of the lipophilic region.

One method that may help to elucidate the nature of the improved binding mediated by the Y47W mutation is a kinetic analysis of antibody E2 binding. However, we have been unable to perform kinetic analysis of the interaction between RH-C and the E2 protein. The HCV E2 protein forms aggregates when purified. Unfortunately, monomeric E2 protein, which so far is unavailable, is necessary to measure binding affinity to antibody.

The data from the peptide analysis suggested that there is very little difference between the binding of heavy chain versions RH-G and RH-H. It would be interesting to test these versions combined with RH-C in the HCV pseudoparticle experiments. It is plausible that there may be a positive effect on binding and inhibition since these residues might help support the H2 and H3 loops respectively.

Example 14

Analysis of the Chimeric Mutants AP33 Y47F and Y47W

In order to further investigate the contribution of residue Y47 to binding, two chimeric heavy chain mutants were made, Y47W and Y47F. Both these mutants were expressed in association with the chimeric light chain, Vl and compared to AP33 in the HCVpp infection assays and peptide binding.

Figure 11:
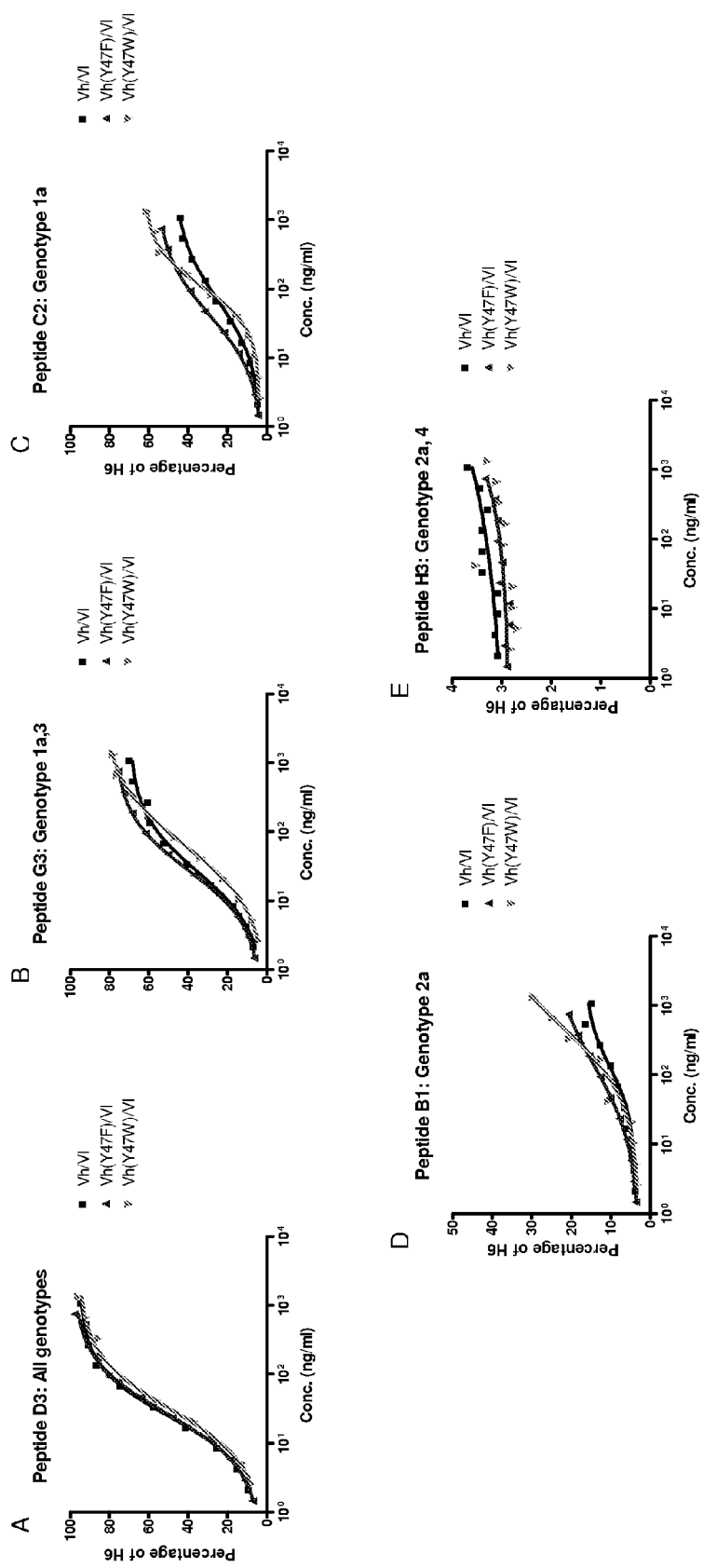
FIGS. 11A-E show the binding of AP33 mutants Y47F and Y47W to E2 peptides. The impact of mutating residue Y47 of the chimeric heavy of AP33. The binding of the E2 peptides shown in Table 5 were used to compare wild type heavy chain AP33 and the mutants Y47F and Y47W. COST cells were transfected with a series of chimeric and mutant antibody constructs. The binding of antibody supernatants to the E2 peptides were measured by ELISA. The data was manipulated by normalizing each data set as a percentage of H6 binding and each genotype grouped together.
Figure 12:
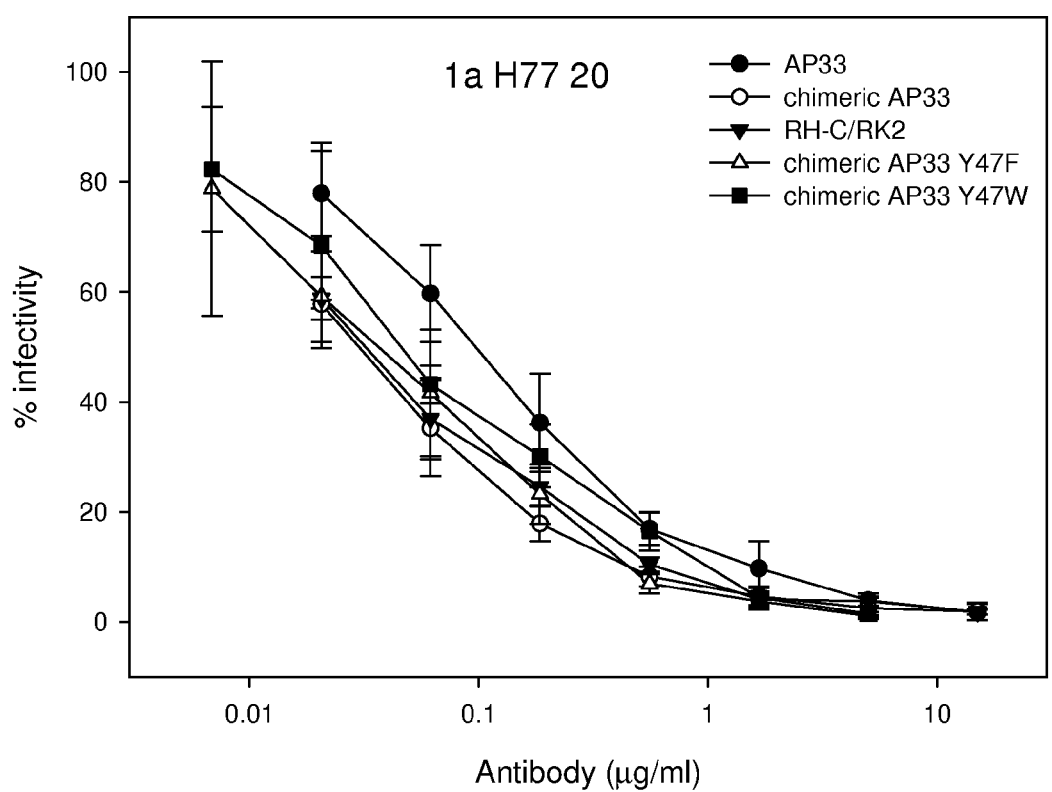
FIG. 12 shows inhibition of HCVpp infection by AP33 mutants Y47F and Y47W. Neutralization by chimeric AP33 or humanized antibodies of HCVpp derived from 1a genotype. HCVpp were preincubated for 1 hour at 37° C. with different concentrations of purified chimeric AP33 or humanized antibodies prior to infection of Huh-7 cells. The neutralizing activity of the antibody is expressed as percentage of inhibition of the infectious titers.

The data from the peptide binding experiments (FIG. 11) suggest that making residue tyrosine 47 more hydrophobic, by substitution with a phenylalanine or tryptophan, may improve binding to some E2 peptides, especially peptide B1 (genotype 2a). However when the antibodies were used in the HCVpp infection assay against a genotype 1a (from isolate 1a H77.20) shown in FIG. 12, there was no enhancement of inhibition by either Y47W or Y47F mutation. It may be concluded therefore that the improved Y47W mutation in RH-C is specific to the humanization although further HCVpp infection assays need to be carried out on a variety of genotypes to determine if the Y47W mutation in AP33 may generally improve the antibody potency of infection inhibition.

Example 15

Materials and Methods

The following materials and methods were used for the experiments described in Example 15A-C.

Generation of Baculovirus Expressed Soluble E2 (sE2)

sE2 expression: Soluble E2 (sE2) were generated by deleting the transmembrane domains by truncating at amino acid 661 (sE2661) as described previously. See Roccasecca, R. et al., *J Virol* 77:1856-67 (2003). sE2661 was cloned into a baculovirus transfer vector co-transfected with BacPak6 linearized viral DNA (BD Clontech) into adherent Sf-9 insect cells cultured in ESF921 protein-free medium (Expression Systems, LLC) at 27° C. The resulting viral stock was amplified twice using standard baculovirus methods before use in large-scale protein production. The production was done in Wave™ bioreactors (GE Bioscience). Ten-liter T.ni Pro cells (Expression Systems, LLC) cultures were grown to $2\times10^6$ cells/mL and infected with 50 mL of the viral stock as prepared above. The supernatant was harvested 48 hours post infection by centrifugation 3000×g for 15 minutes and filtered through a 0.2 μM filter prior to purification.

sE2 purification: The 10 L baculovirus supernatant was batched with 50 mL of Nickel-NTA resin. The HIS-tagged soluble E2 was eluted off of the resin with 250 mM Imidazole in PBS+0.3M NaCl. The elution was diluted into 20 mM NaAcetate, pH 5.0 and loaded over a 34 mL SpFF cation exchange column, and the protein was eluted off in the acetate buffer with 0.3M NaCl. The elution was then loaded over a 24 mL S200 gel filtration column in PBS+0.15M NaCl and dialyzed into PBS buffer. In Source Decay using mass spectrometry, the N-terminus matched the expected N-terminus of the secreted protein.

Determining AP33/RH-C/RK2b Affinity to HCV E2

BIAcore assay: Surface plasmon resonance (SPR) measurements on a BIAcore A100 instrument were used to determine affinity for binding of soluble E2 (sE2) to antibody. A format of capture of the humanized antibody on an anti-human Fc sensor chip surface, followed by injection of a varied concentration of sE2, was employed. The anti-human Fc antibody was covalently linked to the sensor chip surface using amine chemistry, as suggested by the manufacturer. The humanized antibody was captured by injecting 60 μL of a 0.5 μg/mL solution at a flow rate of 30 μL/min. Sensorgrams were collected for 60 μL injections of sE2 solutions followed by monitoring of dissociation for 480 s. The sensor chip surface was regenerated by injection of a 15 μL aliquot of 3 M MgCl2 resulting in dissociation of the antibody-antigen complex from capture antibody. Measurements were repeated with sE2 concentrations ranging from 1.56 nM to 50 nM in 2-fold increments. All measurements included real-time subtraction of data from a reference flow cell with no captured anti-E2 antibody. A sensorgram for injection of buffer alone was also subtracted. The running buffer was Hepes-buffered saline, pH 7.2, and the temperature was 25° C. These data were analyzed with a 1:1 Langmuir binding model, using software supplied by the manufacturer, to determine the kinetics constants.

Scatchard Analysis:

Affinity of RH-C/RK2b to HCV E2, as part of the E1E2 heterodimer expressed on the surface of 293T cells, was determined using a radioligand cell binding assay. The anti-HCV antibodies, RH-C/RK2b and RH-C/RK2b Fab, were iodinated using the Iodogen method. The radiolabeled anti-HCV antibodies were purified from free 125I-Na by gel filtration using a NAP-5 column. The purified RH-C/RK2b and RH-C/RK2b Fab antibodies had a specific activity of 17.96 μCi/μg and 55.21 μCi/μg, respectively. Competition reaction mixtures of 50 μL volume containing a fixed concentration of iodinated antibody and decreasing concentrations of serially diluted unlabeled antibody were placed into 96-well plates. 293T cells were transfected with Fugene6 transfection reagent (Roche) as per manufacturer's recommendations. Cells were transfected with 25 μg/mL plasmids plus 100 μL Fugene6 reagent in a final volume of 25 mL of Freestyle medium (Invitrogen, Gibco) without any supplements. Cells were detached from plates 48 hours post transfection using Sigma Cell Dissociation buffer, washed with binding buffer (50:50 DMEM/F12 with 2% FBS, 50 mM HEPES, pH 7.2, and 2 mM sodium azide) and added at an approximate density of $2\times10^5$ cells in 0.2 mL of binding buffer to the 50 μL competition reaction mixtures. The final concentration of the iodinated antibody in each competition reaction with cells was ~200 pM for RH-C/RK2b and ~500 pM for RH-C/RK2b Fab and the final concentration of the unlabeled antibody in the competition reaction with cells varied, starting at 500 nM and then decreasing by 1:2 fold for 10 concentrations. Competition reactions with cells were incubated at RT for 2 hours. Competition reaction with cells for each concentration of unlabeled antibody was assayed in triplicate. After the incubation, the competition reactions were transferred to a Millipore Multiscreen filter plate and washed 4× with binding buffer to separate the free from bound iodinated antibody. The filters were counted on a Wallac Wizard 1470 gamma counter (PerkinElmer Life and Analytical Sciences Inc.). The binding data was evaluated using NewLigand software (Genentech), which uses the fitting algorithm of Munson and Robard (Munson, P. J., and D. Rodbard, *Anal Biochem* 107:220-39 (1980)) to determine the binding affinity of the antibody.

Generation of Infectious Cell Culture HCV (HCVcc)

Generation of Plasmids Encoding Full Length HCVcc Genomes:

Full length HCV genomes for Jc1 (J6/C3) and Con1/C3 were chemically synthesized by outsourcing to Gene Oracle Inc. (Mountain View, Calif.) using DNA sequences for HC-J6 (CH) (J6), JFH-1 and Con1 as described in the NCBI database [accession numbers AF177036, AJ238799 and AB047639 for HC-J6(CH) (clone pJ6CF), Con1 and JFH-1, respectively] Chimeric HCVcc viruses that encode the J6 and Con1 structural regions (core-E1-E2-p7-part of NS2) fused to the JFH-1 NS2-NS5B region were generated as described previously (Pietschmann, T. et al., *Proc Natl Acad Sci USA* 103:7408-13 (2006)). To make the Con1/C3-neo HCVcc, a DNA fragment containing the 5'-untranslated region (UTR) followed by the neomycin resistance gene and the Encephalomyocarditis virus internal ribosome entry site (EMCV IRES) element flanked by EcoRI and PmeI restriction sites was chemically synthesized by outsourcing to Gene Oracle Inc. (Mountain View, Calif.). The plasmid encoding Con1/C3-neo HCVcc was generated by digesting with EcoRI and PmeI. Both Jc1

(J6/C3) and Con1/C3-neo DNA fragments were ligated into pUC19 vector using unique EcoRI and XbaI restriction sites to generate pUC-Jc1 and pUC-Con1/C3-neo.

In Vitro Transcription Reactions:

pUC-Jc1 and pUC-Con1/C3-neo plasmids were digested with XbaI, which is located at the 3' end of the HCV genome. 30 μg of pUC-Jc1 and pUC-Con1/C3-neo were digested overnight at 37° C. using 20 U XbaI in a final volume of 300 μl. The following day, RNA was extracted using acid phenol as described previously. See Kapadia, S. B. et al, *J Virol* 81:374-83 (2007). In vitro transcription reactions were performed using the T7 Megascript kit (Ambion) as per manufacturer's recommendations. HCV RNA was extracted using phenol/chloroform and ethanol precipitation, as described previously. See Kapadia, S. B. et al., *J Virol* 81:374-83 (2007)). RNA was stored at −70° C.

Generation of HCVcc Stocks:

Huh-7.5 cells were cultured in complete Dulbecco's modified Eagle's medium (c-DMEM) (supplemented with 10% fetal bovine serum [FBS], 100 U/ml penicillin, 100 mg/ml streptomycin, 2 mM L-glutamine, and 0.1 mM nonessential amino acids) under an atmosphere of 5% $CO_2$ at 37° C. On the day of transfection, cells were trypsinized, washed twice with Opti-MEM medium (Gibco) and resuspended at a final concentration of $10^7$ cells/ml in Opti-MEM. 400 μl of cells ($4\times10^6$ cells) plus 10 μg of in vitro transcribed Jc1 or Con1/C3-neo RNA were added to 0.4 cm electroporation cuvettes (BioRad). Electroporation was performed using a Gene Pulser (BioRad) using the following parameters: 0.27 kV, 100 Ohms and 950 μF. The cuvettes were incubated at RT for 10 minutes to allow the cells to recuperate before transferring the cells into one T162 flask containing c-DMEM. Cells were trypsinized and split when cultures reached 80-90% of confluency as required. Supernatants were harvested starting at 3 days post transfection, clarified and infectious viral titers were measured using the $TCID_{50}$ calculation method as described previously. See Lindenbach, B. D., et al., *Science* 309:623-6 (2005). Supernatants were aliquoted and stored at −70° C.

Generation of HCV Pseudoparticles (HCVpp)

Plasmids:

Plasmids expressing E1 and E2 glycoproteins from HCV genotypes 1a (H77), 1b (Con1) and 2a (J6) were generated as previously described (Hsu, M. et al, *Proc Natl Acad Sci USA* 100:7271-6 (2003)) with some modifications. Briefly, the region encoding E1 and E2 (and containing the signal peptide from the C-terminus of HCV core) was cloned into the pRK mammalian expression vector to generate the expression plasmids, pRK-H77, pRK-Con1 and pRK-J6, respectively. The A8.9 packaging plasmid was originally acquired by Genentech from Greg Hannon (Cold Spring Harbor Labs)/David Baltimore (Cal Tech). See Zufferey et al., *Nature Biotechnology* 15:871-875 (1997). The FCMV-Luc-IRES-dsRED plasmid is a modified pFUGW plasmid, which was obtained by Genentech from Greg Hannon at Cold Spring Harbor Labs, and encodes firefly luciferase and DsRed driven by the HCMV promoter and IRES element, respectively.

HCVpp were produced in HEK 293T cells as described previously (Bartosch, B. et al., *J Exp Med* 197:633-42 (2003)) with some modifications. Briefly, $2.5\times10^6$ 293T cells were seeded the day before in 10-cm plates. The following day, the cells were co-transfected with the FCMV-Luc-IRES-DsRed plasmid (5 μg), A8.9 transfer vector (10 μg) and either the pRK-H77, pRK-Con1 or pRK-J6 plasmids (1 μg) using Lipofectamine 2000 (Invitrogen), as per manufacturer's recommendations. Six hours post-transfection the OptiMEM medium (Invitrogen, Gibco) was replaced with c-DMEM. Two days post transfection, supernatants were harvested, clarified and further purified by ultracentrifugation (3000 rpm for 5 minutes) and used in infectivity assays. $5\times10^3$ Huh-7.5 cells were seeded in white walled 96-well plates (Costar). The following day, cells were transduced with appropriate dilution of HCVpp. Seventy-two hours post-infection, cells were lysed in 1× lysis buffer and luciferase activity was measured using the Luciferase Assay System (Promega), as per manufacturer's recommendations.

ELISA Assay to Determine Antibody Binding to HCV E2

Preparation of E2 Lysates:

293T cells were transiently transfected with 10 μg pRK-H77, pRK-Con1 or pRK-J6 μlasmids using Lipofectamine 2000, as per manufacturer's recommendations. Forty-eight hours post transfection, cells were washed with PBS and then lysed in 1 μL lysis buffer (20 mM Tris-HCl, pH 7.4; 150 mM NaCl; 1 mM EDTA; 0.5% NP-40; 20 mM iodoacetamide). The lysate was incubated with shaking at 4° C. for 20 minutes and centrifuged for 5 minutes. The clarified supernatant as then used to coat the ELISA plates.

HCV E2 ELISA: ELISA assay was performed as previously described. See Owsianka, A. et al., *J Virol* 79:11095-104 (2005). Briefly, 96-well Immulon 2 plates were coated with 0.25 μg/well *Galanthus nivalis* lectin (GNA, Sigma) in 100 μL PBS and incubated' at RT overnight. The following day, plates were washed 3× with PBS containing 0.02% Tween-20 (PBST), coated with cell lysate diluted in PBST and incubated at RT for 2 hours. Dilutions of chronic HCV-infected patient sera were diluted in 2% skimmed milk powder/PBST and incubated for 1 hour at RT. After 3× washes with PBST, 100 μL/well of anti-human HRP conjugated secondary antibody was added at a dilution of 1:1000 in PBST and incubated for 1 hour at RT. Wells were washed 6× with PBST and wells were incubated with 100 μL TMB substrate in the dark at RT for 30 minutes. Reactions were stopped by adding 50 μL/well of 0.5M $H_2SO_4$ and $A_{450}$ was measured using a Synergy 2 plate reader (BioTek Instruments).

HCVcc Infection Assays

For infections in 96-well plates, $5\times10^3$ Huh-7.5 cells/well were plated. The following day, the cells were infected with Jc1 or Con1/C3-neo HCVcc at a multiplicity of infection (MOI)=0.3. To identify antibodies that neutralize HCVcc, antibodies were diluted to 150 μg/ml in c-DMEM and seven 3-fold dilutions of the antibody were made in a separate 96-well plate. HCVcc and antibody dilutions were combined and pre-incubated for 1 hour at 37° C. prior to inoculating naïve Huh-7.5 cells. Total RNA was harvested 3 days post infection and HCV RNA replication (measured as a ratio of HCV/GAPDH cDNA) was determined using RT-qPCR, as described below.

Quantitation of HCV Infection

HCVcc RNA replication: For experiments performed in 96-well plates, total RNA was extracted using the SV96 Total RNA Isolation System (Promega), according to manufacturer's instructions. RNA from each well was eluted into 100 μL of RNase-free water and 4 μL of RNA was reverse transcribed using the Taqman Reverse Transcription Reagent Kit (Applied Biosystems). RT-qPCR was performed using 5 μL of cDNA in a 25 μL reaction using TaqMan Universal PCR Master Mix (Applied Biosystems). In all reactions, expression of the housekeeping gene glyceraldehyde-3-phosphate dehydrogenase (GAPDH) was determined as an internal endogenous control for amplification efficiency and normal ization. The primers and probes for HCV and GAPDH are as follows:

```
GT1b sense primer,                          (SEQ ID NO: 55)
5'-CTGCGGAACCGGTGAGTACA-3';

GT1b anti-sense primer,                     (SEQ ID NO: 56)
5'-TGCACGGTCTACGAGACCTCC-3';

GT1b probe,                                 (SEQ ID NO: 57)
6FAM-ACCCGGTCGTCCTGGCAATTCC-MGBNFQ;

GT2a sense primer,                          (SEQ ID NO: 58)
5'-CTTCACGCAGAAAGCGCCTA;

GT2a anti-sense primer,                     (SEQ ID NO: 59)
5'-CAAGCACCCTATCAGGCAGT-3';

GT2a probe,                                 (SEQ ID NO: 60)
6FAM-TATGAGTGTCGTACAGCCTC-MGBNFQ;

GAPDH sense primer,                         (SEQ ID NO: 61)
5'-GAAGGTGAAGGTCGGAGTC-3';

GAPDH anti-sense primer,                    (SEQ ID NO: 62)
5'-GAAGATGGTGATGGGATTTC-3';

GAPDH probe,                                (SEQ ID NO: 63)
VIC-ATGACCCCTTCA TTGACCTC-MGBNFQ.
```

Fluorescence was monitored using a 7500 HT real-time PCR machine (Applied Biosystems, CA).

Titration of Infectious HCVcc:

Infectious HCVcc present in the supernatants of infected cells was measured as described previously, See Lindenbach, B. D. et al., *Science* 309:623-6 (2005). Briefly, titrations were performed by seeding $5 \times 10^3$ Huh-7.5 cells in poly-L-lysine coated 96-well plates. The following day, cells were inoculated with 10-fold dilutions of supernatants in a final volume of 100 μL. Three days later, cells were fixed with 4% paraformaldehyde in PBS and immunostained as described previously (Kapadia, S. B. et al., *J Virol* 81:374-83 (2007)) with an anti-HCV core antibody, C7-50 (Abcam). Titers were calculated according to the method of Reed and Muench as described previously. See Lindenbach, B. D. et al., *Science* 309:623-6 (2005).

Effect of Sera from Chronically HCV-Infected Patients on RH-C/RK2b-Mediated Neutralization To determine whether sera from chronic HCV-infected patients antagonized RH-C/RK2b-mediated neutralization of HCV infection in vitro, neutralization assays were performed using the HCVpp system. HCVpp was incubated with different concentrations of RH-C/RK2b for 1 h at 37° C. in the presence of either 10% fetal bovine serum (FBS), 10% normal human serum (NHS), or 10% of sera from chronic HCV-infected patients (CHCHS-1, 2 and 3). Huh −7.5 cells seeded in 96-well plates were inoculated with the HCVpp: antibody mixture. Four hours post-transduction, the medium was replaced with c-DMEM containing 10% FBS plus supplements for the remainder of the assay. Three days later, cells were lysed and luciferase activity was measured as described above. Levels of anti-HCV E1/E2 antibodies were determined using ELISA as described above.

Example 15A

Neutralization of HCVcc and HCVpp by RH-C/RK2b

To determine whether RH-C/RK2b inhibits HCV entry and infection, a neutralization assay was performed in Huh-7.5 cells using both HCVpp and HCVcc. AP33 was used as a control. To identify the specific inhibition of HCV entry by RH-C/RK2b, HCVpp containing E1E2 sequences from GT1b (Con1) or GT2a (J6) were incubated in the presence of AP33 or RH-C/RK2b. RH-C/RK2b inhibited Con1 and J6 HCVpp entry equivalently ($EC_{50}$=0.511 μg/mL and 0.793 μg/mL for Con1 and J6 HCVpp, respectively). See FIGS. 39A-C. In addition, RH-C/RK2b neutralization of both HCVpp genotypes was comparable to that seen with AP33 ($EC_{50}$=1.417 μg/mL and 2.066 μg/mL for Con1 and J6 HCVpp, respectively (FIGS. 39A-C).

To determine if RH-C/RK2b neutralized the infectious cell culture virus (HCVcc), similar neutralization assays were performed with AP33 and RH-C/RK2b. AP33 inhibited both Con1 and J6 HCVcc to levels comparable to that previously described for HCVpp containing E1E2 sequences from multiple genotypes (Owsianka, A. et al., *J Virol* 79:11095-104 (2005)). While RH-C/RK2b inhibited Con1 HCVcc infection to levels comparable to AP33 (FIGS. 40A and C), RH-C/RK2b inhibited J6 HCVcc at least ~4.7-fold better than AP33 (FIGS. 40B-C).

Example 15B

Affinity Measurements of Anti-HCV E2 Antibodies to E2

In further experiments, the affinity of AP33 and RH-C/RK2b to soluble E2 (sE2) was determined by BIAcore assays. Both AP33 and RH-C/RK2b bound sE2 with similar affinities (~5-8 nM for AP33 and ~3.8 nM for RH-C/RK2b). In comparison, the Fab fragments of each antibody bound sE2 with an affinity of ~50 nM. In addition to binding sE2 protein, binding of AP33 and RH-C/RK2b to E1E2 heterodimers expressed on the surface of 293T cells was determined. Since it is known that 293T cells transfected with plasmids encoding E1E2 express functional E1E2 heterodimers on their cell surface, scatchard analysis was performed to determine affinities of RH-C/RK2b and RH-C/RK2b Fab. Affinities of RH-C/RK2b and RH-C/RK2b Fab to cell surface expressed E2 (~5 and ~50 nM, respectively) were comparable to that seen with sE2 in the BIAcore assay described above. See Table 10.

TABLE 10

| Antibody | Antibody Affinity (nM) | |
|---|---|---|
|  | sE2 | E1E2 Scatchard |
| AP33 | 5-8 |  |
| AP33 Fab | 50 |  |
| RH-C/RK2b | 3.8 ± 0.6 | 5 |
| RH-C/RK2b Fab |  | 50 |

Example 15C

Sera from Chronic HCV-Infected Patients do not Antagonize RH-C/RK2b-Mediated Neutralization In order to determine whether chronic patient sera, which contain anti-HCV antibodies, can antagonize the neutralizing ability of RH-C/RK2b, a neutralization assay was performed using Con1 HCVpp in the presence of 10% normal human serum (NHS) or sera from chronic HCV-infected patients (CHCHS-1 and -2). RH-C/RK2b inhibited HCV infection to comparable levels irrespective of the source of human serum (FIG. 41A). To determine whether these chronic HCV-infected patient sera contained antibodies against genotype 1b, an ELISA assay was performed using lysates from GT1b (Con1) E1E2-transfected 293T cells. 3-fold dilutions of RH-C/RK2b starting at an initial concentration of 10 μg/mL were used as controls. While no binding to E2 was detected with NHS, dose-dependent binding was detected with both chronic HCV-infected patient sera, suggesting that they contained Con1 HCV E1E2-reactive antibodies. See FIG. 41B. These results suggest that while anti-HCV antibodies do exist in patient sera, they do not interfere with the ability of RH-C/RK2b to neutralize HCV in vitro.

REFERENCES

1. Anonymous, *J Viral Hepatology* 6:35-47 (1999).
2. Yagnik A T et al., *Proteins* 40:355-66 (2000).
3. Owsianka A. et al., *J Gen Virol* 82:1877-83 (2001).
4. Patel A. H. et al., *J Gen Virol* 81:2873-83 (2000).
5. Owsianka A. et al., *J Virol* 79:11095-104 (2005).
6. Fiser A et al., *Protein Sci* 9:1753-73 (2000).
7. Fiser A. and Sali A., *Methods Enzymol* 374:461-91 (2003).
8. Sali A, and Blundell T. L., *J Mol Biol* 234:779-815 (1993).
9. Saldanha J. W. et al., *J Mot Biol Immunol* 5391(22436): 487709-99719 (1992).
10. Foote J. and Winter G., *J Mol Biol* 224:487-99 (1992).
11. Chothia C, et al., *J Mol Biol* 186:651-63 (1985).
12. Chothia C, et al., *Nature* 342:877-83 (1989).
13. Tarr A. W. et al., *Hepatology* 43:592-601 (2006).
14. Mierau R. et al., *Rheumatol Int* 12:23-31 (1992).
15. Ghosh S. et al., *J Immunol* 174:2860-9 (2005).
16. Nielsen H. et al., *Protein Eng.* 10:1-6 (1997).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A humanized antibody that binds hepatitis C virus E2 protein or an antigen binding fragment thereof, wherein the humanized antibody or antigen binding fragment thereof comprises a heavy chain variable domain selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

2. A humanized antibody that binds hepatitis C virus E2 protein or an antigen binding fragment thereof, wherein the humanized antibody or the antigen binding fragment thereof comprises a light chain variable domain selected from the group consisting of SEQ ID NO:6, SEQ ID NO:7, SEQ ID NO:19, and SEQ ID NO:20.

3. The humanized antibody or antigen binding fragment thereof of claim 1, wherein the humanized antibody or the antigen binding fragment thereof comprises a light chain variable domain selected from the group consisting of SEQ ID NO:6, SEQ ID NO:7, SEQ ID NO:19, and SEQ ID NO:20.

4. The humanized antibody or antigen binding fragment thereof of claim 3, wherein the antigen binding fragment thereof is selected from the group consisting of a Fab fragment, a Fab' fragment, a F(ab')2 fragment, a scFv, a Fv, and a diabody.

5. A composition comprising the humanized antibody or antigen binding fragment thereof of claim 3 and a carrier or excipient.

6. A kit comprising the humanized antibody or antigen binding fragment thereof of claim 3 and instructions for administering said humanized antibody or antigen binding fragment thereof.

7. An in vitro assay method for identifying an agent that improves or enhances the efficacy of the neutralizing activity of the humanized antibody or antigen binding fragment thereof of claim 3 against hepatitis C virus, comprising the steps of (a) contacting said humanized antibody or antigen binding fragment thereof with an agent to be tested; and (b) determining whether the agent improves or enhances the efficacy of the humanized antibody or antigen binding fragment thereof in neutralizing the infectivity of hepatitis C virus.

8. A method for determining the presence or absence of hepatitis C virus in a sample from a subject, the method comprising the step of: contacting the sample with the humanized antibody or antigen binding fragment thereof of claim 3.

* * * * *

```
                              SEQUENCE LISTING

<160> NUMBER OF SEQ ID NOS: 293

<210> SEQ ID NO 1
<211> LENGTH: 117
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr Tyr Asn Leu Ser Leu Arg
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Leu Ile Thr Thr Thr Thr Tyr Ala Met Asp Tyr Trp Gly Gln Gly Thr
            100                 105                 110

Ser Val Thr Val Ser
        115

<210> SEQ ID NO 2
<211> LENGTH: 111
<212> TYPE: PRT
<213> ORGANISM: Artificial Sequence
<220> FEATURE:
<223> OTHER INFORMATION: Synthetic Construct

<400> SEQUENCE: 2

Asn Ile Val Leu Thr Gln Ser Pro Val Ser Leu Ala Val Ser Leu Gly
 1               5                  10                  15

Gln Arg Ala Thr Ile Ser Cys Arg Ala Ser Glu Ser Val Asp Gly Tyr
            20                  25                  30
```

```
Gly Asn Ser Phe Leu His Trp Phe Gln Gln Lys Pro Gly Gln Pro
            35                  40                  45

Lys Leu Leu Ile Tyr Leu Ala Ser Asn Leu Asn Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                85                  90                  95

Val Asp Pro Trp Thr Phe Gly Gly Gly Thr Lys Leu Glu Ile Lys
            100                 105                 110
```

<210> SEQ ID NO 3
<211> LENGTH: 117
<212> TYPE: PRT
<213> ORGANISM: Artificial Sequence
<220> FEATURE:
<223> OTHER INFORMATION: Synthetic Construct

<400> SEQUENCE: 3

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Gly
                20                  25                  30

Tyr Trp Asn Trp Ile Arg Gln Pro Pro Gly Arg Ala Leu Glu Trp Ile
            35                  40                  45

Gly Tyr Ile Ser Tyr Ser Gly Ser Thr Tyr Tyr Asn Leu Ser Leu Arg
 50                  55                  60

Ser Arg Val Thr Ile Ser Val Asp Thr Ser Lys Asn Gln Phe Ser Leu
 65                  70                  75                  80

Arg Leu Ser Ser Val Thr Ala Ala Asp Thr Ala Met Tyr Tyr Cys Ala
                85                  90                  95

Arg Ile Thr Thr Thr Thr Tyr Ala Met Asp Tyr Trp Gly Gln Gly Thr
            100                 105                 110

Thr Val Thr Val Ser
        115
```

<210> SEQ ID NO 4
<211> LENGTH: 111
<212> TYPE: PRT
<213> ORGANISM: Artificial Sequence
<220> FEATURE:
<223> OTHER INFORMATION: Synthetic Construct

<400> SEQUENCE: 4

```
Asp Ile Val Leu Thr Gln Ser Pro Asp Ser Leu Ser Val Ser Leu Gly
 1               5                  10                  15

Glu Arg Val Thr Val Asn Cys Arg Ala Ser Glu Ser Val Asp Gly Tyr
                20                  25                  30

Gly Asn Ser Phe Leu His Trp Phe Gln Gln Asn Pro Gly Gln Pro Pro
            35                  40                  45

Lys Leu Leu Ile Tyr Leu Ala Ser Asn Leu Asn Ser Gly Val Pro Ala
 50                  55                  60

Arg Phe Met Gly Ser Gly Ser Gly Thr Glu Phe Ser Leu Thr Ile Ser
 65                  70                  75                  80

Ser Leu Gln Ala Glu Asp Val Ala Val Tyr Tyr Cys Gln Gln Asn Asn
                85                  90                  95

Val Asp Pro Trp Thr Phe Gly Gln Gly Thr Lys Leu Glu Ile Asn
```

<210> SEQ ID NO 5
<211> LENGTH: 111
<212> TYPE: PRT
<213> ORGANISM: Artificial Sequence
<220> FEATURE:
<223> OTHER INFORMATION: Synthetic Construct

<400> SEQUENCE: 5

```
Asp Ile Val Leu Thr Gln Ser Pro Asp Ser Leu Ser Val Ser Leu Gly
  1               5                  10                  15

Glu Arg Val Thr Val Asn Cys Arg Ala Ser Glu Ser Val Asp Gly Tyr
             20                  25                  30

Gly Asn Ser Phe Leu His Trp Phe Gln Gln Asn Pro Gly Gln Pro Pro
         35                  40                  45

Lys Leu Leu Ile Tyr Leu Ala Ser Asn Leu Asn Ser Gly Val Pro Ala
     50                  55                  60

Arg Phe Met Gly Ser Gly Ser Arg Thr Glu Phe Ser Leu Thr Ile Ser
 65                  70                  75                  80

Ser Leu Gln Ala Glu Asp Val Ala Val Tyr Tyr Cys Gln Gln Asn Asn
                 85                  90                  95

Val Asp Pro Trp Thr Phe Gly Gln Gly Thr Lys Leu Glu Ile Lys
            100                 105                 110
```

<210> SEQ ID NO 6
<211> LENGTH: 111
<212> TYPE: PRT
<213> ORGANISM: Artificial Sequence
<220> FEATURE:
<223> OTHER INFORMATION: Synthetic Construct

<400> SEQUENCE: 6

```
Glu Ile Val Leu Thr Gln Ser Pro Ser Ser Leu Ser Ala Ser Val Gly
  1               5                  10                  15

Asp Arg Val Thr Ile Thr Cys Arg Ala Ser Glu Ser Val Asp Gly Tyr
             20                  25                  30

Gly Asn Ser Phe Leu His Trp Tyr Gln Gln Lys Pro Gly Lys Ala Pro
         35                  40                  45

Lys Leu Leu Ile Tyr Leu Ala Ser Asn Leu Asn Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Asn
                 85                  90                  95

Val Asp Pro Trp Thr Phe Gly Gln Gly Thr Lys Leu Glu Ile Lys
            100                 105                 110
```

<210> SEQ ID NO 7
<211> LENGTH: 111
<212> TYPE: PRT
<213> ORGANISM: Artificial Sequence
<220> FEATURE:
<223> OTHER INFORMATION: Synthetic Construct

<400> SEQUENCE: 7

```
Glu Ile Val Leu Thr Gln Ser Pro Ser Ser Leu Ser Ala Ser Val Gly
  1               5                  10                  15

Asp Arg Val Thr Ile Thr Cys Arg Ala Ser Glu Ser Val Asp Gly Tyr
             20                  25                  30
```

```
Gly Asn Ser Phe Leu His Trp Phe Gln Gln Lys Pro Gly Lys Ala Pro
            35                  40                  45

Lys Leu Leu Ile Tyr Leu Ala Ser Asn Leu Asn Ser Gly Val Pro Ser
 50                  55                  60

Arg Phe Ser Gly Ser Gly Ser Arg Thr Asp Phe Thr Leu Thr Ile Ser
 65                  70                  75                  80

Ser Leu Gln Pro Glu Asp Phe Ala Thr Tyr Tyr Cys Gln Gln Asn Asn
                 85                  90                  95

Val Asp Pro Trp Thr Phe Gly Gln Gly Thr Lys Leu Glu Ile Lys
            100                 105                 110

<210> SEQ ID NO 8
<211> LENGTH: 117
<212> TYPE: PRT
<213> ORGANISM: Artificial Sequence
<220> FEATURE:
<223> OTHER INFORMATION: Synthetic Construct

<400> SEQUENCE: 8

Glu Ile Val Leu Thr Gln Ser Pro Leu Ser Leu Pro Val Thr Leu Gly
  1               5                  10                  15

Gln Pro Ala Ser Ile Ser Cys Arg Ala Ser Glu Ser Val Asp Gly Tyr
                 20                  25                  30

Gly Asn Ser Phe Leu His Trp Phe Gln Gln Arg Pro Gly Gln Ser Pro
            35                  40                  45

Arg Leu Leu Ile Tyr Leu Ala Ser Asn Leu Asn Ser Gly Val Pro Asp
 50                  55                  60

Arg Phe Ser Gly Ser Gly Ser Arg Thr Asp Phe Thr Leu Lys Ile Ser
 65                  70                  75                  80

Arg Val Glu Ala Glu Asp Val Gly Val Tyr Tyr Cys Gln Gln Asn Asn
                 85                  90                  95

Val Asp Pro Trp Thr Phe Gly Gly Gly Thr Lys Val Glu Ile Lys Arg
            100                 105                 110

Glu Trp Ile Pro Arg
        115

<210> SEQ ID NO 9
<211> LENGTH: 111
<212> TYPE: PRT
<213> ORGANISM: Artificial Sequence
<220> FEATURE:
<223> OTHER INFORMATION: Synthetic Construct

<400> SEQUENCE: 9

Asp Ile Val Met Thr Gln Ser Pro Asp Ser Leu Ala Val Ser Leu Gly
  1               5                  10                  15

Glu Arg Ala Thr Ile Asn Cys Arg Ala Ser Glu Ser Val Asp Gly Tyr
                 20                  25                  30

Gly Asn Ser Phe Leu His Trp Tyr Gln Gln Lys Pro Gly Gln Pro Pro
            35                  40                  45

Lys Leu Leu Ile Tyr Leu Ala Ser Asn Leu Asn Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                 85                  90                  95

Val Asp Pro Trp Thr Phe Gly Gln Gly Thr Lys Leu Glu Ile Lys
```

<210> SEQ ID NO 10
<211> LENGTH: 117
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Arg Ala Leu Glu Tyr Met
        35                  40                  45

Gly Tyr Ile Ser Tyr Ser Gly Ser Thr Tyr Tyr Asn Leu Ser Leu Arg
    50                  55                  60

Ser Arg Ile Thr Ile Ser Arg Asp Thr Ser Lys Asn Gln Tyr Ser Leu
65                  70                  75                  80

Arg Leu Ser Ser Val Thr Ala Ala Asp Thr Ala Met Tyr Tyr Cys Ala
                85                  90                  95

Leu Ile Thr Thr Thr Thr Tyr Ala Met Asp Tyr Trp Gly Gln Gly Thr
                100                 105                 110

Thr Val Thr Val Ser
            115

<210> SEQ ID NO 11
<211> LENGTH: 117
<212> TYPE: PRT
<213> ORGANISM: Artificial Sequence
<220> FEATURE:
<223> OTHER INFORMATION: Synthetic Construct

<400> SEQUENCE: 11

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Thr Ser Gly
            20                  25                  30

Tyr Trp Asn Trp Ile Arg Lys Pro Pro Gly Arg Ala Leu Glu Tyr Met
        35                  40                  45

Gly Tyr Ile Ser Tyr Ser Gly Ser Thr Tyr Tyr Asn Leu Ser Leu Arg
    50                  55                  60

Ser Arg Ile Thr Ile Ser Arg Asp Thr Ser Lys Asn Gln Tyr Ser Leu
65                  70                  75                  80

Arg Leu Ser Ser Val Thr Ala Ala Asp Thr Ala Met Tyr Tyr Cys Ala
                85                  90                  95

Leu Ile Thr Thr Thr Thr Tyr Ala Met Asp Tyr Trp Gly Gln Gly Thr
                100                 105                 110

Thr Val Thr Val Ser
            115

<210> SEQ ID NO 12
<211> LENGTH: 118
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Tyr Trp Asn Trp Ile Arg Gln Pro Pro Gly Arg Ala Leu Glu Tyr Met
        35                  40                  45

Gly Tyr Ile Ser Tyr Ser Gly Ser Thr Tyr Tyr Asn Leu Ser Leu Arg
    50                  55                  60

Ser Arg Ile Thr Ile Ser Arg Asp Thr Ser Lys Asn Gln Tyr Ser Leu
65                  70                  75                  80

Arg Leu Ser Ser Val Thr Ala Ala Asp Thr Ala Met Tyr Tyr Cys Ala
                85                  90                  95

Leu Ile Thr Thr Thr Thr Tyr Ala Met Asp Tyr Trp Gly Gln Gly Thr
            100                 105                 110

Thr Val Thr Val Ser Ser
        115

<210> SEQ ID NO 13
<211> LENGTH: 118
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Arg Ala Leu Glu Trp Met
        35                  40                  45

Gly Tyr Ile Ser Tyr Ser Gly Ser Thr Tyr Tyr Asn Leu Ser Leu Arg
    50                  55                  60

Ser Arg Ile Thr Ile Ser Arg Asp Thr Ser Lys Asn Gln Tyr Ser Leu
65                  70                  75                  80

Arg Leu Ser Ser Val Thr Ala Ala Asp Thr Ala Met Tyr Tyr Cys Ala
                85                  90                  95

Leu Ile Thr Thr Thr Thr Tyr Ala Met Asp Tyr Trp Gly Gln Gly Thr
            100                 105                 110

Thr Val Thr Val Ser Ser
        115

<210> SEQ ID NO 14
<211> LENGTH: 117
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Arg Ala Leu Glu Tyr Ile
        35                  40                  45

Gly Tyr Ile Ser Tyr Ser Gly Ser Thr Tyr Tyr Asn Leu Ser Leu Arg

```
                    50                  55                  60
Ser Arg Ile Thr Ile Ser Arg Asp Thr Ser Lys Asn Gln Tyr Ser Leu
 65                  70                  75                  80

Arg Leu Ser Ser Val Thr Ala Ala Asp Thr Ala Met Tyr Tyr Cys Ala
                 85                  90                  95

Leu Ile Thr Thr Thr Thr Tyr Ala Met Asp Tyr Trp Gly Gln Gly Thr
                100                 105                 110

Thr Val Thr Val Ser
        115

<210> SEQ ID NO 15
<211> LENGTH: 117
<212> TYPE: PRT
<213> ORGANISM: Artificial Sequence
<220> FEATURE:
<223> OTHER INFORMATION: Synthetic Construct

<400> SEQUENCE: 15

Gln Val Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Thr Ser Gly
                 20                  25                  30

Tyr Trp Asn Trp Ile Arg Gln Pro Pro Gly Arg Ala Leu Glu Tyr Met
             35                  40                  45

Gly Tyr Ile Ser Tyr Ser Gly Ser Thr Tyr Tyr Asn Leu Ser Leu Arg
     50                  55                  60

Ser Arg Val Thr Ile Ser Arg Asp Thr Ser Lys Asn Gln Tyr Ser Leu
 65                  70                  75                  80

Arg Leu Ser Ser Val Thr Ala Ala Asp Thr Ala Met Tyr Tyr Cys Ala
                 85                  90                  95

Leu Ile Thr Thr Thr Thr Tyr Ala Met Asp Tyr Trp Gly Gln Gly Thr
                100                 105                 110

Thr Val Thr Val Ser
        115

<210> SEQ ID NO 16
<211> LENGTH: 117
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Thr Ser Gly
                 20                  25                  30

Tyr Trp Asn Trp Ile Arg Gln Pro Pro Gly Arg Ala Leu Glu Tyr Met
             35                  40                  45

Gly Tyr Ile Ser Tyr Ser Gly Ser Thr Tyr Tyr Asn Leu Ser Leu Arg
     50                  55                  60

Ser Arg Ile Thr Ile Ser Val Asp Thr Ser Lys Asn Gln Tyr Ser Leu
 65                  70                  75                  80

Arg Leu Ser Ser Val Thr Ala Ala Asp Thr Ala Met Tyr Tyr Cys Ala
                 85                  90                  95

Leu Ile Thr Thr Thr Thr Tyr Ala Met Asp Tyr Trp Gly Gln Gly Thr
                100                 105                 110
```

-continued

```
Thr Val Thr Val Ser
        115

<210> SEQ ID NO 17
<211> LENGTH: 117
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Thr Ser Gly
             20                  25                  30

Tyr Trp Asn Trp Ile Arg Gln Pro Pro Gly Arg Ala Leu Glu Tyr Met
         35                  40                  45

Gly Tyr Ile Ser Tyr Ser Gly Ser Thr Tyr Tyr Asn Leu Ser Leu Arg
     50                  55                  60

Ser Arg Ile Thr Ile Ser Arg Asp Thr Ser Lys Asn Gln Phe Ser Leu
 65                  70                  75                  80

Arg Leu Ser Ser Val Thr Ala Ala Asp Thr Ala Met Tyr Tyr Cys Ala
                 85                  90                  95

Leu Ile Thr Thr Thr Thr Tyr Ala Met Asp Tyr Trp Gly Gln Gly Thr
            100                 105                 110

Thr Val Thr Val Ser
        115

<210> SEQ ID NO 18
<211> LENGTH: 117
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Thr Ser Gly
             20                  25                  30

Tyr Trp Asn Trp Ile Arg Gln Pro Pro Gly Arg Ala Leu Glu Tyr Met
         35                  40                  45

Gly Tyr Ile Ser Tyr Ser Gly Ser Thr Tyr Tyr Asn Leu Ser Leu Arg
     50                  55                  60

Ser Arg Ile Thr Ile Ser Arg Asp Thr Ser Lys Asn Gln Tyr Ser Leu
 65                  70                  75                  80

Arg Leu Ser Ser Val Thr Ala Ala Asp Thr Ala Met Tyr Tyr Cys Ala
                 85                  90                  95

Arg Ile Thr Thr Thr Thr Tyr Ala Met Asp Tyr Trp Gly Gln Gly Thr
            100                 105                 110

Thr Val Thr Val Ser
        115

<210> SEQ ID NO 19
<211> LENGTH: 111
<212> TYPE: PRT
<213> ORGANISM: Artificial Sequence
<220> FEATURE:
<223> OTHER INFORMATION: Synthetic Construct
```

<400> SEQUENCE: 19

Glu Ile Val Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Gly Tyr
            20                  25                  30

Gly Asn Ser Phe Leu His Trp Phe Gln Gln Lys Pro Gly Lys Ala Pro
        35                  40                  45

Lys Leu Leu Ile Tyr Leu Ala Ser Asn Leu Asn Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Val Asp Pro Trp Thr Phe Gly Gly Gly Thr Lys Leu Glu Ile Lys
            100                 105                 110

<210> SEQ ID NO 20
<211> LENGTH: 111
<212> TYPE: PRT
<213> ORGANISM: Artificial Sequence
<220> FEATURE:
<223> OTHER INFORMATION: Synthetic Construct

<400> SEQUENCE: 20

Glu Ile Val Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Gly Tyr
            20                  25                  30

Gly Asn Ser Phe Leu His Trp Tyr Gln Gln Lys Pro Gly Lys Ala Pro
        35                  40                  45

Lys Leu Leu Ile Tyr Leu Ala Ser Asn Leu Asn Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Val Asp Pro Trp Thr Phe Gly Gln Gly Thr Lys Leu Glu Ile Lys
            100                 105                 110

<210> SEQ ID NO 21
<211> LENGTH: 351
<212> TYPE: DNA
<213> ORGANISM: Artificial Sequence
<220> FEATURE:
<223> OTHER INFORMATION: Synthetic Construct

<400> SEQUENCE: 21
gaggtgcagc ttcaggagtc aggacctagc ctcgtgaaac cttctcagac tctgtccctc     60
acctgttctg tcactggcga ctccatcacc agtggttact ggaactggat ccggaaattc    120
ccagggaata acttgagta catgggatac ataagttaca gtggtagcac ttactacaat    180
ctatctctca gaagtcgcat ctccatcact cgagacacat ccaagaatca gtactacctg    240
cagttgaatt ctgtgactac tgaggacaca gccacatatt actgtgcgct cattactacg    300
actacctatg ctatggacta ctggggtcaa ggaacctcag tcaccgtctc c             351

<210> SEQ ID NO 22
<211> LENGTH: 333

```
<212> TYPE: DNA
<213> ORGANISM: Artificial Sequence
<220> FEATURE:
<223> OTHER INFORMATION: Synthetic Construct

<400> SEQUENCE: 22
aacattgtgc tgacccaatc tccagttttct ttggctgtgt ctctggggca gagggccacc    60
atttcctgca gagccagtga aagtgttgat ggttatggca atagttttct gcactggttc   120
cagcagaaac caggacagcc acccaaactc ctcatctatc ttgcatccaa cctaaactct   180
ggggtccctg ccaggttcag tggcagtggg tctaggacag acttcaccct caccattgat   240
cctgtggagg ctgatgatgc tgcaacctat tactgtcagc aaaataatgt ggacccgtgg   300
acgttcggtg gaggcaccaa gctggaaatc aaa                                333

<210> SEQ ID NO 23
<211> LENGTH: 351
<212> TYPE: DNA
<213> ORGANISM: Artificial Sequence
<220> FEATURE:
<223> OTHER INFORMATION: Synthetic Construct

<400> SEQUENCE: 23
caagtgcagc tgcaggagtc gggaccagga ctggtgaagc cttcggagac cctgtccctc    60
acctgcactg tctctggtga ctccatcagt agtggttact ggaactggat ccggcagccc   120
ccagggaggg cactggagtg gataggatac ataagttaca gtggtagcac ttactacaat   180
ctatctctca gaagtcgggt caccatatca gtagacacct caagaaccca gttctccctg   240
aggctgagct ctgtgaccgc tgcggacacg gccatgtatt actgtgcgag aattactacg   300
actacctatg ctatggacta ctggggccaa gggaccacgg tcaccgtctc c             351

<210> SEQ ID NO 24
<211> LENGTH: 334
<212> TYPE: DNA
<213> ORGANISM: Artificial Sequence
<220> FEATURE:
<223> OTHER INFORMATION: Synthetic Construct

<400> SEQUENCE: 24
gacatcgtgc tgacccagtc tccagactcc ctgtctgtgt ctctgggcga gagggtcacc    60
gtcaactgca gagccagtga aagtgttgat ggttatggca atagttttct gcactggttc   120 cagcaaaaacc caggacagcc tcctaaactc ctcatttatc ttgcatccaa cctaaactct   180
ggggtccctg cccgattcat gggcagcggg tctgggacag aattcagtct caccatcagc   240
agcctgcagg ctgaagatgt ggcagtttat tactgtcagc aaaataatgt ggacccgtgg   300
acctttggcc aggggaccaa gctggagatc aacc                               334

<210> SEQ ID NO 25
<211> LENGTH: 333
<212> TYPE: DNA
<213> ORGANISM: Artificial Sequence
<220> FEATURE:
<223> OTHER INFORMATION: Synthetic Construct

<400> SEQUENCE: 25
gacatcgtgc tgacccagtc tccagactcc ctgtctgtgt ctctgggcga gagggtcacc    60
gtcaactgca gagccagtga aagtgttgat ggttatggca atagttttct gcactggttc   120 cagcaaaaacc caggacagcc tcctaaactc ctcatttatc ttgcatccaa cctaaactct   180
```

```
ggggtccctg cccgattcat gggcagcggg tctcggacag aattcagtct caccatcagc    240
agcctgcagg ctgaagatgt ggcagtttat tactgtcagc aaaataatgt ggacccgtgg    300
acctttggcc aggggaccaa gctggagatc aaa                                 333

<210> SEQ ID NO 26
<211> LENGTH: 334
<212> TYPE: DNA
<213> ORGANISM: Artificial Sequence
<220> FEATURE:
<223> OTHER INFORMATION: Synthetic Construct

<400> SEQUENCE: 26
gaaatagtgt tgacgcagtc tccatcctcc ctgtctgcat ctgtaggaga cagagtcacc    60
atcacttgca gagccagtga agtgttgat ggttatggca atagttttct gcactggtat    120
cagcagaaac cagggaaagc ccctaagctc ctgatctatc ttgcatccaa cctaaactct    180
ggggtcccat caaggttcag tggcagtgga tctgggacag atttcactct caccatcagc    240
agtctgcaac ctgaagattt tgcaacttac tactgtcagc aaaataatgt ggacccgtgg    300
acttttggcc aggggaccaa gctggagatc aaac                                334

<210> SEQ ID NO 27
<211> LENGTH: 333
<212> TYPE: DNA
<213> ORGANISM: Artificial Sequence
<220> FEATURE:
<223> OTHER INFORMATION: Synthetic Construct

<400> SEQUENCE: 27
gaaatagtgt tgacgcagtc tccatcctcc ctgtctgcat ctgtaggaga cagagtcacc    60
atcacttgca gagccagtga agtgttgat ggttatggca atagttttct gcactggttt    120
cagcagaaac cagggaaagc ccctaagctc ctgatctatc ttgcatccaa cctaaactct    180
ggggtcccat caaggttcag tggcagtgga tctcggacag atttcactct caccatcagc    240
agtctgcaac ctgaagattt tgcaacttac tactgtcagc aaaataatgt ggacccgtgg    300
acttttggcc aggggaccaa gctggagatc aaa                                 333

<210> SEQ ID NO 28
<211> LENGTH: 350
<212> TYPE: DNA
<213> ORGANISM: Artificial Sequence
<220> FEATURE:
<223> OTHER INFORMATION: Synthetic Construct

<400> SEQUENCE: 28
gaaattgtgc tgactcagtc tccactctcc ctgcccgtca cccttggaca gccggcctcc    60
atctcctgca gagccagtga agtgttgat ggttatggca atagttttct gcactggttt    120
cagcagaggc caggccaatc tccaaggctc ctaatttatc ttgcatccaa cctaaactct    180
ggggtcccag acagattcag cggcagcgga tcaaggactg atttcacact gaaaatcagc    240
agagtggagg ctgaggatgt tggggtttat tactgccagc aaaataatgt ggacccgtgg    300
acgttcggcg agggaccaa agtggagatc aaacgtgagt ggatcccgcg               350

<210> SEQ ID NO 29
<211> LENGTH: 333
<212> TYPE: DNA
<213> ORGANISM: Artificial Sequence
<220> FEATURE:
<223> OTHER INFORMATION: Synthetic Construct
```

<400> SEQUENCE: 29

```
gacatcgtga tgacccagtc tccagactcc ctggctgtgt ctctgggcga gagggccacc    60
atcaactgca gagccagtga aagtgttgat ggttatggca atagttttct gcactggtat   120
cagcagaaac cgggacagcc tcctaagttg ctcatttacc ttgcatccaa cctaaactct   180
ggggtccctg accgattcag tggcagcggg tctgggacag atttcactct caccatcagc   240
agcctgcagg ccgaagatgt ggcagtgtat tactgtcagc aaaataatgt ggacccgtgg   300
actttggcc aggggaccaa gctggagatc aaa                                  333
```

<210> SEQ ID NO 30
<211> LENGTH: 351
<212> TYPE: DNA
<213> ORGANISM: Artificial Sequence
<220> FEATURE:
<223> OTHER INFORMATION: Synthetic Construct

<400> SEQUENCE: 30

```
caagtgcagc tgcaggagtc gggaccagga ctggtgaagc cttcggagac cctgtccctc    60
acctgcactg tctctggtga ctccatcact agtggttact ggaactggat ccggcagccc   120
ccagggaggg cactggagta catgggatac ataagttaca gtggtagcac ttactacaat   180
ctatctctca gaagtcggat caccatatca gagacacct ctaagaacca gtactccctg    240
aggctgagct ctgtgaccgc tgcggacacg gccatgtatt actgtgcgct gattactacg   300
actacctatg ctatggacta ctggggccaa gggaccacgg tcaccgtctc c            351
```

<210> SEQ ID NO 31
<211> LENGTH: 351
<212> TYPE: DNA
<213> ORGANISM: Artificial Sequence
<220> FEATURE:
<223> OTHER INFORMATION: Synthetic Construct

<400> SEQUENCE: 31

```
caagtgcagc tgcaggagtc gggaccagga ctggtgaagc cttcggagac cctgtccctc    60
acctgcactg tctctggtga ctccatcact agtggttact ggaactggat ccggaagccc   120
ccagggaggg cactggagta catgggatac ataagttaca gtggtagcac ttactacaat   180
ctatctctca gaagtcggat caccatatca gagacacct ctaagaacca gtactccctg    240
aggctgagct ctgtgaccgc tgcggacacg gccatgtatt actgtgcgct gattactacg   300
actacctatg ctatggacta ctggggccaa gggaccacgg tcaccgtctc c            351
```

<210> SEQ ID NO 32
<211> LENGTH: 354
<212> TYPE: DNA
<213> ORGANISM: Artificial Sequence
<220> FEATURE:
<223> OTHER INFORMATION: Synthetic Construct

<400> SEQUENCE: 32

```
caagtgcagc tgcaggagtc gggaccagga ctggtgaagc cttcggagac cctgtccctc    60
acctgcactg tctctggtga ctccatcagt agtggttact ggaactggat ccggcagccc   120
ccagggaggg cactggagta catgggatac ataagttaca gtggtagcac ttactacaat   180
ctatctctca gaagtcggat caccatatca gagacacct ctaagaacca gtactccctg    240
aggctgagct ctgtgaccgc tgcggacacg gccatgtatt actgtgcgct gattactacg   300
```

```
actacctatg ctatggacta ctggggccaa gggaccacgg tcaccgtctc ctca              354

<210> SEQ ID NO 33
<211> LENGTH: 354
<212> TYPE: DNA
<213> ORGANISM: Artificial Sequence
<220> FEATURE:
<223> OTHER INFORMATION: Synthetic Construct

<400> SEQUENCE: 33
caagtgcagc tgcaggagtc gggaccagga ctggtgaagc cttcggagac cctgtccctc         60
acctgcactg tctctggtga ctccatcacc agtggttact ggaactggat ccggcagccc        120
ccagggaggg cactggagtg gatgggatac ataagttaca gtggtagcac ttactacaat        180
ctatctctca gaagtcggat caccatatca agagacacct ctaagaacca gtactccctg        240
aggctgagct ctgtgaccgc tgcggacacg gccatgtatt actgtgcgct gattactacg        300
actacctatg ctatggacta ctggggccaa gggaccacgg tcaccgtctc ctca              354

<210> SEQ ID NO 34
<211> LENGTH: 351
<212> TYPE: DNA
<213> ORGANISM: Artificial Sequence
<220> FEATURE:
<223> OTHER INFORMATION: Synthetic Construct

<400> SEQUENCE: 34
caagtgcagc tgcaggagtc gggaccagga ctggtgaagc cttcggagac cctgtccctc         60
acctgcactg tctctggtga ctccatcacc agtggttact ggaactggat ccggcagccc        120
ccagggaggg cactggagta cataggatac ataagttaca gtggtagcac ttactacaat        180
ctatctctca gaagtcggat caccatatca agagacacct ctaagaacca gtactccctg        240
aggctgagct ctgtgaccgc tgcggacacg gccatgtatt actgtgcgct gattactacg        300
actacctatg ctatggacta ctggggccaa gggaccacgg tcaccgtctc c                 351

<210> SEQ ID NO 35
<211> LENGTH: 351
<212> TYPE: DNA
<213> ORGANISM: Artificial Sequence
<220> FEATURE:
<223> OTHER INFORMATION: Synthetic Construct

<400> SEQUENCE: 35
caagtgcagc tgcaggagtc gggaccagga ctggtgaagc cttcggagac cctgtccctc         60
acctgcactg tctctggtga ctccatcacc agtggttact ggaactggat ccggcagccc        120
ccagggaggg cactggagta catgggatac ataagttaca gtggtagcac ttactacaat        180
ctatctctca gaagtcgggt caccatatca agagacacct ctaagaacca gtactccctg        240
aggctgagct ctgtgaccgc tgcggacacg gccatgtatt actgtgcgct gattactacg        300
actacctatg ctatggacta ctggggccaa gggaccacgg tcaccgtctc c                 351

<210> SEQ ID NO 36
<211> LENGTH: 351
<212> TYPE: DNA
<213> ORGANISM: Artificial Sequence
<220> FEATURE:
<223> OTHER INFORMATION: Synthetic Construct

<400> SEQUENCE: 36
caagtgcagc tgcaggagtc gggaccagga ctggtgaagc cttcggagac cctgtccctc         60
```

```
acctgcactg tctctggtga ctccatcacc agtggttact ggaactggat ccggcagccc    120
ccagggaggg cactggagta catgggatac ataagttaca gtggtagcac ttactacaat    180
ctatctctca gaagtcggat caccatatca gtggacacct ctaagaacca gtactccctg    240
aggctgagct ctgtgaccgc tgcggacacg gccatgtatt actgtgcgct gattactacg    300
actacctatg ctatggacta ctggggccaa gggaccacgg tcaccgtctc c             351

<210> SEQ ID NO 37
<211> LENGTH: 351
<212> TYPE: DNA
<213> ORGANISM: Artificial Sequence
<220> FEATURE:
<223> OTHER INFORMATION: Synthetic Construct

<400> SEQUENCE: 37
caagtgcagc tgcaggagtc gggaccagga ctggtgaagc cttcggagac cctgtccctc     60
acctgcactg tctctggtga ctccatcacc agtggttact ggaactggat ccggcagccc    120
ccagggaggg cactggagta catgggatac ataagttaca gtggtagcac ttactacaat    180
ctatctctca gaagtcggat caccatatca agagacacct ctaagaacca gttctccctg    240
aggctgagct ctgtgaccgc tgcggacacg gccatgtatt actgtgcgct gattactacg    300
actacctatg ctatggacta ctggggccaa gggaccacgg tcaccgtctc c             351

<210> SEQ ID NO 38
<211> LENGTH: 351
<212> TYPE: DNA
<213> ORGANISM: Artificial Sequence
<220> FEATURE:
<223> OTHER INFORMATION: Synthetic Construct

<400> SEQUENCE: 38
caagtgcagc tgcaggagtc gggaccagga ctggtgaagc cttcggagac cctgtccctc     60
acctgcactg tctctggtga ctccatcacc agtggttact ggaactggat ccggcagccc    120
ccagggaggg cactggagta catgggatac ataagttaca gtggtagcac ttactacaat    180
ctatctctca gaagtcggat caccatatca agagacacct ctaagaacca gtactccctg    240
aggctgagct ctgtgaccgc tgcggacacg gccatgtatt actgtgcgag aattactacg    300
actacctatg ctatggacta ctggggccaa gggaccacgg tcaccgtctc c             351

<210> SEQ ID NO 39
<211> LENGTH: 333
<212> TYPE: DNA
<213> ORGANISM: Artificial Sequence
<220> FEATURE:
<223> OTHER INFORMATION: Synthetic Construct

<400> SEQUENCE: 39
gaaatagtgt tgacgcagtc tccatcctcc ctgtctgcat ctgtaggaga cagagtcacc     60
atcacttgca gagccagtga aagtgttgat ggttatggca atagttttct gcactggttt    120
cagcagaaac cagggaaagc ccctaagctc ctgatctatc ttgcatccaa cctaaactct    180
ggggtcccat caaggttcag tggcagtgga tctgggacag atttcactct caccatcagc    240
agtctgcaac ctgaagattt tgcaacttac tactgtcagc aaaataatgt ggacccgtgg    300
acttttggcc aggggaccaa gctggagatc aaa                                 333

<210> SEQ ID NO 40
```

```
<211> LENGTH: 334
<212> TYPE: DNA
<213> ORGANISM: Artificial Sequence
<220> FEATURE:
<223> OTHER INFORMATION: Synthetic Construct

<400> SEQUENCE: 40
gaaatagtgt tgacgcagtc tccatcctcc ctgtctgcat ctgtaggaga cagagtcacc    60
atcacttgca gagccagtga aagtgttgat ggttatggca atagttttct gcactggtat   120
cagcagaaac cagggaaagc ccctaagctc ctgatctatc ttgcatccaa cctaaactct   180
ggggtcccat caaggttcag tggcagtgga tctcggacag atttcactct caccatcagc   240
agtctgcaac tgaagatttt gcaacttac tactgtcagc aaaataatgt ggacccgtgg    300
acttttggcc aggggaccaa gctggagatc aaac                               334

<210> SEQ ID NO 41
<211> LENGTH: 30
<212> TYPE: DNA
<213> ORGANISM: Artificial Sequence
<220> FEATURE:
<223> OTHER INFORMATION: Synthetic Construct

<400> SEQUENCE: 41
aataaacttg agttcatggg atacataagt                                     30

<210> SEQ ID NO 42
<211> LENGTH: 30
<212> TYPE: DNA
<213> ORGANISM: Artificial Sequence
<220> FEATURE:
<223> OTHER INFORMATION: Synthetic Construct

<400> SEQUENCE: 42
acttatgtat cccatgaact caagtttatt                                     30

<210> SEQ ID NO 43
<211> LENGTH: 30
<212> TYPE: DNA
<213> ORGANISM: Artificial Sequence
<220> FEATURE:
<223> OTHER INFORMATION: Synthetic Construct

<400> SEQUENCE: 43
gaataaactt gagtggatgg gatacataag                                     30

<210> SEQ ID NO 44
<211> LENGTH: 30
<212> TYPE: DNA
<213> ORGANISM: Artificial Sequence
<220> FEATURE:
<223> OTHER INFORMATION: Synthetic Construct

<400> SEQUENCE: 44
cttatgtatc ccatccactc aagtttattc                                     30

<210> SEQ ID NO 45
<211> LENGTH: 16
<212> TYPE: PRT
<213> ORGANISM: Artificial Sequence
<220> FEATURE:
<223> OTHER INFORMATION: Synthetic Construct

<400> SEQUENCE: 45

Gln Leu Ile Asn Thr Asn Gly Ser Trp His Ile Asn Gly Ser Gly Lys
```

<210> SEQ ID NO 46
<211> LENGTH: 16
<212> TYPE: PRT
<213> ORGANISM: Artificial Sequence
<220> FEATURE:
<223> OTHER INFORMATION: Synthetic Construct

<400> SEQUENCE: 46

Asn Leu Ile Asn Thr Asn Gly Ser Trp His Ile Asn Gly Ser Gly Lys
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic Construct

<400> SEQUENCE: 47

Gln Leu Ile Asn Thr Asn Gly Ser Trp His Val Asn Gly Ser Gly Lys
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic Construct

<400> SEQUENCE: 48

Gln Leu Ile Asn Ser Asn Gly Ser Trp His Ile Asn Gly Ser Gly Lys
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic Construct

<400> SEQUENCE: 49

Gln Leu Val Asn Ser Asn Gly Ser Trp His Ile Asn Gly Ser Gly Lys
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct

<400> SEQUENCE: 50

Val Glu Leu Arg Asn Leu Gly Gly Thr Trp Arg Pro Gly Ser Gly Lys
1               5                   10                  15

<210> SEQ ID NO 51
<211> LENGTH: 60
<212> TYPE: DNA
<213> ORGANISM: Artificial Sequence
<220> FEATURE:
<223> OTHER INFORMATION: Synthetic Construct

<400> SEQUENCE: 51
atggtgttgc agacccaggt cttcatttct ctgttgctct ggatctctgg ggcttacggg    60

<210> SEQ ID NO 52
<211> LENGTH: 20
<212> TYPE: PRT
<213> ORGANISM: Artificial Sequence
<220> FEATURE:
<223> OTHER INFORMATION: Synthetic Construct

<400> SEQUENCE: 52

Met Val Leu Gln Thr Gln Val Phe Ile Ser Leu Leu Leu Trp Ile Ser
1               5                   10                  15

Gly Ala Tyr Gly
            20

<210> SEQ ID NO 53
<211> LENGTH: 66
<212> TYPE: DNA
<213> ORGANISM: Artificial Sequence
<220> FEATURE:
<223> OTHER INFORMATION: Synthetic Construct

<400> SEQUENCE: 53
atggacatga gggtccccgc tcagctcctg gggctcctgc tgctctggct cccaggcgcc      60
agatgt                                                                66

<210> SEQ ID NO 54
<211> LENGTH: 22
<212> TYPE: PRT
<213> ORGANISM: Artificial Sequence
<220> FEATURE:
<223> OTHER INFORMATION: Synthetic Construct

<400> SEQUENCE: 54

Met Asp Met Arg Val Pro Ala Gln Leu Leu Gly Leu Leu Leu Leu Trp
1               5                   10                  15

Leu Pro Gly Ala Arg Cys
            20

<210> SEQ ID NO 55
<211> LENGTH: 20
<212> TYPE: DNA
<213> ORGANISM: Artificial Sequence
<220> FEATURE:
<223> OTHER INFORMATION: Synthetic Construct

<400> SEQUENCE: 55
ctgcggaacc ggtgagtaca                                                 20

<210> SEQ ID NO 56
<211> LENGTH: 21
<212> TYPE: DNA
<213> ORGANISM: Artificial Sequence
<220> FEATURE:
<223> OTHER INFORMATION: Synthetic Construct

<400> SEQUENCE: 56
tgcacggtct acgagaccto c                                               21

<210> SEQ ID NO 57
<211> LENGTH: 22
<212> TYPE: DNA
<213> ORGANISM: Artificial Sequence
<220> FEATURE:
<223> OTHER INFORMATION: Synthetic Construct

<400> SEQUENCE: 57
acccggtcgt cctggcaatt cc                                          22

<210> SEQ ID NO 58
<211> LENGTH: 20
<212> TYPE: DNA
<213> ORGANISM: Artificial Sequence
<220> FEATURE:
<223> OTHER INFORMATION: Synthetic Construct

<400> SEQUENCE: 58
cttcacgcag aaagcgccta                                             20

<210> SEQ ID NO 59
<211> LENGTH: 20
<212> TYPE: DNA
<213> ORGANISM: Artificial Sequence
<220> FEATURE:
<223> OTHER INFORMATION: Synthetic Construct

<400> SEQUENCE: 59
caagcaccct atcaggcagt                                             20

<210> SEQ ID NO 60
<211> LENGTH: 20
<212> TYPE: DNA
<213> ORGANISM: Artificial Sequence
<220> FEATURE:
<223> OTHER INFORMATION: Synthetic Construct

<400> SEQUENCE: 60
tatgagtgtc gtacagcctc                                             20

<210> SEQ ID NO 61
<211> LENGTH: 19
<212> TYPE: DNA
<213> ORGANISM: Artificial Sequence
<220> FEATURE:
<223> OTHER INFORMATION: Synthetic Construct

<400> SEQUENCE: 61
gaaggtgaag gtcggagtc                                              19

<210> SEQ ID NO 62
<211> LENGTH: 20
<212> TYPE: DNA
<213> ORGANISM: Artificial Sequence
<220> FEATURE:
<223> OTHER INFORMATION: Synthetic Construct

<400> SEQUENCE: 62
gaagatggtg atgggatttc                                             20

<210> SEQ ID NO 63
<211> LENGTH: 20
<212> TYPE: DNA
<213> ORGANISM: Artificial Sequence
<220> FEATURE:
<223> OTHER INFORMATION: Synthetic Construct

<400> SEQUENCE: 63
atgacccctt cattgacctc                                             20

<210> SEQ ID NO 64
<211> LENGTH: 122
<212> TYPE: PRT

<213> ORGANISM: Homo sapiens

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Ser Trp Ile Arg Gln Pro Pro Gly Arg Ala Leu Glu Trp Ile
        35                  40                  45

Gly Tyr Ile Tyr His Gly Ser Thr Asn Tyr Ser Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Met Tyr Tyr Cys Ala
                85                  90                  95

Arg Asp Arg His Cys Ser Gly Gly Thr Cys Tyr Gly Met Asp Val Trp
            100                 105                 110

Gly Gln Gly Thr Thr Val Thr Val Ser Ser
            115                 120

<210> SEQ ID NO 65
<211> LENGTH: 113
<212> TYPE: PRT
<213> ORGANISM: Artificial Sequence
<220> FEATURE:
<223> OTHER INFORMATION: Synthetic Construct

<400> SEQUENCE: 65

Asp Ile Val Leu Thr Gln Ser Pro Asp Ser Leu Ser Val Ser Leu Gly
1               5                   10                  15

Glu Arg Val Thr Val Asn Cys Lys Leu Ser Gln Ser Val Leu His Ser
            20                  25                  30

Ser Asn Lys Gln Asn Tyr Leu Ala Trp Phe Gln Gln Asn Pro Gly Gln
        35                  40                  45

Pro Pro Lys Leu Leu Ile Tyr Trp Ala Ser Ala Arg Gln Ser Gly Val
    50                  55                  60

Pro Ala Arg Phe Met Gly Ser Gly Ser Gly Thr Glu Phe Ser Leu Thr
65                  70                  75                  80

Ile Ser Ser Leu Gln Ala Glu Asp Val Ala Val Tyr Tyr Cys Gln Gln
                85                  90                  95

Tyr Tyr Asp Ser Thr Tyr Thr Phe Gly Gln Gly Thr Lys Leu Glu Ile
            100                 105                 110

Asn

<210> SEQ ID NO 66
<211> LENGTH: 111
<212> TYPE: PRT
<213> ORGANISM: Artificial Sequence
<220> FEATURE:
<223> OTHER INFORMATION: Synthetic Construct

<400> SEQUENCE: 66

Glu Ile Val Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Gly Tyr
            20                  25                  30

Gly Asn Ser Phe Leu His Trp Tyr Gln Gln Lys Pro Gly Lys Ala Pro
        35                  40                  45

```
Lys Leu Leu Ile Tyr Leu Ala Ser Asn Leu Asn Ser Gly Val Pro Ser
             50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Asn
                 85                  90                  95

Val Asp Pro Trp Thr Phe Gly Gln Gly Thr Lys Leu Glu Ile Lys
            100                 105                 110

<210> SEQ ID NO 67
<211> LENGTH: 111
<212> TYPE: PRT
<213> ORGANISM: Artificial Sequence
<220> FEATURE:
<223> OTHER INFORMATION: Synthetic Construct

<400> SEQUENCE: 67

Glu Ile Val Leu Thr Gln Ser Pro Leu Ser Leu Pro Val Thr Leu Gly
  1               5                  10                  15

Gln Pro Ala Ser Ile Ser Cys Arg Ser Gln Ser Leu Val Tyr Ser
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Leu Thr Phe Gly Gly Gly Thr Lys Val Glu Ile Lys
            100                 105                 110

<210> SEQ ID NO 68
<211> LENGTH: 113
<212> TYPE: PRT
<213> ORGANISM: Artificial Sequence
<220> FEATURE:
<223> OTHER INFORMATION: Synthetic Construct

<400> SEQUENCE: 68

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
                 20                  25                  30

Ser Asn Asn Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Ser Tyr Thr Phe Gly Gln Gly Thr Lys Leu Glu Ile
            100                 105                 110

Lys

<210> SEQ ID NO 69
```

```
<211> LENGTH: 5
<212> TYPE: PRT
<213> ORGANISM: Artificial sequence
<220> FEATURE:
<223> OTHER INFORMATION: Synthetic Construct

<400> SEQUENCE: 69

Gly Asp Ser Ile Thr
 1               5

<210> SEQ ID NO 70
<211> LENGTH: 5
<212> TYPE: PRT
<213> ORGANISM: Artificial sequence
<220> FEATURE:
<223> OTHER INFORMATION: Synthetic Construct

<400> SEQUENCE: 70

Gly Asp Ser Ile Ser
 1               5

<210> SEQ ID NO 71
<211> LENGTH: 5
<212> TYPE: PRT
<213> ORGANISM: Artificial sequence
<220> FEATURE:
<223> OTHER INFORMATION: Synthetic Construct

<400> SEQUENCE: 71

Gly Asp Ser Ile Arg
 1               5

<210> SEQ ID NO 72
<211> LENGTH: 5
<212> TYPE: PRT
<213> ORGANISM: Artificial sequence
<220> FEATURE:
<223> OTHER INFORMATION: Synthetic Construct

<400> SEQUENCE: 72

Gly Gly Ser Ile Thr
 1               5

<210> SEQ ID NO 73
<211> LENGTH: 5
<212> TYPE: PRT
<213> ORGANISM: Artificial sequence
<220> FEATURE:
<223> OTHER INFORMATION: Synthetic Construct

<400> SEQUENCE: 73

Gly Asp Ser Phe Thr
 1               5

<210> SEQ ID NO 74
<211> LENGTH: 5
<212> TYPE: PRT
<213> ORGANISM: Artificial sequence
<220> FEATURE:
<223> OTHER INFORMATION: Synthetic Construct

<400> SEQUENCE: 74

Gly Val Ser Ile Thr
 1               5

<210> SEQ ID NO 75
<211> LENGTH: 5
```

```
<212> TYPE: PRT
<213> ORGANISM: Artificial sequence
<220> FEATURE:
<223> OTHER INFORMATION: Synthetic Construct

<400> SEQUENCE: 75

Gly Gly Ser Ile Ser
 1               5

<210> SEQ ID NO 76
<211> LENGTH: 118
<212> TYPE: PRT
<213> ORGANISM: Artificial
<220> FEATURE:
<223> OTHER INFORMATION: Synthetic Construct

<400> SEQUENCE: 76

Ser Glu Val Gln Leu Gln Glu Ser Gly Pro Ser Leu Val Lys Pro Ser
 1               5                  10                  15

Gln Thr Leu Ser Leu Thr Cys Ser Val Thr Gly Asp Ser Ile Thr Ser
                20                  25                  30

Gly Tyr Trp Asn Trp Ile Arg Lys Phe Pro Gly Asn Lys Leu Glu Tyr
            35                  40                  45

Met Gly Tyr Ile Ser Tyr Ser Gly Ser Thr Tyr Tyr Asn Leu Ser Leu
 50                  55                  60

Arg Ser Arg Ile Ser Ile Thr Arg Asp Thr Ser Lys Asn Gln Tyr Tyr
 65                  70                  75                  80

Leu Gln Leu Asn Ser Val Thr Thr Glu Asp Thr Ala Thr Tyr Tyr Cys
                85                  90                  95

Ala Leu Ile Thr Thr Thr Thr Tyr Ala Met Asp Tyr Trp Gly Gln Gly
            100                 105                 110

Thr Ser Val Thr Val Ser
        115

<210> SEQ ID NO 77
<211> LENGTH: 118
<212> TYPE: PRT
<213> ORGANISM: Artificial
<220> FEATURE:
<223> OTHER INFORMATION: Synthetic Construct

<400> SEQUENCE: 77

Ser Gln Val Gln Leu Gln Glu Ser Gly Pro Gly Leu Val Lys Pro Ser
 1               5                  10                  15

Glu Thr Leu Ser Leu Thr Cys Ile Val Ser Gly Asp Ser Ile Ser Ser
                20                  25                  30

Tyr Tyr Trp Ser Trp Ile Arg Gln Ser Pro Gly Lys Gly Leu Glu Trp
            35                  40                  45

Ile Gly Cys Met Ser Tyr Ser Gly Ser Thr Asn Tyr Asn Pro Ser Leu
 50                  55                  60

Arg Ser Arg Val Thr Ile Ser Val Asp Thr Ser Lys Asn Gln Phe Ser
 65                  70                  75                  80

Leu Glu Leu Arg Ser Val Thr Ala Ala Asp Thr Ala Val Tyr Tyr Cys
                85                  90                  95

Ala Arg His Asp Phe Trp Arg Thr Phe Asp Ser Trp Gly Gln Gly Thr
            100                 105                 110

Leu Val Thr Val Ser Ser
        115
```

<210> SEQ ID NO 78
<211> LENGTH: 123
<212> TYPE: PRT
<213> ORGANISM: Artificial
<220> FEATURE:
<223> OTHER INFORMATION: Synthetic Construct

<400> SEQUENCE: 78

```
Ser Gln Val Gln Leu Gln Glu Ser Gly Pro Gly Leu Val Lys Pro Ser
1               5                   10                  15

Glu Thr Leu Ser Leu Thr Cys Thr Val Ser Gly Asp Ser Ile Ser Ser
            20                  25                  30

Tyr Tyr Trp Ser Trp Ile Arg Gln Pro Pro Gly Arg Ala Leu Glu Trp
        35                  40                  45

Ile Gly Tyr Ile Tyr His Gly Gly Ser Thr Asn Tyr Ser Pro Ser Leu
    50                  55                  60

Lys Ser Arg Val Thr Ile Ser Val Asp Thr Ser Lys Asn Gln Phe Ser
65                  70                  75                  80

Leu Arg Leu Ser Ser Val Thr Ala Ala Asp Thr Ala Met Tyr Tyr Cys
                85                  90                  95

Ala Arg Asp Arg His Cys Ser Gly Gly Thr Cys Tyr Gly Met Asp Val
            100                 105                 110

Trp Gly Gln Gly Thr Thr Val Thr Val Ser Ser
        115                 120
```

<210> SEQ ID NO 79
<211> LENGTH: 122
<212> TYPE: PRT
<213> ORGANISM: Artificial
<220> FEATURE:
<223> OTHER INFORMATION: Synthetic Construct

<400> SEQUENCE: 79

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Ser Trp Ile Arg Gln Pro Pro Gly Arg Gly Leu Glu Trp Ile
        35                  40                  45

Gly Tyr Ile Tyr His Gly Gly Ser Thr Asn Tyr Ser Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Met Tyr Tyr Cys Ala
                85                  90                  95

Arg Asp Arg His Cys Ser Gly Gly Thr Cys Tyr Gly Met Asp Val Trp
            100                 105                 110

Gly Gln Gly Thr Thr Val Thr Val Ser Ser
        115                 120
```

<210> SEQ ID NO 80
<211> LENGTH: 122
<212> TYPE: PRT
<213> ORGANISM: Artificial
<220> FEATURE:
<223> OTHER INFORMATION: Synthetic Construct

<400> SEQUENCE: 80

```
Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Asp Ser Ile Ser Ser Tyr
            20                  25                  30

Tyr Trp Ser Trp Ile Arg Gln Pro Pro Gly Arg Ala Leu Glu Trp Ile
        35                  40                  45

Gly Tyr Ile Tyr His Gly Gly Ser Thr Asn Tyr Ser Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Met Tyr Tyr Cys Ala
                85                  90                  95

Arg Asp Arg His Cys Ser Gly Gly Thr Cys Tyr Gly Met Asp Val Trp
                100                 105                 110

Gly Gln Gly Thr Thr Val Thr Val Ser Ser
            115                 120
```

`<210>` SEQ ID NO 81
`<211>` LENGTH: 116
`<212>` TYPE: PRT
`<213>` ORGANISM: Artificial
`<220>` FEATURE:
`<223>` OTHER INFORMATION: Synthetic Construct

`<400>` SEQUENCE: 81

```
Gln Val Gln Leu Gln Glu Ser Gly Pro Gly Leu Met Lys Pro Ser Glu
1               5                   10                  15

Thr Leu Ser Leu Thr Cys Ser Val Ser Gly Asp Ser Ile Arg Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Asp Thr Gly Ser Thr Asn Tyr Asn Pro Ser Leu Lys
    50                  55                  60

Ser Arg Val Thr Ile Ser Val Asp Thr Ser Lys Asn Arg Phe Ser Leu
65                  70                  75                  80

Lys Leu Asn Ser Val Thr Ala Ala Asp Thr Ala Val Tyr Tyr Cys Ala
                85                  90                  95

Arg Tyr Lys Gln Gln Ile Phe Asp Pro Trp Gly Gln Gly Ile Leu Val
                100                 105                 110

Thr Val Ser Ser
            115
```

`<210>` SEQ ID NO 82
`<211>` LENGTH: 122
`<212>` TYPE: PRT
`<213>` ORGANISM: Artificial
`<220>` FEATURE:
`<223>` OTHER INFORMATION: Synthetic Construct

`<400>` SEQUENCE: 82

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Ser Trp Ile Arg Gln Pro Pro Gly Arg Ala Leu Glu Trp Ile
        35                  40                  45

Gly Tyr Ile Tyr His Gly Gly Ser Thr Asn Tyr Ser Pro Ser Leu Lys
    50                  55                  60

Ser Arg Val Thr Ile Ser Val Asp Thr Ser Lys Asn Gln Phe Ser Leu
```

```
                65                  70                  75                  80
Arg Leu Thr Ser Leu Thr Ala Ala Asp Thr Ala Met Tyr Tyr Cys Ala
                    85                  90                  95

Arg Asp Arg His Cys Ser Gly Gly Thr Cys Tyr Gly Met Asp Val Trp
                100                 105                 110

Gly Gln Gly Thr Thr Val Thr Val Ser Ser
                115                 120

<210> SEQ ID NO 83
<211> LENGTH: 122
<212> TYPE: PRT
<213> ORGANISM: Artificial
<220> FEATURE:
<223> OTHER INFORMATION: Synthetic Construct

<400> SEQUENCE: 83

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Tyr
                20                  25                  30

Tyr Trp Ser Trp Ile Arg Gln Pro Pro Gly Arg Gly Leu Glu Trp Ile
            35                  40                  45

Gly Tyr Ile Tyr His Gly Gly Ser Thr Asn Tyr Ser Pro Ser Leu Lys
        50                  55                  60

Ser Arg Val Thr Ile Ser Val Asp Thr Ser Lys Ser Gln Val Ser Leu
65                  70                  75                  80

Arg Leu Ser Ser Val Thr Ala Ala Asp Thr Ala Met Tyr Tyr Cys Ala
                    85                  90                  95

Arg Asp Arg His Cys Ser Gly Gly Thr Cys Tyr Gly Met Asp Val Trp
                100                 105                 110

Gly Gln Gly Thr Thr Val Thr Val Ser Ser
                115                 120

<210> SEQ ID NO 84
<211> LENGTH: 122
<212> TYPE: PRT
<213> ORGANISM: Artificial
<220> FEATURE:
<223> OTHER INFORMATION: Synthetic Construct

<400> SEQUENCE: 84

Glu Val Gln Leu Leu Glu Ser Gly Pro Gly Leu Val Lys Pro Ser Glu
 1               5                  10                  15

Thr Leu Ser Leu Thr Cys Thr Val Ser Gly Gly Ser Ile Thr Ser Tyr
                20                  25                  30

Tyr Trp Thr Trp Ile Arg Gln Pro Pro Gly Lys Gly Leu Glu Trp Ile
            35                  40                  45

Gly Tyr Ile Tyr Asn Ser Val Ser Thr Asn Tyr Asn Pro Ser Val Lys
        50                  55                  60

Ser Arg Val Thr Ile Ser Ala His Thr Ser Thr Asn Gln Phe Ser Leu
65                  70                  75                  80

Asn Leu Phe Ser Val Thr Ala Ala Asp Thr Ala Val Tyr Tyr Cys Ala
                    85                  90                  95

Arg Gly Arg Arg Ala Tyr Ser Ser Ser Trp Tyr Pro Pro Asp Tyr Trp
                100                 105                 110

Gly Gln Gly Thr Leu Val Thr Val Ser Ser
                115                 120
```

```
<210> SEQ ID NO 85
<211> LENGTH: 123
<212> TYPE: PRT
<213> ORGANISM: Artificial
<220> FEATURE:
<223> OTHER INFORMATION: Synthetic Construct

<400> SEQUENCE: 85

Ser Arg Val Gln Leu Gln Glu Ser Gly Pro Gly Leu Val Lys Ala Ser
  1               5                  10                  15

Glu Thr Leu Ser Leu Thr Cys Thr Val Ser Gly Asp Ser Ile Thr Asn
             20                  25                  30

Tyr Tyr Trp Ser Trp Ile Arg Gln Pro Pro Gly Lys Gly Leu Glu Trp
         35                  40                  45

Ile Gly Asn Thr Tyr Ser Ser Gly Asn Ala Asn Tyr Asn Pro Ser Phe
     50                  55                  60

Glu Ser Arg Val Thr Met Ser Val Asp Thr Ser Arg Ser Gln Phe Ser
 65                  70                  75                  80

Leu Lys Leu Ser Ser Val Thr Ala Ala Asp Thr Ala Val Tyr Tyr Cys
                 85                  90                  95

Ala Arg Val His Phe Asp Phe Gly Ala Lys Arg Lys Thr Phe Asp Tyr
            100                 105                 110

Trp Gly Gln Gly Thr Leu Val Thr Val Ser Ser
        115                 120

<210> SEQ ID NO 86
<211> LENGTH: 119
<212> TYPE: PRT
<213> ORGANISM: Artificial
<220> FEATURE:
<223> OTHER INFORMATION: Synthetic Construct

<400> SEQUENCE: 86

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Asp Ser Phe Thr Asp Tyr
             20                  25                  30

Tyr Trp Ser Trp Ile Arg Gln Pro Pro Gly Lys Asp Leu Glu Trp Ile
         35                  40                  45

Gly Glu Ile Asn His Ser Gly Asn Thr Asn Tyr Asn Pro Ser Leu Thr
     50                  55                  60

Ser Arg Val Thr Ile Ser Val Asp Thr Ser Lys Asn Gln Phe Ser Leu
 65                  70                  75                  80

Lys Met Asn Ser Val Thr Ala Ala Asp Thr Ala Val Tyr Tyr Cys Ala
                 85                  90                  95

Arg Leu Arg Gln Tyr Gly Ala Lys Ala Gly Tyr Trp Gly Gln Gly
            100                 105                 110

Thr Leu Val Thr Val Ser Ser
        115

<210> SEQ ID NO 87
<211> LENGTH: 123
<212> TYPE: PRT
<213> ORGANISM: Artificial
<220> FEATURE:
<223> OTHER INFORMATION: Synthetic Construct

<400> SEQUENCE: 87

Gln Val Gln Leu Gln Glu Ser Gly Pro Gly Leu Val Lys Pro Ser Glu
```

```
                1               5                   10                  15
            Thr Leu Ser Leu Thr Cys Thr Val Ser Gly Val Ser Ile Thr Asn Tyr
                            20                  25                  30

Phe Trp Ser Trp Ile Arg Gln Thr Pro Gly Lys Gly Leu Asp Trp Ile
                            35                  40                  45

Gly Tyr Ile Tyr Tyr Ser Gly Ser Arg Asn Tyr Asn Pro Ser Val Lys
                        50                  55                  60

Ser Arg Val Val Ile Ser Leu Asp Thr Thr Lys Asn His Phe Ser Leu
            65                  70                  75                  80

Lys Leu Arg Ser Val Thr Ala Ala Asp Thr Gly Val Tyr Tyr Cys Ala
                            85                  90                  95

Arg His Val Arg Gly Gly Arg Leu Gly Asp Leu Ser Ser Ala Asp Ser
                            100                 105                 110

Trp Gly Pro Gly Thr Leu Val Thr Val Ser Ser
                        115                 120
```

<210> SEQ ID NO 88
<211> LENGTH: 124
<212> TYPE: PRT
<213> ORGANISM: Artificial
<220> FEATURE:
<223> OTHER INFORMATION: Synthetic Construct

<400> SEQUENCE: 88

```
            Gln Val Gln Leu Gln Glu Ser Gly Pro Gly Leu Val Lys Pro Ser Glu
            1               5                   10                  15

Thr Leu Ser Leu Thr Cys Thr Val Ser Gly Gly Ser Ile Ser Ser Tyr
                            20                  25                  30

Tyr Trp Ser Trp Ile Arg Gln Pro Pro Gly Lys Gly Leu Glu Trp Ile
                            35                  40                  45

Gly Tyr Thr Tyr Tyr Ser Gly Ser Thr Asn Tyr Asn Pro Ser Leu Lys
                        50                  55                  60

Ser Arg Val Thr Ile Leu Val Asp Thr Ser Lys Asn Gln Phe Ser Leu
            65                  70                  75                  80

Arg Leu Ser Ser Val Thr Ala Ala Asp Thr Ala Val Tyr Tyr Cys Ala
                            85                  90                  95

Arg Asp Pro Gly Asn Ala Trp Val Gly Glu Leu Ser Gly Gly Met Asp
                            100                 105                 110

Val Trp Gly Gln Gly Thr Thr Val Thr Val Ser Ser
                        115                 120
```

<210> SEQ ID NO 89
<211> LENGTH: 127
<212> TYPE: PRT
<213> ORGANISM: Artificial
<220> FEATURE:
<223> OTHER INFORMATION: Synthetic Construct

<400> SEQUENCE: 89

```
            Glu Val Gln Leu Gln Glu Ser Gly Pro Ser Leu Val Lys Pro Ser Gln
            1               5                   10                  15

Thr Leu Ser Leu Thr Cys Ser Val Thr Gly Asp Ser Ile Thr Ser Gly
                            20                  25                  30

Tyr Trp Asn Trp Ile Arg Lys Phe Pro Gly Asn Lys Leu Glu Tyr Met
                            35                  40                  45

Gly Tyr Ile Ser Tyr Ser Gly Ser Thr Tyr Tyr Asn Leu Ser Leu Arg
                        50                  55                  60
```

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
            85                  90                  95

Leu Ile Thr Thr Thr Thr Tyr Ala Met Asp Tyr Trp Gly Gln Gly Thr
            100                 105                 110

Ser Val Thr Val Ser Ala Ser Thr Lys Gly Pro Ser Val Phe Pro
            115                 120                 125

<210> SEQ ID NO 90
<211> LENGTH: 142
<212> TYPE: PRT
<213> ORGANISM: Homo sapiens

<400> SEQUENCE: 90

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Asp Ser Ile
        35                  40                  45

Ser Ser Tyr Tyr Trp Ser Trp Ile Arg Gln Pro Pro Gly Arg Ala Leu
50                  55                  60

Glu Trp Ile Gly Tyr Ile Tyr His Gly Gly Ser Thr Asn Tyr Ser Pro
65                  70                  75                  80

Ser Leu Lys Ser Arg Val Thr Ile Ser Val Asp Thr Ser Lys Asn Gln
            85                  90                  95

Phe Ser Leu Arg Leu Ser Ser Val Thr Ala Ala Asp Thr Ala Met Tyr
            100                 105                 110

Tyr Cys Ala Arg Asp Arg His Cys Ser Gly Gly Thr Cys Tyr Gly Met
            115                 120                 125

Asp Val Trp Gly Gln Gly Thr Thr Val Thr Val Ser Ser Gly
            130                 135                 140

<210> SEQ ID NO 91
<211> LENGTH: 118
<212> TYPE: PRT
<213> ORGANISM: Homo sapiens

<400> SEQUENCE: 91

Ser Gln Val Gln Leu Gln Glu Ser Gly Pro Gly Leu Val Lys Pro Ser
1               5                   10                  15

Glu Thr Leu Ser Leu Thr Cys Ile Val Ser Gly Asp Ser Ile Ser Ser
            20                  25                  30

Tyr Tyr Trp Ser Trp Ile Arg Gln Ser Pro Gly Lys Gly Leu Glu Trp
            35                  40                  45

Ile Gly Cys Met Ser Tyr Ser Gly Ser Thr Asn Tyr Asn Pro Ser Leu
50                  55                  60

Arg Ser Arg Val Thr Ile Ser Val Asp Thr Ser Lys Asn Gln Phe Ser
65                  70                  75                  80

Leu Glu Leu Arg Ser Val Thr Ala Ala Asp Thr Ala Val Tyr Tyr Cys
            85                  90                  95

Ala Arg His Asp Phe Trp Arg Thr Phe Asp Ser Trp Gly Gln Gly Thr
            100                 105                 110

Leu Val Thr Val Ser Ser
            115

<210> SEQ ID NO 92
<211> LENGTH: 122
<212> TYPE: PRT
<213> ORGANISM: Homo sapiens

<400> SEQUENCE: 92

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Ser Trp Ile Arg Gln Pro Pro Gly Arg Gly Leu Glu Trp Ile
        35                  40                  45

Gly Tyr Ile Tyr His Gly Gly Ser Thr Asn Tyr Ser Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Met Tyr Tyr Cys Ala
                85                  90                  95

Arg Asp Arg His Cys Ser Gly Gly Thr Cys Tyr Gly Met Asp Val Trp
            100                 105                 110

Gly Gln Gly Thr Thr Val Thr Val Ser Ser
        115                 120

<210> SEQ ID NO 93
<211> LENGTH: 123
<212> TYPE: PRT
<213> ORGANISM: Homo sapiens

<400> SEQUENCE: 93

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Ser Trp Ile Arg Gln Pro Pro Gly Arg Ala Leu Glu Trp Ile
        35                  40                  45

Gly Tyr Ile Tyr His Gly Gly Ser Thr Asn Tyr Ser Pro Ser Leu Lys
    50                  55                  60

Ser Arg Val Thr Ile Ser Val Asp Thr Ser Lys Asn Gln Phe Ser Leu
65                  70                  75                  80

Arg Leu Thr Ser Leu Thr Ala Ala Asp Thr Ala Met Tyr Tyr Cys Ala
                85                  90                  95

Arg Asp Arg His Cys Ser Gly Gly Thr Cys Tyr Gly Met Asp Val Trp
            100                 105                 110

Gly Gln Gly Thr Thr Val Thr Val Ser Ser Gly
        115                 120

<210> SEQ ID NO 94
<211> LENGTH: 57
<212> TYPE: DNA
<213> ORGANISM: Artificial
<220> FEATURE:
<223> OTHER INFORMATION: Synthetic Construct

<400> SEQUENCE: 94
atgaaacatc tgtggttctt ccttctgctg gtggcagctc ccagatgggt cctgtcc      57

<210> SEQ ID NO 95
<211> LENGTH: 47

<212> TYPE: PRT
<213> ORGANISM: Artificial
<220> FEATURE:
<223> OTHER INFORMATION: Synthetic Construct

<400> SEQUENCE: 95

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Asp Ser
        35                  40                  45

<210> SEQ ID NO 96
<211> LENGTH: 5
<212> TYPE: PRT
<213> ORGANISM: Artificial
<220> FEATURE:
<223> OTHER INFORMATION: Synthetic Construct

<400> SEQUENCE: 96

Val Leu Ser Gln Val
1               5

<210> SEQ ID NO 97
<211> LENGTH: 5
<212> TYPE: PRT
<213> ORGANISM: Artificial
<220> FEATURE:
<223> OTHER INFORMATION: Synthetic Construct

<400> SEQUENCE: 97

Ser Gly Tyr Trp Asn
1               5

<210> SEQ ID NO 98
<211> LENGTH: 16
<212> TYPE: PRT
<213> ORGANISM: Artificial
<220> FEATURE:
<223> OTHER INFORMATION: Synthetic Construct

<400> SEQUENCE: 98

Tyr Ile Ser Tyr Ser Gly Ser Thr Tyr Tyr Asn Leu Ser Leu Arg Ser
1               5                   10                  15

<210> SEQ ID NO 99
<211> LENGTH: 10
<212> TYPE: PRT
<213> ORGANISM: Artificial
<220> FEATURE:
<223> OTHER INFORMATION: Synthetic Construct

<400> SEQUENCE: 99

Ile Thr Thr Thr Thr Tyr Ala Met Asp Tyr
1               5                   10

<210> SEQ ID NO 100
<211> LENGTH: 118
<212> TYPE: PRT
<213> ORGANISM: Artificial
<220> FEATURE:
<223> OTHER INFORMATION: Synthetic Construct

<400> SEQUENCE: 100

Gln Val Gln Leu Gln Glu Ser Gly Pro Gly Leu Val Lys Pro Ser Glu

```
                1               5                  10                 15
Thr Leu Ser Leu Thr Cys Thr Val Ser Gly Asp Ser Ile Ser Ser Gly
                20                  25                 30

Tyr Trp Asn Trp Ile Arg Gln Pro Pro Gly Arg Ala Leu Glu Trp Ile
            35                  40                 45

Gly Tyr Ile Ser Tyr Ser Gly Ser Thr Tyr Tyr Asn Leu Ser Leu Arg
    50                  55                 60

Ser Arg Val Thr Ile Ser Val Asp Thr Ser Lys Asn Gln Phe Ser Leu
65                  70                  75                 80

Arg Leu Ser Ser Val Thr Ala Ala Asp Thr Ala Met Tyr Tyr Cys Ala
                85                  90                 95

Arg Ile Thr Thr Thr Thr Tyr Ala Met Asp Tyr Trp Gly Gln Gly Thr
            100                 105                110

Thr Val Thr Val Ser Ser
            115

<210> SEQ ID NO 101
<211> LENGTH: 87
<212> TYPE: PRT
<213> ORGANISM: Artificial
<220> FEATURE:
<223> OTHER INFORMATION: Synthetic Construct

<400> SEQUENCE: 101

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Trp Ile
                20                  25                 30

Arg Gln Pro Pro Gly Arg Ala Leu Glu Trp Ile Gly Arg Val Thr Ile
            35                  40                 45

Ser Val Asp Thr Ser Lys Asn Gln Phe Ser Leu Arg Leu Ser Ser Val
    50                  55                 60

Thr Ala Ala Asp Thr Ala Met Tyr Tyr Cys Ala Arg Trp Gly Gln Gly
65                  70                  75                 80

Thr Thr Val Thr Val Ser Ser
            85

<210> SEQ ID NO 102
<211> LENGTH: 19
<212> TYPE: PRT
<213> ORGANISM: Artificial sequence
<220> FEATURE:
<223> OTHER INFORMATION: Synthetic Construct

<400> SEQUENCE: 102

Met Lys His Leu Trp Phe Phe Leu Leu Leu Val Ala Ala Pro Arg Trp
1               5                   10                  15

Val Leu Ser

<210> SEQ ID NO 103
<211> LENGTH: 90
<212> TYPE: DNA
<213> ORGANISM: Artificial
<220> FEATURE:
<223> OTHER INFORMATION: Synthetic Construct

<400> SEQUENCE: 103
caggtgcagc tgcaggagtc gggcccagga ctggtgaagc cttcggagac cctgtccctc    60
acctgcactg tctctggtga ctccatcagt                                     90
```

<210> SEQ ID NO 104
<211> LENGTH: 30
<212> TYPE: PRT
<213> ORGANISM: Artificial
<220> FEATURE:
<223> OTHER INFORMATION: Synthetic Construct

<400> SEQUENCE: 104

Gln Val Gln Leu Gln Glu Ser Gly Pro Gly Leu Val Lys Pro Ser Glu
 1               5                  10                  15
Thr Leu Ser Leu Thr Cys Thr Val Ser Gly Asp Ser Ile Ser
            20                  25                  30

<210> SEQ ID NO 105
<211> LENGTH: 15
<212> TYPE: DNA
<213> ORGANISM: Artificial
<220> FEATURE:
<223> OTHER INFORMATION: Synthetic Construct

<400> SEQUENCE: 105
agtggttact ggaac                                                    15

<210> SEQ ID NO 106
<211> LENGTH: 39
<212> TYPE: DNA
<213> ORGANISM: Artificial
<220> FEATURE:
<223> OTHER INFORMATION: Synthetic Construct

<400> SEQUENCE: 106
atccggcagc ccccagggag ggcactggag tggatagga                          39

<210> SEQ ID NO 107
<211> LENGTH: 14
<212> TYPE: PRT
<213> ORGANISM: Artificial
<220> FEATURE:
<223> OTHER INFORMATION: Synthetic Construct

<400> SEQUENCE: 107

Trp Ile Arg Gln Pro Pro Gly Arg Ala Leu Glu Trp Ile Gly
 1               5                  10

<210> SEQ ID NO 108
<211> LENGTH: 48
<212> TYPE: DNA
<213> ORGANISM: Artificial
<220> FEATURE:
<223> OTHER INFORMATION: Synthetic Construct

<400> SEQUENCE: 108
tacataagtt acagtggtag cacttactac aatctatctc tcagaagt                48

<210> SEQ ID NO 109
<211> LENGTH: 96
<212> TYPE: DNA
<213> ORGANISM: Artificial
<220> FEATURE:
<223> OTHER INFORMATION: Synthetic Construct

<400> SEQUENCE: 109
cgggtcacca tatcagtaga cacgtctaag aaccagttct ccctgaggct gagctctgtg   60
accgctgcgg acacggccat gtattactgt gcgaga                             96

<210> SEQ ID NO 110
<211> LENGTH: 32
<212> TYPE: PRT
<213> ORGANISM: Artificial
<220> FEATURE:
<223> OTHER INFORMATION: Synthetic Construct

<400> SEQUENCE: 110

Arg Val Thr Ile Ser Val Asp Thr Ser Lys Asn Gln Phe Ser Leu Arg
 1               5                  10                  15

Leu Ser Ser Val Thr Ala Ala Asp Thr Ala Met Tyr Tyr Cys Ala Arg
                20                  25                  30

<210> SEQ ID NO 111
<211> LENGTH: 30
<212> TYPE: DNA
<213> ORGANISM: Artificial
<220> FEATURE:
<223> OTHER INFORMATION: Synthetic Construct

<400> SEQUENCE: 111
attactacga ctacctatgc tatggactac                                          30

<210> SEQ ID NO 112
<211> LENGTH: 30
<212> TYPE: DNA
<213> ORGANISM: Artificial
<220> FEATURE:
<223> OTHER INFORMATION: Synthetic Construct

<400> SEQUENCE: 112
tggggccaag ggaccacggt caccgtctcc                                          30

<210> SEQ ID NO 113
<211> LENGTH: 10
<212> TYPE: PRT
<213> ORGANISM: Artificial
<220> FEATURE:
<223> OTHER INFORMATION: Synthetic Construct

<400> SEQUENCE: 113

Trp Gly Gln Gly Thr Thr Val Thr Val Ser
 1               5                  10

<210> SEQ ID NO 114
<211> LENGTH: 405
<212> TYPE: DNA
<213> ORGANISM: Artificial sequence
<220> FEATURE:
<223> OTHER INFORMATION: Synthetic Construct

<400> SEQUENCE: 114
atgaaacatc tgtggttctt ccttctgctg gtggcagctc ccagatgggt cctgtcccag         60
gtgcagctgc aggagtcggg cccaggactg gtgaagcctt cggagaccct gtccctcacc        120
tgcactgtct ctggtgactc catcagtagt ggttactgga acatccggca gcccccaggg        180
agggcactgg agtggatagg atacataagt acagtggta gcacttacta caatctatct         240
ctcagaagtc gggtcaccat atcagtagac acgtctaaga accagttctc cctgaggctg        300
agctctgtga ccgctgcgga cacggccatg tattactgtg cgagaattac tacgactacc        360
tatgctatgg actactgggg ccaagggacc acggtcaccg tctcc                        405

<210> SEQ ID NO 115
<211> LENGTH: 453
<212> TYPE: DNA
<213> ORGANISM: Artificial sequence
<220> FEATURE:
<223> OTHER INFORMATION: Synthetic Construct

<400> SEQUENCE: 115

```
cacgccaagc ttgccgccac catgaaacat ctgtggttct tccttctgct ggtggcagct    60
cccagatggg tcctgtccca agtgcagctg caggagtcgg gaccaggact ggtgaagcct   120
tcggagaccc tgtccctcac ctgcactgtc tctggtgact ccatcagtag tggttactgg   180
aactggatcc ggcagccccc agggagggca ctggagtgga taggatacat aagttacagt   240
ggtagcactt actacaatct atctctcaga agtcgggtca ccatatcagt agacacctct   300
aagaaccagt tctccctgag gctgagctct gtgaccgctg cggacacggc catgtattac   360
tgtgcgagaa ttactacgac tacctatgct atggactact ggggccaagg gaccacggtc   420
accgtctcct cagcctccac caagggccca tcg                                453
```

<210> SEQ ID NO 116
<211> LENGTH: 151
<212> TYPE: PRT
<213> ORGANISM: Artificial sequence
<220> FEATURE:
<223> OTHER INFORMATION: Synthetic Construct

<400> SEQUENCE: 116

His Ala Lys Leu Ala Ala Thr Met Lys His Leu Trp Phe Phe Leu Leu
1               5                   10                  15

Leu Val Ala Ala Pro Arg Trp Val Leu Ser Gln Val Gln Leu Gln Glu
            20                  25                  30

Ser Gly Pro Gly Leu Val Lys Pro Ser Glu Thr Leu Ser Leu Thr Cys
        35                  40                  45

Thr Val Ser Gly Asp Ser Ile Ser Ser Gly Tyr Trp Asn Trp Ile Arg
    50                  55                  60

Gln Pro Pro Gly Arg Ala Leu Glu Trp Ile Gly Tyr Ile Ser Tyr Ser
65                  70                  75                  80

Gly Ser Thr Tyr Tyr Asn Leu Ser Leu Arg Ser Arg Val Thr Ile Ser
                85                  90                  95

Val Asp Thr Ser Lys Asn Gln Phe Ser Leu Arg Leu Ser Ser Val Thr
            100                 105                 110

Ala Ala Asp Thr Ala Met Tyr Tyr Cys Ala Arg Ile Thr Thr Thr Thr
        115                 120                 125

Tyr Ala Met Asp Tyr Trp Gly Gln Gly Thr Thr Val Thr Val Ser Ser
    130                 135                 140

Ala Ser Thr Lys Gly Pro Ser
145                 150

<210> SEQ ID NO 117
<211> LENGTH: 99
<212> TYPE: PRT
<213> ORGANISM: Artificial
<220> FEATURE:
<223> OTHER INFORMATION: Synthetic Construct

<400> SEQUENCE: 117

Asn Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Gly Tyr

```
                    20                  25                  30
Gly Asn Ser Phe Leu His Trp Phe Gln Gln Lys Pro Gly Gln Pro
            35                  40                  45
Lys Leu Leu Ile Tyr Leu Ala Ser Asn Leu Asn Ser Gly Val Pro Ala
 50                  55                  60
Arg Phe Ser Gly Ser Gly Ser Arg Thr Asp Phe Thr Leu Thr Ile Asp
 65                  70                  75                  80
Pro Val Glu Ala Asp Asp Ala Ala Thr Tyr Tyr Cys Gln Gln Asn Asn
                 85                  90                  95
Val Asp Pro

<210> SEQ ID NO 118
<211> LENGTH: 95
<212> TYPE: PRT
<213> ORGANISM: Homo sapiens

<400> SEQUENCE: 118

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro
                 85                  90                  95

<210> SEQ ID NO 119
<211> LENGTH: 95
<212> TYPE: PRT
<213> ORGANISM: Homo sapiens

<400> SEQUENCE: 119

Asp Ile Gln Met Thr Gln Ser Pro Ser Ser Leu Ser Ala Ser Val Gly
 1               5                  10                  15
Asp Arg Val Thr Ile Thr Cys Gln Ala Ser Gln Asp Ile Ser Asn Tyr
                20                  25                  30
Leu Asn Trp Tyr Gln Gln Lys Pro Gly Lys Ala Pro Lys Leu Leu Ile
            35                  40                  45
Tyr Asp Ala Ser Asn Leu Glu Thr Gly Val Pro Ser Arg Phe Ser Gly
 50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Gln Gln Tyr Asp Asn Leu Pro
                 85                  90                  95

<210> SEQ ID NO 120
<211> LENGTH: 95
<212> TYPE: PRT
<213> ORGANISM: Homo sapiens

<400> SEQUENCE: 120

Asp Ile Gln Met Thr Gln Ser Pro Ser Ser Leu Ser Ala Ser Val Gly
 1               5                  10                  15
```

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 121
<211> LENGTH: 95
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 122
<211> LENGTH: 95
<212> TYPE: PRT
<213> ORGANISM: Homo sapiens

<400> SEQUENCE: 122

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 123
<211> LENGTH: 95
<212> TYPE: PRT
<213> ORGANISM: Homo sapiens

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr

```
                    20                  25                  30

Leu Ala Trp Phe Gln Gln Lys Pro Gly Lys Ala Pro Lys Ser Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                    85                  90                  95

<210> SEQ ID NO 124
<211> LENGTH: 95
<212> TYPE: PRT
<213> ORGANISM: Homo sapiens

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                    85                  90                  95

<210> SEQ ID NO 125
<211> LENGTH: 95
<212> TYPE: PRT
<213> ORGANISM: Homo sapiens

<400> SEQUENCE: 125

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                    85                  90                  95

<210> SEQ ID NO 126
<211> LENGTH: 95
<212> TYPE: PRT
<213> ORGANISM: Homo sapiens

<400> SEQUENCE: 126

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30
```

```
Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95
```

<210> SEQ ID NO 127
<211> LENGTH: 95
<212> TYPE: PRT
<213> ORGANISM: Homo sapiens

<400> SEQUENCE: 127

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95
```

<210> SEQ ID NO 128
<211> LENGTH: 95
<212> TYPE: PRT
<213> ORGANISM: Homo sapiens

<400> SEQUENCE: 128

```
Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
                20                  25                  30

Leu Ala Trp Tyr Gln Gln Lys Pro Ala Lys Ala Pro Lys Leu Phe Ile
            35                  40                  45

Tyr Tyr Ala Ser Ser Leu Gln Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95
```

<210> SEQ ID NO 129
<211> LENGTH: 95
<212> TYPE: PRT
<213> ORGANISM: Homo sapiens

<400> SEQUENCE: 129

```
Ala Ile Arg Met Thr Gln Ser Pro Ser Phe Ser Ala Ser Thr Gly
1               5                   10                  15

Asp Arg Val Thr Ile Thr Cys Arg Ala Ser Gln Gly Ile Ser Ser Tyr
                20                  25                  30
```

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Tyr Pro
                 85                  90                  95

<210> SEQ ID NO 130
<211> LENGTH: 95
<212> TYPE: PRT
<213> ORGANISM: Homo sapiens

<400> SEQUENCE: 130

Val Ile Trp Met Thr Gln Ser Pro Ser Leu Ser Ala Ser Thr Gly
 1               5                  10                  15

Asp Arg Val Thr Ile Ser Cys Arg Met Ser Gln Gly Ile Ser Ser Tyr
                 20                  25                  30

Leu Ala Trp Tyr Gln Gln Lys Pro Gly Lys Ala Pro Glu Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Phe Pro
                 85                  90                  95

<210> SEQ ID NO 131
<211> LENGTH: 95
<212> TYPE: PRT
<213> ORGANISM: Homo sapiens

<400> SEQUENCE: 131

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro
                 85                  90                  95

<210> SEQ ID NO 132
<211> LENGTH: 95
<212> TYPE: PRT
<213> ORGANISM: Homo sapiens

<400> SEQUENCE: 132

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile

```
            35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser
                 85                  90                  95
```

<210> SEQ ID NO 133
<211> LENGTH: 101
<212> TYPE: PRT
<213> ORGANISM: Homo sapiens

<400> SEQUENCE: 133

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu Asp Ser
                 20                  25                  30

Asp Asp Gly Asn Thr Tyr Leu Asp Trp Tyr Leu Gln Lys Pro Gly Gln
             35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Ile Glu Phe Pro
            100
```

<210> SEQ ID NO 134
<211> LENGTH: 100
<212> TYPE: PRT
<213> ORGANISM: Homo sapiens

<400> SEQUENCE: 134

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro
            100
```

<210> SEQ ID NO 135
<211> LENGTH: 100
<212> TYPE: PRT
<213> ORGANISM: Homo sapiens

<400> SEQUENCE: 135

```
Asp Val Val Met Thr Gln Ser Pro Leu Ser Leu Pro Val Thr Leu Gly
 1               5                  10                  15
```

Gln Pro Ala Ser Ile Ser Cys Arg Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 136
<211> LENGTH: 100
<212> TYPE: PRT
<213> ORGANISM: Homo sapiens

<400> SEQUENCE: 136

Asp Ile Val Met Thr Gln Thr Pro Leu Ser Leu Ser Val Thr Pro Gly
 1               5                  10                  15

Gln Pro Ala Ser Ile Ser Cys Lys Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 137
<211> LENGTH: 100
<212> TYPE: PRT
<213> ORGANISM: Homo sapiens

<400> SEQUENCE: 137

Asp Ile Val Met Thr Gln Thr Pro Leu Ser Leu Ser Val Thr Pro Gly
 1               5                  10                  15

Gln Pro Ala Ser Ile Ser Cys Lys Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 138

```
<211> LENGTH: 100
<212> TYPE: PRT
<213> ORGANISM: Homo sapiens

<400> SEQUENCE: 138

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 139
<211> LENGTH: 100
<212> TYPE: PRT
<213> ORGANISM: Homo sapiens

<400> SEQUENCE: 139

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100

<210> SEQ ID NO 140
<211> LENGTH: 96
<212> TYPE: PRT
<213> ORGANISM: Homo sapiens

<400> SEQUENCE: 140

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Ser Pro
                85                  90                  95
```

<210> SEQ ID NO 141
<211> LENGTH: 96
<212> TYPE: PRT
<213> ORGANISM: Homo sapiens

<400> SEQUENCE: 141

```
Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser
                20                  25                  30

Tyr Leu Ala Trp Tyr Gln Gln Lys Pro Gly Leu Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 142
<211> LENGTH: 95
<212> TYPE: PRT
<213> ORGANISM: Homo sapiens

<400> SEQUENCE: 142

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 143
<211> LENGTH: 95
<212> TYPE: PRT
<213> ORGANISM: Homo sapiens

<400> SEQUENCE: 143

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 144
<211> LENGTH: 95
<212> TYPE: PRT
<213> ORGANISM: Homo sapiens

<400> SEQUENCE: 144

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Gly Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Pro Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp His
                85                  90                  95

<210> SEQ ID NO 145
<211> LENGTH: 96
<212> TYPE: PRT
<213> ORGANISM: Homo sapiens

<400> SEQUENCE: 145

Glu Ile Val Met Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ser Trp Tyr Gln Gln Lys Pro Gly Gln Ala Pro Arg Leu Leu
        35                  40                  45
Ile Tyr Gly Ala Ser Thr Arg Ala Thr Gly Ile Pro Ala Arg Phe Ser
    50                  55                  60
Gly Ser Gly Ser Gly Thr Asp Phe Thr Leu Thr Ile Ser Ser Leu Gln
65                  70                  75                  80
Pro Glu Asp Phe Ala Val Tyr Tyr Cys Gln Gln Asp Tyr Asn Leu Pro
                85                  90                  95

<210> SEQ ID NO 146
<211> LENGTH: 101
<212> TYPE: PRT
<213> ORGANISM: Homo sapiens

<400> SEQUENCE: 146

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95

-continued

```
Tyr Tyr Ser Thr Pro
            100

<210> SEQ ID NO 147
<211> LENGTH: 95
<212> TYPE: PRT
<213> ORGANISM: Homo sapiens

<400> SEQUENCE: 147

Glu Thr Thr Leu Thr Gln Ser Pro Ala Phe Met Ser Ala Thr Pro Gly
 1               5                  10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 148
<211> LENGTH: 95
<212> TYPE: PRT
<213> ORGANISM: Homo sapiens

<400> SEQUENCE: 148

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 149
<211> LENGTH: 95
<212> TYPE: PRT
<213> ORGANISM: Homo sapiens

<400> SEQUENCE: 149

Asp Val Val Met Thr Gln Ser Pro Ala Phe Leu Ser Val Thr Pro Gly
 1               5                  10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Phe Thr Ile Ser Ser Leu Glu Ala
65                  70                  75                  80
```

Glu Asp Ala Ala Thr Tyr Tyr Cys Gln Gln Gly Asn Lys His Pro
                85                  90                  95

<210> SEQ ID NO 150
<211> LENGTH: 4
<212> TYPE: PRT
<213> ORGANISM: Artificial sequence
<220> FEATURE:
<223> OTHER INFORMATION: Synthetic Construct

<400> SEQUENCE: 150

Leu Leu Ile Tyr
 1

<210> SEQ ID NO 151
<211> LENGTH: 4
<212> TYPE: PRT
<213> ORGANISM: Artificial sequence
<220> FEATURE:
<223> OTHER INFORMATION: Synthetic Construct

<400> SEQUENCE: 151

Leu Leu Ile Lys
 1

<210> SEQ ID NO 152
<211> LENGTH: 4
<212> TYPE: PRT
<213> ORGANISM: Artificial sequence
<220> FEATURE:
<223> OTHER INFORMATION: Synthetic Construct

<400> SEQUENCE: 152

Ile Ile Ile Tyr
 1

<210> SEQ ID NO 153
<211> LENGTH: 114
<212> TYPE: PRT
<213> ORGANISM: Artificial sequence
<220> FEATURE:
<223> OTHER INFORMATION: Synthetic construct

<400> SEQUENCE: 153

Gly Asp Ile Val Leu Thr Gln Ser Pro Asp Ser Leu Ser Val Ser Leu
 1               5                  10                  15

Gly Glu Arg Val Thr Val Asn Cys Lys Leu Ser Gln Ser Val Leu His
                20                  25                  30

Ser Ser Asn Lys Gln Asn Tyr Leu Ala Trp Phe Gln Asn Pro Gly
            35                  40                  45

Gln Pro Pro Lys Leu Leu Ile Tyr Trp Ala Ser Ala Arg Gln Ser Gly
        50                  55                  60

Val Pro Ala Arg Phe Met Gly Ser Gly Ser Gly Thr Glu Phe Ser Leu
65                  70                  75                  80

Thr Ile Ser Ser Leu Gln Ala Glu Asp Val Ala Val Tyr Tyr Cys Gln
                85                  90                  95

Gln Tyr Tyr Asp Ser Thr Tyr Thr Phe Gly Gln Gly Thr Lys Leu Glu
                100                 105                 110

Ile Asn

<210> SEQ ID NO 154
<211> LENGTH: 107
<212> TYPE: PRT

<213> ORGANISM: Homo sapiens

<400> SEQUENCE: 154

Asp Ile Val Leu Thr Gln Ser Pro Ser Ser Val Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ser Ala Ser Tyr Tyr Cys Gln Gln Thr Asn Ser Phe Pro Ile
                85                  90                  95

Thr Phe Gly Gln Gly Thr Arg Leu Glu Ile Lys
            100                 105

<210> SEQ ID NO 155
<211> LENGTH: 108
<212> TYPE: PRT
<213> ORGANISM: Artificial sequence
<220> FEATURE:
<223> OTHER INFORMATION: Synthetic construct

<400> SEQUENCE: 155

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Met
                85                  90                  95

Tyr Thr Phe Gly Gln Gly Thr Lys Leu Glu Ile Lys
            100                 105

<210> SEQ ID NO 156
<211> LENGTH: 107
<212> TYPE: PRT
<213> ORGANISM: Artificial sequence
<220> FEATURE:
<223> OTHER INFORMATION: Synthetic construct

<400> SEQUENCE: 156

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro

```
              65                  70                  75                  80
Glu Asp Phe Gly Thr Tyr Tyr Cys Gln Gln Tyr Asn Thr Tyr Pro Leu
                    85                  90                  95

Thr Phe Gly Gly Gly Thr Lys Leu Glu Ile Lys
                100                 105
```

<210> SEQ ID NO 157
<211> LENGTH: 107
<212> TYPE: PRT
<213> ORGANISM: Artificial sequence
<220> FEATURE:
<223> OTHER INFORMATION: Synthetic construct

<400> SEQUENCE: 157

```
Asp Ile Glu Leu Thr Gln Ser Pro Ser Thr Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
                100                 105
```

<210> SEQ ID NO 158
<211> LENGTH: 107
<212> TYPE: PRT
<213> ORGANISM: Artificial sequence
<220> FEATURE:
<223> OTHER INFORMATION: Synthetic construct

<400> SEQUENCE: 158

```
Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Asn Tyr Pro Leu
                85                  90                  95

Thr Phe Gly Gly Gly Thr Lys Val Asp Ile Lys
                100                 105
```

<210> SEQ ID NO 159
<211> LENGTH: 107
<212> TYPE: PRT
<213> ORGANISM: Homo sapiens

<400> SEQUENCE: 159

```
Asp Ile Arg Leu Thr Gln Ser Pro Ser Phe Leu Ser Ala Ser Val Gly
```

```
              1               5                  10                 15
            Asp Arg Val Thr Ile Thr Cys Arg Ala Ser Gln Gly Ile Ser Thr Tyr
                            20                  25                 30

Leu Ala Trp Tyr Gln Gln Lys Pro Gly Lys Ala Pro Lys Leu Leu Ile
                            35                  40                 45

Tyr Ala Ala Ser Thr Leu Gln Ser Gly Val Pro Ser Arg Phe Ser Gly
                        50                  55                 60

Ser Gly Ser Gly Thr Asp Phe Thr Leu Thr Ile Ser Thr Leu Gln Pro
            65                  70                  75                 80

Glu Asp Phe Ala Thr Tyr Tyr Cys Gln Gln Phe Asn Ser Asn Pro Tyr
                            85                  90                 95

Thr Phe Gly Gln Gly Thr Lys Leu Glu Ile Lys
                        100                 105

<210> SEQ ID NO 160
<211> LENGTH: 109
<212> TYPE: PRT
<213> ORGANISM: Homo sapiens

<400> SEQUENCE: 160

Gly Glu Ile Val Leu Thr Gln Ser Pro Gly Thr Leu Ser Leu Ser Ala
            1               5                  10                 15

Gly Glu Arg Ala Thr Leu Ser Cys Arg Ala Ser Gln Ser Val Ser Ser
                            20                  25                 30

Arg Tyr Leu Ala Trp Tyr Gln Gln Lys Pro Gly Gln Ala Pro Arg Leu
                            35                  40                 45

Leu Ile Tyr Gly Ala Ser Ser Arg Ala Thr Gly Ile Pro Asp Arg Phe
                        50                  55                 60

Ser Gly Ser Gly Ser Gly Thr Asp Phe Thr Leu Thr Ile Ser Arg Val
            65                  70                  75                 80

Glu Pro Glu Asp Phe Ala Val Tyr Tyr Cys Gln Gln Tyr Asp Asn Ser
                            85                  90                 95

Val Cys Thr Phe Gly Gln Gly Thr Lys Leu Glu Ile Lys
                        100                 105

<210> SEQ ID NO 161
<211> LENGTH: 107
<212> TYPE: PRT
<213> ORGANISM: Homo sapiens

<400> SEQUENCE: 161

Asp Ile Gln Leu Thr Gln Ser Pro Ser Phe Leu Ser Ala Ser Ile Gly
            1               5                  10                 15

Asp Arg Val Thr Ile Thr Cys Arg Ala Ser Gln Gly Ile Asn Ser Tyr
                            20                  25                 30

Leu Ala Trp Tyr Gln Gln Lys Pro Gly Lys Ala Pro Lys Leu Leu Ile
                            35                  40                 45

Tyr Val Ala Ser Thr Leu Gln Ser Gly Val Pro Ser Arg Phe Ser Gly
                        50                  55                 60

Ser Gly Ser Gly Thr Glu Phe Thr Leu Thr Ile Ser Ser Leu Gln Pro
            65                  70                  75                 80

Glu Asp Phe Ala Ser Tyr Tyr Cys Gln Gln Phe Asn Ser Tyr Pro Phe
                            85                  90                 95

Thr Phe Gly Gly Gly Thr Lys Val Glu Ile Arg
                        100                 105
```

```
<210> SEQ ID NO 162
<211> LENGTH: 108
<212> TYPE: PRT
<213> ORGANISM: Homo sapiens

<400> SEQUENCE: 162

Cys Asp Ile Gln Leu Thr Gln Ser Pro Ser Phe Leu Ser Ala Ser Ile
1               5                   10                  15

Gly Asp Arg Val Thr Ile Thr Cys Arg Ala Ser Gln Gly Ile Asn Ser
            20                  25                  30

Tyr Leu Ala Trp Tyr Gln Gln Lys Pro Gly Lys Ala Pro Lys Leu Leu
        35                  40                  45

Ile Tyr Val Ala Ser Thr Leu Gln Ser Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Glu Asp Phe Ala Ser Tyr Tyr Cys Gln Gln Phe Asn Ser Tyr Pro
                85                  90                  95

Phe Thr Phe Gly Gly Gly Thr Lys Val Glu Ile Arg
            100                 105

<210> SEQ ID NO 163
<211> LENGTH: 107
<212> TYPE: PRT
<213> ORGANISM: Homo sapiens

<400> SEQUENCE: 163

Glu Ile Val Leu Thr Gln Ser Pro Ser Ser Leu Ser Ala Tyr Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Gln Leu Thr Val Leu
            100                 105

<210> SEQ ID NO 164
<211> LENGTH: 108
<212> TYPE: PRT
<213> ORGANISM: Homo sapiens

<400> SEQUENCE: 164

Glu Ile Val Leu Thr Gln Ser Pro Gly Thr Leu Ser Leu Ser Gln Gly
1               5                   10                  15

Glu Arg Val Thr Leu Ser Cys Arg Ala Ser Gln Thr Ile Asn Ser His
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Val Pro Asp Arg Phe Ser
50                  55                  60

Gly Ser Gly Ser Gly Thr Asp Phe Ile Leu Thr Ile Ser Gly Leu Glu
65                  70                  75                  80
```

-continued

```
Pro Glu Asp Phe Ala Val Tyr Tyr Cys Gln Gln Tyr Gly Thr Ser Pro
                85                  90                  95

Leu Thr Phe Gly Gly Gly Thr Lys Val Glu Ile Lys
            100                 105

<210> SEQ ID NO 165
<211> LENGTH: 108
<212> TYPE: PRT
<213> ORGANISM: Homo sapiens

<400> SEQUENCE: 165

Cys Asp Ile Gln Leu Thr Gln Ser Pro Ser Phe Leu Ser Ala Ser Val
1               5                   10                  15

Gly Asp Arg Val Thr Ile Thr Cys Arg Ala Ser Gln Gly Ile Ser Ser
            20                  25                  30

Tyr Leu Ala Trp Tyr Gln Gln Lys Pro Gly Lys Ala Pro Asn Leu Leu
        35                  40                  45

Ile Tyr Ala Ala Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Leu Asn Ser Ser Pro
                85                  90                  95

Pro Thr Phe Gly Gly Gly Thr Lys Val Glu Ile Lys
            100                 105

<210> SEQ ID NO 166
<211> LENGTH: 107
<212> TYPE: PRT
<213> ORGANISM: Homo sapiens

<400> SEQUENCE: 166

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Thr Thr Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 167
<211> LENGTH: 107
<212> TYPE: PRT
<213> ORGANISM: Homo sapiens

<400> SEQUENCE: 167

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30
```

```
Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Ile
                85                  90                  95

Thr Phe Gly Gln Gly Thr Arg Leu Glu Ile Lys
            100                 105

<210> SEQ ID NO 168
<211> LENGTH: 107
<212> TYPE: PRT
<213> ORGANISM: Homo sapiens

<400> SEQUENCE: 168

Glu Ile Val Leu Thr Gln Ser Pro Ser Ser Leu Ser Ala Ser Val Gly
 1               5                  10                  15

Asp Arg Val Thr Ile Thr Cys Arg Ser Ser Gln Gly Ile Gly Asp Asp
            20                  25                  30

Leu Gly Trp Tyr Gln Gln Lys Pro Gly Lys Ala Pro Ile Leu Leu Ile
            35                  40                  45

Tyr Gly Thr Ser Thr Leu Gln Ser Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys
            100                 105

<210> SEQ ID NO 169
<211> LENGTH: 131
<212> TYPE: PRT
<213> ORGANISM: Artificial sequence
<220> FEATURE:
<223> OTHER INFORMATION: Synthetic construct

<400> SEQUENCE: 169

Met Glu Thr Asp Thr Leu Leu Leu Trp Val Leu Leu Leu Trp Val Pro
 1               5                  10                  15

Gly Ser Thr Gly Asn Ile Val Leu Thr Gln Ser Pro Val Ser Leu Ala
            20                  25                  30

Val Ser Leu Gly Gln Arg Ala Thr Ile Ser Cys Arg Ala Ser Glu Ser
            35                  40                  45

Val Asp Gly Tyr Gly Asn Ser Phe Leu His Trp Phe Gln Gln Lys Pro
 50                  55                  60

Gly Gln Pro Pro Lys Leu Leu Ile Tyr Leu Ala Ser Asn Leu Asn Ser
 65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Asp Ala Ala Thr Tyr Tyr Cys
            100                 105                 110

Gln Gln Asn Asn Val Asp Pro Trp Thr Phe Gly Gly Gly Thr Lys Leu
            115                 120                 125

Glu Ile Lys
```

```
                130

<210> SEQ ID NO 170
<211> LENGTH: 136
<212> TYPE: PRT
<213> ORGANISM: Homo sapiens

<400> SEQUENCE: 170

Ser Lys Met Val Leu Gln Thr Gln Val Phe Ile Ser Leu Leu Leu Trp
  1               5                  10                  15

Ile Ser Gly Ala Ser Gly Asp Ile Val Leu Thr Gln Ser Pro Asp Ser
             20                  25                  30

Leu Ser Val Ser Leu Gly Glu Arg Val Thr Val Asn Cys Lys Leu Ser
         35                  40                  45

Gln Ser Val Leu His Ser Ser Asn Lys Gln Asn Tyr Leu Ala Trp Phe
     50                  55                  60

Gln Gln Asn Pro Gly Gln Pro Pro Lys Leu Leu Ile Tyr Trp Ala Ser
 65                  70                  75                  80

Ala Arg Gln Ser Gly Val Pro Ala Arg Phe Met Gly Ser Gly Ser Gly
                 85                  90                  95

Thr Glu Phe Ser Leu Thr Ile Ser Ser Leu Gln Ala Glu Asp Val Ala
            100                 105                 110

Val Tyr Tyr Cys Gln Gln Tyr Tyr Asp Ser Tyr Thr Tyr Thr Phe Gln
        115                 120                 125

Gly Gly Thr Lys Leu Glu Ile Asn
    130                 135

<210> SEQ ID NO 171
<211> LENGTH: 4
<212> TYPE: PRT
<213> ORGANISM: Artificial sequence
<220> FEATURE:
<223> OTHER INFORMATION: Synthetic construct

<400> SEQUENCE: 171

Arg Leu Ile Tyr
  1

<210> SEQ ID NO 172
<211> LENGTH: 112
<212> TYPE: PRT
<213> ORGANISM: Homo sapiens

<400> SEQUENCE: 172

Ala Glu Ile Val Leu Thr Gln Ser Pro Leu Ser Leu Pro Val Thr Leu
  1               5                  10                  15

Gly Gln Pro Ala Ser Ile Ser Cys Arg Ser Ser Gln Ser Leu Val Tyr
             20                  25                  30

Ser Asp Gly Asn Thr Tyr Leu Asn Trp Phe Gln Gln Arg Pro Gly Gln
         35                  40                  45

Ser Pro Arg Arg Leu Ile Tyr Lys Val Ser Asn Trp Asp Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Gly Thr His Trp Leu Thr Phe Gly Gly Gly Thr Lys Val Glu Ile Lys
            100                 105                 110
```

<210> SEQ ID NO 173
<211> LENGTH: 113
<212> TYPE: PRT
<213> ORGANISM: Homo sapiens

<400> SEQUENCE: 173

Gly Asp Ile Val Leu Thr Gln Ser Pro Leu Ser Leu Pro Val Thr Leu
1               5                   10                  15

Gly Gln Pro Ala Ser Ile Ser Cys Arg Ser Ser Gln Asn Leu Val Tyr
            20                  25                  30

Ser Asp Gly Asn Thr Tyr Leu Asn Trp Phe Gln Gln Arg Pro Gly Gln
        35                  40                  45

Ser Pro Arg Arg Leu Ile Tyr Lys Val Ser Asn Arg Asp Ser Gly Val
    50                  55                  60

Pro Asp Ser Phe Ser Gly Ser Gly Ser Gly Thr Asp Phe Thr Leu Thr
65                  70                  75                  80

Ile Ser Arg Val Glu Ala Glu Asp Val Gly Ile Tyr Tyr Cys Met Gln
                85                  90                  95

Gly Thr Arg Trp Pro Tyr Thr Phe Gly Glu Gly Thr Lys Leu Glu Ile
            100                 105                 110

Lys

<210> SEQ ID NO 174
<211> LENGTH: 112
<212> TYPE: PRT
<213> ORGANISM: Homo sapiens

<400> SEQUENCE: 174

Asp Ile Val Leu Thr Gln Ser Pro Leu Ser Leu Pro Val Thr Leu Gly
1               5                   10                  15

Gln Pro Ala Ser Ile Ser Cys Arg Ser Ser Gln Asn Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Ser Phe Ser Gly Ser Gly Ser Gly Thr Asp Phe Thr Leu Thr Ile
65                  70                  75                  80

Ser Arg Val Glu Ala Glu Asp Val Gly Ile Tyr Tyr Cys Met Gln Gly
                85                  90                  95

Thr Arg Trp Pro Tyr Thr Phe Gly Glu Gly Thr Lys Leu Glu Ile Lys
            100                 105                 110

<210> SEQ ID NO 175
<211> LENGTH: 113
<212> TYPE: PRT
<213> ORGANISM: Homo sapiens

<400> SEQUENCE: 175

Asp Ile Val Met Thr Gln Thr Pro Leu Ser Leu Ser Val Ser Pro Gly
1               5                   10                  15

Gln Ala Ala Ser Ile Ser Cys Lys Ser Ser Gln Ser Leu Gln His Pro
            20                  25                  30

Asn Gly Lys Thr Tyr Leu Tyr Trp Phe Leu Gln Lys Pro Gly Gln Pro
        35                  40                  45

Pro Gln Leu Leu Ile Tyr Glu Leu Ser Arg Arg Phe Ser Gly Val Pro
    50                  55                  60

```
Ala Arg Phe Ser Gly Ser Gly Ser Gly Thr Glu Phe Thr Leu Lys Ile
 65                  70                  75                  80

Ser Arg Val Glu Ala Glu Asp Val Gly Val Tyr Tyr Cys Met Glu Thr
                 85                  90                  95

Met Glu Leu Arg Ser Ile Thr Phe Gly Gln Gly Thr Arg Leu Glu Ile
            100                 105                 110

Lys

<210> SEQ ID NO 176
<211> LENGTH: 113
<212> TYPE: PRT
<213> ORGANISM: Homo sapiens

<400> SEQUENCE: 176

Ala Glu Ile Val Leu Thr Gln Ser Pro Leu Ser Leu Pro Val Thr Leu
 1               5                  10                  15

Gly Gln Pro Ala Ser Ile Ser Cys Arg Ser Ser Gln Ser Leu Val Asp
             20                  25                  30

Ser Asn Gly Arg Ile Tyr Leu Ala Trp Phe Gln Gln Arg Pro Gly Gln
         35                  40                  45

Ser Pro Arg Arg Leu Ile Tyr Pro Val Ser Lys Arg Asp Ser Gly Val
     50                  55                  60

Pro Asp Arg Phe Ser Gly Ser Gly Ser Gly Thr Glu Phe Thr Leu Lys
 65                  70                  75                  80

Ile Ser Arg Val Glu Ala Glu Asp Val Gly Val Tyr Tyr Cys Met Gln
                 85                  90                  95

His Thr His Trp Pro His Thr Phe Gly Gln Gly Thr Lys Leu Glu Ile
            100                 105                 110

Lys

<210> SEQ ID NO 177
<211> LENGTH: 112
<212> TYPE: PRT
<213> ORGANISM: Homo sapiens

<400> SEQUENCE: 177

Asp Ile Gln Leu Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Arg
             20                  25                  30

Asn Gly Asn Thr Tyr Leu His Trp Phe Gln Gln Arg Pro Gly Gln Ser
         35                  40                  45

Pro Arg Leu Leu Ile Tyr Thr Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Ser His Val Pro Pro Thr Phe Gly Ala Gly Thr Arg Leu Glu Ile Lys
            100                 105                 110

<210> SEQ ID NO 178
<211> LENGTH: 113
<212> TYPE: PRT
<213> ORGANISM: Homo sapiens

<400> SEQUENCE: 178
```

Ala Glu Ile Val Leu Thr Gln Ser Pro Leu Ser Leu Pro Val Thr Leu
1               5                   10                  15

Gly Gln Pro Ala Ser Ile Ser Cys Arg Ser Ser Gln Ser Leu Val Tyr
            20                  25                  30

Ser Asp Gly Asn Thr Tyr Leu Asn Trp Phe Gln Gln Arg Pro Gly Gln
        35                  40                  45

Ser Pro Arg Arg Leu Ile Tyr Lys Val Ser Asn Trp Asp Ser Gly Val
50                  55                  60

Pro Asp Arg Phe Ser Gly Ser Gly Ser Gly Thr Asp Phe Ala Leu Lys
65                  70                  75                  80

Ile Ser Arg Val Glu Ala Glu Asp Val Gly Val Tyr Tyr Cys Met Gln
                85                  90                  95

Gly Thr His Trp Pro Leu Thr Phe Gly Gln Gly Thr Arg Leu Glu Ile
            100                 105                 110

Lys

<210> SEQ ID NO 179
<211> LENGTH: 113
<212> TYPE: PRT
<213> ORGANISM: Homo sapiens

<400> SEQUENCE: 179

Ala Glu Ile Val Leu Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Pro His Thr Phe Gly Gln Gly Thr Lys Leu Glu Ile
            100                 105                 110

Lys

<210> SEQ ID NO 180
<211> LENGTH: 113
<212> TYPE: PRT
<213> ORGANISM: Homo sapiens

<400> SEQUENCE: 180

Ala Glu Ile Val Leu Thr Gln Ser Pro Leu Ser Leu Pro Val Thr Pro
1               5                   10                  15

Gly Glu Pro Ala Ser Ile Ser Cys Lys Ser Ser Gln Ser Leu Leu His
            20                  25                  30

Met Asn Gly Ala Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
50                  55                  60

Pro Asp Arg Phe Ser Gly Ser Gly Ser Glu Thr Asp Phe Thr Leu Lys
65                  70                  75                  80

Ile Thr Arg Val Glu Ala Asp Asp Val Gly Val Tyr Tyr Cys Met Gln

```
                    85                  90                  95

Ser Leu Gln Asn Pro Leu Thr Phe Gly Gly Gly Thr Lys Val Glu Ile
                100                 105                 110

Arg

<210> SEQ ID NO 181
<211> LENGTH: 113
<212> TYPE: PRT
<213> ORGANISM: Homo sapiens

<400> SEQUENCE: 181

Ala Glu Ile Val Leu Thr Gln Ser Pro Leu Ser Leu Pro Val Thr Pro
 1               5                  10                  15

Gly Glu Pro Ala Ser Ile Ser Cys Arg Ser Ser Gln Ser Leu Leu His
                20                  25                  30

Ser Asn Gly Tyr Asn Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Pro Arg Thr Phe Gly Gln Gly Thr Lys Val Glu Ile
                100                 105                 110

Lys

<210> SEQ ID NO 182
<211> LENGTH: 112
<212> TYPE: PRT
<213> ORGANISM: Homo sapiens

<400> SEQUENCE: 182

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
                20                  25                  30

Asp Gly Asn Thr Tyr Leu Asn Trp Phe His Gln Arg Pro Gly Gln Pro
            35                  40                  45

Pro Arg Leu Leu Ile Tyr Lys Ile Ser Ser Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro His Thr Phe Gly Gln Gly Thr Lys Leu Glu Ile Lys
                100                 105                 110

<210> SEQ ID NO 183
<211> LENGTH: 112
<212> TYPE: PRT
<213> ORGANISM: Homo sapiens

<400> SEQUENCE: 183

Glu Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
```

```
                20                  25                  30
Asn Gly Tyr Thr Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Lys Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Glu Thr Pro Gln Thr Phe Gly Gln Gly Thr Arg Leu Glu Ile Lys
            100                 105                 110

<210> SEQ ID NO 184
<211> LENGTH: 112
<212> TYPE: PRT
<213> ORGANISM: Homo sapiens

<400> SEQUENCE: 184

Asp Ile Gln Leu Thr Gln Ser Pro Ser Ser Leu Ser Ala Ser Val Gly
1               5                   10                  15

Asp Arg Val Thr Ile Thr Cys Lys Ser Ser Gln Ser Val Leu Tyr Ser
                20                  25                  30

Ser Asn Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gln Gly Thr Lys Val Glu Ile Lys
            100                 105                 110

<210> SEQ ID NO 185
<211> LENGTH: 106
<212> TYPE: PRT
<213> ORGANISM: Homo sapiens

<400> SEQUENCE: 185

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Phe Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Arg Trp Thr Phe Gly Gln
            100                 105

<210> SEQ ID NO 186
<211> LENGTH: 112
<212> TYPE: PRT
```

<213> ORGANISM: Homo sapiens

<400> SEQUENCE: 186

Glu Ile Val Leu Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Val Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr His Trp Pro Leu Tyr Thr Phe Gly Gln Gly Thr Lys Val Glu Ile
            100                 105                 110

<210> SEQ ID NO 187
<211> LENGTH: 106
<212> TYPE: PRT
<213> ORGANISM: Homo sapiens

<400> SEQUENCE: 187

Glu Ile Val Leu Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Phe Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Arg Trp Thr Phe Gly Gln
            100                 105

<210> SEQ ID NO 188
<211> LENGTH: 106
<212> TYPE: PRT
<213> ORGANISM: Homo sapiens

<400> SEQUENCE: 188

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Phe Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

```
Ile Gln Pro Pro Arg Trp Thr Phe Gly Gln
            100                 105
```

```
<210> SEQ ID NO 189
<211> LENGTH: 113
<212> TYPE: PRT
<213> ORGANISM: Homo sapiens

<400> SEQUENCE: 189
```

```
Glu Ile Val Leu Thr Gln Ser Pro Leu Ser Leu Pro Val Thr Pro Gly
1               5                   10                  15

Glu Pro Ala Pro Ile Ser Cys Arg Ser Ser Gln Ser Leu Leu His Ser
            20                  25                  30

Asp Gly Tyr Asn Tyr Leu Asp Trp Tyr Val Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Val Gly Val Tyr Tyr Cys Thr Gln Ala
                85                  90                  95

Leu Gln Thr Pro Gly Trp Thr Phe Gly Gln Gly Thr Lys Val Glu Ile
            100                 105                 110

Lys
```

```
<210> SEQ ID NO 190
<211> LENGTH: 112
<212> TYPE: PRT
<213> ORGANISM: Homo sapiens

<400> SEQUENCE: 190
```

```
Glu Ile Val Leu Thr Gln Ser His Leu Ser Leu Pro Val Thr Pro Gly
1               5                   10                  15

Glu Pro Ala Ser Ile Ser Cys Arg Ser Ser Gln Ser Phe Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Arg Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Gln Gly Thr Phe Gly Gln Gly Thr Lys Val Glu Ile Lys
            100                 105                 110
```

```
<210> SEQ ID NO 191
<211> LENGTH: 112
<212> TYPE: PRT
<213> ORGANISM: Homo sapiens

<400> SEQUENCE: 191
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Ser Leu Asp Trp Phe Leu Gln Arg Pro Gly Gln Ser
```

```
                35                  40                  45
Pro Gln Leu Leu Ile Tyr Leu Gly Ser Asn Arg Ala Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Val
                85                  90                  95
Leu Gln Thr Pro Phe Thr Phe Gly Pro Gly Thr Lys Val Asp Ile Lys
                100                 105                 110
```

<210> SEQ ID NO 192
<211> LENGTH: 111
<212> TYPE: PRT
<213> ORGANISM: Homo sapiens

<400> SEQUENCE: 192

```
Glu Ile Val Leu Thr Gln Ser Pro Leu Ser Leu Pro Val Thr Leu Gly
1               5                   10                  15
Gln Pro Ala Ser Ile Ser Cys Arg Ser Ser Gln Ser Leu Val Tyr Ser
                20                  25                  30
Asp Gly Asn Thr Tyr Leu Asn Trp Phe Gln Gln Arg Pro Gly Gln Ser
                35                  40                  45
Pro Arg Arg Leu Ile Tyr Lys Val Ser Asn Trp Asp Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Thr His Trp Leu Thr Phe Gly Gly Gly Thr Lys Val Glu Ile Lys
                100                 105                 110
```

<210> SEQ ID NO 193
<211> LENGTH: 112
<212> TYPE: PRT
<213> ORGANISM: Homo sapiens

<400> SEQUENCE: 193

```
Asp Ile Val Leu Thr Gln Ser Pro Leu Ser Leu Pro Val Thr Leu Gly
1               5                   10                  15
Gln Pro Ala Ser Ile Ser Cys Arg Ser Ser Gln Asn Leu Val Tyr Ser
                20                  25                  30
Asp Gly Asn Thr Tyr Leu Asn Trp Phe Gln Gln Arg Pro Gly Gln Ser
                35                  40                  45
Pro Arg Arg Leu Ile Tyr Lys Val Ser Asn Arg Asp Ser Gly Val Pro
        50                  55                  60
Asp Ser Phe Ser Gly Ser Gly Ser Gly Ile Asp Phe Thr Leu Thr Ile
65                  70                  75                  80
Ser Arg Val Glu Ala Glu Asp Val Gly Ile Tyr Tyr Cys Met Gln Gly
                85                  90                  95
Thr Arg Trp Pro Tyr Thr Phe Gly Glu Gly Thr Lys Leu Glu Ile Lys
                100                 105                 110
```

<210> SEQ ID NO 194
<211> LENGTH: 112
<212> TYPE: PRT
<213> ORGANISM: Homo sapiens

<400> SEQUENCE: 194

-continued

Glu Ile Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Asp Ser
            20                  25                  30

Asn Gly Arg Ile Tyr Leu Ala Trp Phe Gln Gln Arg Pro Gly Gln Ser
        35                  40                  45

Pro Arg Arg Leu Ile Tyr Pro Val Ser Lys Arg Asp Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Val Gly Val Tyr Tyr Cys Met Gln His
                85                  90                  95

Thr His Trp Pro His Thr Phe Gly Gln Gly Thr Lys Leu Glu Ile Lys
            100                 105                 110

<210> SEQ ID NO 195
<211> LENGTH: 112
<212> TYPE: PRT
<213> ORGANISM: Homo sapiens

<400> SEQUENCE: 195

Glu Ile Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Ala Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Arg Leu Glu Ile Lys
            100                 105                 110

<210> SEQ ID NO 196
<211> LENGTH: 112
<212> TYPE: PRT
<213> ORGANISM: Homo sapiens

<400> SEQUENCE: 196

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro His Thr Phe Gly Gln Gly Thr Lys Leu Glu Ile Lys
            100                 105                 110

<210> SEQ ID NO 197
<211> LENGTH: 112
<212> TYPE: PRT
<213> ORGANISM: Homo sapiens

<400> SEQUENCE: 197

Glu Ile Val Leu Thr Gln Ser Pro Leu Ser Leu Pro Val Thr Pro Gly
1               5                   10                  15

Glu Pro Ala Ser Ile Ser Cys Lys Ser Gln Ser Leu Leu His Met
            20                  25                  30

Asn Gly Ala Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Glu Thr Asp Phe Thr Leu Lys Ile
65                  70                  75                  80

Thr Arg Val Glu Ala Asp Asp Val Gly Val Tyr Tyr Cys Met Gln Ser
                85                  90                  95

Leu Gln Asn Pro Leu Thr Phe Gly Gly Gly Thr Lys Val Glu Ile Arg
            100                 105                 110

<210> SEQ ID NO 198
<211> LENGTH: 112
<212> TYPE: PRT
<213> ORGANISM: Homo sapiens

<400> SEQUENCE: 198

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Ile Asp Phe Ile Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 199
<211> LENGTH: 107
<212> TYPE: PRT
<213> ORGANISM: Homo sapiens

<400> SEQUENCE: 199

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Phe Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Arg Trp Thr Phe Gly Gln Gly
            100                 105

<210> SEQ ID NO 200
<211> LENGTH: 107
<212> TYPE: PRT
<213> ORGANISM: Homo sapiens

<400> SEQUENCE: 200

Glu Ile Val Leu Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Phe Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Arg Trp Thr Phe Gly Gln Gly
            100                 105

<210> SEQ ID NO 201
<211> LENGTH: 107
<212> TYPE: PRT
<213> ORGANISM: Homo sapiens

<400> SEQUENCE: 201

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Phe Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Pro Pro Arg Trp Thr Phe Gly Gln Gly
            100                 105

<210> SEQ ID NO 202
<211> LENGTH: 113
<212> TYPE: PRT
<213> ORGANISM: Homo sapiens

<400> SEQUENCE: 202

Glu Ile Val Leu Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser

```
                    20                  25                  30
Asn Gly Tyr Asn Tyr Leu Asp Trp Tyr Leu Gln Lys Pro Gly Gln Ser
                35                  40                  45

Pro Gln Leu Leu Ile Tyr Val Gly Ser Ser Arg Ala Ser Gly Val Pro
            50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Thr
                85                  90                  95

Thr His Trp Pro Leu Tyr Thr Phe Gly Gln Gly Thr Lys Val Glu Ile
            100                 105                 110

Lys

<210> SEQ ID NO 203
<211> LENGTH: 43
<212> TYPE: PRT
<213> ORGANISM: Artificial sequence
<220> FEATURE:
<223> OTHER INFORMATION: Synthetic Construct

<400> SEQUENCE: 203

Met Val Leu Gln Thr Gln Val Phe Ile Ser Leu Leu Trp Ile Ser
 1               5                  10                  15

Gly Ala Tyr Gly Asp Ile Val Leu Thr Gln Ser Pro Asp Ser Leu Ser
                20                  25                  30

Val Ser Leu Gly Glu Arg Val Thr Val Asn Cys
            35                  40

<210> SEQ ID NO 204
<211> LENGTH: 43
<212> TYPE: PRT
<213> ORGANISM: Artificial sequence
<220> FEATURE:
<223> OTHER INFORMATION: Synthetic Construct

<400> SEQUENCE: 204

Met Asp Met Arg Val Pro Ala Gln Leu Leu Gly Leu Leu Leu Leu Trp
 1               5                  10                  15

Leu Arg Gly Ala Arg Cys Glu Ile Val Leu Thr Gln Ser Pro Ser Ser
                20                  25                  30

Leu Ser Ala Ser Val Gly Asp Arg Val Thr Ile
            35                  40

<210> SEQ ID NO 205
<211> LENGTH: 49
<212> TYPE: PRT
<213> ORGANISM: Artificial sequence
<220> FEATURE:
<223> OTHER INFORMATION: Synthetic Construct

<400> SEQUENCE: 205

Met Arg Leu Pro Ala Gln Leu Leu Gly Leu Leu Met Leu Trp Val Pro
 1               5                  10                  15

Gly Ser Ser Gly Glu Ile Val Leu Thr Gln Ser Pro Leu Ser Leu Pro
                20                  25                  30

Val Thr Leu Gly Gln Pro Ala Ser Ile Ser Cys Arg Ser Ser Gln Ser
            35                  40                  45

Leu
```

```
<210> SEQ ID NO 206
<211> LENGTH: 15
<212> TYPE: PRT
<213> ORGANISM: Artificial sequence
<220> FEATURE:
<223> OTHER INFORMATION: Synthetic Construct

<400> SEQUENCE: 206

Arg Ala Ser Glu Ser Val Asp Gly Tyr Gly Asn Ser Phe Leu His
1               5                   10                  15

<210> SEQ ID NO 207
<211> LENGTH: 7
<212> TYPE: PRT
<213> ORGANISM: Artificial sequence
<220> FEATURE:
<223> OTHER INFORMATION: Synthetic Construct

<400> SEQUENCE: 207

Leu Ala Ser Asn Leu Asn Ser
1               5

<210> SEQ ID NO 208
<211> LENGTH: 9
<212> TYPE: PRT
<213> ORGANISM: Artificial sequence
<220> FEATURE:
<223> OTHER INFORMATION: Synthetic Construct

<400> SEQUENCE: 208

Gln Gln Asn Asn Val Asp Pro Trp Thr
1               5

<210> SEQ ID NO 209
<211> LENGTH: 80
<212> TYPE: PRT
<213> ORGANISM: Artificial sequence
<220> FEATURE:
<223> OTHER INFORMATION: Synthetic Construct

<400> SEQUENCE: 209

Asp Ile Val Leu Thr Gln Ser Pro Asp Ser Leu Ser Val Ser Leu Gly
1               5                   10                  15

Glu Arg Val Thr Val Asn Cys Trp Phe Gln Gln Asn Pro Gly Gln Pro
                20                  25                  30

Pro Lys Leu Leu Ile Tyr Gly Val Pro Ala Arg Phe Met Gly Ser Gly
                35                  40                  45

Ser Gly Thr Glu Phe Ser Leu Thr Ile Ser Ser Leu Gln Ala Glu Asp
            50                  55                  60

Val Ala Val Tyr Tyr Cys Phe Gly Gln Gly Thr Lys Leu Glu Ile Asn
65                  70                  75                  80

<210> SEQ ID NO 210
<211> LENGTH: 114
<212> TYPE: PRT
<213> ORGANISM: Homo sapiens

<400> SEQUENCE: 210

Asp Ile Val Leu Thr Gln Ser Pro Asp Ser Leu Ser Val Ser Leu Gly
1               5                   10                  15

Glu Arg Val Thr Val Asn Cys Lys Leu Ser Gln Ser Val Leu His Ser
                20                  25                  30

Ser Asn Lys Gln Asn Tyr Leu Ala Trp Phe Gln Gln Asn Pro Gly Gln
                35                  40                  45
```

```
Pro Pro Lys Leu Leu Ile Tyr Trp Ala Ser Ala Arg Gln Ser Gly Val
    50                  55                  60

Pro Ala Arg Phe Met Gly Ser Gly Ser Gly Thr Glu Phe Ser Leu Thr
65                  70                  75                  80

Ile Ser Ser Leu Gln Ala Glu Asp Val Ala Val Tyr Tyr Cys Gln Gln
                85                  90                  95

Tyr Tyr Asp Ser Thr Tyr Trp Thr Phe Gln Gly Gly Thr Lys Leu Glu
                100                 105                 110

Ile Asn
```

<210> SEQ ID NO 211
<211> LENGTH: 66
<212> TYPE: DNA
<213> ORGANISM: Artificial sequence
<220> FEATURE:
<223> OTHER INFORMATION: Synthetic Construct

<400> SEQUENCE: 211
atggacatga gggtccctgc tcagctcctg gggctcctgc agctctggct ctccggcgcc   60
agatgt                                                             66

<210> SEQ ID NO 212
<211> LENGTH: 69
<212> TYPE: DNA
<213> ORGANISM: Artificial sequence
<220> FEATURE:
<223> OTHER INFORMATION: Synthetic Construct

<400> SEQUENCE: 212
gacatcgtgc tgacccagtc tccagactcc ctgtctgtgt ctctgggcga gagggtcacc   60
gtcaactgc                                                          69

<210> SEQ ID NO 213
<211> LENGTH: 45
<212> TYPE: DNA
<213> ORGANISM: Artificial sequence
<220> FEATURE:
<223> OTHER INFORMATION: Synthetic Construct

<400> SEQUENCE: 213
agagccagtg aaagtgttga tggttatggc aatagttttc tgcac                  45

<210> SEQ ID NO 214
<211> LENGTH: 21
<212> TYPE: DNA
<213> ORGANISM: Artificial sequence
<220> FEATURE:
<223> OTHER INFORMATION: Synthetic Construct

<400> SEQUENCE: 214
cttgcatcca acctaaactc t                                            21

<210> SEQ ID NO 215
<211> LENGTH: 96
<212> TYPE: DNA
<213> ORGANISM: Artificial sequence
<220> FEATURE:
<223> OTHER INFORMATION: Synthetic Construct

<400> SEQUENCE: 215
ggggtccctg cccgattcat gggcagcggg tctgggacag aattcagtct caccatcagc   60
agcctgcagg ctgaagatgt ggcagtttat tactgt                              96

<210> SEQ ID NO 216
<211> LENGTH: 27
<212> TYPE: DNA
<213> ORGANISM: Artificial sequence
<220> FEATURE:
<223> OTHER INFORMATION: Synthetic Construct

<400> SEQUENCE: 216
cagcaaaata atgtggaccc gtggacg                                         27

<210> SEQ ID NO 217
<211> LENGTH: 30
<212> TYPE: DNA
<213> ORGANISM: Artificial sequence
<220> FEATURE:
<223> OTHER INFORMATION: Synthetic Construct

<400> SEQUENCE: 217
tttggccagg ggaccaagct ggagatcaac                                      30

<210> SEQ ID NO 218
<211> LENGTH: 22
<212> TYPE: PRT
<213> ORGANISM: Artificial sequence
<220> FEATURE:
<223> OTHER INFORMATION: Synthetic Construct

<400> SEQUENCE: 218

Met Asp Met Arg Val Pro Ala Gln Leu Leu Gly Leu Leu Gln Leu Trp
 1               5                  10                  15

Leu Ser Gly Ala Arg Cys
            20

<210> SEQ ID NO 219
<211> LENGTH: 23
<212> TYPE: PRT
<213> ORGANISM: Artificial sequence
<220> FEATURE:
<223> OTHER INFORMATION: Synthetic Construct

<400> SEQUENCE: 219

Asp Ile Val Leu Thr Gln Ser Pro Asp Ser Leu Ser Val Ser Leu Gly
 1               5                  10                  15

Glu Arg Val Thr Val Asn Cys
            20

<210> SEQ ID NO 220
<211> LENGTH: 15
<212> TYPE: PRT
<213> ORGANISM: Artificial sequence
<220> FEATURE:
<223> OTHER INFORMATION: Synthetic Construct

<400> SEQUENCE: 220

Trp Phe Gln Gln Asn Pro Gly Gln Pro Pro Lys Leu Leu Ile Tyr
 1               5                  10                  15

<210> SEQ ID NO 221
<211> LENGTH: 32
<212> TYPE: PRT
<213> ORGANISM: Artificial sequence
<220> FEATURE:
<223> OTHER INFORMATION: Synthetic Construct

<400> SEQUENCE: 221

Gly Val Pro Ala Arg Phe Met Gly Ser Gly Ser Gly Thr Glu Phe Ser
1               5                   10                  15

Leu Thr Ile Ser Ser Leu Gln Ala Glu Asp Val Ala Val Tyr Tyr Cys
            20                  25                  30

<210> SEQ ID NO 222
<211> LENGTH: 10
<212> TYPE: PRT
<213> ORGANISM: Artificial sequence
<220> FEATURE:
<223> OTHER INFORMATION: Synthetic Construct

<400> SEQUENCE: 222

Phe Gly Gln Gly Thr Lys Leu Glu Ile Asn
1               5                   10

<210> SEQ ID NO 223
<211> LENGTH: 111
<212> TYPE: PRT
<213> ORGANISM: Artificial sequence
<220> FEATURE:
<223> OTHER INFORMATION: Synthetic Construct

<400> SEQUENCE: 223

Glu Ile Val Leu Thr Gln Ser Pro Ser Leu Ser Ala Ser Val Gly
1               5                   10                  15

Asp Arg Val Thr Ile Thr Cys Arg Ala Ser Glu Ser Val Asp Gly Tyr
            20                  25                  30

Gly Asn Ser Phe Leu His Trp Phe Gln Gln Lys Pro Gly Lys Ala Pro
        35                  40                  45

Lys Leu Leu Ile Tyr Leu Ala Ser Asn Leu Asn Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Val Asp Pro Trp Thr Phe Gly Gln Gly Thr Lys Leu Glu Ile Lys
            100                 105                 110

<210> SEQ ID NO 224
<211> LENGTH: 80
<212> TYPE: PRT
<213> ORGANISM: Artificial sequence
<220> FEATURE:
<223> OTHER INFORMATION: Synthetic Construct

<400> SEQUENCE: 224

Glu Ile Val Leu Thr Gln Ser Pro Ser Leu Ser Ala Ser Val Gly
1               5                   10                  15

Asp Arg Val Thr Ile Thr Cys Trp Phe Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Arg Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Leu Glu Ile Lys
65                  70                  75                  80

<210> SEQ ID NO 225

```
<211> LENGTH: 66
<212> TYPE: DNA
<213> ORGANISM: Artificial sequence
<220> FEATURE:
<223> OTHER INFORMATION: Synthetic Construct

<400> SEQUENCE: 225
atggacatga gggtccccgc tcagctcctg gggctcctgc tactctggct ccgaggtgcc     60
agatgt                                                                66

<210> SEQ ID NO 226
<211> LENGTH: 69
<212> TYPE: DNA
<213> ORGANISM: Artificial sequence
<220> FEATURE:
<223> OTHER INFORMATION: Synthetic Construct

<400> SEQUENCE: 226
gaaatagtgt tgacgcagtc tccatcctcc ctgtctgcat ctgtaggaga cagagtcacc     60
atcacttgc                                                             69

<210> SEQ ID NO 227
<211> LENGTH: 45
<212> TYPE: DNA
<213> ORGANISM: Artificial sequence
<220> FEATURE:
<223> OTHER INFORMATION: Synthetic Construct

<400> SEQUENCE: 227
tggtttcagc agaaaccagg gaaagcccct aagctcctga tctat                     45

<210> SEQ ID NO 228
<211> LENGTH: 96
<212> TYPE: DNA
<213> ORGANISM: Artificial sequence
<220> FEATURE:
<223> OTHER INFORMATION: Synthetic Construct

<400> SEQUENCE: 228
ggggtcccat caaggttcag tggcagtgga tctcggacag atttcactct caccatcagc     60
agtctgcaac ctgaagattt tgcaacttac tactgt                               96

<210> SEQ ID NO 229
<211> LENGTH: 30
<212> TYPE: DNA
<213> ORGANISM: Artificial sequence
<220> FEATURE:
<223> OTHER INFORMATION: Synthetic Construct

<400> SEQUENCE: 229
tttggccagg ggaccaagct ggagatcaaa                                      30

<210> SEQ ID NO 230
<211> LENGTH: 22
<212> TYPE: PRT
<213> ORGANISM: Artificial sequence
<220> FEATURE:
<223> OTHER INFORMATION: Synthetic Construct

<400> SEQUENCE: 230

Met Asp Met Arg Val Pro Ala Gln Leu Leu Gly Leu Leu Leu Leu Trp
1               5                   10                  15

Leu Arg Gly Ala Arg Cys
            20
```

<210> SEQ ID NO 231
<211> LENGTH: 23
<212> TYPE: PRT
<213> ORGANISM: Artificial sequence
<220> FEATURE:
<223> OTHER INFORMATION: Synthetic Construct

<400> SEQUENCE: 231

Glu Ile Val Leu Thr Gln Ser Pro Ser Ser Leu Ser Ala Ser Val Gly
1               5                   10                  15

Asp Arg Val Thr Ile Thr Cys
            20

<210> SEQ ID NO 232
<211> LENGTH: 15
<212> TYPE: PRT
<213> ORGANISM: Artificial sequence
<220> FEATURE:
<223> OTHER INFORMATION: Synthetic Construct

<400> SEQUENCE: 232

Trp Phe Gln Gln Lys Pro Gly Lys Ala Pro Lys Leu Leu Ile Tyr
1               5                   10                  15

<210> SEQ ID NO 233
<211> LENGTH: 32
<212> TYPE: PRT
<213> ORGANISM: Artificial sequence
<220> FEATURE:
<223> OTHER INFORMATION: Synthetic Construct

<400> SEQUENCE: 233

Gly Val Pro Ser Arg Phe Ser Gly Ser Gly Ser Arg Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 234
<211> LENGTH: 111
<212> TYPE: PRT
<213> ORGANISM: Artificial sequence
<220> FEATURE:
<223> OTHER INFORMATION: Synthetic Construct

<400> SEQUENCE: 234

Glu Ile Val Leu Thr Gln Ser Pro Leu Ser Leu Pro Val Thr Leu Gly
1               5                   10                  15

Gln Pro Ala Ser Ile Ser Cys Arg Ala Ser Glu Ser Val Asp Gly Tyr
            20                  25                  30

Gly Asn Ser Phe Leu His Trp Phe Gln Gln Arg Pro Gly Gln Ser Pro
        35                  40                  45

Arg Arg Leu Ile Tyr Leu Ala Ser Asn Leu Asn Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Val Asp Pro Trp Thr Phe Gly Gly Gly Thr Lys Val Glu Ile Lys
            100                 105                 110

<210> SEQ ID NO 235

<211> LENGTH: 80
<212> TYPE: PRT
<213> ORGANISM: Artificial sequence
<220> FEATURE:
<223> OTHER INFORMATION: Synthetic Construct

<400> SEQUENCE: 235

Glu Ile Val Leu Thr Gln Ser Pro Leu Ser Leu Pro Val Thr Leu Gly
1               5                   10                  15

Gln Pro Ala Ser Ile Ser Cys Trp Phe Gln Gln Arg Pro Gly Gln Ser
            20                  25                  30

Pro Arg Arg Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gly Gly Thr Lys Val Glu Ile Lys
65                  70                  75                  80

<210> SEQ ID NO 236
<211> LENGTH: 60
<212> TYPE: DNA
<213> ORGANISM: Artificial sequence
<220> FEATURE:
<223> OTHER INFORMATION: Synthetic Construct

<400> SEQUENCE: 236
atgaggctcc ctgctcagct cctggggctg ctaatgctct gggtcccagg atccagtggg      60

<210> SEQ ID NO 237
<211> LENGTH: 69
<212> TYPE: DNA
<213> ORGANISM: Artificial sequence
<220> FEATURE:
<223> OTHER INFORMATION: Synthetic Construct

<400> SEQUENCE: 237
gaaattgtgc tgactcagtc tccactctcc ctgcccgtca cccttggaca gccggcctcc      60
atctcctgc                                                             69

<210> SEQ ID NO 238
<211> LENGTH: 45
<212> TYPE: DNA
<213> ORGANISM: Artificial sequence
<220> FEATURE:
<223> OTHER INFORMATION: Synthetic Construct

<400> SEQUENCE: 238
tggtttcagc agaggccagg ccaatctcca aggcgcctaa tttat                     45

<210> SEQ ID NO 239
<211> LENGTH: 96
<212> TYPE: DNA
<213> ORGANISM: Artificial sequence
<220> FEATURE:
<223> OTHER INFORMATION: Synthetic Construct

<400> SEQUENCE: 239
ggggtcccag acagattcag cggcagtggg tcaggcactg atttcacact gaaaatcagc      60
agggtggagg ctgaggatgt tggggtttat tactgc                               96

<210> SEQ ID NO 240
<211> LENGTH: 30
<212> TYPE: DNA

<213> ORGANISM: Artificial sequence
<220> FEATURE:
<223> OTHER INFORMATION: Synthetic Construct

<400> SEQUENCE: 240
ttcggcggag ggaccaaggt ggagatcaaa                30

<210> SEQ ID NO 241
<211> LENGTH: 20
<212> TYPE: PRT
<213> ORGANISM: Artificial sequence
<220> FEATURE:
<223> OTHER INFORMATION: Synthetic Construct

<400> SEQUENCE: 241

Met Arg Leu Pro Ala Gln Leu Leu Gly Leu Leu Met Leu Trp Val Pro
1               5                   10                  15

Gly Ser Ser Gly
            20

<210> SEQ ID NO 242
<211> LENGTH: 23
<212> TYPE: PRT
<213> ORGANISM: Artificial sequence
<220> FEATURE:
<223> OTHER INFORMATION: Synthetic Construct

<400> SEQUENCE: 242

Glu Ile Val Leu Thr Gln Ser Pro Leu Ser Leu Pro Val Thr Leu Gly
1               5                   10                  15

Gln Pro Ala Ser Ile Ser Cys
            20

<210> SEQ ID NO 243
<211> LENGTH: 15
<212> TYPE: PRT
<213> ORGANISM: Artificial sequence
<220> FEATURE:
<223> OTHER INFORMATION: Synthetic Construct

<400> SEQUENCE: 243

Trp Phe Gln Gln Arg Pro Gly Gln Ser Pro Arg Arg Leu Ile Tyr
1               5                   10                  15

<210> SEQ ID NO 244
<211> LENGTH: 32
<212> TYPE: PRT
<213> ORGANISM: Artificial sequence
<220> FEATURE:
<223> OTHER INFORMATION: Synthetic Construct

<400> SEQUENCE: 244

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 245
<211> LENGTH: 10
<212> TYPE: PRT
<213> ORGANISM: Artificial sequence
<220> FEATURE:
<223> OTHER INFORMATION: Synthetic Construct

<400> SEQUENCE: 245

```
Phe Gly Gly Gly Thr Lys Val Glu Ile Lys
  1               5                  10
```

<210> SEQ ID NO 246
<211> LENGTH: 66
<212> TYPE: DNA
<213> ORGANISM: Artificial sequence
<220> FEATURE:
<223> OTHER INFORMATION: Synthetic Construct

<400> SEQUENCE: 246

```
atggacatga gggtccctgc tcagctcctg gggctcctgc agctctggct ctcaggtgcc    60
agatgt                                                               66
```

<210> SEQ ID NO 247
<211> LENGTH: 69
<212> TYPE: DNA
<213> ORGANISM: Artificial sequence
<220> FEATURE:
<223> OTHER INFORMATION: Synthetic Construct

<400> SEQUENCE: 247

```
gacatcgtga tgacccagtc tccagactcc ctggctgtgt ctctgggtga gagggccacc    60
atcaactgc                                                            69
```

<210> SEQ ID NO 248
<211> LENGTH: 45
<212> TYPE: DNA
<213> ORGANISM: Artificial sequence
<220> FEATURE:
<223> OTHER INFORMATION: Synthetic Construct

<400> SEQUENCE: 248

```
tggtaccagc agaaaccggg acagcctcct aagttgctca tttac                    45
```

<210> SEQ ID NO 249
<211> LENGTH: 96
<212> TYPE: DNA
<213> ORGANISM: Artificial sequence
<220> FEATURE:
<223> OTHER INFORMATION: Synthetic Construct

<400> SEQUENCE: 249

```
ggggtccctg accgattcag tggcagcggg tctgggacag atttcactct caccatcagc    60
agcctgcagg ccgaagatgt ggcagtgtat tactgt                              96
```

<210> SEQ ID NO 250
<211> LENGTH: 30
<212> TYPE: DNA
<213> ORGANISM: Artificial sequence
<220> FEATURE:
<223> OTHER INFORMATION: Synthetic Construct

<400> SEQUENCE: 250

```
tttggccagg ggaccaagct ggagatcaaa                                     30
```

<210> SEQ ID NO 251
<211> LENGTH: 23
<212> TYPE: PRT
<213> ORGANISM: Artificial sequence
<220> FEATURE:
<223> OTHER INFORMATION: Synthetic Construct

<400> SEQUENCE: 251

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 252
<211> LENGTH: 15
<212> TYPE: PRT
<213> ORGANISM: Artificial sequence
<220> FEATURE:
<223> OTHER INFORMATION: Synthetic Construct

<400> SEQUENCE: 252

```
Trp Tyr Gln Gln Lys Pro Gly Gln Pro Pro Lys Leu Leu Ile Tyr
1               5                   10                  15
```

<210> SEQ ID NO 253
<211> LENGTH: 32
<212> TYPE: PRT
<213> ORGANISM: Artificial sequence
<220> FEATURE:
<223> OTHER INFORMATION: Synthetic Construct

<400> SEQUENCE: 253

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 254
<211> LENGTH: 10
<212> TYPE: PRT
<213> ORGANISM: Artificial sequence
<220> FEATURE:
<223> OTHER INFORMATION: Synthetic Construct

<400> SEQUENCE: 254

```
Phe Gly Gln Gly Thr Lys Leu Glu Ile Lys
1               5                   10
```

<210> SEQ ID NO 255
<211> LENGTH: 399
<212> TYPE: DNA
<213> ORGANISM: Artificial sequence
<220> FEATURE:
<223> OTHER INFORMATION: Synthetic Construct

<400> SEQUENCE: 255

```
atggacatga gggtccctgc tcagctcctg gggctcctgc agctctggct ctccggcgcc    60
agatgtgaca tcgtgctgac ccagtctcca gactccctgt ctgtgtctct gggcgagagg   120
gtcaccgtca actgcagagc cagtgaaagt gttgatggtt atggcaatag tttctgcac   180 agagccagtg aaagtgttga tggttatggc aatagttttc tgcacttgc atccaaccta   240 aactctgggg tccctgcccg attcatgggc agcgggtctg gacagaatt cagtctcacc   300 atcagcagcc tgcaggctga agatgtggca gtttattact gtcagcaaaa taatgtggac   360
ccgtggacgt tggccaggg gaccaagctg gagatcaac                            399
```

<210> SEQ ID NO 256
<211> LENGTH: 399
<212> TYPE: DNA
<213> ORGANISM: Artificial sequence
<220> FEATURE:
<223> OTHER INFORMATION: Synthetic Construct

<400> SEQUENCE: 256

```
atggacatga gggtccccgc tcagctcctg gggctcctgc tactctggct ccgaggtgcc    60
agatgtgaaa tagtgttgac gcagtctcca tcctccctgt ctgcatctgt aggagacaga   120
gtcaccatca cttgcagagc cagtgaaagt gttgatggtt atggcaatag ttttctgcac   180
tggtttcagc agaaaccagg gaaagcccct aagctcctga tctatcttgc atccaaccta   240
aactctgggg tcccatcaag gttcagtggc agtggatctc ggacagattt cactctcacc   300
atcagcagtc tgcaacctga agattttgca acttactact gtcagcaaaa taatgtggac   360
ccgtggacgt ttggccaggg gaccaagctg gagatcaaa                          399
```

<210> SEQ ID NO 257
<211> LENGTH: 393
<212> TYPE: DNA
<213> ORGANISM: Artificial sequence
<220> FEATURE:
<223> OTHER INFORMATION: Synthetic Construct

<400> SEQUENCE: 257

```
atgaggctcc ctgctcagct cctggggctg ctaatgctct gggtcccagg atccagtggg    60
gaaattgtgc tgactcagtc tccactctcc ctgcccgtca cccttggaca gccggcctcc   120
atctcctgca gagccagtga aagtgttgat ggttatggca atagttttct gcactggttt   180
cagcagaggc caggccaatc tccaaggcgc ctaatttatc ttgcatccaa cctaaactct   240
ggggtcccag acagattcag cggcagtggg tcaggcactg atttcacact gaaaatcagc   300
agggtggagg ctgaggatgt tggggtttat tactgccagc aaaataatgt ggacccgtgg   360
acgttcggcg agggaccaa ggtggagatc aaa                                 393
```

<210> SEQ ID NO 258
<211> LENGTH: 399
<212> TYPE: DNA
<213> ORGANISM: Artificial sequence
<220> FEATURE:
<223> OTHER INFORMATION: Synthetic Construct

<400> SEQUENCE: 258

```
atggacatga gggtccctgc tcagctcctg gggctcctgc agctctggct ctcaggggcc    60
agatgtgaca tcgtgatgac ccagtctcca gactccctgg ctgtgtctct gggcgagagg   120
gccaccatca actgcagagc cagtgaaagt gttgatggtt atggcaatag ttttctgcac   180
tggtatcagc agaaaccggg acagcctcct aagttgctca tttaccttgc atccaaccta   240
aactctgggg tccctgaccg attcagtggc agcgggtctg ggacagattt cactctcacc   300
atcagcagcc tgcaggccga agatgtggca gtgtattact gtcagcaaaa taatgtggac   360
ccgtggacgt ttggccaggg gaccaagctg gagatcaaa                          399
```

<210> SEQ ID NO 259
<211> LENGTH: 394
<212> TYPE: DNA
<213> ORGANISM: Artificial sequence
<220> FEATURE:
<223> OTHER INFORMATION: Synthetic Construct

<400> SEQUENCE: 259

```
atggtgttgc agacccaggt cttcatttct ctgttgctct ggatctctgg ggcttacggg    60
gacatcgtgc tgacccagtc tccagactcc ctgtctgtgt ctctgggcga gagggtcacc   120
```

```
gtcaactgca gagccagtga aagtgttgat ggttatggca atagttttct gcactggttc    180
cagcaaaacc caggacagcc tcctaaactc ctcatttatc ttgcatccaa cctaaactct    240
ggggtccctg cccgattcat gggcagcggg tctgggacag aattcagtct caccatcagc    300
agcctgcagg ctgaagatgt ggcagtttat tactgtcagc aaaataatgt ggacccgtgg    360
acctttggcc aggggaccaa gctggagatc aacc                                394
```

<210> SEQ ID NO 260
<211> LENGTH: 131
<212> TYPE: PRT
<213> ORGANISM: Artificial sequence
<220> FEATURE:
<223> OTHER INFORMATION: Synthetic Construct

<400> SEQUENCE: 260

```
Met Val Leu Gln Thr Gln Val Phe Ile Ser Leu Leu Trp Ile Ser
 1               5                  10                  15

Gly Ala Tyr Gly Asp Ile Val Leu Thr Gln Ser Pro Asp Ser Leu Ser
                20                  25                  30

Val Ser Leu Gly Glu Arg Val Thr Val Asn Cys Arg Ala Ser Glu Ser
            35                  40                  45

Val Asp Gly Tyr Gly Asn Ser Phe Leu His Trp Phe Gln Gln Asn Pro
        50                  55                  60

Gly Gln Pro Pro Lys Leu Leu Ile Tyr Leu Ala Ser Asn Leu Asn Ser
65                  70                  75                  80

Gly Val Pro Ala Arg Phe Met Gly Ser Gly Ser Gly Thr Glu Phe Ser
                85                  90                  95

Leu Thr Ile Ser Ser Leu Gln Ala Glu Asp Val Ala Val Tyr Tyr Cys
                100                 105                 110

Gln Gln Asn Asn Val Asp Pro Trp Thr Phe Gly Gln Gly Thr Lys Leu
            115                 120                 125

Glu Ile Asn
        130
```

<210> SEQ ID NO 261
<211> LENGTH: 400
<212> TYPE: DNA
<213> ORGANISM: Artificial sequence
<220> FEATURE:
<223> OTHER INFORMATION: Synthetic Construct

<400> SEQUENCE: 261

```
atggacatga gggtccccgc tcagctcctg gggctcctgc tactctggct ccgaggtgcc     60
agatgtgaaa tagtgttgac gcagtctcca tcctccctgt ctgcatctgt aggagacaga    120
gtcaccatca cttgcagagc cagtgaaagt gttgatggtt atggcaatag ttttctgcac    180
tggtatcagc agaaaccagg gaaagcccct aagctcctga tctatcttgc atccaaccta    240
aactctgggg tccatcaag gttcagtggc agtggatctg gacagatttc actctcacc     300 atcagcagtc tgcaacctga agattttgca acttactact gtcagcaaaa taatgtggac    360
ccgtggactt ttggccaggg gaccaagctg gagatcaaac                          400
```

<210> SEQ ID NO 262
<211> LENGTH: 400
<212> TYPE: DNA
<213> ORGANISM: Artificial sequence
<220> FEATURE:
<223> OTHER INFORMATION: Synthetic Construct

<400> SEQUENCE: 262

```
gtttgatctc cagcttggtc ccctggccaa aagtccacgg gtccacatta ttttgctgac      60
agtagtaagt tgcaaaatct tcaggttgca gactgctgat ggtgagagtg aaatctgtcc     120
cagatccact gccactgaac cttgatggga ccccagagtt taggttggat gcaagataga    180
tcaggagctt aggggctttc cctggttcct gctgatacca gtgcagaaaa ctattgccat    240
aaccatcaac actttcactg gctctgcaag tgatggtgac tctgtctcct acagatgcag    300
acagggagga tggagactgc gtcaacacta tttcacatct ggcacctcgg agccagagta    360
gcaggagccc caggagctga gcggggaccc tcatgtccat                          400
```

<210> SEQ ID NO 263
<211> LENGTH: 133
<212> TYPE: PRT
<213> ORGANISM: Artificial sequence
<220> FEATURE:
<223> OTHER INFORMATION: Synthetic Construct

<400> SEQUENCE: 263

```
Met Asp Met Arg Val Pro Ala Gln Leu Leu Gly Leu Leu Leu Leu Trp
 1               5                  10                  15
Leu Arg Gly Ala Arg Cys Glu Ile Val Leu Thr Gln Ser Pro Ser Ser
                20                  25                  30
Leu Ser Ala Ser Val Gly Asp Arg Val Thr Ile Thr Cys Arg Ala Ser
            35                  40                  45
Glu Ser Val Asp Gly Tyr Gly Asn Ser Phe Leu His Trp Tyr Gln Gln
        50                  55                  60
Lys Pro Gly Lys Ala Pro Lys Leu Leu Ile Tyr Leu Ala Ser Asn Leu
65                  70                  75                  80
Asn Ser Gly Val Pro Ser Arg Phe Ser Gly Ser Gly Ser Gly Thr Asp
                85                  90                  95
Phe Thr Leu Thr Ile Ser Ser Leu Gln Pro Glu Asp Phe Ala Thr Tyr
            100                 105                 110
Tyr Cys Gln Gln Asn Asn Val Asp Pro Trp Thr Phe Gly Gln Gly Thr
        115                 120                 125
Lys Leu Glu Ile Lys
    130
```

<210> SEQ ID NO 264
<211> LENGTH: 425
<212> TYPE: DNA
<213> ORGANISM: Artificial sequence
<220> FEATURE:
<223> OTHER INFORMATION: Synthetic Construct

<400> SEQUENCE: 264

```
aagcttgccg ccaccatgag gctccctgct cagctcctgg ggctgctaat gctctgggtc      60
ccagggtcca gcgggaaat tgtgctgact cagtctccac tctccctgcc cgtcacccctt    120
ggacagccgg cctccatctc ctgcagagcc agtgaaagtg ttgatggtta tggcaatagt    180
tttctgcact ggtttcagca gaggccaggc caatctccaa ggcgcctaat ttatcttgca    240
tccaacctaa actctggggt cccagacaga ttcagcggca gcggatcagg cactgatttc    300
acactgaaaa tcagcagagt ggaggctgag gatgttgggg tttattactg ccagcaaaat    360
aatgtggacc cgtggacgtt cggcggaggg accaaagtgg agatcaaacg tgagtggatc    420
ccgcg                                                                  425
```

<210> SEQ ID NO 265
<211> LENGTH: 142
<212> TYPE: PRT
<213> ORGANISM: Artificial sequence
<220> FEATURE:
<223> OTHER INFORMATION: Synthetic Construct

<400> SEQUENCE: 265

```
Lys Leu Ala Ala Thr Met Arg Leu Pro Ala Gln Leu Leu Gly Leu Leu
 1               5                  10                  15

Met Leu Trp Val Pro Gly Ser Ser Gly Glu Ile Val Leu Thr Gln Ser
            20                  25                  30

Pro Leu Ser Leu Pro Val Thr Leu Gly Gln Pro Ala Ser Ile Ser Cys
        35                  40                  45

Arg Ala Ser Glu Ser Val Asp Gly Tyr Gly Asn Ser Phe Leu His Trp
    50                  55                  60

Phe Gln Gln Arg Pro Gly Gln Ser Pro Arg Arg Leu Ile Tyr Leu Ala
65                  70                  75                  80

Ser Asn Leu Asn Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Val
            100                 105                 110

Gly Val Tyr Tyr Cys Gln Gln Asn Asn Val Asp Pro Trp Thr Phe Gly
        115                 120                 125

Gly Gly Thr Lys Val Glu Ile Lys Arg Glu Trp Ile Pro Arg
    130                 135                 140
```

<210> SEQ ID NO 266
<211> LENGTH: 399
<212> TYPE: DNA
<213> ORGANISM: Artificial sequence
<220> FEATURE:
<223> OTHER INFORMATION: Synthetic Construct

<400> SEQUENCE: 266

```
atggacatga gggtccctgc tcagctcctg gggctcctgc agctctggct ctcaggggcc      60
agatgtgaca tcgtgatgac ccagtctcca gactccctgg ctgtgtctct gggcgagagg     120
gccaccatca actgcagagc cagtgaaagt gttgatggtt atggcaatag ttttctgcac     180
tggtatcagc agaaaccggg acagcctcct aagttgctca tttaccttgc atccaaccta     240
aactctgggg tccctgaccg attcagtggc agcgggtctg gacagatttt cactctcacc     300
atcagcagcc tgcaggccga agatgtggca gtgtattact gtcagcaaaa taatgtggac     360
ccgtggactt ttggccaggg gaccaagctg gagatcaaa                            399
```

<210> SEQ ID NO 267
<211> LENGTH: 399
<212> TYPE: DNA
<213> ORGANISM: Artificial sequence
<220> FEATURE:
<223> OTHER INFORMATION: Synthetic Construct

<400> SEQUENCE: 267

```
tttgatctcc agcttggtcc cctggccaaa agtccacggg tccacattat tttgctgaca      60
gtaatacact gccacatctt cggcctgcag gctgctgatg gtgagagtga aatctgtccc     120
agacccgctg ccactgaatc ggtcagggac cccagagttt aggttggatg caaggtaaat     180
gagcaactta ggaggctgtc ccggtttctg ctgataccag tgcagaaaac tattgccata     240
```
accatcaaca ctttcactgg ctctgcagtt gatggtggcc ctctcgccca gagacacagc    300
cagggagtct ggagactggg tcatcacgat gtcacatctg gcccctgaga gccagagctg    360
caggagcccc aggagctgag cagggaccct catgtccat                           399

<210> SEQ ID NO 268
<211> LENGTH: 133
<212> TYPE: PRT
<213> ORGANISM: Artificial sequence
<220> FEATURE:
<223> OTHER INFORMATION: Synthetic Construct

<400> SEQUENCE: 268

Met Asp Met Arg Val Pro Ala Gln Leu Leu Gly Leu Leu Gln Leu Trp
 1               5                  10                  15

Leu Ser Gly Ala Arg Cys Asp Ile Val Met Thr Gln Ser Pro Asp Ser
                20                  25                  30

Leu Ala Val Ser Leu Gly Glu Arg Ala Thr Ile Asn Cys Arg Ala Ser
            35                  40                  45

Glu Ser Val Asp Gly Tyr Gly Asn Ser Phe Leu His Trp Tyr Gln Gln
        50                  55                  60

Lys Pro Gly Gln Pro Pro Lys Leu Leu Ile Tyr Leu Ala Ser Asn Leu
65                  70                  75                  80

Asn Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
               100                 105                 110

Tyr Cys Gln Gln Asn Asn Val Asp Pro Trp Thr Phe Gly Gln Gly Thr
            115                 120                 125

Lys Leu Glu Ile Lys
        130

<210> SEQ ID NO 269
<211> LENGTH: 351
<212> TYPE: DNA
<213> ORGANISM: Artificial sequence
<220> FEATURE:
<223> OTHER INFORMATION: Synthetic Construct

<400> SEQUENCE: 269
ggagacggtg actgaggttc cttgacccca gtagtccata gcataggtag tcgtagtaat     60
gagcgcacag taatatgtgg ctgtgtcctc agtagtcaca gaattcaact gcaggtagta    120
ctgattcttg gatgtgtctc gagtgatgga gatgcgactt ctgagagata gattgtagta    180
agtgctacca ctgtaactta tgtatcccat gtactcaagt ttattccctg gaatttccg     240 gatccagttc cagtaaccac tggtgatgga gtcgccagtg acagaacagg tgagggacag    300
agtctgagaa ggtttcacga ggctaggtcc tgactcctga agctgcacct c              351

<210> SEQ ID NO 270
<211> LENGTH: 333
<212> TYPE: DNA
<213> ORGANISM: Artificial sequence
<220> FEATURE:
<223> OTHER INFORMATION: Synthetic Construct

<400> SEQUENCE: 270
tttgatttcc agcttggtgc ctccaccgaa cgtccacggg tccacattat tttgctgaca     60
gtaataggtt gcagcatcat cagcctccac aggatcaatg gtgagggtga agtctgtcct    120

```
agacccactg ccactgaacc tggcagggac cccagagttt aggttggatg caagatagat    180
gaggagtttg ggtggctgtc ctggtttctg ctggaaccag tgcagaaaac tattgccata    240
accatcaaca ctttcactgg ctctgcagga aatggtggcc ctctgcccca gagacacagc    300
caaagaaact ggagattggg tcagcacaat gtt                                 333
```

<210> SEQ ID NO 271
<211> LENGTH: 351
<212> TYPE: DNA
<213> ORGANISM: Artificial sequence
<220> FEATURE:
<223> OTHER INFORMATION: Synthetic Construct

<400> SEQUENCE: 271

```
ggagacggtg accgtggtcc cttggcccca gtagtccata gcataggtag tcgtagtaat     60
tctcgcacag taatacatgg ccgtgtccgc agcggtcaca gagctcagcc tcagggagaa    120
ctggttctta gaggtgtcta ctgatatggt gacccgactt ctgagagata gattgtagta    180
agtgctacca ctgtaactta tgtatcctat ccactccagt gccctccctg ggggctgccg    240
gatccagttc cagtaaccac tactgatgga gtcaccagag acagtgcagg tgagggacag    300
ggtctccgaa ggcttcacca gtcctggtcc cgactcctgc agctgcactt g             351
```

<210> SEQ ID NO 272
<211> LENGTH: 334
<212> TYPE: DNA
<213> ORGANISM: Artificial sequence
<220> FEATURE:
<223> OTHER INFORMATION: Synthetic Construct

<400> SEQUENCE: 272

```
ggttgatctc cagcttggtc ccctggccaa aggtccacgg gtccacatta ttttgctgac     60
agtaataaac tgccacatct tcagcctgca ggctgctgat ggtgagactg aattctgtcc    120
cagacccgct gccatgaatc gggcaggga ccccagagtt taggttggat gcaagataaa    180
tgaggagttt aggaggctgt cctgggtttt gctggaacca gtgcagaaaa ctattgccat    240
aaccatcaac actttcactg ctctgcagt tgacggtgac cctctcgccc agagacacag    300
acagggagtc tggagactgg gtcagcacga tgtc                                334
```

<210> SEQ ID NO 273
<211> LENGTH: 333
<212> TYPE: DNA
<213> ORGANISM: Artificial sequence
<220> FEATURE:
<223> OTHER INFORMATION: Synthetic Construct

<400> SEQUENCE: 273

```
tttgatctcc agcttggtcc cctggccaaa ggtccacggg tccacattat tttgctgaca     60
gtaataaact gccacatctt cagcctgcag gctgctgatg gtgagactga attctgtccg    120
agacccgctg cccatgaatc gggcagggac cccagagttt aggttggatg caagataaat    180
gaggagttta ggaggctgtc ctgggttttg ctggaaccag tgcagaaaac tattgccata    240
accatcaaca ctttcactgg ctctgcagtt gacggtgacc ctctcgccca gagacacaga    300
cagggagtct ggagactggg tcagcacgat gtc                                 333
```

<210> SEQ ID NO 274
<211> LENGTH: 334
<212> TYPE: DNA
<213> ORGANISM: Artificial sequence
<220> FEATURE:
<223> OTHER INFORMATION: Synthetic Construct

<400> SEQUENCE: 274

```
gtttgatctc cagcttggtc ccctggccaa aagtccacgg gtccacatta ttttgctgac      60
agtagtaagt tgcaaaatct tcaggttgca gactgctgat ggtgagagtg aaatctgtcc     120
cagatccact gccactgaac cttgatggga ccccagagtt taggttggat gcaagataga    180
tcaggagctt aggggctttc cctggtttct gctgatacca gtgcagaaaa ctattgccat    240
aaccatcaac actttcactg gctctgcaag tgatggtgac tctgtctcct acagatgcag   300
acagggagga tggagactgc gtcaacacta tttc                                 334
```

<210> SEQ ID NO 275
<211> LENGTH: 333
<212> TYPE: DNA
<213> ORGANISM: Artificial sequence
<220> FEATURE:
<223> OTHER INFORMATION: Synthetic Construct

<400> SEQUENCE: 275

```
tttgatctcc agcttggtcc cctggccaaa agtccacggg tccacattat tttgctgaca     60
gtagtaagtt gcaaaatctt caggttgcag actgctgatg gtgagagtga aatctgtccg    120
agatccactg ccactgaacc ttgatgggac cccagagttt aggttggatg caagatagat    180
caggagctta ggggctttcc ctggtttctg ctgaaaccag tgcagaaaac tattgccata    240
accatcaaca ctttcactgg ctctgcaagt gatggtgact ctgtctccta cagatgcaga    300
cagggaggat ggagactgcg tcaacactat ttc                                  333
```

<210> SEQ ID NO 276
<211> LENGTH: 350
<212> TYPE: DNA
<213> ORGANISM: Artificial sequence
<220> FEATURE:
<223> OTHER INFORMATION: Synthetic Construct

<400> SEQUENCE: 276

```
cgcgggatcc actcacgttt gatctccact ttggtccctc cgccgaacgt ccacgggtcc     60
acattatttt gctggcagta ataaccccca acatcctcag cctccactct gctgattttc    120
agtgtgaaat cagtccttga tccgctgccg ctgaatctgt ctgggacccc agagtttagg    180
ttggatgcaa gataaattag gagccttgga gattggcctg gcctctgctg aaaccagtgc    240
agaaaactat tgccataacc atcaacactt tcactggctc tgcaggagat ggaggccggc    300
tgtccaaggg tgacgggcag ggagagtgga gactgagtca gcacaatttc                350
```

<210> SEQ ID NO 277
<211> LENGTH: 333
<212> TYPE: DNA
<213> ORGANISM: Artificial sequence
<220> FEATURE:
<223> OTHER INFORMATION: Synthetic Construct

<400> SEQUENCE: 277

```
tttgatctcc agcttggtcc cctggccaaa agtccacggg tccacattat tttgctgaca     60
gtaatacact gccacatctt cggcctgcag gctgctgatg gtgagagtga aatctgtccc    120
agacccgctg ccactgaatc ggtcagggac cccagagttt aggttggatg caaggtaaat    180
gagcaactta ggaggctgtc ccggtttctg ctgataccag tgcagaaaac tattgccata    240
```

```
accatcaaca ctttcactgg ctctgcagtt gatggtggcc ctctcgccca gagacacagc    300
cagggagtct ggagactggg tcatcacgat gtc                                333
```

<210> SEQ ID NO 278
<211> LENGTH: 351
<212> TYPE: DNA
<213> ORGANISM: Artificial sequence
<220> FEATURE:
<223> OTHER INFORMATION: Synthetic Construct

<400> SEQUENCE: 278

```
ggagacggtg accgtggtcc cttggcccca gtagtccata gcataggtag tcgtagtaat     60
cagcgcacag taatacatgg ccgtgtccgc agcggtcaca gagctcagcc tcagggagta    120
ctggttctta gaggtgtctc ttgatatggt gatccgactt ctgagagata gattgtagta    180
agtgctacca ctgtaactta tgtatcccat gtactccagt gccctccctg ggggctgccg    240
gatccagttc cagtaaccac tagtgatgga gtcaccagag acagtgcagg tgagggacag    300
ggtctccgaa ggcttcacca gtcctggtcc cgactcctgc agctgcactt g             351
```

<210> SEQ ID NO 279
<211> LENGTH: 351
<212> TYPE: DNA
<213> ORGANISM: Artificial sequence
<220> FEATURE:
<223> OTHER INFORMATION: Synthetic Construct

<400> SEQUENCE: 279

```
ggagacggtg accgtggtcc cttggcccca gtagtccata gcataggtag tcgtagtaat     60
cagcgcacag taatacatgg ccgtgtccgc agcggtcaca gagctcagcc tcagggagta    120
ctggttctta gaggtgtctc ttgatatggt gatccgactt ctgagagata gattgtagta    180
agtgctacca ctgtaactta tgtatcccat gtactccagt gccctccctg gggcttccg     240 gatccagttc cagtaaccac tagtgatgga gtcaccagag acagtgcagg tgagggacag    300
ggtctccgaa ggcttcacca gtcctggtcc cgactcctgc agctgcactt g             351
```

<210> SEQ ID NO 280
<211> LENGTH: 354
<212> TYPE: DNA
<213> ORGANISM: Artificial sequence
<220> FEATURE:
<223> OTHER INFORMATION: Synthetic Construct

<400> SEQUENCE: 280

```
tgaggagacg gtgaccgtgg tcccttggcc ccagtagtcc atagcatagg tagtcgtagt     60
aatcagcgca cagtaataca tggccgtgtc cgcagcggtc acagagctca gcctcaggga    120
gtactggttc ttagaggtgt ctcttgatat ggtgatccga cttctgagag atagattgta    180
gtaagtgcta ccactgtaac ttatgtatcc catgtactcc agtgccctcc ctggggctg     240 ccggatccag ttcagtaac cactactgat ggagtcacca gagacagtgc aggtgaggga    300
cagggtctcc gaaggcttca ccagtcctgg tcccgactcc tgcagctgca cttg          354
```

<210> SEQ ID NO 281
<211> LENGTH: 354
<212> TYPE: DNA
<213> ORGANISM: Artificial sequence
<220> FEATURE:
<223> OTHER INFORMATION: Synthetic Construct

<400> SEQUENCE: 281

```
tgaggagacg gtgaccgtgg tcccttggcc ccagtagtcc atagcatagg tagtcgtagt    60
aatcagcgca cagtaataca tggccgtgtc cgcagcggtc acagagctca gcctcaggga   120
gtactggttc ttagaggtgt ctcttgatat ggtgatccga cttctgagag atagattgta   180
gtaagtgcta ccactgtaac ttatgtatcc catccactcc agtgccctcc ctggggctg    240 ccggatccag ttccagtaac cactggtgat ggagtcacca gagacagtgc aggtgaggga   300
cagggtctcc gaaggcttca ccagtcctgg tcccgactcc tgcagctgca cttg         354
```

<210> SEQ ID NO 282
<211> LENGTH: 351
<212> TYPE: DNA
<213> ORGANISM: Artificial sequence
<220> FEATURE:
<223> OTHER INFORMATION: Synthetic Construct

<400> SEQUENCE: 282

```
ggagacggtg accgtggtcc cttggcccca gtagtccata gcataggtag tcgtagtaat    60
cagcgcacag taatacatgg ccgtgtccgc agcggtcaca gagctcagcc tcagggagta   120
ctggttctta gaggtgtctc ttgatatggt gatccgactt ctgagagata gattgtagta   180
agtgctacca ctgtaactta tgtatcctat gtactccagt gccctccctg ggggctgccg   240
gatccagttc cagtaaccac tggtgatgga gtcaccagag acagtgcagg tgagggacag   300
ggtctccgaa ggcttcacca gtcctggtcc cgactcctgc agctgcactt g             351
```

<210> SEQ ID NO 283
<211> LENGTH: 351
<212> TYPE: DNA
<213> ORGANISM: Artificial sequence
<220> FEATURE:
<223> OTHER INFORMATION: Synthetic Construct

<400> SEQUENCE: 283

```
ggagacggtg accgtggtcc cttggcccca gtagtccata gcataggtag tcgtagtaat    60
cagcgcacag taatacatgg ccgtgtccgc agcggtcaca gagctcagcc tcagggagta   120
ctggttctta gaggtgtctc ttgatatggt gacccgactt ctgagagata gattgtagta   180
agtgctacca ctgtaactta tgtatcccat gtactccagt gccctccctg ggggctgccg   240
gatccagttc cagtaaccac tggtgatgga gtcaccagag acagtgcagg tgagggacag   300
ggtctccgaa ggcttcacca gtcctggtcc cgactcctgc agctgcactt g             351
```

<210> SEQ ID NO 284
<211> LENGTH: 351
<212> TYPE: DNA
<213> ORGANISM: Artificial sequence
<220> FEATURE:
<223> OTHER INFORMATION: Synthetic Construct

<400> SEQUENCE: 284

```
ggagacggtg accgtggtcc cttggcccca gtagtccata gcataggtag tcgtagtaat    60
cagcgcacag taatacatgg ccgtgtccgc agcggtcaca gagctcagcc tcagggagta   120
ctggttctta gaggtgtcca ctgatatggt gatccgactt ctgagagata gattgtagta   180
agtgctacca ctgtaactta tgtatcccat gtactccagt gccctccctg ggggctgccg   240
gatccagttc cagtaaccac tggtgatgga gtcaccagag acagtgcagg tgagggacag   300
ggtctccgaa ggcttcacca gtcctggtcc cgactcctgc agctgcactt g             351
```

<210> SEQ ID NO 285
<211> LENGTH: 351
<212> TYPE: DNA
<213> ORGANISM: Artificial sequence
<220> FEATURE:
<223> OTHER INFORMATION: Synthetic Construct

<400> SEQUENCE: 285
ggagacggtg accgtggtcc cttggcccca gtagtccata gcataggtag tcgtagtaat     60
cagcgcacag taatacatgg ccgtgtccgc agcggtcaca gagctcagcc tcagggagaa    120
ctggttctta gaggtgtctc ttgatatggt gatccgactt ctgagagata gattgtagta    180
agtgctacca ctgtaactta tgtatcccat gtactccagt gccctccctg ggggctgccg    240
gatccagttc cagtaaccac tggtgatgga gtcaccagag acagtgcagg tgagggacag    300
ggtctccgaa ggcttcacca gtcctggtcc cgactcctgc agctgcactt g             351

<210> SEQ ID NO 286
<211> LENGTH: 351
<212> TYPE: DNA
<213> ORGANISM: Artificial sequence
<220> FEATURE:
<223> OTHER INFORMATION: Synthetic Construct

<400> SEQUENCE: 286
ggagacggtg accgtggtcc cttggcccca gtagtccata gcataggtag tcgtagtaat     60
tctcgcacag taatacatgg ccgtgtccgc agcggtcaca gagctcagcc tcagggagta    120
ctggttctta gaggtgtctc ttgatatggt gatccgactt ctgagagata gattgtagta    180
agtgctacca ctgtaactta tgtatcccat gtactccagt gccctccctg ggggctgccg    240
gatccagttc cagtaaccac tggtgatgga gtcaccagag acagtgcagg tgagggacag    300
ggtctccgaa ggcttcacca gtcctggtcc cgactcctgc agctgcactt g             351

<210> SEQ ID NO 287
<211> LENGTH: 333
<212> TYPE: DNA
<213> ORGANISM: Artificial sequence
<220> FEATURE:
<223> OTHER INFORMATION: Synthetic Construct

<400> SEQUENCE: 287
tttgatctcc agcttggtcc cctggccaaa agtccacggg tccacattat tttgctgaca     60
gtagtaagtt gcaaaatctt caggttgcag actgctgatg gtgagagtga aatctgtccc    120
agatccactg ccactgaacc ttgatgggac cccagagttt aggttggatg caagatagat    180
caggagctta ggggctttcc ctggtttctg ctgaaaccag tgcagaaaac tattgccata    240
accatcaaca ctttcactgg ctctgcaagt gatggtgact ctgtctccta cagatgcaga    300
cagggaggat ggagactgcg tcaacactat ttc                                 333

<210> SEQ ID NO 288
<211> LENGTH: 334
<212> TYPE: DNA
<213> ORGANISM: Artificial sequence
<220> FEATURE:
<223> OTHER INFORMATION: Synthetic Construct

<400> SEQUENCE: 288
gtttgatctc cagcttggtc ccctggccaa aagtccacgg gtccacatta ttttgctgac     60
agtagtaagt tgcaaaatct tcaggttgca gactgctgat ggtgagagtg aaatctgtcc    120

```
gagatccact gccactgaac cttgatggga ccccagagtt taggttggat gcaagataga    180
tcaggagctt aggggctttc cctggtttct gctgatacca gtgcagaaaa ctattgccat   240
aaccatcaac actttcactg gctctgcaag tgatggtgac tctgtctcct acagatgcag   300
acagggagga tggagactgc gtcaacacta tttc                              334

<210> SEQ ID NO 289
<211> LENGTH: 5
<212> TYPE: PRT
<213> ORGANISM: Artificial sequence
<220> FEATURE:
<223> OTHER INFORMATION: Synthetic Construct

<400> SEQUENCE: 289

Lys Leu Glu Ile Asn
 1               5

<210> SEQ ID NO 290
<211> LENGTH: 5
<212> TYPE: PRT
<213> ORGANISM: Artificial sequence
<220> FEATURE:
<223> OTHER INFORMATION: Synthetic Construct

<400> SEQUENCE: 290

Lys Leu Glu Ile Lys
 1               5

<210> SEQ ID NO 291
<211> LENGTH: 5
<212> TYPE: PRT
<213> ORGANISM: Artificial sequence
<220> FEATURE:
<223> OTHER INFORMATION: Synthetic Construct

<400> SEQUENCE: 291

Ala Tyr Gly Asp Ile
 1               5

<210> SEQ ID NO 292
<211> LENGTH: 5
<212> TYPE: PRT
<213> ORGANISM: Artificial sequence
<220> FEATURE:
<223> OTHER INFORMATION: Synthetic Construct

<400> SEQUENCE: 292

Ala Arg Cys Glu Ile
 1               5

<210> SEQ ID NO 293
<211> LENGTH: 5
<212> TYPE: PRT
<213> ORGANISM: Artificial sequence
<220> FEATURE:
<223> OTHER INFORMATION: Synthetic Construct

<400> SEQUENCE: 293

Ser Ser Gly Glu Ile
 1               5
```